(12) United States Patent
Johnson et al.

(10) Patent No.: US 7,786,270 B2
(45) Date of Patent: Aug. 31, 2010

(54) HUMANIZED FCγRIIB-SPECIFIC ANTIBODIES AND METHODS OF USE THEREOF

(75) Inventors: Leslie S. Johnson, Darnestown, MD (US); Ling Huang, Bethesda, MD (US)

(73) Assignee: MacroGenics, Inc., Rockville, MD (US)

( * ) Notice: Subject to any disclaimer, the term of this patent is extended or adjusted under 35 U.S.C. 154(b) by 121 days.

(21) Appl. No.: 11/754,015

(22) Filed: May 25, 2007

(65) Prior Publication Data

US 2008/0044417 A1 Feb. 21, 2008

Related U.S. Application Data

(60) Provisional application No. 60/809,116, filed on May 26, 2006, provisional application No. 60/816,126, filed on Jun. 23, 2006.

(51) Int. Cl.
*C12P 21/08* (2006.01)
(52) U.S. Cl. .................. 530/387.3; 530/350; 530/387.1
(58) Field of Classification Search ................. 530/350, 530/387.1, 387.3
See application file for complete search history.

(56) References Cited

U.S. PATENT DOCUMENTS

| | | | |
|---|---|---|---|
| 4,179,337 A | 12/1979 | Davis et al. | |
| 4,752,601 A | 6/1988 | Hahn | |
| 5,348,876 A | 9/1994 | Michaelsen et al. | |
| 5,576,184 A | 11/1996 | Better et al. | |
| 5,585,089 A | 12/1996 | Queen et al. | |
| 5,624,821 A | 4/1997 | Winter et al. | |
| 5,648,260 A | 7/1997 | Winter et al. | |
| 5,693,761 A | 12/1997 | Queen et al. | |
| 5,693,762 A | 12/1997 | Queen et al. | |
| 5,698,449 A | 12/1997 | Baumann et al. | |
| 5,711,944 A | 1/1998 | Gilbert et al. | |
| 5,723,584 A | 3/1998 | Schatz | |
| 5,736,135 A | 4/1998 | Goeddel et al. | |
| 5,736,137 A | 4/1998 | Anderson et al. | |
| 5,837,243 A | 11/1998 | Deo et al. | |
| 5,874,239 A | 2/1999 | Schatz | |
| 5,888,533 A | 3/1999 | Dunn | |
| 5,932,433 A | 8/1999 | Schatz | |
| 5,945,115 A | 8/1999 | Dunn et al. | |
| 5,985,599 A | 11/1999 | McKenzie et al. | |
| 6,019,968 A | 2/2000 | Platz et al. | |
| 6,025,485 A | 2/2000 | Kamb et al. | |
| 6,114,147 A | 9/2000 | Frenken et al. | |
| 6,132,764 A | 10/2000 | Li et al. | |
| 6,165,745 A | 12/2000 | Ward et al. | |
| 6,180,370 B1 | 1/2001 | Queen et al. | |
| 6,194,551 B1 | 2/2001 | Idusogie et al. | |
| 6,218,149 B1 | 4/2001 | Morrison et al. | |
| 6,242,195 B1 | 6/2001 | Idusogie et al. | |
| 6,277,375 B1 | 8/2001 | Ward | |
| 6,300,065 B1 | 10/2001 | Kieke et al. | |
| 6,339,069 B1 | 1/2002 | Meers et al. | |
| 6,420,149 B1 | 7/2002 | Fukuda et al. | |
| 6,423,538 B1 | 7/2002 | Wittrup et al. | |
| 6,455,263 B2 | 9/2002 | Payan | |
| 6,472,511 B1 | 10/2002 | Leung et al. | |
| 6,528,624 B1 | 3/2003 | Idusogie et al. | |
| 6,538,124 B1 | 3/2003 | Idusogie et al. | |
| 6,548,640 B1 | 4/2003 | Winter | |
| 6,737,056 B1 | 5/2004 | Presta | |
| 6,821,505 B2 | 11/2004 | Ward | |
| 6,982,321 B2 | 1/2006 | Winter | |
| 7,315,786 B2 | 1/2008 | Dahiyat et al. | |
| 7,317,091 B2 | 1/2008 | Lazar et al. | |
| 7,355,008 B2 | 4/2008 | Stavenhagen et al. | |
| 7,655,229 B2 | 2/2010 | Chan et al. | |
| 7,662,926 B2 | 2/2010 | Chan et al. | |
| 2001/0036459 A1 | 11/2001 | Ravetch | |
| 2002/0028486 A1 | 3/2002 | Morrison et al. | |
| 2003/0077282 A1 | 4/2003 | Bigler et al. | |

(Continued)

FOREIGN PATENT DOCUMENTS

EP 0 327 378 8/1989

(Continued)

OTHER PUBLICATIONS

Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Rudikoff et al (PNAS, 79:1979-1983, 1982).*
Alt et al., "Novel Tetravalent and Bispecific IgG-Like Antibody Molecules Combining Single-Chain Diabodies With the Immunoglobin Gamma 1 Fc or CH3 Region," FEBS Letters 454: 90-94, 1999.

(Continued)

*Primary Examiner*—Stephen L Rawlings
*Assistant Examiner*—Brad Duffy
(74) *Attorney, Agent, or Firm*—Jeffrey I. Auerbach; Edell, Shapiro & Finnan, LLC

(57) ABSTRACT

The present invention relates to humanized FcγRIIB antibodies, fragments, and variants thereof that bind human FcγRIIB with a greater affinity than said antibody binds FcγRIIA. The invention encompasses the use of the humanized antibodies of the invention for the treatment of any disease related to loss of balance of Fc receptor mediated signaling, such as cancer, autoimmune and inflammatory disease. The invention provides methods of enhancing the therapeutic effect of therapeutic antibodies by administering the humanized antibodies of the invention to enhance the effector function of the therapeutic antibodies. The invention also provides methods of enhancing the efficacy of a vaccine composition by administering the humanized antibodies of the invention. The invention encompasses methods for treating an autoimmune disease and methods for elimination of cancer cells that express FcγRIIB.

5 Claims, 10 Drawing Sheets

U.S. PATENT DOCUMENTS

Figure 3:
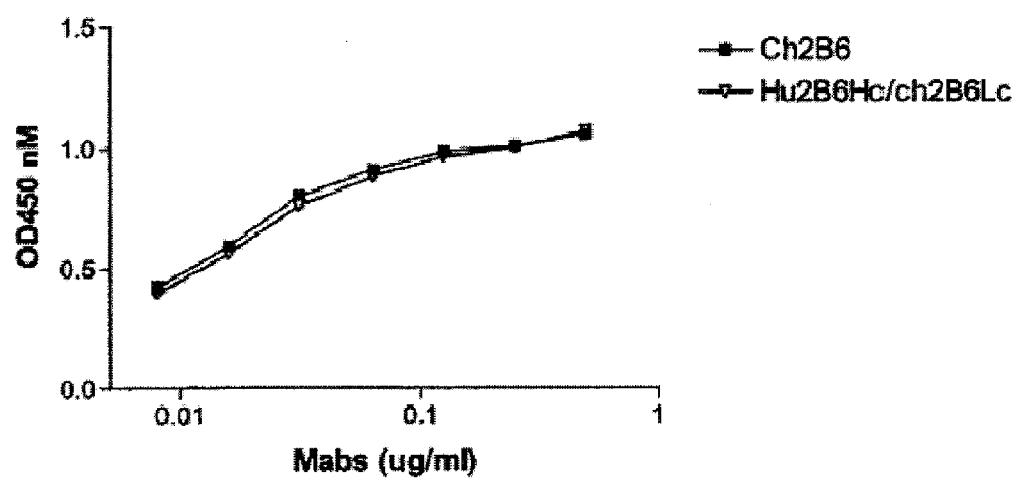

| | | |
|---|---|---|
| 2003/0115614 A1 | 6/2003 | Kanda et al. |
| 2003/0158389 A1 | 8/2003 | Idusogie et al. |
| 2003/0190319 A1 | 10/2003 | Adolf et al. |
| 2004/0002587 A1 | 1/2004 | Watkins et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0191244 A1 | 9/2004 | Presta |
| 2004/0220388 A1 | 11/2004 | Mertens et al. |
| 2004/0236078 A1 | 11/2004 | Carter et al. |
| 2005/0037000 A1 | 2/2005 | Stavenhagen et al. |
| 2005/0037358 A1* | 2/2005 | Muyldermans |
| 2005/0054832 A1 | 3/2005 | Lazar et al. |
| 2005/0064514 A1 | 3/2005 | Stavenhagen et al. |
| 2005/0215767 A1 | 9/2005 | Koenig et al. |
| 2005/0260213 A1 | 11/2005 | Koenig et al. |
| 2006/0013810 A1 | 1/2006 | Johnson et al. |
| 2006/0018899 A1 | 1/2006 | Kao et al. |
| 2006/0024298 A1 | 2/2006 | Lazar et al. |
| 2006/0073142 A1 | 4/2006 | Chan et al. |
| 2006/0134709 A1 | 6/2006 | Stavenhagen et al. |
| 2006/0177439 A1 | 8/2006 | Koenig et al. |
| 2007/0004909 A1 | 1/2007 | Johnson et al. |
| 2007/0036799 A1* | 2/2007 | Stavenhagen et al. |
| 2007/0253948 A1 | 11/2007 | Chan et al. |
| 2008/0131435 A1 | 6/2008 | Stavenhagen et al. |
| 2008/0138344 A1 | 6/2008 | Stavenhagen et al. |
| 2008/0286819 A1 | 11/2008 | Ravetch et al. |
| 2009/0053218 A1 | 2/2009 | Koenig et al. |

FOREIGN PATENT DOCUMENTS

| | | |
|---|---|---|
| EP | 0 332 865 | 9/1989 |
| EP | 0 629 703 | 12/1994 |
| EP | 0 359 096 | 11/1997 |
| EP | 0 953 639 | 11/1999 |
| EP | 1 006 183 | 6/2000 |
| EP | 0 343 950 | 10/2000 |
| WO | WO 88/07089 | 9/1988 |
| WO | WO 89/07142 | 8/1989 |
| WO | WO 92/16562 | 10/1992 |
| WO | WO 93/22332 | 11/1993 |
| WO | WO 94/18330 | 8/1994 |
| WO | WO 94/29351 | 12/1994 |
| WO | WO 95/05468 | 2/1995 |
| WO | WO 97/28267 | 8/1997 |
| WO | WO 97/34631 | 9/1997 |
| WO | WO 97/44362 | 11/1997 |
| WO | WO 98/05787 | 2/1998 |
| WO | WO 98/23289 | 6/1998 |
| WO | WO 98/52975 | 11/1998 |
| WO | WO 99/19362 | 4/1999 |
| WO | WO 99/41285 | 8/1999 |
| WO | WO 99/43713 | 9/1999 |
| WO | WO 99/51642 | 10/1999 |
| WO | WO 99/58572 | 11/1999 |
| WO | WO 00/09560 | 2/2000 |
| WO | WO 00/42072 | 7/2000 |
| WO | WO 01/79299 | 10/2001 |
| WO | WO 02/060919 | 8/2002 |
| WO | WO 02/086070 | 10/2002 |
| WO | WO 03/035835 | 5/2003 |
| WO | WO 03/066095 | 8/2003 |
| WO | WO 03/074679 | 9/2003 |
| WO | WO 2004/016750 | 2/2004 |
| WO | WO 2004/029207 | 4/2004 |
| WO | WO 2004/063351 | 7/2004 |
| WO | WO 2004/065423 | 8/2004 |
| WO | WO 2004/074455 | 9/2004 |
| WO | WO 2004/099249 | 11/2004 |
| WO | WO 2005/070963 | 8/2005 |
| WO | WO 2005/110474 | 11/2005 |
| WO | WO 2005/115452 | 12/2005 |
| WO | WO 2006/020114 | 2/2006 |
| WO | WO 2006/028956 | 3/2006 |
| WO | WO 2006/066078 | 6/2006 |
| WO | WO 2006/088494 | 8/2006 |
| WO | WO 2006/113665 | 10/2006 |
| WO | WO 2007/021841 | 2/2007 |
| WO | 2007/024249 A2 | 3/2007 |
| WO | WO 2007/106707 | 9/2007 |
| WO | WO 2008/002933 | 1/2008 |
| WO | WO 2008/019199 | 2/2008 |
| WO | WO 2009/083009 | 7/2009 |

OTHER PUBLICATIONS

Altman et al., "Phenotypic Analysis of Antigen-Specific T Lymphocytes", Science 274:94-96, 1996.

Angal et al., "A single amino acid substitution abolishes the heterogeneity of chimeric mouse/human (IgG4) antibody," Mol Immunol 30 :105-108, 1993.

Armour et al., "The contrasting IgG-binding interactions of human and herpes simplex virus Fc receptors," Biochemical Society Transactions 30:495-500, 2002.

Armour et al., "Recombinant human IgG molecules lacking Fcgamma receptor I binding and monocyte triggering activities," Eur J Immunol 29:2613-2624, 1999.

Armour et al., "Differential binding to human FcgammaRIIa and FcgammaRIIb receptors by human IgG wildtype and mutant antibodies," Mol Immunol 40 :585-593, 2003.

Armstrong, S. et al. "Heterogeneity of IgG1 monoclonal anti-Rh(D): an investigation using ADCC and macrophage binding assays," Brit. J. Haematol. 66:257-262 (1987).

Baggiolini M, Dewald B. "Cellular models for the detection and evaluation of drugs that modulate human phagocyte activity," Experientia. Oct. 15;44(10):841-848, 1988.

Boder and Wittrup, 1997, "Yeast surface display for screening combinatorial polypeptide libraries", Nature Biotechnology 15:553-557.

Boder and Wittrup, "Optimal screening of surface-displayed polypeptide libraries," Biotechnol Prog 14:55-62, 1998.

Boder and Wittrup, "Yeast surface display for directed evolution of protein expression, affinity, and stability," Methods in Enzymology 328:430-444, 2000.

Boder et al., "Directed evolution of antibody fragments with monovalent femtomolar antigen-binding affinity," Proc. Natl. Acad. Sci. USA 97:10701-10705, 2000.

Bredius et al., "Role of neutrophil Fc gamma RIIa (CD32) and Fc gamma RIIIb (CD16) polymorphic forms in phagocytosis of human IgG1- and IgG3-opsonized bacteria and erythrocytes," Immunology 83:624-630, 1994.

Brekke et al., "Human IgG isotype-specific amino acid residues affecting complement-mediated cell lysis and phagocytosis.," Eur J Immunol 24:2542-2547, 1994.

Brown EJ., vol. 45 (Microbes as Tools for Cell Biology) in *Methods in Cell Biololgy*, Russell ed. Academic Press Inc. pp. 147-164, 1994.

Burlmeister et al., "Crystal structure of the complex of rat neonatal Fc receptor with Fc," Nature 372:379-383, 1994.

Burton and Woof, "Human antibody effector function," Advances in Immunology 51:1-84, 1992.

Burton et al., "Molecular recognition of antibody (IgG) by cellular Fc receptor (FcRI)," Mol Immunol 25:1175-1181, 1988.

Burton, "Immunoglobulin G: functional sites," Mol Immunol 22:161-206, 1985.

Canfield and Morrison, "The binding affinity of human IgG for its high affinity Fc receptor is determined by multiple amino acids in the CH2 domain and is modulated by the hinge region," J Exp Med 173:1483-1491, 1991.

Caron et al., "Engineered humanized dimeric forms of IgG are more effective antibodies," J Exp Med 176 :1191-5, 1992.

Carter et al., "Humanization of an anti-p185HER2 antibody for human cancer therapy," Proc. Natl. Acad. Sci. USA 89:4285-4289, 1992.

Cartron et al., "Therapeutic activity of humanized anti-CD20 monoclonal antibody and polymorphism in IgG Fc receptor FcgammaRIIIa gene," Blood 99 :754-758, 2002.

Chappel et al., "Identification of the Fc gamma receptor class I binding site in human IgG through the use of recombinant IgG1/IgG2 hybrid and point-mutated antibodies," Proc. Natl. Acad. Sci USA 88:9036-9040, 1991.

Chappel et al., "Identification of a secondary Fc gamma RI binding site within a genetically engineered human IgG antibody," J Biol. Chem 268:25124-25131, 1993.

Ciccimarra et al., "Localization of the IgG effector site for monocyte receptors," Proc. Natl. Acad. Sci. U.S.A. 72 :2081-2083, 1975.

Clynes and Ravetch, "Cytotoxic antibodies trigger inflammation through Fc receptors," Immunity 3:21-26, 1995.

Clynes et al., "Modulation of immune complex-induced inflammation in vivo by the coordinate expression of activation and inhibitory Fc receptors," J Exp Med 189:179-185, 1999.

Clynes et al., "Inhibitory Fc receptors modulate in vivo cytoxicity against tumor targets," Nature Medicine 6 :443-446, 2000.

Clynes et al., "Fc receptors are required in passive and active immunity to melanoma," Proc. Natl. Acad. Sci USA 95:652-656, 1998.

Clynes et al., "Uncoupling of immune complex formation and kidney damage in autoimmune glomerulonephritis," Science 279:1052-1054, 1998.

de Haas, Wien Kin "IgG-Fc receptors and the clinical relevance of their polymorphisms," Wien Klin Wochenscha 113:825-831, 2001.

Deisenhofer, "Crystallographic refinement and atomic models of a human Fc fragment and its complex with fragment B of protein A from *Staphylococcus aureus* at 2.9- and 2.8-A resolution," Biochem. 20:2361-2370, 1981.

Deo et al., "Clinical significance of IgG Fc receptors and Fc gamma R-directed immunotherapies," Immunology Today 18:127-135, 1997.

Duncan and Winter, "The binding site for C1q on IgG," Nature 332 :738-740, 1988.

Duncan and Winter, "Localization of the binding site for the human high-affinity Fc receptor on IgG," Nature 332:563-564, 1988.

Edberg et al., "Modulation of Fcgamma and Complement Receptor Function by the Glycosyl-Phosphatidylinositol-Anchored Form of FcgammaRIII," Journal of Immunology 152: 5826-5835, 1994.

Flesch and Neppert, "Functions of the Fc receptors for immunoglobulin G," J Clin Lab Anal 14:141-156, 2000.

Gergeley et al., "Fc receptors on lymphocytes and K cells," Biochemical Society Transactions 12:739-743, 1984.

Gergely and Sarmay, "The two binding-site models of human IgG binding Fc gamma receptors," FASEB J 4:3275-3283, 1990.

Greenwood and Clark, Effector functions of matched sets of recombinant human IgG subclass antibodies. (final version edited Feb. 11, 1993).

Greenwood et al., "Structural motifs involved in human IgG antibody effector functions," Eur J Immunol 23:1098-1104, 1993.

Greenwood et al., "Engineering multiple-domain forms of the therapeutic antibody CAMPATH-1H: effects on complement lysis," Therapeutic Immunology 1:247-255, 1994.

Hadley et al., "The functional activity of Fc gamma RII and Fc gamma RIII on subsets of human lymphocytes," Immunology 76:446-451, 1992.

Hatta et al., "Association of Fc gamma receptor IIIB, but not of Fc gamma receptor IIA and IIIA polymorphisms with systemic lupus erythematosus in Japanese," Genes and Immunity 1:53-60, 1999.

Hayes, Fc Engineering to Enhance Monoclonal Antibody Effector Functions. (Presentation) Xecor, CA, 2003.

Herzenberg et al., "The history and future of the fluorescence activated cell sorter and flow cytometry: a view from Stanford," Clinical Chem. 2002:48:1819-1827, 2002.

Heyman, "Regulation of antibody responses via antibodies, complement, and Fc receptors," Annu Rev Immunol 18:709-737, 2000.

Hogarth et al., "Characterization of FcR Ig-binding sites and epitope mapping," Immunomethods 4 :17-24, 1994.

Holler et al., "In vitro evolution of a T cell receptor with high affinity for peptide/MHC," Proc. Natl. Acad. Sci. U.S.A. 97 :5387-92, 2000.

Hulett et al., "Identification of the IgG binding site of the human low affinity receptor for IgG Fc gamma RII. Enhancement and ablation of binding by site-directed mutagenesis," J. Biol. Chem. 269:15287-15293, 1994.

Hulett et al., "Multiple regions of human Fc gamma RII (CD32) contribute to the binding of IgG," J. Biol. Chem. 270:21188-21194, 1995.

Hulett et al., "Chimeric Fc receptors identify functional domains of the murine high affinity receptor for IgG," J Immunol 147 :1863-1868, 1991.

Idusogie et al., "Mapping of the C1q binding site on rituxan, a chimeric antibody with a human IgG1 Fc," J Immunol 164: 4178-4184, 2000.

Idusogie et al., "Engineered antibodies with increased activity to recruit complement," J Immunol 166 :2571-2575, 2001.

Isaacs et al., "A therapeutic human IgG4 monoclonal antibody that depletes target cells in humans," Clin Exp Immunol 106 :427-433, 1996.

Isaacs et al., "Therapy with monoclonal antibodies. An in vivo model for the assessment of therapeutic potential," J Immunol 148 :3062-3071, 1992.

Isaacs et al., "Therapy with monoclonal antibodies. II. The contribution of Fc gamma receptor binding and the influence of C(H)1 and C(H)3 domains on in vivo effector function," J Immunol 161 :3862-3869, 1998.

Jassal et al., "Remodeling glycans on IgG by genetic re-engineering," Biochem Soc Trans 26 :S113, 1998.

Jefferis and Lund, "Interaction sites on human IgG-Fc for FcgammaR: current models," Immunology Letters 82 :57-65, 2002.

Jefferis et al., "Recognition sites on human IgG for Fc gamma receptors: the role of glycosylation," Immunol Lett 44 :111-7, 1995.

Jefferis et al., "IgG-Fc-mediated effector functions: molecular definition of interaction sites for effector ligands and the role of glycosylation," Immunol Rev 163:59-76, 1998.

Jefferis et al., "Molecular definition of interaction sites on human IgG for Fc receptors (huFc gamma R)," Mol Immunol 27 :1237-1240, 1990.

Jendeberg et al., "Engineering of Fc(1) and Fc(3) from human immunoglobulin G to analyse subclass specificity for staphylococcal protein A," J Immunological Methods 201 :25-34, 1997.

Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.

Kadar et al., "Modulatory effect of synthetic human IgG Fc peptides on the in vitro immune response of murine spleen cells," Int J Immunpharmacol 13 :1147-55, 1991.

Kato et al., "Structural basis of the interaction between IgG and Fcγ receptors," J Mol Biol 295:213-224, 2000.

Keler et al., "Differential effect of cytokine treatment on Fc alpha receptor I- and Fc gamma receptor I-mediated tumor cytotoxicity by monocyte-derived macrophages," J. of Immunol. 164:5746-52, 2000.

Kieke et al., "Selection of functional T cell receptor mutants from a yeast surface-display library," Proc. Natl. Acad. Sci. U.S.A. 96 :5651-56, 1999.

Kim et al., "Analysis of FcγRIII and IgG Fc polymorphism reveals functional and evolutionary implications of protein-protein interaction," J Mol Evol 53:1-9, 2001.

Klein et al., "Expression of biological effector functions by immunoglobulin G molecules lacking the hinge region," Proc. Natl. Acad. Sci. U.S.A. 78 :524-528, 1981.

Koene et al., "Fc gammaRIIIa-158V/F polymorphism influences the binding of IgG by natural killer cell Fc gammaRIIIa, independently of the Fc gammaRIIIa-48L/R/H phenotype," Blood 90 :1109-1114, 1997.

Kranz et al., "Mechanisms of ligand binding by monoclonal anti-fluorescyl antibodies," J. Biol. Chem. 257:6987-6995, 1982.

Kumpel, B.M. Brit. "Human monoclonal anti-D antibodies," J. Haematol. 71:415-420 (1989).

Lehmann et al., "Phagocytosis: measurement by flow cytometry," J Immunol Methods. 243(1-2):229-42, 2000.

Lehrnbecher et al., "Variant genotypes of the low-affinity Fcgamma receptors in two control populations and a review of low-affinity Fcgamma receptor polymorphisms in control and disease populations," Blood 94:4220-4232, 1999.

Li et al., "Reconstitution of human Fc gamma RIII cell type specificity in transgenic mice," J Exp Med 183 :1259-1263, 1996.

Liu et al., "Production of a mouse-human chimeric monoclonal antibody to CD20 with potent Fc-dependent biologic activity," J. Immunol. 139:3521-3526, 1987.

Lund et al., "Expression and characterization of truncated forms of humanized L243 IgG1. Architectural features can influence synthesis of its oligosaccharide chains and affect superoxide production triggered through human Fcgamma receptor I," Eur J Biochem 267 :7246-57, 2000.

Lund et al., "Oligosaccharide-protein interactions in IgG can modulate recognition by Fc gamma receptors," FASEB J 9 :115-119, 1995.

Lund et al., "Human Fc gamma RI and Fc gamma RII interact with distinct but overlapping sites on human IgG," J Immunol 147 :2657-62, 1991.

Lund et al., "Multiple interactions of IgG with its core oligosaccharide can modulate recognition by complement and human Fc gamma receptor I and influence the synthesis of its oligosaccharide chains," J Immunol 157 :4963-4969, 1996.

Lund et al., "Multiple binding sites on the CH2 domain of IgG for mouse Fc gamma R11," Molecular Immunology 29:53-59, 1992.

Maenaka et al., "The human low affinity Fcgamma receptors IIa, IIb, and III bind IgG with fast kinetics and distinct thermodynamic properties," J Biol Chem 48 :44898-904, 2001.

Michaelsen et al., "One disulfide bond in front of the second heavy chain constant region is necessary and sufficient for effector functions of human IgG3 without a genetic hinge," Immunolgy 91 :9243-9247, 1994.

Morgan et al., "The N-terminal end of the CH2 domain of chimeric human IgG1 anti-HLA-DR is necessary for Clq, Fc gamma RI and Fc gamma RIII binding," Immunology 86 :319-324, 1995.

Morrison et al., "Structural determinants of IgG structure," Immunologist 2 :119-124, 1994.

Munn et al., "Phagocytosis of tumor cells by human monocytes cultured in recombinant macrophage colony-stimulating factor," J Exp Med. 172(1):231-7, 1990.

Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.

Neuberger et al., "Recombinant antibodies possessing novel effector functions," Nature 312 :604-608, 1984.

Norderhaug et al., "Chimeric mouse human IgG3 antibodies with an IgG4-like hinge region induce complement-mediated lysis more efficiently than IgG3 with normal hinge," Eur J Immunol 21:2379-84, 1991.

Nose and Leanderson, "Substitution of asparagine324 with aspartic acid in the Fc portion of mouse antibodies reduces their capacity for Clq binding," Eur J Immunol 19 :2179-81, 1989.

Okazaki et al., "Fucose depletion from human IgG1 oligosaccharide enhances binding enthalpy and association rate between IgG1 and FcgammaRIIIa," J Mol Biol 336 :1239-1249, 2004.

Orfao and Ruiz-Arguelles, "General concepts about cell sorting techniques," Clinical Biochem. 29:5-9, 1996.

Partridge et al., "The use of anti-IgG monoclonal antibodies in mapping the monocyte receptor site on IgG," Mol Immunol. 23(12):1365-72, 1986.

Perussia "Human Natural Killer Cell Protocols" in *Methods Molecular Biology*. vol. 121 (Campbell et al. eds.) Humana Press Inc., Totowa, NJ. 179-92, 2000.

Radaev and Sun, "Recognition of immunoglobulins by Fcgamma receptors," Molecular Immunology 38 :1073-1083, 2001.

Ravetch and Bolland, "IgG Fc receptors," Annu Rev Immunol 19:275-90, 2001.

Ravetch and Clynes, "Divergent roles for Fc receptors and complement in vivo," Annu Rev Immunol 16:421-432, 1998.

Ravetch and Kinet, "Fc receptors," Annu Rev Immunol 9:457-492, 1991.

Ravetech and Lanier, "Immune inhibitory receptors," Science 290:84-89, 2000.

Redpath et al., "The influence of the hinge region length in binding of human IgG to human Fcgamma receptors," Hum Immunol 59 :720-727, 1998.

Reff et al., "Depletion of B cells in vivo by a chimeric mouse human monoclonal antibody to CD20," Blood 83:435-445, 1994.

Riechmann et al., "Reshaping human antibodies for therapy," Nature. 332(6162):323-7, 1988.

Sarmay et al., "The effect of synthetic peptides corresponding to Fc sequences in human IgG1 on various steps in the B cell activation pathway," Eur J Immunol 18 :289-294, 1988.

Sarmay et al., "Ligand inhibition studies on the role of Fc receptors in antibody-dependent cell-mediated cytotoxicity," Mol Immunol 21 :43-51, 1984.

Sarmay et al., "Mapping and comparison of the interaction sites on the Fc region of IgG responsible for triggering antibody dependent cellular cytotoxicity (ADCC) through different types of human Fc gamma receptor," Mol Immunol 29 :633-639, 1992.

Sautes-Fridman et al., "Fc gamma receptors: a magic link with the outside world," ASHI Quarterley, 4th Quarter:148-151, 2003.

Schaffner et al., "Chimeric interleukin 2 receptor alpha chain antibody derivatives with fused mu and gamma chains permit improved recruitment of effector functions," Mol Immunol 32 :9-20, 1995 (Erratum in 32 :1299, 1995).

Schatz et al., "Use of peptide libraries to map the substrate specificity of a peptide-modifying enzyme: a 13 residue consensus peptide specifies biotinylation in *Escherichia coli*," Bio/Technology 11:1138-1143, 2000.

Sensel et al., "Amino acid differences in the N-terminus of C(H)2 influence the relative abilities of IgG2 and IgG3 to activate complement," Molecular Immunology 34:1019-1029, 1997.

Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276 :6591-6604, 2001.

Shopes et al., "Recombinant human IgG1-murine IgE chimeric Ig. Construction, expression, and binding to human Fc gamma receptors," J Immunol 145 :3842-3848, 1990.

Shopes, "A genetically engineered human IgG mutant with enhanced cytolytic activity," J Immunol 148 :2918-2922, 1992.

Shopes, "A genetically engineered human IgG with limited flexibility fully initiates cytolysis via complement," Molecular Immunology 30 :603-609, 1993.

Shusta et al., "Yeast polypeptide fusion surface display levels predict thermal stability and soluble secretion efficiency," J Mol Biol 292:949-956, 1999.

Shusta et al., "Increasing the secretory capacity of *Saccharomyces cerevisiae* for production of single-chain antibody fragments," Nature Biotechnology 16:773-777, 1998.

Shusta et al., "Directed evolution of a stable scaffold for T-cell receptor engineering," Nature Biotechnology 18:754-759, 2000.

Smith and Morrison, "Recombinant polymeric IgG: an approach to engineering more potent antibodies," Bio/Technology 12:683-688, 1994.

Sondermann and Oosthuizen, "The structure of Fc receptor/Ig complexes: considerations on stoichiometry and potential inhibitors," Immunology Letters, 82:51-56, 2002.

Sondermann et al., "Molecular basis for immune complex recognition: a comparison of Fc-receptor structures," J. Mol. Biol. 309:737-749, 2001.

Sondermann et al., "Crystal structure of the soluble form of the human fcgamma-receptor IIb: a new member of the immunoglobulin superfamily at 1.7 A resolution," EMBO J 18:1095-1103, 1999.

Sondermann et al., "The 3.2-A crystal structure of the human IgG1 Fc fragment-Fc gammaRIII complex," Nature 406:267-273, 2000.

Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.

Strohmeier et al., "Role of the Fc gamma R subclasses Fc gamma RII and Fc gamma RIII in the activation of human neutrophils by low and high valency immune complexes," J Leukocyte Biol 58:415-422, 1995.

Sylvestre and Ravetch, "A dominant role for mast cell Fc receptors in the Arthus reaction," Immunity 5:387-390, 1996.

Sylvestre and Ravetch, "Fc receptors initiate the Arthus reaction: redefining the inflammatory cascade," Science 265:1095-1098, 1994.

Takai et al., "FcR gamma chain deletion results in pleiotrophic effector cell defects," Cell 76 :519-529, 1994.

Takai et al., "Augmented humoral and anaphylactic responses in Fc gamma RII-deficient mice," Nature 379:346-349, 1996.

Takai, "Roles of Fc receptors in autoimmunity," Nature Reviews 2:580-592, 2002.

Tamm et al., "The IgG binding site of human FcγRIIIB receptor involves CC' and FG loops of the membrane-proximal domain," J Biol Chem 271:3659-3666, 1996.

Tao et al., "The differential ability of human IgG1 and IgG4 to activate complement is determined by the COOH-terminal sequence of the CH2 domain," J Exp Med 173:1025-1028, 1991.

Tao et al., "Structural features of human immunoglobulin G that determine isotype-specific differences in complement activation," J Exp Med 178:661-667, 1993.

Tridandapandi et al., "Regulated Expression and Inhibitory Function of FcgammaRIIB in Human Monocytic Cells," Journal of Biological Chemistry 277(7): 5082-5089, 2002.

Van Sorge et al., "FcgammaR polymorphisms: Implications for function, disease susceptibility and immunotherapy," Tissue Antigens 61:189-202, 2003.

VanAntwerp and Wittrup, "Fine affinity discrimination by yeast surface display and flow cytometry," Biotechnol Prog 16:31-37, 2000.

Vidarte, "Serine 132 is the C3 covalent attachment point on the CH1 domain of human IgG1," J Biol Chem 276:38217-38233, 2001.

Ward and Ghetie, "The effector functions of immunoglobulins: implications for therapy," Therapeutic Immunology 2:77-94, 1995.

Weng and Levy, "Two immunoglobulin G fragment C receptor polymorphisms independently predict response to rituximab in patients with follicular lymphoma," J Clin Oncol 21:3940-3947, 2003.

Wiener, E. et al. "Differences between the activities of human monoclonal IgG1 and IgG3 anti-D antibodies of the Rh blood group system in their abilities to mediate effector functions of monocytes," Immunol. 65:159-163 (1988).

Wing et al., "Mechanism of first-dose cytokine-release syndrome by CAMPATH 1-H: Involvement ofCD16 (FcγRIII) and CD11a/CD18 (LFA-1) on NK cells," J Clin Invest 98 :2819-2826, 1996.

Wingren et al., "Comparison of surface properties of human IgA, IgE, IgG and IgM antibodies with identical and different specificities," Scand J Immunol 44:430-436, 1996.

Wittrup, "The single cell as a microplate well," Nat Biotechnol 18:1039-1040, 2000.

Witttrup, "Protein engineering by cell-surface display," Curr, Opin. Biotechnol. 12:395-399, 2001.

Woof et al., "Localisation of the monocyte-binding region on human immunoglobulin G," Mol Immunol 23 :319-330, 1986.

Wu et al., "a novel polymorphism of FcγRIIIa (CD16) alters receptor function and predisposes to autoimmune disease," J Clin Invst 100 :1059-1070, 1997.

Xu et al., "Residue at position 331 in the IgG1 and IgG4 CH2 domains contributes to their differential ability to bind and activate complement," J Biol Chem 269 :3469-3474, 1994.

Yeung and Wittrup, "Quantitative screening of yeast surface-displayed polypeptide libraries by magnetic bead capture," Biotechnol Prog 18:212-220, 2002.

Zeidler et al., "The Fc-region of a new class of intact bispecific antibody mediates activation of accessory cells and NK cells and induces direct phagocytosis of tumour cells," British J Cancer 83:261-266, 2000.

Zuckier et al., "Chimeric human-mouse IgG antibodies with shuffled constant region exons demonstrate that multiple domains contribute to in vivo half-life," Cancer Res 58 :3905-3908, 1998.

Bernard et al. (1986) "A unique epitope on the CD2 molecule defined by the monoclonal antibody 9-1: epitope-specific modulation of the E-rosette receptor and effects on T-cell functions," Hum. Immunol. 17(4):388-405.

Boyer et al. (1999) "Relative cytotoxic activity of immunotoxins reactive with different epitopes on the extracellular domain of the c-erbB-2 (HER-2/neu) gene product p185," Int. J. Cancer. 82(4):525-531.

Campbell et al. (2003) "Monoclonal antibody therapy for lymphoma," Blood Rev. 17(3):143-152.

De Santes et al. (1992) "Radiolabeled Antibody Targeting of the Her-2/neu Oncoprotein," Cancer Res. 52:1916-1923.

Henry et al. (2004) "A prostate-specific membrane antigen-targeted monoclonal antibody-chemotherapeutic conjugate designed for the treatment of prostate cancer," Cancer Res. 64(21):7995-8001.

Jiang et al. (Epub Nov. 9, 2004) "A novel peptide isolated from a phage display peptide library with trastuzumab can mimic antigen epitope of HER-2," J Biol Chem. 280(6):4656-4662.

Kim et al. (2002) "Both the epitope specificity and isotype are important in the antitumor effect of monoclonal antibodies against Her-2/neu antigen," Int. J. Cancer. 102(4):428-434.

Kipps et al. (1985) "Importance of Immunoglobin Isotype in Human Antibody-Dependent, Cell-Mediated Cytotoxicity Directed by Murine Monoclonal Antbodies," J. Exper. Med. 161:1-17.

Lewis et al. (1993) "Differential responses of human tumor cell lines to anti-p185HER2 monoclonal antibodies," Cancer Immunol Immunother. 37(4):255-263.

Masui et al. (1986) "Mechanism of antitumor activity in mice for anti-epidermal growth factor receptor monoclonal antibodies with different isotypes.," Canc. Res. 46:5592-5598.

McDevitt et al. "An alpha-particle emitting antibody ([213Bi]J591) for radioimmunotherapy of prostate cancer.," Cancer Res. 60(21):6095-6100.

Pettersen et al. (1999) "CD47 Signals T Cell Death," J. Immunol. 162(12):7031-7040.

Press et al. (1988) "Ricin A-chain containing immunotoxins directed against different epitopes on the CD2 molecule differ in their ability to kill normal and malignant T cells," J. Immunol. 141(12):4410-4417.

Riemer et al. (Epub Jan. 8, 2005) "Matching of trastuzumab (Herceptin) epitope mimics onto the surface of Her-2/neu—a new method of epitope definition.," Mol Immunol. 42(9):1121-1124.

Stancovski et al. (1991) "Mechanistic aspects of the opposing effects of monoclonal antibodies to the ERBB2 receptor on tumor growth," Proc Natl Acad Sci U S A. 88(19):8691-8695.

Vuist et al. (1990) "Two distinct mechanisms of antitumor activity mediated by the combination of interleukin 2 and monoclonal antibodies," Canc. Res. 50:5767-5772.

Xu et al. (1993) "Antibody-induced growth inhibition is mediated through immunochemically and functionally distinct epitopes on the extracellular domain of the c-erbB-2 (HER-2/neu) gene product p. 185," Int. J. Cancer. 53(3):401-8.

Casset et al. (2003) A peptide mimetic of an anti-CD4 monoclonal antibody by rational design, Biochem. Biophs. Res. Commun. 307:198-205.

Chattergee et al. (1994) "Idiotypic Antibody Immunotherapy of Cancer," Cancer Immuno. Immunother. 38:75-82.

Dermer (1994) "Another Anniversary for the War on Cancer," Biotechnology 12:320 (1994).

Gura (1997) "Systems for Identifying New Drugs Are Often Faulty," Science 278:1041-1042.

Ibragimova et al. (1999) "Stability of the beta-sheet of the WW domain: A molecular dynamics simulation study," Biophys. J. 77(4):2191-2198.

Jain et al. "Barriers to Drug Delivery in Solid Tumors," Scientific American Jul. 1994:58-65.

Seaver (1994) "Monoclonal Antibodies in Industry: More Difficult than Originally Thought," Genetic Engineering News 14(14):10, 21.

Veri, M.C. et al. (2007) "Monoclonal antibodies capable of discriminating the human inhibitory Fcgamma-receptor IIB (CD32B) from the activating Fcgamma-receptor IIA (CD32A): biochemical, biological and functional characterization," Immunology 121(3):392-404.

Cavacini et al. (1995) "Influence of heavy chain constant regions on antigen binding and HIV-1 neutralization by a human monoclonal antibody," J Immunol. 155(7):3638-3644.

Lu, D. et al. (2003) "Di-Diabody: A Novel Tetravalent Bispecific Antibody Molecule by Design."J. Immunol. Meth 279: 219-232.

Abra et al. The next generation of liposome delivery systems: recent experience with tumor-targeted, sterically-stabilized immunoliposomes and active-loading gradients. J Liposome Res. Feb.-May 2002;12(1-2):1-3.

Amit et al. (1986) Three-dimensional structure of an antigen-antibody complex at 2.8 A resolution.; Science 233:747-753.

Bachmann et al. (2005) "Recall Proliferation of Memory CD8+ T Cells and Antiviral Protection," J. Immunol. 175:4677-4685.

Bendas G, Immunoliposomes: a promising approach to targeting cancer therapy. BioDrugs. 2001;15(4):215-24.

Bendig, M.M. (1995) Methods: A Companion to Methods in Enzymology 8:83-93.

Bewarder et al., 1996, "In vivo and in vitro specificity of protein tyrosine kinases for immunoglobulin G receptor (FcgammaRII) phosphorylation," Mol. Cell. Biol. 16 (9):4735-43.

Billadeau et al., ITAMs versus ITIMs: striking a balance during cell regulation, J Clin Invest. Jan. 2002;109(2):161-8.

Bolland et al., Genetic modifiers of systemic lupus erythematosus in Fc.gamma.RIIB(-/-) mice. J Exp Med. May 6, 2002;195(9):1167-74.

Bolland and Ravetch., Inhibitory pathways triggered by ITIM-containing receptors. Adv Immunol. 1999;72:149-177.

Boruchov et al., Activating and inhibitory IgG Fc receptors on human DCs mediate opposing functions. The Journal of Clinical Investigation 115; 10:2914-2923.

Boruchov et al., "Expression and Modulation of the Inhibitory Fcγ Receptor, FcγRIIB (CD32B), on Human Dendritic Cells (DCs)," Blood 102(11):Abstract #1908, 2003.

Brauweiler et al., Partially distinct molecular mechanisms mediate inhibitory Fc.gamma.RIIB signaling in resting and activated B cells. J Immunol. 2001;167:204-211.

Brown (2001) "Factors Modifying the Migration of Lymphocytes Across the Blood-Brain Barrier," Int Immunopharmacol. Nov. 2001;1(12):2043-62.

Budde et al., Specificity of CD32 mAB for Fc.gamma.RIIa, Fc.gamma.RIIb1, and Fc.gamma.RIIb2 expressed in transfected mouse B cells and BHK-21 cells. Leukocyte Typing V: White cell differentiation antigens. 1995;828-832 (Schlossman, Boumsell, Gilks, Harlan, Kishomoto, eds.).

Burgess et al. (1990) "Possible dissociation of the heparin-binding and mitogenic activities of the heparin-binding (acidic fibroblast) growth factor-1 from its receptor binding activities by site directed mutagenesis of a single lysine residue," J. Cell Biol. 111:2129-2138.

Callanan et al., The IgG Fc Receptor, Fc.gamma.RIIB is a target for deregulation by chromosomal translocation in malignant lymphoma. PNAS. Jan. 2000;97(1):309-314.

Cameron et al., Differentiation of the human monocyte cell line, U937, with dibutyryl cyclicAMP induces the expression of the inhibitory Fc receptor, Fc.gamma.RIIb. Immunol Lett. Oct. 1, 2002;83(3):171-9.

Camilleri-Broet et al., Fc.gamma.RIIB is differentially expressed during B cell maturation and in B-cell lymphomas. Br J Haematol. 2004;124(1):55-62.

Cassard et al., Modulation of tumor growth by inhibitory Fc.gamma. receptor expressed by human melanoma cells. The J Clin Invest. Nov. 2002;110(10):1549-1557.

Chen, et al. (1999) "Selection and Analysis of an Optimized Anti-VEGF Antibody: Crystal Structure of an Affinity-Matured Fab in Complex with Antigen," J. Molec. Biol. 293:865-881.

Colman, P.M. (1994) "Effects of amino acid sequence changes on antibody-antigen complexes," Res. Immunol. 145:33-36.

Daeron et al., The Same Tyrosine Based Inhibition Motif, in the Intracytoplasmic Domain of Fc.gamma.RIIB, regulates negatively BCR, TCR- and FcR dependent cell activation. Immunity. Nov. 1995;3: 635-646.

Damle et al., B-cell chronic lymphocytic leukemia cells express a surface membrane phenotype of activated, antigen-experienced B lymphocytes. Blood Jun. 1, 2002;99(11):4087-4093.

Davies et al., Expression of GnTIII in a recombinant anti-CD20 CHO production cell line: Expression of antibodies with altered glycoforms leads to an increase in ADCC through higher affinity for FC.sub.gamma. RIII. Biotechnol Bioeng. Aug. 20, 2001;74(4):288-94.

Davies et al. (1995) Antibody VH domains as small recognition units, Bio/Technology 13:475-479.

DePascalis et al. (2002) "Grafting of Abbreviated Complementarity Determining Regions Containing Specificity Determining Residues Essential for Ligand Contact to Engineer a Less Immunogenic humanized monoclonal antibody," J. Immunol. 169:3076-3084.

Ding et al., Inhibition of the function of the Fc.gamma.RIIB by a monoclonal antibody to thymic shared antigen-1, a Ly-6 family antigen. Immunology. Sep. 2001;104(1):28-36.

Dumoulin et al. (2002) Single-domain antibody fragments with high conformational stability, Protein Science 11:500-512.

Efferson et al. (2005) "Stimulation of Human T Cells by an Influenza A Vector Expressing a CTL Epitope from the HER-2/neu Protooncogene Results in Higher Numbers of Antigen Specific TCRhi Cells than Stimulation with Peptide," Anticancer Research 25:715-724.

Ellman, J. et al. "Biosynthetic Method for Introducing Unnatural Amino Acids Site-Specifically into Proteins," Methods Enzymol. 202:301-336, 1991.

Eppstein et al., Biological activity of liposome-encapsulated murine interferon .gamma. is mediated by a cell membrane receptor. Proc Natl Acad Sci U S A. Jan. 1985;82(11):3688-9.

Fanger et al., Production and use of anti-FcR bispecific antibodies. Immunomethods. Feb. 1994;4(1):72-81.

Farag, et al., Fc.gamma.RIIIa and Fc.gamma.RIIIa polymorphisms do not predict response to Rituximab in B-cell chronic lymphocytic leukemia. Blood. Oct. 16, 2003 (15 pp.).

Fidler, I. J., Macrophages and metastasis—a biological approach to cancer therapy. Cancer Res. Oct. 1985;45(10):4714-26.

Fleit et al., 1995 "Cross-linking of mAb to FC.gamma.RII results in tyrosine phosphorylation of multiple polypeptides including FC.gamma.RII itself." Leukocyte Typing V: White cell differentiation antigens 826-827 (Schlossman, Boumsell, Gilks, Harlan, Kishomoto, eds.).

Gamberale et al., 2003, "To the Editor: Expression of Fc.gamma. receptors type II (Fc.gamma.RII) in chronic lymphocytic leukemia B cells." Blood (Correspondence) 102(7):2698-2699.

Gerber et al., Stimulatory and inhibitory signals originating from the macrophage Fc.gamma. receptors. Microbes Infect. Feb. 2001;3(2):131-9.

Holm et al, (2007) "Functional Mapping and Single Chain Construction of the Anti-Cytokeratin 8 Monoclonal Antibody TS1," Molecular Immunology 44:1075-1084.

Holmes et al., Alleles of the Ly-17 alloantigen define polymorphisms of the murine IgG Fc receptor. Proc Natl Acad Sci USA. Nov. 1985;82(22):7706-10.

Holt, L.J. (2003) "Domain Antibodies: Proteins for Therapy," TRENDS in Biochemistry 21(11)484-490.

Hwang et al., Hepatic uptake and degradation of unilamellar sphingomyelin/cholesterol liposomes: a kinetic study. Proc Natl Acad Sci U S A. Jul. 1980;77(7):4030-4.

Kagari et al., Essential Role of Fc.gamma. Receptors in anti-type II collagen antibody induced arthritis. J. Immunol. Apr. 2003;170:4318-24.

Kang, C.Y. et al. (1988) "Inhibition of Self-Binding Antibodies (Autobodies) by a VH-Derived Peptide," Science 240(4855):1034-1036.

Kepley et al. "Co-aggregation of FcgammaRII with FcepsilonRI on human mast cells inhibits antigeninduced secretion and involves SHIP-Grb2-Dok complexes" J. Biol. Chem. 279(34) 35139-35149.

Kimura et al. (1981) "A new mouse cell-surface antigen (Ly-m20) controlled by a gene linked to Mls locus and defined by monoclonal antibodies," Immunogenetics. 14(1-2):3-14.

Kurlander et al., 1986, "Comparison of intravenous gamma globulin and a monoclonal anti-Fc receptor antibody as inhibitors of immune clearance in vivo in mice." J. Clin. Invest. 77(6):2010-2018.

Lazar et al. (1988) Transforming growth factor a: mutation of aspartic acid 47 and leucine 48 results in different biological activities, Molec. Cell. Biol. 8:1247-1252.

Li et al. (2007) Regeneration of nigrostriatal dopaminergic axons by degradation of chondroitin sulfate is accompanied by elimination of the fibrotic scar and glia limitans in the lesion site. J. Neurosci. Res. 85:636-547.

Lifely et al., Glycosylation and biological activity of CAMPATH-1H expressed in different cell lines and grown under different culture conditions. Glycobiology. Dec. 1995;5(8):813-22.

Lin et al., Colony-stimulating factor 1 promotes progression of mammary tumors to malignancy. J Exp Med. 2001;193(6):727-739.

Lin et al., The macrophage growth factor CSF-1 in mammary gland development and tumor progression. J Mammary Gland Biol Neoplasia. 2002;7(2):147-62.

Looney et al., 1986, "Human Monocytes and U(#& Cells Bear Two Distinct Fc Receptors for IgG." J. Immunol. 136(5):1641-1647.

Lyden et al., The Fc receptor for IgG expressed in the villus endothelium of human placenta is Fc.gamma. RIIb2. J Immunol. Mar. 15, 2001;166(6):3882-9.

MacCallum et al. (1996) "Antibody-Antigen Interactions: Contact Analysis and Binding Site Topography," J. Molec. Biol. 262:732-745.

Malbec et al., Fcs receptor I-associated lyn-dependent phosphorylation of Fc.gamma. receptor IIB during negative regulation of mast cell activation. J Immunol. Feb. 15, 1998;160(4):1647-58.

Maresco et al., 1999, "The SH2-Containing 5'-Inositol Phosphatase (SHIP) Is Tyrosine Phosphorylated after Fc.gamma. Receptor Clustering in Monocytes." J. Immunol. 162:6458-6465.

Maruyama K, In vivo targeting by liposomes. Biol Pharm Bull. Jul. 2000;23(7):791-9.

Melero et al. (1998) The frequent expansion of a subpopulation of B cells that express RF-associated cross-reactive idiotypes: evidence from analysis of a panel autoreactive monoclonal antibodies; Scand. J. Immunol. 48:152-158 1998.

Metcalfe, Mast Cells, Physiol Rev. Oct. 1997;77(4):1033-79.

Micklem et al., Different isoforms of human FcRII distinguished by CDw32 antibodies. J Immunol. Mar. 1990;144:2295-2303.

Nakamura et al., Fc.gamma. receptor IIB-deficient mice develop Goodpasture's Syndrome upon immunization with Type IV collagen: a novel murine model for Autoimmune Glomerular Basement Membrane Disease. J. Exp. Med. Mar. 6, 2000;191(5):899-905.

Noren, C.J. et al. "A General Method for Site-Specific Incorporation of Unnatural Amino Acids into Proteins," Science 244:182-188, 1989.

Norris et al., A naturally occurring mutation in Fc.gamma.RIIA: A Q to K.sup.127 change confers unique IgG binding properties to the R.sup.131 allelic form of the receptor. Blood. Jan. 15, 1998;91(2):656-662.

Ott, V.L. et al. "FcgammaRIIB as a potential molecular target for intravenous gamma globulin therapy," J. Allergy Clin Immunol. Oct. 2001:S95-S98.

Ott et al., Downstream of Kinase, p62.sup.dok, Is a mediator of Fc.gamma.RIIB inhibition of Fc.epsilon.RI signaling. J. of Immunol. 2002;168:4430-9.

Panka et al. (1988) Variable region framework differences result in decreased or increased affinity of variant anti-digoxin antibodies. Proc. Natl. Acad. Sci. USA 85:30803084.

Pardridge et al., Blood-brain barrier drug targeting: The future of brain drug development. Molecular Interventions. 2003, 3;2:90-105. See particularly pp. 91-96.

Park YS, Tumor-directed targeting of liposomes. Biosci Rep. Apr. 2002;22(2):267-81.

Park et al., Immunoliposomes for cancer treatment. Adv Pharmacol. 1997;40:399-435.

Paul, William E, (1993) "Fundamental Microbiology, 3 Ed." pf. 242, 292-296.

Pereira et al. (1998) Cardiolipin Binding a light Chain from Lupus-prone Mice; Biochem. 37:1460-1437.

Pluckthun, A. et al. (1997) "New protein engineering approaches to multivalent and bispecific antibody fragments," Immunotechnology 3(2):83-105.

Presta, L.G. et al. (2005) "Selection, Design and Engineering of Therapeutic Antibodies," J. Allergy Clin. Immunol. 116(4):731-736.

Presta LG, Engineering antibodies for therapy. Curr Pharm Biotechnol. Sep. 2002;3(3):237-56.

Pricop et al., differential modulation of stimulatory and inhibitory Fc.gamma. receptors on human monocytes by Th1 and Th2 cytokines. J Immunol. Jan. 1, 2001;166(1):531-7.

Pulford et al., 1995 "M6.5: The immunocytochemical distribution of CD16, CD32, and CD64 antigens." Leukocyte Typing V: White cell differentiation antigens 817-821 (Schlossman, Boumsell, Gilks, Harlan, Kishomoto, eds.) pp. 817-821.

Pulford et al., A new monoclonal antibody (KB61) recognizing a novel antigen which is selectively expressed on a subpopulation of human B lymphocytes. Immunology. Jan. 1986;57(1):71-6.

Qin et al., Fc.gamma. receptor IIB on follicular dendritic cells regulates the B cell recall response. J Immunol. 2000;164:6268-6275.

Ravetch et al., Fc receptors: rubor redux. Cell. Aug. 26, 1994;78(4):553-60.

Reali et al., IgEs targeted on tumor cells: therapeutic activity and potential in the design of tumor vaccines. Cancer Res. 2001;61(14): 5517-22.

Reff et al., "A review of modifications to recombinant antibodies: attempt to increase efficacy in oncology applications," Critical Reviews in Oncology/Hematology 40: 25-35; 2001.

Routledge et al., The effect of aglycosylation on the immunogenicity of a humanized therapeutic CD3 monoclonal antibody. Transplantation. Oct. 27, 1995;60(8):847-53.

Rudikoff et al. (1982) "Single amino acid substitution altering antigen-binding specificity" Proc. Natl. Acad. Sci. USA 79:1979-1983.

Samsom et al. (2005) Fc gamma RIIB regulates nasal and oral tolerance: a role for dendritic cells Immunol. 174:5279-5287.

Samuelsson et al., Anti-inflammatory activity of IVIG mediated through the inhibitory Fc receptor. Science. Jan. 19, 2001; 291:484-486.

Sarkar et al., Negative signaling via Fc.gamma.RIIB1 in B cells blocks phospholipase C.sub..gamma.2 tyrosine phosphorylation but not Syk or Lyn activation. J Biol Chem. Aug. 16, 1996;271(33):20182-6.

Scholl et al., Is colony-stimulating factor-1 a key mediator of breast cancer invasion and metastasis? Mol Carcinog. 7(4):207-11.

Schuna et al., 2000, "New Drugs for the treatment of rheumatoid arthritis." Am J. Health Syst. Phar, 57:225-237.

Shields et al., Lack of fucose on human IgG1 N-linked oligosaccharide improves binding to human Fc.gamma. RIII and antibody-dependent cellular toxicity. J Biol Chem. Jul. 26, 2002;277(30):26733-40.

Siberil, S. et al. (2006) "Molecular Aspects of Human FcgammaR Interactions with IgG: Functional and Therapeutic Consequences," Immunol. Lett. 106:111-118 (2006).

Skolnick et al. (2000) From Genes to Protein Structure and Function: Novel Aspects of Computational Approaches in the Genomic Era, Trends in Biotechnology 18:34-39.

Su et al., Expression profile of Fc.gamma.RIIB on leukocytes and its dysregulation in systemic lupus erythematosus. J. Immunol. 178:3272-3280, 2007.

Tam et al., A bispecific antibody against human IgE and human Fc.gamma.RII that inhibits antigen-induced histamine release by human mast cells and basophils. Allergy 2004;59:772-780.

Tao and Morrison, Studies of aglycosylated chimeric mouse-human IgG. Role of carbohydrate in the structure and effector functions mediated by the human IgG constant region. J Immunol. Oct. 15, 1989;143(8):2595-601.

Todorovska et al., Design and application of diabodies, triabodies and tetrabodies for cancer targeting. J Immunol Methods. Feb. 1, 2001;248(1-2):47-66.

Umana et al., Engineered glycoforms of an antineuroblastoma IgG1 with optimized antibody-dependent cellular cytotoxic activity. Nat Biotechnol. Feb. 1999;17(2):176-80.

Vajdos et al. (2002) "Comprehensive Functional Maps of the Antigen-Binding Site of an Anti-ErbB2 Antibody Obtained with Shotgun Scanning Mutagenesis," J. Molec. Biol. 320:415-428.

Van den Beuken et al. (2001) Building novel binding ligands to B7.1 and B7.2 based on human antibody single variable light chain domains; J. Molec. Biol. 310:591-601.

Van De Winkel et al., 1995, "CD32 cluster workshop report." Leukocyte Typing V: White Cell differentiation antigens 823-825 (Schlossman, Boumsell, Gilks, Harlan, Kishomoto, eds.).

Van Nguyen et al., Colony stimulating factor-1 is required to recruit macrophages into the mammary gland to facilitate mammary ductal outgrowth. Dev Biol. 2002;247(1):11-25.

Vely et al., 1997, "A new set of monoclonal antibodies against human Fc gamma RII (CD32) and Fc gamma RIII (CD16): characterization and use in various assays." Hybridoma 16(6):519-28.

Vingerhoeds et al., Immunoliposomes in vivo. Immunomethods. Jun. 1994;4(3):259-72.

Vitetta, E.S. et al. (2006) "Immunology. Cnsidering Therapeutic Antibodies," Science 313:308-309.

Wallick et al., Glycosylation of a VH residue of a monoclonal antibody against {acute over(.alpha.)}(1.fwdarw.6) dextran increases its affinity for antigen. J Exp Med. Sep. 1, 1988;168(3):1099-109.

Ward et al. (1989) Building Activities of a repertoire of single immunoglobulin variable domains secreted from *Escherichia coli*, Nature 341:544-546 (1989).

Warmerdam et al., Molecular basis for a polymorphism of human Fc gamma receptor II (CD32). J Exp Med. Jul. 1, 1990;172(1):19-25.

Warren, HS et al.(1999) "NK cells and apoptosis," Immunol. Cell Biol. 77(1):64-75.

Wheeler, "Preventive Vaccines for Cervical Cancer," Salud Publica d Mexico, 1997, vol. 39, pp. 1-9.

Weinrich, V. et al. "Epitope Mapping of New Monoclonal Antibodies Recognizing Distinct Human FCRII (CD32) Isoforms," Hybridoma 15(2):109-116.

Wright and Morrison, Effect of glycosylation on antibody function: implications for genetic engineering. Trends Biotechnol. Jan. 1997;15(1):26-32.

Wu et al., "Humanization of a Murine Monoclonal Antibody by Simultaneous Optimization of Framework and CDR Residues," Journal of Molecular Biology, 1999, vol. 294, pp. 151-162.

Xu et al., Fc.gamma.Rs Modulate Cytotoxicity of Anti-Fas Antibodies: Implications for Agonistic Antibody Based Therapeutics. J Immunol. 2003;171:562-68.

Zola et al., 2000, "CD32 (FcgammaRII)." J Biol Regul Homeost Agents 14(4):311-6.

US 6,331,391, 12/2001, Wittrup et al. (withdrawn)

* cited by examiner

```
              0                                    3         3
              1                                    1         6
Mu2B6VH    QVQLQQPVTELVRPGASVMLSCKASDYPFT    NYWIH    WVKQRPGQGLEWIG
Hu2B6VH-1  ----V-SGA-VKK-----KV-----G-T--    -----    --R-A-------M-
VH1-18     ----V-SGA-VKK-----KV-----G-T--    S-G-S    --R-A-------M-
                      FR1                    CDR1         FR2

5                  6
              0                  6
Mu2B6VH    VIDPSDTYPNYNKKFKG    KATLTVVVSSSTAYMQLSSLTSDDSAVYYCAR
Hu2B6VH-1  ----------------    RV-M-TDT-T------E-R--R---T--------
VH1-18     W-SAYNGNT---AQ-LQ-  RV-M-TDT-T------E-R--R---T--------
                  CDR2                         FR3

1
              9               0
              5               3
Mu2B6VH    NGDSDYYSGMDY    WGQGTSVTVSS
Hu2B6VH-1  ------------    -----T-----
HuJH5         --Y---V      -----T-----
              CDR3            FR4
```

FIG. 1A

```
                    0                    2            3
                    1                    4            5
Mu2B6VL   DILLTQSPAILSVSPGERVSFSC   RTSQSIGTNIH   WYQQRTNGFPRLLIK
Hu2B6VL-1 E-V-----DFQ--T-K-K-TIT-   -----------   ----KPDQS-K----
Hu2B6VL-2 E-V-----DFQ--T-K-K-TIT-   -----------   ----KPDQS-K----
Hu2B6VL-3 E-V-----DFQ--T-K-K-TIT-   -----------   ----KPDQS-K----
VK-A26    E-V-----DFQ--T-K-K-TIT-   -A-----SSL-   ----KPDQS-K----
                    FR1                  CDR1          FR2

5       5
             0       7
Mu2B6VL   NVSESIS  GIPSRFSGSGSGTDFILSINSVESEDIADYYC
Hu2B6VL-1 -------  -V-------------T-T---L-A--A-T---
Hu2B6VL-2 Y------  -V-------------T-T---L-A--A-T---
Hu2B6VL-3 YA-----  -V-------------T-T---L-A--A-T---
VK-A26    YA-Q-F-  -V-------------T-T---L-A--A-T---
            CDR2            FR3

8        9
             9        8
Mu2B6VL   QQSNTWPFT  FGGGTKLEIK
Hu2B6VL-1 ---------  ------V---
Hu2B6VL-2 ---------  ------V---
Hu2B6VL-3 ---------  ------V---
VK-A26    H-SSL-
HuJK4                L- ------V---
            CDR3           FR4
```

FIG. 1B

```
           1         10        20        30        40        50
           |         |         |         |         |         |
h2B6VH-1   QVQLVQSGAEVKKPGASVKVSCKASGYTFTNYWIHWVRQAPGQGLEWMGVIDPSDTYPN
h2B6VH-3   QVQLVQSGAEVKKPGASVKVSCKASGYTFTNYWIHWVRQAPGQGLEWIGVIDPSDTYPN 60        70        80        90        100       110
           |         |         |         |         |         |
           YNKKFKGRVTMTTDTSTSTAYMELRSLRSDDTAVYYCARNGDSDYYSGMDYWGQGTTVT
           YNKKFKGRVTMTVDTSTSTAYMELRSLRSDDTAVYYCARNGDSDYYSGMDYWGQGTTVT

120
|
VSS
VSS
```

FIG. 2A

```
           1         10        20        30        40        50
           |         |         |         |         |         |
H2B6VL-1   EIVLTQSPDFQSVTPKEKVTITCRTSQSIGTNIHWYQQKPDQSPKLLIKNVSESISGVP
H2B6VL-2   EIVLTQSPDFQSVTPKEKVTITCRTSQSIGTNIHWYQQKPDQSPKLLIKYASESISGVP
H2B6VL-3   EIVLTQSPDFQSVTPKEKVTITCRTSQSIGTNIHWYQQKPDQSPKLLIKYVSESISGVP
H2B6VL-5   EIVLTQSPDFQSVTPKEKVTFTCRTSQSIGTNIHWYQQKPDQSPKLLIKEVSESISGVP 60        70        80        90        100       107
           |         |         |         |         |         |
           SRFSGSGSGTDFTLTINSLEAEDAATYYCQQSNTWPFTFGGGTKVEIK
           SRFSGSGSGTDFTLTINSLEAEDAATYYCQQSNTWPFTFGGGTKVEIK
           SRFSGSGSGTDFTLTINSLEAEDAATYYCQQSNTWPFTFGGGTKVEIK
           SRFSGSGSGTDFTLTINSLEAEDAATYYCQQSNTWPFTFGGGTKVEIK
```

FIG. 2B

SEQUENCE LISTING

```
<160> NUMBER OF SEQ ID NOS: 76

<210> SEQ ID NO 1
<211> LENGTH: 5
<212> TYPE: PRT
<213> ORGANISM: Artificial Sequence
<220> FEATURE:
<223> OTHER INFORMATION: 2B6 Heavy Chain Variable Region -CDR1

<400> SEQUENCE: 1

Asn Tyr Trp Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: 2B6 Heavy Chain Variable Region -CDR2

<400> SEQUENCE: 2

Val Ile Asp Pro Ser Asp Thr Tyr Pro Asn Tyr Asn Lys Lys Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: 2B6 Heavy Chain Variable Region - CDR3

<400> SEQUENCE: 3

Asn Gly Asp Ser Asp Tyr Tyr Ser Gly Met Asp Tyr
1               5                   10

<210> SEQ ID NO 4
<211> LENGTH: 24
<212> TYPE: PRT
<213> ORGANISM: Homo sapiens
<220> FEATURE:
<221> NAME/KEY: MISC_FEATURE
<223> OTHER INFORMATION: Framework Sequence from human germline VH1-18
      and JH6 -FR1

<400> SEQUENCE: 4

Gln Gly Ala Glu Val Lys Lys Pro Gly Ala Ser Val Lys Val Ser Cys
```

-continued

```
                1               5                  10                  15
Lys Ala Ser Gly Tyr Thr Phe Thr
            20

<210> SEQ ID NO 5
<211> LENGTH: 14
<212> TYPE: PRT
<213> ORGANISM: Homo sapiens
<220> FEATURE:
<221> NAME/KEY: MISC_FEATURE
<223> OTHER INFORMATION: Framework Sequence from human germline VH1-18
      and JH6 - FR2

<400> SEQUENCE: 5

Trp Val Arg Gln Ala Pro Gly Gln Gly Leu Glu Trp Met Gly
1               5                  10

<210> SEQ ID NO 6
<211> LENGTH: 32
<212> TYPE: PRT
<213> ORGANISM: Homo sapiens
<220> FEATURE:
<221> NAME/KEY: MISC_FEATURE
<223> OTHER INFORMATION: Framework Sequence from human germline VH1-18
      and JH6 - FR3

<400> SEQUENCE: 6

Arg Val Thr Met Thr Thr Asp Thr Ser Thr Ser Thr Ala Tyr Met Glu
1               5                  10                  15

Leu Arg Ser Leu Arg Ser Asp Asp Thr Ala Val Tyr Tyr Cys Ala Arg
            20                  25                  30

<210> SEQ ID NO 7
<211> LENGTH: 11
<212> TYPE: PRT
<213> ORGANISM: Homo sapiens
<220> FEATURE:
<221> NAME/KEY: MISC_FEATURE
<223> OTHER INFORMATION: Framework Sequence from human germline VH1-18
      and JH6 - FR4

<400> SEQUENCE: 7

Trp Gly Gln Gly Thr Thr Val Thr Val Ser Ser
1               5                  10

<210> SEQ ID NO 8
<211> LENGTH: 11
<212> TYPE: PRT
<213> ORGANISM: Artificial Sequence
<220> FEATURE:
<223> OTHER INFORMATION: 2B6 Light Chain Variable Region - CDR1

<400> SEQUENCE: 8

Arg Thr Ser Gln Ser Ile Gly Thr Asn Ile His
1               5                  10

<210> SEQ ID NO 9
<211> LENGTH: 7
<212> TYPE: PRT
<213> ORGANISM: Artificial Sequence
<220> FEATURE:
<223> OTHER INFORMATION: 2B6 Light Chain Variable Region - CDR2

<400> SEQUENCE: 9

Asn Val Ser Glu Ser Ile Ser
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: 2B6 Light Chain Variable Region - CDR2

<400> SEQUENCE: 10

Tyr Val Ser Glu Ser Ile Ser
1               5

<210> SEQ ID NO 11
<211> LENGTH: 7
<212> TYPE: PRT
<213> ORGANISM: Artificial Sequence
<220> FEATURE:
<223> OTHER INFORMATION: 2B6 Light Chain Variable Region - CDR2

<400> SEQUENCE: 11

Tyr Ala Ser Glu Ser Ile Ser
1               5

<210> SEQ ID NO 12
<211> LENGTH: 9
<212> TYPE: PRT
<213> ORGANISM: Artificial Sequence
<220> FEATURE:
<223> OTHER INFORMATION: 2B6 Light Chain Variable Region - CDR3

<400> SEQUENCE: 12

Gln Gln Ser Asn Thr Trp Pro Phe Thr
1               5

<210> SEQ ID NO 13
<211> LENGTH: 23
<212> TYPE: PRT
<213> ORGANISM: Homo sapiens
<220> FEATURE:
<221> NAME/KEY: MISC_FEATURE
<223> OTHER INFORMATION: Framework Sequence from human germline VK-A26
      and JK4 - FR1

<400> SEQUENCE: 13

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 14
<211> LENGTH: 15
<212> TYPE: PRT
<213> ORGANISM: Homo sapiens
<220> FEATURE:
<221> NAME/KEY: MISC_FEATURE
<223> OTHER INFORMATION: Framework Sequence from human germline VK-A26
      and JK4 - FR2

<400> SEQUENCE: 14

Trp Tyr Gln Gln Lys Pro Asp Gln Ser Pro Lys Leu Leu Ile Lys
1               5                   10                  15

<210> SEQ ID NO 15
<211> LENGTH: 32
<212> TYPE: PRT
<213> ORGANISM: Homo sapiens
<220> FEATURE:
<221> NAME/KEY: MISC_FEATURE
```

-continued

<223> OTHER INFORMATION: Framework Sequence from human germline VK-A26
      and JK4 - FR3

<400> SEQUENCE: 15

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 16
<211> LENGTH: 10
<212> TYPE: PRT
<213> ORGANISM: Homo sapiens
<220> FEATURE:
<221> NAME/KEY: MISC_FEATURE
<223> OTHER INFORMATION: Framework Sequence from human germline VK-A26
      and JK4 - FR4

<400> SEQUENCE: 16

Phe Gly Gly Gly Thr Lys Val Glu Ile Lys
1               5                   10

<210> SEQ ID NO 17
<211> LENGTH: 321
<212> TYPE: DNA
<213> ORGANISM: Artificial Sequence
<220> FEATURE:
<223> OTHER INFORMATION: Humanized 2B6 Light Chain Variable Region -
      Hu2B6VL-1

<400> SEQUENCE: 17
gaaattgtgc tgactcagtc tccagacttt cagtctgtga ctccaaagga gaaagtcacc      60
atcacctgca ggaccagtca gagcattggc acaaacatac actggtacca gcagaaacca    120
gatcagtctc caaagctcct catcaagaat gtttctgagt ctatctctgg agtcccatcg    180
aggttcagtg gcagtggatc tgggacagat ttcaccctca ccatcaatag cctggaagct    240
gaagatgctg caacgtatta ctgtcaacaa agtaatacct ggccgttcac gttcggcgga    300
gggaccaagg tggagatcaa a                                              321

<210> SEQ ID NO 18
<211> LENGTH: 107
<212> TYPE: PRT
<213> ORGANISM: Artificial Sequence
<220> FEATURE:
<223> OTHER INFORMATION: Humanized 2B6 Light Chain Variable Region -
      Hu2B6VL-1

<400> SEQUENCE: 18

Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Asn Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys

<210> SEQ ID NO 19
<211> LENGTH: 321
<212> TYPE: DNA
<213> ORGANISM: Artificial Sequence
<220> FEATURE:
<223> OTHER INFORMATION: Humanized 2B6 Light Chain Variable Region - Hu2B6VL-2

<400> SEQUENCE: 19

```
gaaattgtgc tgactcagtc tccagacttt cagtctgtga ctccaaagga gaaagtcacc      60
atcacctgca ggaccagtca gagcattggc acaaacatac actggtacca gcagaaacca    120
gatcagtctc caaagctcct catcaagtat gtttctgagt ctatctctgg agtcccatcg    180
aggttcagtg gcagtggatc tgggacagat ttcaccctca ccatcaatag cctggaagct    240
gaagatgctg caacgtatta ctgtcaacaa agtaatacct ggccgttcac gttcggcgga    300
gggaccaagg tggagatcaa a                                              321
```

<210> SEQ ID NO 20
<211> LENGTH: 107
<212> TYPE: PRT
<213> ORGANISM: Artificial Sequence
<220> FEATURE:
<223> OTHER INFORMATION: Humanized 2B6 Light Chain Variable Region - Hu2B6VL-2

<400> SEQUENCE: 20

Glu Ile Val Leu Thr Gln Ser Pro Asp Phe Gln Ser Val Thr Pro Lys
1               5                   10                  15
Glu Lys Val Thr Ile Thr Cys Arg Thr Ser Gln Ser Ile Gly Thr Asn
            20                  25                  30
Ile His Trp Tyr Gln Gln Lys Pro Asp Gln Ser Pro Lys Leu Leu Ile
        35                  40                  45
Lys Tyr Val Ser Glu Ser Ile Ser Gly Val Pro Ser Arg Phe Ser Gly
    50                  55                  60
Ser Gly Ser Gly Thr Asp Phe Thr Leu Thr Ile Asn Ser Leu Glu Ala
65                  70                  75                  80
Glu Asp Ala Ala Thr Tyr Tyr Cys Gln Gln Ser Asn Thr Trp Pro Phe
                85                  90                  95
Thr Phe Gly Gly Gly Thr Lys Val Glu Ile Lys
            100                 105

<210> SEQ ID NO 21
<211> LENGTH: 321
<212> TYPE: DNA
<213> ORGANISM: Artificial Sequence
<220> FEATURE:
<223> OTHER INFORMATION: Humanized 2B6 Light Chain Variable Region - Hu2B6VL-3

<400> SEQUENCE: 21

```
gaaattgtgc tgactcagtc tccagacttt cagtctgtga ctccaaagga gaaagtcacc      60
atcacctgca ggaccagtca gagcattggc acaaacatac actggtacca gcagaaacca    120
gatcagtctc caaagctcct catcaagtat gcttctgagt ctatctctgg agtcccatcg    180
aggttcagtg gcagtggatc tgggacagat ttcaccctca ccatcaatag cctggaagct    240
gaagatgctg caacgtatta ctgtcaacaa agtaatacct ggccgttcac gttcggcgga    300
gggaccaagg tggagatcaa a                                              321
```

<210> SEQ ID NO 22
<211> LENGTH: 107
<212> TYPE: PRT
<213> ORGANISM: Artificial Sequence
<220> FEATURE:
<223> OTHER INFORMATION: Humanized 2B6 Light Chain Variable Region - Hu2B6VL-3

<400> SEQUENCE: 22

Glu Ile Val Leu Thr Gln Ser Pro Asp Phe Gln Ser Val Thr Pro Lys
1               5                   10                  15
Glu Lys Val Thr Ile Thr Cys Arg Thr Ser Gln Ser Ile Gly Thr Asn
            20                  25                  30
Ile His Trp Tyr Gln Gln Lys Pro Asp Gln Ser Pro Lys Leu Leu Ile
        35                  40                  45
Lys Tyr Ala Ser Glu Ser Ile Ser Gly Val Pro Ser Arg Phe Ser Gly
    50                  55                  60
Ser Gly Ser Gly Thr Asp Phe Thr Leu Thr Ile Asn Ser Leu Glu Ala
65                  70                  75                  80
Glu Asp Ala Ala Thr Tyr Tyr Cys Gln Gln Ser Asn Thr Trp Pro Phe
                85                  90                  95
Thr Phe Gly Gly Gly Thr Lys Val Glu Ile Lys
            100                 105

<210> SEQ ID NO 23
<211> LENGTH: 363
<212> TYPE: DNA
<213> ORGANISM: Artificial Sequence
<220> FEATURE:
<223> OTHER INFORMATION: Humanized 2B6 heavy chain variable region - Hu2B6VH-1

<400> SEQUENCE: 23
caggttcagc tggtgcagtc tggagctgag gtgaagaagc ctggggcctc agtgaaggtc      60
tcctgcaagg cttctggtta cacctttacc aactactgga tacactgggt gcgacaggcc     120
cctggacaag ggcttgagtg gatgggagtg attgatcctt ctgatactta tccaaattac     180
aataaaaagt tcaagggcag agtcaccatg accacagaca catccacgag cacagcctac     240
atggagctga ggagcctgag atctgacgac acggccgtgt attactgtgc gagaaacggt     300
gattccgatt attactctgg tatggactac tgggggcaag gaccacggtc accgtctcc     360
tca                                                                   363

<210> SEQ ID NO 24
<211> LENGTH: 121
<212> TYPE: PRT
<213> ORGANISM: Artificial Sequence
<220> FEATURE:
<223> OTHER INFORMATION: Humanized 2B6 Heavy Chain Variable Region - Hu2B6VH-1

<400> SEQUENCE: 24

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Trp Ile His Trp Val Arg Gln Ala Pro Gly Gln Gly Leu Glu Trp Met
        35                  40                  45
Gly Val Ile Asp Pro Ser Asp Thr Tyr Pro Asn Tyr Asn Lys Lys Phe

```
              50                  55                  60
Lys Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser
            115                 120

<210> SEQ ID NO 25
<211> LENGTH: 321
<212> TYPE: DNA
<213> ORGANISM: Mus musculus
<220> FEATURE:
<221> NAME/KEY: misc_feature
<223> OTHER INFORMATION: Mouse 2B6 Light Chain Variable Region

<400> SEQUENCE: 25
gacatcttgc tgactcagtc tccagccatc ctgtctgtga gtccaggaga gagagtcagt    60
ttttcctgca ggaccagtca gagcattggc acaaacatac actggtatca gcaaagaaca   120
aatggttttc caaggcttct cataaagaat gtttctgagt ctatctctgg gatcccttcc   180
aggtttagtg gcagtggatc aggaacagat tttattctta gcatcaacag tgtggagtct   240
gaagatattg cagattatta ttgtcaacaa agtaataccT ggccgttcac gttcggaggg   300
gggaccaagc tggaaataaa a                                             321

<210> SEQ ID NO 26
<211> LENGTH: 107
<212> TYPE: PRT
<213> ORGANISM: Mus musculus
<220> FEATURE:
<221> NAME/KEY: MISC_FEATURE
<223> OTHER INFORMATION: Mouse 2B6 Light Chain Variable Region

<400> SEQUENCE: 26

Asp Ile Leu Leu Thr Gln Ser Pro Ala Ile Leu Ser Val Ser Pro Gly
  1               5                  10                  15

Glu Arg Val Ser Phe Ser Cys Arg Thr Ser Gln Ser Ile Gly Thr Asn
                 20                  25                  30

Ile His Trp Tyr Gln Gln Arg Thr Asn Gly Phe Pro Arg Leu Leu Ile
             35                  40                  45

Lys Asn Val Ser Glu Ser Ile Ser Gly Ile Pro Ser Arg Phe Ser Gly
 50                  55                  60

Ser Gly Ser Gly Thr Asp Phe Ile Leu Ser Ile Asn Ser Val Glu Ser
 65                  70                  75                  80

Glu Asp Ile Ala Asp Tyr Tyr Cys Gln Gln Ser Asn Thr Trp Pro Phe
                 85                  90                  95

Thr Phe Gly Gly Gly Thr Lys Leu Glu Ile Lys
            100                 105

<210> SEQ ID NO 27
<211> LENGTH: 363
<212> TYPE: DNA
<213> ORGANISM: Mus musculus
<220> FEATURE:
<221> NAME/KEY: misc_feature
<223> OTHER INFORMATION: Mouse 2B6 Heavy Chain Variable Region

<400> SEQUENCE: 27
```

```
caggtccaat tgcagcagcc tgtgactgag ctggtgaggc cggggcttc agtgatgttg      60 tcctgcaagg cttctgacta ccccttcacc aactactgga tacactgggt aaagcagagg    120
cctggacaag gcctggagtg gatcggagtg attgatcctt ctgatactta tccaaattac    180
aataaaaagt tcaagggcaa ggccacattg actgtagtcg tatcctccag cacagcctac    240
atgcagctca gcagcctgac atctgacgat tctgcggtct attactgtgc aagaaacggt    300
gattccgatt attactctgg tatggactac tggggtcaag gaacctcagt caccgtctcc    360
tca                                                                 363
```

```
<210> SEQ ID NO 28
<211> LENGTH: 121
<212> TYPE: PRT
<213> ORGANISM: Mus musculus
<220> FEATURE:
<221> NAME/KEY: MISC_FEATURE
<223> OTHER INFORMATION: Mouse 2B6 Heavy Chain Variable Region

<400> SEQUENCE: 28
```

Gln Val Gln Leu Gln Gln Pro Val Thr Glu Leu Val Arg Pro Gly Ala
1               5                   10                  15

Ser Val Met Leu Ser Cys Lys Ala Ser Asp Tyr Pro Phe Thr Asn Tyr
            20                  25                  30

Trp Ile His Trp Val Lys Gln Arg Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Lys Ala Thr Leu Thr Val Val Val Ser Ser Ser Thr Ala Tyr
65                  70                  75                  80

Met Gln Leu Ser Ser Leu Thr Ser Asp Asp Ser Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Ser Val Thr Val Ser Ser
        115                 120

```
<210> SEQ ID NO 29
<211> LENGTH: 5
<212> TYPE: PRT
<213> ORGANISM: Artificial Sequence
<220> FEATURE:
<223> OTHER INFORMATION: 3H7 Heavy Chain Variable Region - CDR1

<400> SEQUENCE: 29
```

Asp Ala Trp Met Asp
1               5

```
<210> SEQ ID NO 30
<211> LENGTH: 19
<212> TYPE: PRT
<213> ORGANISM: Artificial Sequence
<220> FEATURE:
<223> OTHER INFORMATION: 3H7 Heavy Chain Variable Region - CDR2

<400> SEQUENCE: 30
```

Glu Ile Arg Asn Lys Ala Asn Asn Leu Ala Thr Tyr Tyr Ala Glu Ser
1               5                   10                  15

Val Lys Gly

```
<210> SEQ ID NO 31
<211> LENGTH: 6
<212> TYPE: PRT
<213> ORGANISM: Artificial Sequence
<220> FEATURE:
<223> OTHER INFORMATION: 3H7 Heavy Chain Variable Region - CDR3

<400> SEQUENCE: 31

Tyr Ser Pro Phe Ala Tyr
1               5

<210> SEQ ID NO 32
<211> LENGTH: 30
<212> TYPE: PRT
<213> ORGANISM: Artificial Sequence
<220> FEATURE:
<223> OTHER INFORMATION: 3H7 Heavy Chain Variable Region - FWR1

<400> SEQUENCE: 32

Glu Val Lys Phe Glu Glu Ser Gly Gly Gly Leu Val Gln Pro Gly Gly
1               5                   10                  15

Ser Met Lys Leu Ser Cys Ala Ala Ser Gly Phe Thr Phe Ser
            20                  25                  30

<210> SEQ ID NO 33
<211> LENGTH: 14
<212> TYPE: PRT
<213> ORGANISM: Artificial Sequence
<220> FEATURE:
<223> OTHER INFORMATION: 3H7 Heavy Chain Variable Region - FWR2

<400> SEQUENCE: 33

Trp Val Arg Gln Gly Pro Glu Lys Gly Leu Glu Trp Val Ala
1               5                   10

<210> SEQ ID NO 34
<211> LENGTH: 30
<212> TYPE: PRT
<213> ORGANISM: Artificial Sequence
<220> FEATURE:
<223> OTHER INFORMATION: 3H7 Heavy Chain Variable Region - FWR3

<400> SEQUENCE: 34

Arg Phe Thr Ile Pro Arg Asp Asp Ser Lys Ser Ser Val Tyr Leu His
1               5                   10                  15

Met Asn Ser Leu Arg Ala Glu Asp Thr Gly Ile Tyr Tyr Cys
            20                  25                  30

<210> SEQ ID NO 35
<211> LENGTH: 11
<212> TYPE: PRT
<213> ORGANISM: Artificial Sequence
<220> FEATURE:
<223> OTHER INFORMATION: 3H7 Heavy Chain Variable Region - FWR4

<400> SEQUENCE: 35

Trp Gly Gln Gly Thr Leu Val Thr Val Ser Ala
1               5                   10

<210> SEQ ID NO 36
<211> LENGTH: 345
<212> TYPE: DNA
<213> ORGANISM: Mus musculus
<220> FEATURE:
<221> NAME/KEY: misc_feature
<223> OTHER INFORMATION: mouse 3H7 Heavy Chain Variable Region
```

<400> SEQUENCE: 36

```
gaagtgaagt tgaggagtc tggaggaggc ttggtgcaac ctggaggatc catgaaactc      60
tcttgtgctg cctctggatt cactttagt gacgcctgga tggactgggt ccgccaggt     120 ccagagaagg ggcttgagtg ggttgctgaa attagaaaca aagctaataa tcttgcaaca    180
tactatgctg agtctgtgaa agggaggttc accatcccaa gagatgattc caaaagtagt    240
gtctacctgc acatgaacag cttaagagct gaagacactg gcatttatta ctgttatagt    300 cccttttgctt actggggcca agggactctg gtcactgtct ctgca                   345
```

<210> SEQ ID NO 37
<211> LENGTH: 115
<212> TYPE: PRT
<213> ORGANISM: Mus musculus
<220> FEATURE:
<221> NAME/KEY: MISC_FEATURE
<223> OTHER INFORMATION: Mouse 3H7 Heavy Chain Variable Region

<400> SEQUENCE: 37

```
Glu Val Lys Phe Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Gly Pro Glu Lys Gly Leu Glu Trp Val
        35                  40                  45

Ala Glu Ile Arg Asn Lys Ala Asn Asn Leu Ala Thr Tyr Tyr Ala Glu
    50                  55                  60

Ser Val Lys Gly Arg Phe Thr Ile Pro Arg Asp Asp Ser Lys Ser Ser
65                  70                  75                  80

Val Tyr Leu His Met Asn Ser Leu Arg Ala Glu Asp Thr Gly Ile Tyr
                85                  90                  95

Tyr Cys Tyr Ser Pro Phe Ala Tyr Trp Gly Gln Gly Thr Leu Val Thr
            100                 105                 110

Val Ser Ala
        115
```

<210> SEQ ID NO 38
<211> LENGTH: 11
<212> TYPE: PRT
<213> ORGANISM: Artificial Sequence
<220> FEATURE:
<223> OTHER INFORMATION: 3H7 Light Chain Variable Region - CDR1

<400> SEQUENCE: 38

```
Arg Ala Ser Gln Glu Ile Ser Gly Tyr Leu Ser
1               5                   10
```

<210> SEQ ID NO 39
<211> LENGTH: 7
<212> TYPE: PRT
<213> ORGANISM: Artificial Sequence
<220> FEATURE:
<223> OTHER INFORMATION: 3H7 Light Chain Variable Region - CDR2

<400> SEQUENCE: 39

```
Ala Ala Ser Thr Leu Asp Ser
1               5
```

<210> SEQ ID NO 40
<211> LENGTH: 9
<212> TYPE: PRT

<213> ORGANISM: Artificial Sequence
<220> FEATURE:
<223> OTHER INFORMATION: 3H7 Light Chain Variable Region - CDR3

<400> SEQUENCE: 40

Leu Gln Tyr Val Ser Tyr Pro Tyr Thr
1               5

<210> SEQ ID NO 41
<211> LENGTH: 23
<212> TYPE: PRT
<213> ORGANISM: Artificial Sequence
<220> FEATURE:
<223> OTHER INFORMATION: 3H7 Light Chain Variable Region - FWR1

<400> SEQUENCE: 41

Asp Ile Gln Met Thr Gln Ser Pro Ser Ser Leu Ser Ala Ser Leu Gly
1               5                   10                  15

Glu Arg Val Ser Leu Thr Cys
            20

<210> SEQ ID NO 42
<211> LENGTH: 15
<212> TYPE: PRT
<213> ORGANISM: Artificial Sequence
<220> FEATURE:
<223> OTHER INFORMATION: 3H7 Light Chain Variable Region - FWR2

<400> SEQUENCE: 42

Trp Leu Gln Gln Lys Pro Asp Gly Thr Ile Arg Arg Leu Ile Tyr
1               5                   10                  15

<210> SEQ ID NO 43
<211> LENGTH: 32
<212> TYPE: PRT
<213> ORGANISM: Artificial Sequence
<220> FEATURE:
<223> OTHER INFORMATION: 3H7 Light Chain Variable Region - FWR3

<400> SEQUENCE: 43

Gly Val Pro Lys Arg Phe Ser Gly Ser Trp Ser Gly Ser Asp Tyr Ser
1               5                   10                  15

Leu Thr Ile Ser Ser Leu Glu Ser Glu Asp Phe Ala Asp Tyr Tyr Cys
            20                  25                  30

<210> SEQ ID NO 44
<211> LENGTH: 10
<212> TYPE: PRT
<213> ORGANISM: Artificial Sequence
<220> FEATURE:
<223> OTHER INFORMATION: 3H7 Light Chain Variable Region - FWR4

<400> SEQUENCE: 44

Phe Gly Gly Gly Thr Lys Leu Glu Ile Lys
1               5                   10

<210> SEQ ID NO 45
<211> LENGTH: 321
<212> TYPE: DNA
<213> ORGANISM: Mus musculus
<220> FEATURE:
<221> NAME/KEY: misc_feature
<223> OTHER INFORMATION: mouse 3H7 Light Chain Variable Region

<400> SEQUENCE: 45
gacatccaga tgacccagtc tccatcctcc ttatctgcct ctctgggaga aagagtcagt     60

```
ctcacttgtc gggcaagtca ggaaattagt ggttacttaa gctggcttca gcagaaacca      120
gatggaacta ttagacgcct gatctacgcc gcatccactt tagattctgg tgtcccaaaa      180
aggttcagtg gcagttggtc tgggtcagat tattctctca ccatcagcag ccttgagtct      240
gaagattttg cagactatta ctgtctacaa tatgttagtt atccgtatac gttcggaggg      300
gggaccaagc tggaaataaa a                                                 321
```

<210> SEQ ID NO 46
<211> LENGTH: 107
<212> TYPE: PRT
<213> ORGANISM: Mus musculus
<220> FEATURE:
<221> NAME/KEY: MISC_FEATURE
<223> OTHER INFORMATION: mouse 3H7 Light Chain Variable Region

<400> SEQUENCE: 46

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Arg Arg Leu Ile
        35                  40                  45

Tyr Ala Ala Ser Thr Leu Asp Ser Gly Val Pro Lys Arg Phe Ser Gly
    50                  55                  60

Ser Trp Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Val Ser Tyr Pro Tyr
                85                  90                  95

Thr Phe Gly Gly Gly Thr Lys Leu Glu Ile Lys
            100                 105

<210> SEQ ID NO 47
<211> LENGTH: 22
<212> TYPE: DNA
<213> ORGANISM: Artificial Sequence
<220> FEATURE:
<223> OTHER INFORMATION: Primer - SJ15R

<400> SEQUENCE: 47

```
ggtcactgtc actggctcag gg                                                22
```

<210> SEQ ID NO 48
<211> LENGTH: 28
<212> TYPE: DNA
<213> ORGANISM: Artificial Sequence
<220> FEATURE:
<223> OTHER INFORMATION: Primer - SJ16R

<400> SEQUENCE: 48

```
aggcggatcc aggggccagt ggatagac                                          28
```

<210> SEQ ID NO 49
<211> LENGTH: 26
<212> TYPE: DNA
<213> ORGANISM: Artificial Sequence
<220> FEATURE:
<223> OTHER INFORMATION: Primer - SJ17R

<400> SEQUENCE: 49

```
gcacacgact gaggcacctc cagatg                                            26
```

```
<210> SEQ ID NO 50
<211> LENGTH: 34
<212> TYPE: DNA
<213> ORGANISM: Artificial Sequence
<220> FEATURE:
<223> OTHER INFORMATION: Primer - SJ18R

<400> SEQUENCE: 50
cggcggatcc gatggataca gttggtgcag catc                                34

<210> SEQ ID NO 51
<211> LENGTH: 9
<212> TYPE: PRT
<213> ORGANISM: Artificial Sequence
<220> FEATURE:
<223> OTHER INFORMATION: Fusion protein - partial sequence

<400> SEQUENCE: 51

Lys Lys Phe Ser Arg Ser Asp Pro Asn
1               5

<210> SEQ ID NO 52
<211> LENGTH: 9
<212> TYPE: PRT
<213> ORGANISM: Artificial Sequence
<220> FEATURE:
<223> OTHER INFORMATION: fusion protein - partial sequence

<400> SEQUENCE: 52

Gln Lys Phe Ser Arg Leu Asp Pro Asn
1               5

<210> SEQ ID NO 53
<211> LENGTH: 9
<212> TYPE: PRT
<213> ORGANISM: Artificial Sequence
<220> FEATURE:
<223> OTHER INFORMATION: fusion protein - partial sequence

<400> SEQUENCE: 53

Gln Lys Phe Ser Arg Leu Asp Pro Thr
1               5

<210> SEQ ID NO 54
<211> LENGTH: 9
<212> TYPE: PRT
<213> ORGANISM: Artificial Sequence
<220> FEATURE:
<223> OTHER INFORMATION: fusion protein - partial sequence

<400> SEQUENCE: 54

Lys Lys Phe Ser Arg Leu Asp Pro Thr
1               5

<210> SEQ ID NO 55
<211> LENGTH: 9
<212> TYPE: PRT
<213> ORGANISM: Artificial Sequence
<220> FEATURE:
<223> OTHER INFORMATION: fusion protein - partial sequence

<400> SEQUENCE: 55

Gln Lys Phe Ser His Leu Asp Pro Thr
1               5

<210> SEQ ID NO 56
```

```
<211> LENGTH: 9
<212> TYPE: PRT
<213> ORGANISM: Artificial Sequence
<220> FEATURE:
<223> OTHER INFORMATION: fusion protein - partial sequence

<400> SEQUENCE: 56

Lys Lys Phe Ser His Leu Asp Pro Thr
1               5

<210> SEQ ID NO 57
<211> LENGTH: 5
<212> TYPE: PRT
<213> ORGANISM: Artificial Sequence
<220> FEATURE:
<223> OTHER INFORMATION: fusion protein - partial sequence

<400> SEQUENCE: 57

Ala Pro Ser Ser Ser
1               5

<210> SEQ ID NO 58
<211> LENGTH: 8
<212> TYPE: PRT
<213> ORGANISM: Artificial Sequence
<220> FEATURE:
<223> OTHER INFORMATION: fusion protein - partial sequence

<400> SEQUENCE: 58

Val Pro Ser Met Gly Ser Ser Ser
1               5

<210> SEQ ID NO 59
<211> LENGTH: 363
<212> TYPE: DNA
<213> ORGANISM: Artificial Sequence
<220> FEATURE:
<223> OTHER INFORMATION: Humanized 2B6 Heavy Chain Variable Domain -
      H2B6VH-A

<400> SEQUENCE: 59
caggttcagc tggtgcagtc tggagctgag gtgaagaagc ctggggcctc agtgaaggtc      60
tcctgcaagg cttctggtta cacctttacc aactactgga tacactgggt gcgacaggcc     120
cctggacaag ggcttgagtg gattggagtg attgatcctt ctgatactta tccaaattac     180
aataaaaagt tcaagggcag agtcaccatg accgtagtcg tatccacgag cacagcctac     240
atggagctga ggagcctgag atctgacgac acggccgtgt attactgtgc gagaaacggt     300
gattccgatt attactctgg tatggactac tggggcaag ggaccacggt caccgtctcc     360
tca                                                                  363

<210> SEQ ID NO 60
<211> LENGTH: 121
<212> TYPE: PRT
<213> ORGANISM: Artificial Sequence
<220> FEATURE:
<223> OTHER INFORMATION: Humanized 2B6 Heavy Chain Variable Domain -
      H2B6VH-A

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

```
Trp Ile His Trp Val Arg Gln Ala Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Arg Val Thr Met Thr Val Val Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
                100                 105                 110

Gln Gly Thr Thr Val Thr Val Ser Ser
        115                 120

<210> SEQ ID NO 61
<211> LENGTH: 321
<212> TYPE: DNA
<213> ORGANISM: Artificial Sequence
<220> FEATURE:
<223> OTHER INFORMATION: Humanized 2B6 Light Chain Variable Domain -
      H2B6VL-5

<400> SEQUENCE: 61
gaaattgtgc tgactcagtc tccagacttt cagtctgtga ctccaaagga gaaagtcacc    60
ttcacctgca ggaccagtca gagcattggc acaaacatac actggtacca gcagaaacca   120
gatcagtctc caaagctcct catcaaggag gtttctgagt ctatctctgg agtcccatcg   180
aggttcagtg gcagtggatc tgggacagat ttcaccctca ccatcaatag cctggaagct   240
gaagatgctg caacgtatta ctgtcaacaa agtaatacct ggccgttcac gttcggcgga   300
gggaccaagg tggagatcaa a                                             321

<210> SEQ ID NO 62
<211> LENGTH: 107
<212> TYPE: PRT
<213> ORGANISM: Artificial Sequence
<220> FEATURE:
<223> OTHER INFORMATION: Humanized 2B6 Light Chain Variable Domain -
      H2B6VL-5

<400> SEQUENCE: 62

Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
                20                  25                  30

Ile His Trp Tyr Gln Gln Lys Pro Asp Gln Ser Pro Lys Leu Leu Ile
            35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
                100                 105

<210> SEQ ID NO 63
<211> LENGTH: 1356
<212> TYPE: DNA
<213> ORGANISM: Artificial Sequence
<220> FEATURE:
```

<223> OTHER INFORMATION: Humanized 2B6 Heavy Chain - H2B6Hc-A

<400> SEQUENCE: 63

| | | |
|---|---|---|
| caggttcagc tggtgcagtc tggagctgag gtgaagaagc ctggggcctc agtgaaggtc | 60 |
| tcctgcaagg cttctggtta cacctttacc aactactgga tacactgggt gcgacaggcc | 120 |
| cctggacaag gcttgagtg gattggagtg attgatcctt ctgatactta tccaaattac | 180 |
| aataaaaagt tcaagggcag agtcaccatg accgtagtcg tatccacgag cacagcctac | 240 |
| atggagctga ggagcctgag atctgacgac acggccgtgt attactgtgc gagaaacggt | 300 |
| gattccgatt attactctgg tatggactac tgggggcaag ggaccacggt caccgtctcc | 360 |
| tcagcctcca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt accccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgccgga ggagcagtac | 900 |
| aacagcacgc tccgtgtggt cagcatcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggat | 1080 |
| gagctgacca agaaccaggt cagcctgacc tgcctggtca aaggcttcta tcccagcgac | 1140 |
| atcgccgtgg agtgggagag caatgggcag ccggagaaca actacaagac cacgcctctc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaatga | 1356 |

<210> SEQ ID NO 64
<211> LENGTH: 451
<212> TYPE: PRT
<213> ORGANISM: Artificial Sequence
<220> FEATURE:
<223> OTHER INFORMATION: Humanized 2B6 Heavy Chain - H2B6Hc-A

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Arg Val Thr Met Thr Val Val Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly

```
                100                 105                 110
Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Leu Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Glu Glu Gln Tyr Asn Ser Thr Leu
    290                 295                 300

Arg Val Val Ser Ile Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Leu
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 65
<211> LENGTH: 645
<212> TYPE: DNA
<213> ORGANISM: Artificial Sequence
<220> FEATURE:
<223> OTHER INFORMATION: Humanized 2B6 Light Chain H2B6 Lc-5

<400> SEQUENCE: 65
gaaattgtgc tgactcagtc tccagacttt cagtctgtga ctccaaagga gaaagtcacc     60
```

```
ttcacctgca ggaccagtca gagcattggc acaaacatac actggtacca gcagaaacca    120
gatcagtctc caaagctcct catcaaggag gtttctgagt ctatctctgg agtcccatcg    180
aggttcagtg gcagtggatc tgggacagat ttcacccctca ccatcaatag cctggaagct    240
gaagatgctg caacgtatta ctgtcaacaa gtaatacct ggccgttcac gttcggcgga    300
gggaccaagg tggagatcaa acgaactgtg gctgcaccat ctgtcttcat cttcccgcca    360
tctgatcagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 66
<211> LENGTH: 214
<212> TYPE: PRT
<213> ORGANISM: Artificial Sequence
<220> FEATURE:
<223> OTHER INFORMATION: Humanized 2B6 Light Chain H2B6 Lc-5

<400> SEQUENCE: 66

```
Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 67
<211> LENGTH: 363
<212> TYPE: DNA
<213> ORGANISM: Artificial Sequence
<220> FEATURE:

<223> OTHER INFORMATION: Humanized 2B6 Heavy Chain Variable Domain -
     H2B6VH-3

<400> SEQUENCE: 67
caggttcagc tggtgcagtc tggagctgag gtgaagaagc ctggggcctc agtgaaggtc    60
tcctgcaagg cttctggtta cacctttacc aactactgga tacactgggt gcgacaggcc   120
cctggacaag gcttgagtg gattggagtg attgatcctt ctgatactta tccaaattac   180
aataaaaagt tcaagggcag agtcaccatg accgtagaca catccacgag cacagcctac   240
atggagctga ggagcctgag atctgacgac acggccgtgt attactgtgc gagaaacggt   300
gattccgatt attactctgg tatggactac tgggggcaag gaccacggt caccgtctcc   360 tca                                                                 363

<210> SEQ ID NO 68
<211> LENGTH: 121
<212> TYPE: PRT
<213> ORGANISM: Artificial Sequence
<220> FEATURE:
<223> OTHER INFORMATION: Humanized 2B6 Heavy Chain Variable Domain
     H2B6VH-3

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Ile His Trp Val Arg Gln Ala Pro Gly Gln Gly Leu Glu Trp Ile
            35                  40                  45

Gly Val Ile Asp Pro Ser Asp Thr Tyr Pro Asn Tyr Asn Lys Lys Phe
        50                  55                  60

Lys Gly Arg Val Thr Met Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser
        115                 120

<210> SEQ ID NO 69
<211> LENGTH: 1356
<212> TYPE: DNA
<213> ORGANISM: Artificial Sequence
<220> FEATURE:
<223> OTHER INFORMATION: Humanized 2B6 Heavy Chain H2B6Hc-3

<400> SEQUENCE: 69
caggttcagc tggtgcagtc tggagctgag gtgaagaagc ctggggcctc agtgaaggtc    60
tcctgcaagg cttctggtta cacctttacc aactactgga tacactgggt gcgacaggcc   120
cctggacaag gcttgagtg gattggagtg attgatcctt ctgatactta tccaaattac   180
aataaaaagt tcaagggcag agtcaccatg accgtagaca catccacgag cacagcctac   240
atggagctga ggagcctgag atctgacgac acggccgtgt attactgtgc gagaaacggt   300
gattccgatt attactctgg tatggactac tgggggcaag gaccacggt caccgtctcc   360 tcagcctcca ccaagggccc atcggtcttc cccctggcac cctcctccaa gagcacctct   420
gggggcacag cggccctggg ctgcctggtc aaggactact ccccgaacc ggtgacggtg    480

```
tcgtggaact caggcgccct gaccagcggc gtgcacacct tcccggctgt cctacagtcc      540
tcaggactct actccctcag cagcgtggtg accgtgccct ccagcagctt gggcacccag      600
acctacatct gcaacgtgaa tcacaagccc agcaacacca aggtggacaa gagagttgag      660
cccaaatctt gtgacaaaac tcacacatgc ccaccgtgcc cagcacctga actcctgggg      720
ggaccgtcag tcttcctctt accccccaaa acccaaggac acctcatgat ctcccggacc      780
cctgaggtca catgcgtggt ggtggacgtg agccacgaag accctgaggt caagttcaac      840
tggtacgtgg acggcgtgga ggtgcataat gccaagacaa agccgccgga ggagcagtac      900
aacagcacgc tccgtgtggt cagcatcctc accgtcctgc accaggactg gctgaatggc      960
aaggagtaca agtgcaaggt ctccaacaaa gccctcccag cccccatcga gaaaaccatc     1020
tccaaagcca agggcagccc cgagaaccac aggtgtacac cctgccccc atcccgggat      1080 gagctgacca gaaccaggt cagcctgacc tgcctggtca aaggcttcta tcccagcgac     1140
atcgccgtgg agtgggagag caatgggcag ccggagaaca actacaagac cacgcctctc     1200
gtgctggact ccgacggctc cttcttcctc tacagcaagc tcaccgtgga caagagcagg     1260
tggcagcagg ggaacgtctt ctcatgctcc gtgatgcatg aggctctgca caaccactac     1320
acgcagaaga gcctctccct gtctccgggt aaatga                               1356
```

<210> SEQ ID NO 70
<211> LENGTH: 451
<212> TYPE: PRT
<213> ORGANISM: Artificial Sequence
<220> FEATURE:
<223> OTHER INFORMATION: Humanized 2B6 Heavy Chain H2B6Hc-3

<400> SEQUENCE: 70

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Arg Val Thr Met Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Leu Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Leu
    290                 295                 300
Arg Val Val Ser Ile Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Leu
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 71
<211> LENGTH: 5
<212> TYPE: PRT
<213> ORGANISM: Homo sapiens
<220> FEATURE:
<221> NAME/KEY: MISC_FEATURE
<223> OTHER INFORMATION: CDR 1 from human germline VH1-18 and JH6

<400> SEQUENCE: 71

Ser Tyr Gly Ile Ser
1               5

<210> SEQ ID NO 72
<211> LENGTH: 17
<212> TYPE: PRT
<213> ORGANISM: Homo sapiens
<220> FEATURE:
<221> NAME/KEY: MISC_FEATURE
<223> OTHER INFORMATION: CDR2 from human germline VH1-18 and JH6

<400> SEQUENCE: 72

Trp Ile Ser Ala Tyr Asn Gly Asn Thr Asn Tyr Ala Gln Lys Leu Gln
1               5                   10                  15
Gly
```

```
<210> SEQ ID NO 73
<211> LENGTH: 7
<212> TYPE: PRT
<213> ORGANISM: Homo sapiens
<220> FEATURE:
<221> NAME/KEY: MISC_FEATURE
<223> OTHER INFORMATION: CDR3 from human germline JH6

<400> SEQUENCE: 73

Tyr Tyr Tyr Gly Met Asp Val
1               5

<210> SEQ ID NO 74
<211> LENGTH: 11
<212> TYPE: PRT
<213> ORGANISM: Homo sapiens
<220> FEATURE:
<221> NAME/KEY: MISC_FEATURE
<223> OTHER INFORMATION: CDR1 from human germline VK-A26 and JK4

<400> SEQUENCE: 74

Arg Ala Ser Gln Ser Ile Gly Ser Ser Leu His
1               5                   10

<210> SEQ ID NO 75
<211> LENGTH: 7
<212> TYPE: PRT
<213> ORGANISM: Homo sapiens
<220> FEATURE:
<221> NAME/KEY: MISC_FEATURE
<223> OTHER INFORMATION: CDR2 from human germline VK-A26 and JK4

<400> SEQUENCE: 75

Tyr Ala Ser Gln Ser Phe Ser
1               5

<210> SEQ ID NO 76
<211> LENGTH: 6
<212> TYPE: PRT
<213> ORGANISM: Homo sapiens
<220> FEATURE:
<221> NAME/KEY: MISC_FEATURE
<223> OTHER INFORMATION: CDR3 from human germline VK-A26

<400> SEQUENCE: 76

His Gln Ser Ser Leu Thr
1               5
```

HUMANIZED FCγRIIB-SPECIFIC ANTIBODIES AND METHODS OF USE THEREOF

1. CROSS REFERENCE TO RELATED APPLICATIONS

This application claims benefit of U.S. Provisional Patent Application Ser. No. 60/809,116, filed May 26, 2006 and U.S. Provisional Patent Application No. 60/816,126, filed Jun. 23, 2006, the entire contents of each of which are incorporated herein by reference for all purposes.

2. FIELD OF THE INVENTION

The present invention relates to humanized FcγRIIB antibodies, fragments, and variants thereof that bind human FcγRIIB with a greater affinity than said antibody binds FcγRIIA. The invention encompasses the use of the humanized antibodies of the invention for the treatment of any disease related to loss of balance of Fc receptor mediated signaling, such cancer (preferably a B-cell malignancy, particularly, B-cell chronic lymphocytic leukemia or non-Hodgkin's lymphoma), autoimmune disease, inflammatory disease or IgE-mediated allergic disorder. The present invention also encompasses the use of a humanized FcγRIIB antibody or an antigen-binding fragment thereof, in combination with other cancer therapies. The invention provides methods of enhancing the therapeutic effect of therapeutic antibodies by administering the humanized antibodies of the invention to enhance the effector function of the therapeutic antibodies. The invention also provides methods of enhancing the efficacy of a vaccine composition by administering the humanized antibodies of the invention with a vaccine composition.

3. BACKGROUND OF THE INVENTION

3.1 Fc Receptors and their Roles in the Immune System

The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. The diversity of cellular responses triggered by antibodies and immune complexes results from the structural heterogeneity of Fc receptors. Fc-receptors share structurally related ligand binding domains which presumably mediate intracellular signaling.

The Fc receptors, members of the immunoglobulin gene superfamily of proteins, are surface glycoproteins that can bind the Fc portion of immunoglobulin molecules. Each member of the family recognizes immunoglobulins of one or more isotypes through a recognition domain on the α chain of the Fc receptor. Fc receptors are defined by their specificity for immunoglobulin subtypes. Fc receptors for IgG are referred to as FcγR, for IgE as FcεR, and for IgA as FcαR. Different accessory cells bear Fc receptors for antibodies of different isotype, and the isotype of the antibody determines which accessory cells will be engaged in a given response (reviewed by Ravetch J. V. et al. 1991, *Annu. Rev. Immunol.* 9: 457-92; Gerber J. S. et al. 2001 *Microbes and Infection*, 3: 131-139; Billadeau D. D. et al. 2002, *The Journal of Clinical Investigation*, 2(109): 161-168; Ravetch J. V. et al. 2000, *Science*, 290: 84-89; Ravetch J. V. et al., 2001 *Annu. Rev. Immunol.* 19:275-90; Ravetch J. V. 1994, *Cell*, 78(4): 553-60; each of which is incorporated by reference herein in its entirety). The different Fc receptors, the cells that express them, and their isotype specificity is summarized in Table 1 (adapted from Immunobiology: The Immune System in Health and Disease, 4th ed. 1999, Elsevier Science Ltd/Garland Publishing, New York, incorporated herein by reference in its entirety).

Fcγ Receptors

Each member of this family is an integral membrane glycoprotein, possessing extracellular domains related to a C2-set of immunoglobulin-related domains, a single membrane spanning domain and an intracytoplasmic domain of variable length. There are three known FcγRs, designated FcγRI(CD64), FcγRII(CD32), and FcγRIII(CD16). The three receptors are encoded by distinct genes; however, the extensive homology among the three family members suggest they arose from a common progenitor perhaps by gene duplication. This invention specifically focuses on FcγRII(CD32).

FcγRII(CD32)

FcγRII proteins are 40 KDa integral membrane glycoproteins which bind only the complexed IgG due to a low affinity for monomeric Ig ($10^6 M^{-1}$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three human FcγRII genes (FcγRII-A, FcγRII-B, FcγRII-C), all of which bind IgG in aggregates or immune complexes.

Distinct differences within the cytoplasmic domains of FcγRII-A (CD32A) and FcγRII-B (CD32B) create two functionally heterogeneous responses to receptor ligation. The fundamental difference is that the A isoform initiates intracellular signaling leading to cell activation such as phagocytosis and respiratory burst, whereas the β isoform initiates inhibitory signals, e.g., inhibiting B-cell activation.

Signaling through FcγRs

Both activating and inhibitory signals are transduced through the FcγRs following ligation. These diametrically opposing functions result from structural differences among the different receptor isoforms. Two distinct domains within the cytoplasmic signaling domains of the receptor called immunoreceptor tyrosine based activation motifs (ITAMs) or immunoreceptor tyrosine based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB.

Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., $PI_3K$). Cellular activation leads to release of proinflammatory mediators.

The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular $Ca^{++}$. Thus, crosslinking of FcγRIIB dampens the activating response to FcγR ligation and inhibits cellular responsiveness. B cell activation, B cell proliferation and antibody secretion is thus aborted.

(1998 data), with an estimated 25,000 deaths per year. This represents 4% of cancer incidence and 4% of all cancer-related deaths in the U.S. population. The revised European-American classification of lymphoid neoplasms (1994 REAL classification, modified 1999; incorporated herein by reference in its entirety) grouped lymphomas based on their origin as either B cell lineage lymphoma, T cell lineage lymphoma, or Hodgkin's lymphoma. Lymphoma of the B cell lineage is

TABLE 1

Receptors for the Fc Regions of Immunoglobulin Isotypes

| | Receptor | | | | | | |
|---|---|---|---|---|---|---|---|
| | FcγRI (CD64) | FcγRII-A (CD32) | FcγRII-B2 (CD32) | FcγRII-BI (CD32) | FcγRIII (CD16) | FcεRI | FcαRI (CD89) |
| Binding | IgG1 $10^8 M^{-1}$ | IgG1 $2 \times 10^6 M^{-1}$ | IgG1 $2 \times 10^6 M^{-1}$ | IgG1 $2 \times 10^6 M^{-1}$ | IgG1 $5 \times 10^5 M^{-1}$ | IgG1 $10^{10} M^{-1}$ | IgG1, IgA2 $10^7 M^{-1}$ |
| Cell Type | Macrophages Neutrophils Eosinophils Dendritic cells | Macrophages Neutrophils Eosinophils Dendritic cells Platelets Langerhan cells | Macrophages Neutrophils Eosinophils | B cells Mast cells | NK cells Eosinophil macrophages Neutrophils Mast Cells | Mast cells Eosinophil Basophils | Macrophages Neutropils Eosinophils |
| Effect of Ligation | Uptake Stimulation Activation of respiratory burst Induction of killing | Uptake Granule release | Uptake Inhibition of Stimulation | No uptake Inhibition of Stimulation | Induction of Killing | Secretion of granules | Uptake Induction of killing |

3.2 Diseases of Relevance 3.2.1 Cancer

A neoplasm, or tumor, is a neoplastic mass resulting from abnormal uncontrolled cell growth which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W.B. Saunders Co., Philadelphia, pp. 68-122, incorporated herein by reference in its entirety). Cancer can arise in many sites of the body and behave differently depending upon its origin. Cancerous cells destroy the part of the body in which they originate and then spread to other part(s) of the body where they start new growth and cause more destruction.

More than 1.2 million Americans develop cancer each year. Cancer is the second leading case of death in the United States and if current trends continue, cancer is expected to be the leading cause of the death by the year 2010. Lung and prostate cancer are the top cancer killers for men in the United States. Lung and breast cancer are the top cancer killers for women in the United States. One in two men in the United States will be diagnosed with cancer at some time during his lifetime. One in three women in the United States will be diagnosed with cancer at some time during her lifetime.

A cure for cancer has yet to be found. Current treatment options, such as surgery, chemotherapy and radiation treatment, are oftentimes either ineffective or present serious side effects.

3.2.1.1 B-Cell Malignancies

B cell malignancies, including, but not limited to, B-cell lymphomas and leukemias, are neoplastic diseases with significant incidence in the United States. There are approximately 55,000 new lymphoma cases of per year in the U.S.

the most common type of non-Hodgkin's lymphoma (NHL) diagnosed in the U.S. (Williams, Hematology 6th ed. (Beutler et al. Ed.), McGraw Hill 2001; incorporated herein by reference in its entirety).

Chronic lymphocytic leukemia (CLL) is a neoplastic disease characterized by the accumulation of small, mature-appearing lymphocytes in the blood, marrow, and lymphoid tissues. CLL has an incidence of 2.7 cases per 100,000 in the U.S. The risk increases progressively with age, particularly in men. It accounts for 0.8% of all cancers and is the most common adult leukemia, responsible for 30% of all leukemias. In nearly all cases (>98%) the diseased cells belong to the B lymphocyte lineage. A non-leukemic variant, small lymphocytic lymphoma, constitutes 5-10% of all lymphomas, has histological, morphological and immunological features indistinguishable from that of involved lymph nodes in patients with B-CLL (Williams, 2001).

The natural history of chronic lymphocytic leukemia falls into several phases. In the early phase, chronic lymphocytic leukemia is an indolent disease, characterized by the accumulation of small, mature, functionally-incompetent malignant B-cells having a lengthened life span. Eventually, the doubling time of the malignant B-cells decreases and patients become increasingly symptomatic. While treatment with chemotherapeutic agents can provide symptomatic relief, the overall survival of the patients is only minimally extended. The late stages of chronic lymphocytic leukemia are characterized by significant anemia and/or thrombocytopenia. At this point, the median survival is less than two years (Foon et al., 1990, Annals Int. Medicine 113:525; incorporated herein by reference in its entirety). Due to the very low rate of cellular proliferation, chronic lymphocytic leukemia is resistant to treatment with chemotherapeutic agents.

Recently, gene expression studies have identified several genes that may be up regulated in lymphoproliferative disorders. One molecule thought to be over-expressed in patients with B-cell chronic lymphocytic leukemia (B-CLL) and in a large fraction of non-Hodgkin lymphoma patients is CD32B (Alizadeh et al., 2000, Nature 403:503-511; Rosenwald et al., 2001, J. Exp. Med. 184:1639-1647; each of which is incorporated herein by reference in its entirety). However, the role of CD32B is B-CLL is unclear since one report demonstrates that CD32B was expressed on a low percentage of B-CLL cells and at a low density (Damle et al., 2002, Blood 99:4087-4093; incorporated herein by reference in its entirety). CD32B is a B cell lineage surface antigen, whose over-expression in B cell neoplasia makes it a suitable target for therapeutic antibodies. In addition, CD32B belongs to the category of inhibitory receptors, whose ligation delivers a negative signal. Therefore, antibodies directed against CD32B could function to eliminate tumor cells by mechanisms that include complement dependent cytotoxicity (CDC), antibody-dependent cellular cytotoxicity (ADCC), but also triggering an apoptotic signal. The high homology of CD32B with its counterpart, CD32A, an activating Fc receptor, has thus far hampered the generation of antibodies that selectively recognize one but not the other form of the molecule.

3.2.1.2 Cancer Therapy

Currently, cancer therapy may involve surgery, chemotherapy, hormonal therapy and/or radiation treatment to eradicate neoplastic cells in a patient (See, for example, Stockdale, 1998, "Principles of Cancer Patient Management", in Scientific American: Medicine, vol. 3, Rubenstein and Federman, eds., Chapter 12, Section IV; each of which is incorporated herein by reference in its entirety). Cancer therapy can also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and, although it can be effective alone, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division (See, for example, Gilman et al., Goodman and Gilman's: The Pharmacological Basis of Therapeutics, Eighth Ed. (Pergamom Press, New York, 1990); incorporated herein by reference in its entirety). These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest. Chemotherapy protocols generally involve administration of a combination of chemotherapeutic agents to increase the efficacy of treatment.

Despite the availability of a variety of chemotherapeutic agents, chemotherapy has many drawbacks (See, for example, Stockdale, 1998, "Principles Of Cancer Patient Management" in Scientific American Medicine, vol. 3, Rubenstein and Federman, eds., ch. 12, sect. 10; incorporated herein by reference in its entirety). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multi-drug resistance. Thus, because of drug resistance, many cancers prove refractory to standard chemotherapeutic treatment protocols.

B cell malignancy is generally treated with single agent chemotherapy, combination chemotherapy and/or radiation therapy. These treatments can reduce morbidity and/or improve survival, albeit they carry significant side effects. The response of B-cell malignancies to various forms of treatment is mixed. For example, in cases in which adequate clinical staging of non-Hodgkin's lymphoma is possible, field radiation therapy can provide satisfactory treatment. Certain patients, however, fail to respond and disease recurrence with resistance to treatment ensues with time, particularly with the most aggressive variants of the disease. About one-half of the patients die from the disease (Devesa et al., 1987, J. Nat'l Cancer Inst. 79:701; incorporated herein by reference in its entirety).

Investigational therapies for the treatment of refractory B cell neoplasia include autologous and allogeneic bone marrow or stem cell transplantation and gene therapies. Recently, immunotherapy using monoclonal antibodies to target B-cell specific antigens has been introduced in the treatment of B cell neoplasia. The use of monoclonal antibodies to direct radionuclides, toxins, or other therapeutic agents offers the possibility that such agents can be delivered selectively to tumor sites, thus limiting toxicity to normal tissues.

There is a significant need for alternative cancer treatments, particularly for treatment of cancer that has proved refractory to standard cancer treatments, such as surgery, radiation therapy, chemotherapy, and hormonal therapy. A promising alternative is immunotherapy, in which cancer cells are specifically targeted by cancer antigen-specific antibodies. Major efforts have been directed at harnessing the specificity of the immune response, for example, hybridoma technology has enabled the development of tumor selective monoclonal antibodies (See Green M. C. et al., 2000 Cancer Treat Rev., 26: 269-286; Weiner L M, 1999 Semin Oncol. 26(suppl. 14):43-51; each of which is incorporated herein by reference in its entirety), and in the past few years, the Food and Drug Administration has approved the first MAbs for cancer therapy: Rituxin (anti-CD20) for non-Hodgkin's Lymphoma, Campath (anti-CD52) for B-cell chronic lymphocytic leukemia (B-CLL) and Herceptin [anti-(c-erb-2/HER-2)] for metastatic breast cancer (Suzanne A. Eccles, 2001, Breast Cancer Res. 3: 86-90; incorporated herein by reference in its entirety). However, the potency of antibody effector function, e.g., to mediate antibody dependent cellular cytotoxicity ("ADCC") is an obstacle to such treatment. Furthermore, with Rituxan and Campath, at least half the patients fail to respond and a fraction of responders may be refractory to subsequent treatments. Methods to improve the efficacy of such treatment are thus needed.

There is a need for alternative therapies for cancer, particularly, B-cell malignancies, especially for patients that are refractory for standard cancer treatments and new immunotherapies such as Rituxan.

3.2.2 Inflammatory Diseases and Autoimmune Diseases

Inflammation is a process by which the body's white blood cells and chemicals protect our bodies from infection by foreign substances, such as bacteria and viruses. It is usually characterized by pain, swelling, warmth and redness of the affected area. Chemicals known as cytokines and prostaglandins control this process, and are released in an ordered and self-limiting cascade into the blood or affected tissues. This release of chemicals increases the blood flow to the area of injury or infection, and may result in the redness and warmth. Some of the chemicals cause a leak of fluid into the tissues, resulting in swelling. This protective process may stimulate nerves and cause pain. These changes, when occurring for a limited period in the relevant area, work to the benefit of the body.

In autoimmune and/or inflammatory disorders, the immune system triggers an inflammatory response when there are no foreign substances to fight and the body's normally protective immune system causes damage to its own tissues by mistakenly attacking itself. There are many different autoimmune disorders that affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress, destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders include, but are not limited to, Hashimoto's thyroiditis, pernicious anemia, Addison's disease, type 1 diabetes, rheumatoid arthritis, systemic lupus erythematosus, dermatomyositis, Sjogren's syndrome, multiple sclerosis, autoimmune inner ear disease, inflammatory bowel disease, arthritis, myasthenia gravis, Reiter's syndrome, Graves disease, autoimmune hepatitis, familial adenomatous polyposis and ulcerative colitis.

Rheumatoid arthritis (RA) and juvenile rheumatoid arthritis are types of inflammatory arthritis. Arthritis is a general term that describes inflammation in joints. Some, but not all, types of arthritis are the result of misdirected inflammation. Besides rheumatoid arthritis, other types of arthritis associated with inflammation include the following: psoriatic arthritis, Reiter's syndrome, ankylosing spondylitis arthritis, and gouty arthritis. Rheumatoid arthritis is a type of chronic arthritis that occurs in joints on both sides of the body (such as both hands, wrists or knees). This symmetry helps distinguish rheumatoid arthritis from other types of arthritis. In addition to affecting the joints, rheumatoid arthritis may occasionally affect the skin, eyes, lungs, heart, blood or nerves.

Rheumatoid arthritis affects about 1% of the world's population and is potentially disabling. There are approximately 2.9 million incidences of rheumatoid arthritis in the United States. Two to three times more women are affected than men. The typical age that rheumatoid arthritis occurs is between 25 and 50. Juvenile rheumatoid arthritis affects 71,000 young Americans (aged eighteen and under), affecting six times as many girls as boys.

Rheumatoid arthritis is an autoimmune disorder where the body's immune system improperly identifies the synovial membranes that secrete the lubricating fluid in the joints as foreign. Inflammation results, and the cartilage and tissues in and around the joints are damaged or destroyed. In severe cases, this inflammation extends to other joint tissues and surrounding cartilage, where it may erode or destroy bone and cartilage and lead to joint deformities. The body replaces damaged tissue with scar tissue, causing the normal spaces within the joints to become narrow and the bones to fuse together. Rheumatoid arthritis creates stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing.

The diagnosis of rheumatoid arthritis is based on a combination of factors, including: the specific location and symmetry of painful joints, the presence of joint stiffness in the morning, the presence of bumps and nodules under the skin (rheumatoid nodules), results of X-ray tests that suggest rheumatoid arthritis, and/or positive results of a blood test called the rheumatoid factor. Many, but not all, people with rheumatoid arthritis have the rheumatoid-factor antibody in their blood. The rheumatoid factor may be present in people who do not have rheumatoid arthritis. Other diseases can also cause the rheumatoid factor to be produced in the blood. That is why the diagnosis of rheumatoid arthritis is based on a combination of several factors and not just the presence of the rheumatoid factor in the blood.

The typical course of the disease is one of persistent but fluctuating joint symptoms, and after about 10 years, 90% of sufferers will show structural damage to bone and cartilage. A small percentage will have a short illness that clears up completely, and another small percentage will have very severe disease with many joint deformities, and occasionally other manifestations of the disease. The inflammatory process causes erosion or destruction of bone and cartilage in the joints. In rheumatoid arthritis, there is an autoimmune cycle of persistent antigen presentation, T-cell stimulation, cytokine secretion, synovial cell activation, and joint destruction. The disease has a major impact on both the individual and society, causing significant pain, impaired function and disability, as well as costing millions of dollars in healthcare expenses and lost wages (see, for example, the NIH website and the NIAID website).

Currently available therapy for arthritis focuses on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. "Second line drugs" include gold, methotrexate and steroids. Although these are well-established treatments for arthritis, very few patients remit on these lines of treatment alone. Recent advances in the understanding of the pathogenesis of rheumatoid arthritis have led to the use of methotrexate in combination with antibodies to cytokines or recombinant soluble receptors. For example, recombinant soluble receptors and monoclonal antibodies for tumor necrosis factor (TNF)-a have been used in combination with methotrexate in the treatment of arthritis. However, only about 50% of the patients treated with a combination of methotrexate and anti-TNF-α agents such as recombinant soluble receptors for TNF-α show clinically significant improvement. Many patients remain refractory despite treatment. Difficult treatment issues still remain for patients with rheumatoid arthritis. Many current treatments have a high incidence of side effects or cannot completely prevent disease progression. So far, no treatment is ideal, and there is no cure. Novel therapeutics are needed that more effectively treat rheumatoid arthritis and other autoimmune disorders.

3.2.3 Allergy

Immune-mediated allergic (hypersensitivity) reactions are classified into four types (I-IV) according to the underlying mechanisms leading to the expression of the allergic symptoms. Type I allergic reactions are characterized by IgE-mediated release of vasoactive substances such as histamine from mast cells and basophils. The release of these substances and the subsequent manifestation of allergic symptoms are initiated by the cross-linking of allergen-bound IgE to its receptor on the surface of mast cells and basophils. In individuals suffering from type I allergic reactions, exposure to an allergen for a second time leads to the production of high levels of IgE antibodies specific for the allergen as a result of the involvement of memory B and T cells in the 3-cell interaction required for IgE production. The high levels of IgE antibodies produced cause an increase in the cross-linking of IgE receptors on mast cells and basophils by allergen-bound IgE, which in turn leads to the activation of these cells and the release of the pharmacological mediators that are responsible for the clinical manifestations of type I allergic diseases.

Two receptors with differing affinities for IgE have been identified and characterized. The high affinity receptor (FcεRI) is expressed on the surface of mast cells and basophils. The low affinity receptor (FcεII/CD23) is expressed on many cell types including B cells, T cells, macrophages, eosinophils and Langerhan cells. The high affinity IgE receptor consists of three subunits (alpha, beta and gamma chains). Several studies demonstrate that only the alpha chain is involved in the binding of IgE, whereas the beta and gamma chains (which are either transmembrane or cytoplasmic proteins) are required for signal transduction events. The identification of IgE structures required for IgE to bind to the FcεRI on mast cells and basophils is of utmost importance in devising strategies for treatment or prevention of IgE-mediated allergies. For example, the elucidation of the IgE receptor-binding site could lead to the identification of peptides or small molecules that block the binding of IgE to receptor-bearing cells in vivo.

Currently, IgE-mediated allergic reactions are treated with drugs such as antihistamines and corticosteroids which attempt to alleviate the symptoms associated with allergic reactions by counteracting the effects of the vasoactive substances released from mast cells and basophils. High doses of antihistamines and corticosteroids have deleterious side effects (e.g., central nervous system disturbance, constipation, etc). Thus, other methods for treating type I allergic reactions are needed.

One approach to the treatment of type I allergic disorders has been the production of monoclonal antibodies which react with soluble (free) IgE in serum, block IgE from binding to its receptor on mast cells and basophils, and do not bind to receptor-bound IgE (i.e., they are non-anaphylactogenic). Two such monoclonal antibodies are in advanced stages of clinical development for treatment of IgE-mediated allergic reactions (see, e.g., Chang, T. W., 2000, Nat. Biotech. 18:157-162; incorporated herein by reference in its entirety).

One of the most promising treatments for IgE-mediated allergic reactions is the active immunization against appropriate non-anaphylactogenic epitopes on endogenous IgE. Stanworth et al. (U.S. Pat. No. 5,601,821; incorporated herein by reference in its entirety) described a strategy involving the use of a peptide derived from the CεH4 domain of the human IgE coupled to a heterologous carrier protein as an allergy vaccine. However, this peptide has been shown not to induce the production of antibodies that react with native soluble IgE. Further, Hellman (U.S. Pat. No. 5,653,980) proposed anti-IgE vaccine compositions based on fusion of full length CεH2-CεH3 domains (approximately 220 amino acid long) to a foreign carrier protein. However, the antibodies induced by the anti-IgE vaccine compositions proposed in Hellman will most likely it result in anaphylaxis since antibodies against some portions of the CεH2 and CεH3 domains of the IgE molecule have been shown to cross-link the IgE receptor on the surface of mast cell and basophils and lead to production of mediators of anaphylaxis (See, e.g., Stadler et al., 1993, Int. Arch. Allergy and Immunology 102:121-126; incorporated herein by reference in its entirety). Therefore, a need remains for treatment of IgE-mediated allergic reactions which do not induce anaphylactic antibodies.

The significant concern over induction of anaphylaxis has resulted in the development of another approach to the treatment of type I allergic disorders consisting of mimotopes that could induce the production of anti-IgE polyclonal antibodies when administered to animals (See, e.g., Rudolf, et al., 1998, Journal of Immunology 160:3315-3321; incorporated herein by reference in its entirety). Kricek et al. (International Publication No. WO 97/31948; incorporated herein by reference in its entirety) screened phage-displayed peptide libraries with the monoclonal antibody BSW17 to identify peptide mimotopes that could mimic the conformation of the IgE receptor binding. These mimotopes could presumably be used to induce polyclonal antibodies that react with free native IgE, but not with receptor-bound IgE as well as block IgE from binding to its receptor. Kriek et al. disclosed peptide mimotopes that are not homologous to any part of the IgE molecule and are thus different from peptides disclosed in the present invention.

As evidenced by a survey of the art, there remains a need for enhancing the therapeutic efficacy of current methods of treating or preventing disorders such as cancer, autoimmune disease, inflammatory disorder, or allergy. In particular, there is a need for enhancing the effector function, particularly, the cytotoxic effect of therapeutic antibodies used in treatment of cancer. The current state of the art is also lacking in treating or preventing allergy disorders (e.g., either by antibody therapy or vaccine therapy).

4. SUMMARY OF THE INVENTION

The instant invention provides humanized FcγRIIB antibodies, an isolated antibody or a fragment thereof that specifically binds FcγRIIB, particularly human FcγRIIB, more particularly native human FcγRIIB, with a greater affinity than said antibody or a fragment thereof binds FcγRIIA, particularly human FcγRIIA, more particularly native human FcγRIIA. As used herein, "native FcγRIIB or FcγRIIA" means FcγRIIB or FcγRIIA which is endogenously expressed in a cell and is present on the cell surface of that cell or recombinantly expressed in a mammalian cell and present on the cell surface, but is not FcγRIIB or FcγRIIA expressed in a bacterial cell or denatured, isolated FcγRIIB or FcγRIIA. The instant invention encompasses humanized antibodies, and antigen binding fragments thereof, derived from antibodies that bind FcγRIIB, particularly human FcγRIIB, more particularly native human FcεRIIB, with a greater affinity than said antibody or a fragment thereof binds FcγRIIA, particularly human FcγRIIA, more particularly native human FcγRIIA. In most preferred embodiments, the instant invention relates to humanized 2B6 or 3H7 antibodies or fragments thereof, preferably antigen binding fragments thereof. In another preferred embodiments, the invention relates to humanized 1D5, 2E1, 2H9, 2D11, or 1F2 antibodies and fragments thereof, preferably antigen binding fragments thereof.

Preferably the humanized antibodies of the invention bind the extracellular domain of native human FcγRIIB. The humanized anti-FcγRIIB antibodies of the invention may have a heavy chain variable region comprising the amino acid sequence of a CDR1 (e.g., SEQ ID NO:1, SEQ ID NO:29, an amino acid sequence corresponding to amino acids 31-35 as set forth in SEQ ID NO:60, or an amino acid sequence corresponding to amino acids 31-35 as set forth in SEQ ID NO:68) and/or a CDR2 (e.g., SEQ ID NO:2, SEQ ID NO:30, an amino acid sequence corresponding to amino acids 50-66 as set forth in SEQ ID NO:60, or an amino acid sequence corresponding to amino acids 50-66 as set forth in SEQ ID NO:68) and/or a CDR3 (e.g., SEQ ID NO:3, SEQ ID NO:31, an amino acid sequence corresponding to amino acids 99-110 as set forth in SEQ ID NO:60, or an amino acid sequence corresponding to amino acids 99-110 as set forth in SEQ ID NO:68) and/or a light chain variable region comprising the amino acid sequence of a CDR1 (e.g., SEQ ID NO:8, SEQ ID NO:38, or an amino acid sequence corresponding to amino acids 24-34 as set forth in SEQ ID NO:62) and/or a CDR2 (e.g., SEQ ID NO:9, SEQ ID NO:10, SEQ ID NO:11, SEQ ID NO:39, or an amino acid sequence corresponding to amino acids 50-56 as set forth in SEQ ID NO:62) and/or a CDR3 (e.g., SEQ ID NO:12, SEQ ID NO:40, or an amino acid sequence corresponding to amino acids 89-97 as set forth in SEQ ID NO:62).

In other embodiments, the humanized antibodies of the invention comprise a light chain variable region comprising the amino acid sequence of SEQ ID NO. 18, SEQ ID NO:20, SEQ ID NO:22, SEQ ID NO:46, or SEQ ID NO:62, and/or a heavy chain variable region comprising the amino acid sequence of SEQ ID NO:24, SEQ ID NO:37, SEQ ID NO:60, or SEQ ID NO:68 and/or amino acid sequence variants thereof. In a preferred embodiment, the humanized antibodies of the invention comprise a light chain variable region comprising the amino the amino acid sequence of SEQ ID NO:62 and a heavy chain variable region comprising the amino acid sequence of SEQ ID NO:68.

In particular, the invention provides a humanized antibody that immunospecifically binds to extracellular domain of native human FcγRIIB, said antibody comprising (or alternatively, consisting of) a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR2, a VH CDR3 and a VL CDR1; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR1, a VH CDR3, a VL CDR2, and a VL CDR3; a VH CDR2, a VH CDR3, a VL CDR1, a VL CDR2, and a VL CDR3; a VH CDR2, a VH CDR3, a VL CDR1, a VL CDR2, and a VL CDR3; a VH CDR2, a VH CDR3, a VL CDR1, a VL CDR2, and a VL CDR3; a VH CDR1, a VH CDR2, a VH CDR3, a VL CDR1, a VL CDR2, and a VL CDR3; or any combination thereof of the VH CDRs and VL CDRs disclosed herein.

In one specific embodiment, the invention provides a humanized 2B6 antibody, wherein a VH region consists of the FR segments from the human germline VH segment VH1-18 and JH6, and the CDR regions of the 2B6 VH, having the amino acid sequence of SEQ ID NO. 24. In another embodiment, the invention provides a humanized 2B6 antibody wherein a VH region comprises the amino acid sequence SEQ ID NO:60. In yet other embodiments, the invention provides a humanized 2B6 antibody wherein a VH region comprises the amino acid sequence SEQ ID NO:68. In another specific embodiment, the invention provided a humanized 2B6 antibody wherein a VL region consists of the FR segments of the human germline VL segment VK-A26 and JK4 and the CDR regions of 2B6 VL, having an amino acid sequence of SEQ ID NO. 18, SEQ ID NO. 20, or SEQ ID NO. 22. In other embodiments, the invention provides a humanized 2B6 antibody wherein the VL region comprises the amino acid sequence SEQ ID NO:62.

In one specific embodiment, the invention provides a humanized 3H7 antibody, wherein a VH region consists of the FR segments from a human germline VH segment, and the CDR regions of 3H7 VH, having the amino acid sequence of SEQ ID NO:37. In another specific embodiment, the humanized 3H7 antibody further comprises a VL region, which consists of the FR segments of the human germline VL segment, and the CDR regions of 3H7 VL, having an amino acid sequence of SEQ ID NO:46.

The present invention provides humanized antibody molecules specific for FcγRIIB in which one or more regions of one or more CDRs of the heavy and/or light chain variable regions of a human antibody (the recipient antibody) have been substituted by analogous parts of one or more CDRs of a donor monoclonal antibody which specifically binds FcγRIIB with a greater affinity than FcγRIIA, e.g., of the monoclonal antibody produced by clone 2B6 or 3H7 that bind FcγRIIB, having ATCC accession numbers PTA-4591 and PTA-4592, respectively, or a monoclonal antibody produced by clone 1D5, 2E1, 2H9, 2D11 or 1F2, having ATCC Accession numbers, PTA-5958, PTA-5961, PTA-5962, PTA-5960, and PTA-5959, respectively. In a most preferred embodiment, the humanized antibody can specifically bind to the same epitope as the donor murine antibody. It will be appreciated by one skilled in the art that the invention encompasses CDR grafting of antibodies in general. Thus, the donor and acceptor antibodies may be derived from animals of the same species and even same antibody class or sub-class. More usually, however, the donor and acceptor antibodies are derived from animals of different species. Typically the donor antibody is a non-human antibody, such as a rodent MAb, and the acceptor antibody is a human antibody.

In some embodiments, at least one CDR from the donor antibody is grafted onto the human antibody. In other embodiments, at least two and preferably all three CDRs of each of the heavy and/or light chain variable regions are grafted onto the human antibody. The CDRs may comprise the Kabat CDRs, the structural loop CDRs ("Chothia CDRs") or a combination thereof. In some embodiments, the invention encompasses a humanized FcγRIIB antibody comprising at least one CDR grafted heavy chain and at least one CDR-grafted light chain.

In a preferred embodiment, the CDR regions of the humanized FcγRIIB specific antibody are derived from a murine antibody against FcγRIIB. In some embodiments, the humanized antibodies described herein comprise alterations, including, but not limited to, amino acid deletions, insertions, and modifications, of the acceptor antibody, i.e., human, heavy and/or light chain variable domain framework regions that are necessary for retaining an/or altering and/or improving binding specificity of the donor monoclonal antibody. Such modifications may modify the amino acid sequence of the framework region to correspond to the framework region of the donor, e.g. murine, antibody. In certain embodiments, the invention encompasses a humanized antibody having phenylalanine at amino acid number 21 of the light chain variable domain framework region 1 (e.g., corresponding to amino acid number 21 of SEQ ID NO:62). In other embodiments, the invention encompasses a humanized antibody having one or more of an isoleucine at amino acid number 13 of the heavy chain variable domain framework region 2 (e.g., corresponding to amino acid number 48 of SEQ ID NO:60), a valine at amino acid number 6 of the heavy chain variable domain framework region 3 (e.g., corresponding to amino acid number 72 of SEQ ID NO:60), a valine at amino acid number 7 of the heavy chain variable domain framework region 3 (e.g., corresponding to amino acid number 73 of SEQ ID NO:60), a valine at amino acid number 8 of the heavy chain variable domain framework region 3 (e.g., corresponding to amino acid number 74 of SEQ ID NO:60), or any combination thereof. In still other embodiments, the invention encompasses a humanized antibody having one or more of an isoleucine at amino acid number 13 of the heavy chain variable domain framework region 2 (e.g., corresponding to amino acid number 48 of SEQ ID NO:68), a valine at amino acid number 6 of the heavy chain variable domain framework region 3 (e.g., corresponding to amino acid number 72 of SEQ ID NO:68), an aspartic acid at amino acid number 7 of the heavy chain variable domain framework region 3 (e.g., corresponding to amino acid number 73 of SEQ ID NO:68), a threonine at amino acid number 8 of the heavy chain variable domain framework region 3 (e.g., corresponding to amino acid number 74 of SEQ ID NO:68), or any combination thereof. In certain embodiments, the invention encompasses humanized antibodies comprising at least one amino acid modification (e.g., insertion, deletion, substitution) in one or more of the light chain variable domain framework regions. In certain embodiments, the invention encompasses a humanized antibody comprising a modification at amino acid 21 of the light chain variable domain framework region 1 (e.g., corresponding to amino acid number 21 in SEQ ID NO:62), which modification is preferably a substitution with phenylalanine. In other embodiments, the invention encompasses humanized antibodies comprising at least one amino acid modification (e.g., insertion, deletion, substitution) in one or more of the heavy chain variable domain framework regions. In certain embodiments, the invention encompasses a humanized antibody comprising a modification at amino acid 13 of the heavy chain variable domain framework region 2, which modification is preferably a substitution with isoleucine (e.g., corresponding to amino acid number 48 in SEQ ID NO:68), and/or a modification at amino acid 6 of the heavy chain variable domain framework region 3, which modification is preferably a substitution with valine (e.g., corresponding to amino acid number 72 in SEQ ID NO:68), and/or a modification at amino acid 7 of the heavy chain variable domain framework region 3, which modification is preferably a substitution with aspartic acid (e.g., corresponding to amino acid number 73 in SEQ ID NO:68), and/or a modification at amino acid 8 of the heavy chain variable domain framework region 3, which modification is preferably a substitution with threonine (e.g., corresponding to amino acid number 74 in SEQ ID NO:68). In another specific example in accordance with this embodiment, the invention encompasses a humanized antibody comprising a modification at amino acid 13 of the heavy chain variable domain framework region 2, which modification is preferably a substitution with isoleucine (e.g., corresponding to amino acid number 48 in SEQ ID NO:60), and/or a modification at amino acid 6 of the heavy chain variable domain framework region 3, which modification is preferably a substitution with valine (e.g., corresponding to amino acid number 72 in SEQ ID NO:60), and/or a modification at amino acid 7 of the heavy chain variable domain framework region 3, which modification is preferably a substitution with valine (e.g., corresponding to amino acid number 73 in SEQ ID NO:60), and/or a modification at amino acid 8 of the heavy chain variable domain framework region 3, which modification is preferably a substitution with valine (e.g., corresponding to amino acid number 74 in SEQ ID NO:60). Non-limiting examples of humanized 2B6 heavy chain and light chain variable domains amino acid sequences are set forth in FIG. 2A and FIG. 2B, respectively. The invention further encompasses any combination of the foregoing amino acid modifications the heavy and or light chain variable domain framework regions. In some embodiments, the framework regions of the humanized antibodies described herein do not necessarily consist of the precise amino acid sequence of the framework region of a natural occurring human antibody variable region, but contain various alterations, including, but not limited to, amino acid deletions, insertions, modifications that alter the property of the humanized antibody, for example, improve the binding properties of a humanized antibody region that is specific for the same target as the murine FcγRIIB specific antibody. In most preferred embodiments, a minimal number of alterations are made to the framework region in order to avoid large-scale introductions of non-human framework residues and to ensure minimal immunogenicity of the humanized antibody in humans. In some embodiments, the framework residues are derived from the human germline VH segment VH1-18 and JH6 and/or the human germline VL segment VK-A26 and JK4. In certain embodiments of the invention, there are no alterations made to the framework regions. In specific embodiments, the donor monoclonal antibody of the present invention is a monoclonal antibody produced by clone 2B6 or 3H7 which binds FcγRIIB, having ATCC accession number PTA-4591 and PTA-4592, respectively, or a monoclonal antibody produced by clone 1D5, 2E1, 2H9, 2D11 or 1F2 having ATCC Accession number PTA-5958, PTA-5961, PTA-5962, PTA-5960 and PTA-5959, respectively.

The humanized antibodies of the present invention include complete antibody molecules having full length heavy and light chains, or any fragment thereof, such as the Fab or (Fab')$_2$ fragments, a heavy chain and light chain dimer, or any minimal fragment thereof such as an Fv, an SCA (single chain antibody), and the like that exhibits immunospecific binding for the FcγRIIB.

In certain embodiments, the Fc region comprises at least one amino acid modification relative to a wild-type Fc region, such that the modified Fc region has an altered binding affinity to a Fc receptor. In a specific embodiment, the amino acid modification of the Fc regions of the humanized antibodies of the invention relative to a wild-type Fc region comprise a substitution at position 243, 292, 300, 305 and 396. In a certain embodiment, the amino acid modification of the Fc regions of the humanized antibodies of the invention relative to a wild-type Fc region comprise a substitution at position 243 with leucine, at position 292 with proline, at position 300 with leucine, at position 305 with isoleucine and at position 396 with leucine. In other embodiments, the Fc domain of the antibody or fragment thereof has an increased binding affinity to FcγRIIB and/or FcγRIII relative to that of the wild-type antibody.

In a specific embodiment, the Fc region of the humanized antibody of the invention comprises a leucine at position 243, a proline at position 292, a leucine at position 300, an isoleucine at position 305 and a leucine at position 396.

In a specific embodiment, a humanized 2B6 antibody of the invention comprises a heavy chain having the amino acid sequence SEQ ID NO:64. In another specific embodiment, a humanized 2B6 antibody of the invention comprises a heavy chain having the amino acid sequence SEQ ID NO:70. In still other embodiments, the humanized 2B6 antibody comprises a light chain having the amino acid sequence SEQ ID NO:66. In a preferred embodiment, a humanized 2B6 antibody of the invention comprises a heavy chain containing the amino acid sequence SEQ ID NO:70 and a light chain containing the sequence SEQ ID NO:66. In a specific aspect of the invention, plasmid pMGxO675 comprises the nucleotide sequences SEQ ID NO:69 and SEQ ID NO:65 that encode the heavy chain amino acid sequence SEQ ID NO:70 and the light chain amino acid sequence SEQ ID NO:66, respectively. Plasmid pMGxO675 been deposited with the American Type Culture Collection (10801 University Blvd., Manassas, Va. 20110-2209) on May 23, 2006 under the provisions of the Budapest Treaty on the International Recognition of the Deposit of Microorganisms for the Purposes of Patent Procedures, and assigned accession number PTA-7609, and is incorporated herein by reference.

In a particular embodiment, the invention relates to an isolated antibody or a fragment thereof that specifically binds FcγRIIB via the variable domain with a greater affinity than said antibody or a fragment thereof binds FcγRIIA, and the constant domain of said antibody further has an enhanced affinity for at least one or more Fc activation receptors relative to an isotype control antibody. In yet another specific embodiment, said Fc activation receptor is FcγRIIIA or FcγRIIA.

The invention encompasses methods for the production of antibodies of the invention or fragments thereof, particularly for the production of humanized anti-FcγRIIB specific antibodies, such that the FcγRIIB specific antibodies have an enhanced specificity for FcγRIIB relative to FcγRIIA. The invention encompasses any method known in the art useful for the production of polypeptides, e.g., in vitro synthesis, recombinant DNA production, and the like. Preferably, the humanized antibodies are produced by recombinant DNA technology. The humanized FcγRIIB specific antibodies of the invention may be produced using recombinant immunoglobulin expression technology. Exemplary methods for the production of recombinant humanized antibodies of the invention may comprise the following: a) constructing, by conventional molecular biology methods, an expression vector comprising an operon that encodes an antibody heavy chain in which the CDRs and a minimal portion of the variable region framework that are required to retain donor antibody binding specificity are derived from a non-human immunoglobulin, such as the murine FcγRIIB specific monoclonal antibody, e.g., the monoclonal antibody produced by clone 2B6 or 3H7 which binds FcγRIIB, having ATCC accession numbers PTA-4591 and PTA-4592, respectively, or the monoclonal antibody produced by clone 1D5, 2E1, 2H9, 2D11 or 1F2 having ATCC Accession number PTA-5958, PTA-5961, PTA-5962, PTA-5960 and PTA-5959, respectively, and the remainder of the antibody is derived from a human immunoglobulin, thereby producing a vector for the expression of a humanized antibody heavy chain, e.g., the plasmid pMGx0675 comprising nucleic acid sequence SEQ ID NO:69 encoding the amino acid sequence SEQ ID NO:70, said plasmid having the ATCC Accession number PTA-7609, deposited May 23, 2006; b) constructing, by conventional molecular biology methods, an expression vector comprising an operon that encodes an antibody light chain in which the CDRs and a minimal portion of the variable region framework that are required to retain donor antibody binding specificity are derived from a non-human immunoglobulin, such as the murine FcγRIIB monoclonal antibody, e.g., the monoclonal antibody produced by clone 2B6 or 3H7 which binds FcγRIIB, having ATCC accession numbers PTA-4591 and PTA-4592, respectively, or the monoclonal antibody produced by clone 1D5, 2E1, 2H9, 2D11 or 1F2 having ATCC Accession number PTA-5958, PTA-5961, PTA-5962, PTA-5960 and PTA-5959, respectively, and the remainder of the antibody is derived from a human immunoglobulin, thereby producing a vector for the expression of humanized antibody light chain, e.g., the plasmid pMGxO675 comprising nucleic acid sequence SEQ ID NO:65 encoding the amino acid sequence SEQ ID NO:66, said plasmid having the ATCC Accession number PTA-7609, deposited May 23, 2006; c) transferring the expression vectors to a host cell by conventional molecular biology methods to produce a transfected host cell for the expression of humanized anti-FcγRIIB antibodies; d) culturing the transfected cell by conventional cell culture techniques so as to produce humanized anti-FcγRIIB antibodies; and e) recovery of the anti-FcγRIIB antibodies from the culture by conventional means. Host cells may be cotransfected with two expression vectors of the invention, the first vector containing an operon encoding a heavy chain derived polypeptide and the second containing an operon encoding a light chain derived polypeptide. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides, e.g., the plasmid pMGxO675, having ATCC Accession number PTA-7609, deposited May 23, 2006, which comprises the nucleic acid sequences SEQ ID NO:69 and SEQ ID NO:65 that encode the amino acid sequences of the heavy chain and light chain of a humanized 2B6 antibody (i.e., SEQ ID NO:70 and SEQ ID NO:66, respectively). The coding sequences for the heavy and light chains may comprise cDNA or genomic DNA or both. The host cell used to express the recombinant antibody of the invention may be either a bacterial cell such as *Escherichia coli*, or, preferably, a eukaryotic cell. Preferably, a mammalian cell such as a Chinese hamster ovary cell or HEK-293 may be used. The choice of expression vector is dependent upon the choice of host cell, and may be selected so as to have the desired expression and regulatory characteristics in the selected host cell. The general methods for construction of the vector of the invention, transfection of cells to produce the host cell of the invention, culture of cells to produce the antibody of the invention are all conventional molecular biology methods. Likewise, once produced, the recombinant antibodies of the invention may be purified by standard procedures of the art, including cross-flow filtration, ammonium sulphate precipitation, affinity column chromatography, gel electrophoresis and the like.

In some embodiments, cell fusion methods for making monoclonal antibodies may be used in the methods of the invention such as those disclosed in U.S. Pat. No. 5,916,771, incorporated herein by reference in its entirety. Briefly, according to this method, DNA encoding the desired heavy chain (or a fragment of the heavy chain) is introduced into a first mammalian host cell, while DNA encoding the desired light chain (or a fragment of the light chain) is introduced into a second mammalian host cell. The first transformed host cell and the second transformed host cell are then combined by cell fusion to form a third cell. Prior to fusion of the first and second cells, the transformed cells may be selected for specifically desired characteristics, e.g., high levels of expression. After fusion, the resulting hybrid cell contains and expresses both the DNA encoding the desired heavy chain and the DNA encoding the desired light chain, resulting in production of the multimeric antibody.

The invention encompasses using the humanized antibodies of the present invention in conjunction with, or attached to, other antibodies or fragments thereof such as human or humanized monoclonal antibodies. These other antibodies may be reactive with other markers (epitopes) characteristic for the disease against which the antibodies of the invention are directed or may have different specificities chosen, for example, to recruit molecules or cells of the human immune system to the diseased cells. The antibodies of the invention (or parts thereof) may be administered with such antibodies (or parts thereof) as separately administered compositions or as a single composition with the two agents linked by conventional chemical or by molecular biological methods. Additionally the diagnostic and therapeutic value of the antibodies of the invention may be augmented by labeling the humanized antibodies with labels that produce a detectable signal (either in vitro or in vivo) or with a label having a therapeutic property. Some labels, e.g., radionuclides may produce a detectable signal and have a therapeutic property. Examples of radionuclide labels include $^{125}$I, $^{131}$I, $^{14}$C. Examples of other detectable labels include a fluorescent chromophore such as fluorescein, phycobiliprotein or tetraethyl rhodamine for fluorescence microscopy; an enzyme which produces a fluorescent or colored product for detection by fluorescence, absorbance, visible color or agglutination, or which produces an electron dense product for demonstration by electron microscopy; or an electron dense molecule such as ferritin, peroxidase or gold beads for direct or indirect electron microscopic visualization. Labels having therapeutic properties include drugs for the treatment of cancer, such as methotrexate and the like.

The methods of the invention also encompass polynucleotides that encode the humanized antibodies of the invention or fragments thereof. In one embodiment, the invention provides an isolated nucleic acid comprising a nucleotide sequence encoding the heavy chain variable domain and/or the light chain variable domain of an antibody of the invention. In a specific embodiment, the invention provides an isolated nucleic acid comprising a nucleotide sequence encoding a heavy chain variable domain having the amino acid sequence SEQ ID NO:60. In accordance with this embodiment, the nucleic acid comprising the nucleotide sequence encoding the heavy chain variable domain, amino acid sequence SEQ ID NO:60, may, for example, comprise the nucleotide sequence SEQ ID NO:59. In another specific embodiment, the invention provides an isolated nucleic acid comprising a nucleotide sequence encoding a heavy chain variable domain having the amino acid sequence SEQ ID NO:68. In accordance with this embodiment, the nucleic acid comprising the nucleotide sequence encoding the heavy chain variable domain, amino acid sequence SEQ ID NO:68, may, for example, comprise the nucleotide sequence SEQ ID NO:67. In still other embodiments, the invention provides an isolated nucleic acid comprising a nucleotide sequence encoding a light chain variable domain having the amino acid sequence SEQ ID NO:62. In accordance with these embodiments, the nucleic acid comprising the nucleotide sequence encoding the light chain variable domain, amino acid sequence SEQ ID NO:62, may, for example, comprise the nucleotide sequence SEQ ID NO:61. In yet other embodiments, the invention provides an isolated nucleic acid comprising a nucleotide sequence encoding a heavy chain or a light chain of an antibody or a fragment thereof that specifically binds FcγRIIB with greater affinity than said antibody or a fragment thereof binds FcγRIIA. In another embodiment, the invention provides an isolated nucleic acid comprising a nucleotide sequence encoding a heavy chain or a light chain of an antibody or a fragment thereof that specifically binds FcγRIIB and blocks the Fc binding domain of FcγRIIB. The invention also relates to a vector comprising said nucleic acid. The invention further provides a vector comprising a first nucleic acid molecule comprising a nucleotide sequence encoding a heavy chain and a second nucleic acid molecule comprising a nucleotide sequence encoding a light chain, said heavy chain and light chain being of an antibody or a fragment thereof that specifically binds FcγRIIB with greater affinity than said antibody or a fragment thereof binds FcγRIIA. In one specific embodiment, said vector is an expression vector. The invention further provides host cells containing the vectors or nucleotide sequences encoding the antibodies of the invention. In specific embodiments, the invention encompasses nucleotide sequences encoding heavy and light chains of the antibodies produced by the deposited hybridoma clones having ATCC accession numbers PTA-4591, PTA-4592, PTA-5958, PTA-5961, PTA-5962, PTA-5960, and PTA-5959, or portions and/or variants/derivatives thereof (e.g., CDRs, variable domains, etc. and humanized versions thereof). In a specific embodiment, the invention provides the nucleotide sequence SEQ ID NO:63, which encodes a h2B6 heavy chain, amino acid sequence SEQ ID NO:64. In another specific embodiment, the invention provides the nucleotide sequence SEQ ID NO:69, which encodes a h2B6 heavy chain, amino acid sequence SEQ ID NO:70. In still another specific embodiment, the invention provides the nucleotide sequence SEQ ID NO:65, which encodes a h2B6 light chain, amino acid sequence SEQ ID NO:66. In preferred embodiments, the invention encompasses nucleotide sequences encoding a heavy chain and/or light chain having the amino acid sequences of SEQ ID NO:70 and SEQ ID NO:66, respectively.

The invention encompasses the use of the humanized antibodies of the invention to detect the presence of FcγRIIB specifically (i.e., FcγRIIB and not FcγRIIA) in a biological sample.

Activating and inhibitory Fc receptors, e.g., FcγRIIA and FcγRIIB, are critical for the balanced function of these receptors and proper cellular immune responses. The invention encompasses the use of the humanized antibodies of the invention for the treatment of any disease related to loss of such balance and regulated control in the Fc receptor signaling pathway. Thus, the humanized FcγRIIB antibodies of the invention have uses in regulating the immune response, e.g., in inhibiting immune response in connection with autoimmune or inflammatory disease, or allergic response. The humanized FcγRIIB antibodies of the invention can also be used to alter certain effector functions to enhance, for example, therapeutic antibody-mediated cytotoxicity.

The humanized antibodies of the invention are useful for prevention or treatment of cancer, for example, in one embodiment, as a single agent therapy. In one embodiment of the invention, the humanized antibodies of the invention are useful for prevention or treatment of B-cell malignancies, particularly non-Hodgkin's lymphoma or chronic lymphocytic leukemia. In particular embodiments, the cancer of the subject is refractory to one or more standard or experimental therapies, particularly, to Rituxan treatment. The methods of the invention may be used for the treatment, management, prevention, or amelioration of B-cell diseases, such as, B-cell chronic lymphocytic leukemia (B-CLL), non-Hodgkin's lymphoma, diffuse large B cell lymphoma, follicular lymphoma with areas of diffuse large B cell lymphoma, small lymphocytic lymphoma, mantle cell lymphoma, and diffuse small cleaved cell lymphoma.

In one embodiment, the invention provides for the use of a humanized FcγRIIB-specific antibody in combination with a standard or experimental treatment regimen for B-cell malignancies (e.g., chemotherapy, radioimmunotherapy, or radiotherapy). Such combination therapy may enhance the efficacy of standard or experimental treatment. Examples of therapeutic agents that are particularly useful in combination with a FcγRIIB-specific antibody or an antigen-binding fragment thereof, for the prevention, treatment, management, or amelioration of B-cell malignancies, include, but are not limited to, Rituxan, interferon-alpha, and anti-cancer agents. Chemotherapeutic agents that can be used in combination with a FcγRIIB-specific antibody or an antigen-binding fragment thereof, include, but are not limited to alkylating agents, antimetabolites, natural products, and hormones. The combination therapies of the invention enable lower dosages of an anti-FcγRIIB antibody or an antigen-binding fragment thereof and/or less frequent administration of anti-FcγRIIB antibody or an antigen-binding fragment thereof to a subject with a B-cell malignancy, to achieve a therapeutic or prophylactic effect.

In another embodiment, the use of a humanized FcγRIIB antibody or an antigen-binding fragment thereof prolongs the survival of a subject diagnosed with a B-cell malignancy.

In a preferred embodiment, the humanized antibodies of the invention are used for the treatment and/or prevention of melanoma. In another embodiment, the humanized antibodies are useful for prevention and/or treatment of cancer, particularly in potentiating the cytotoxic activity of cancer antigen-specific therapeutic antibodies with cytotoxic activity to enhance tumor cell killing and/or enhancing antibody dependent cytotoxic cellular ("ADCC") activity, complement dependent cytotoxic ("CDC") activity, or phagocytosis of the therapeutic antibodies.

The invention provides a method of treating cancer in a patient having a cancer characterized by a cancer antigen, said method comprising administering to said patient a therapeutically effective amount of a first humanized antibody or a fragment thereof that specifically binds FcγRIIB with greater affinity than said antibody or a fragment thereof binds FcγRIIA, and a second antibody that specifically binds said cancer antigen and is cytotoxic. The invention also provides a method of treating cancer in a patient having a cancer characterized by a cancer antigen, said method comprising administering to said patient a therapeutically effective amount of an humanized antibody or a fragment thereof that specifically binds FcγRIIB, particularly native human FcγRIIB, with greater affinity than said antibody or a fragment thereof binds FcγRIIA, preferably native human FcγRIIA, and the constant domain of which further has an increased affinity for one or more Fc activation receptors, when the antibody is monomeric, such as FcγRIIIA, and an antibody that specifically binds said cancer antigen and is cytotoxic. In one particular embodiment, said Fc activation receptor is FcγRIIIA.

In some embodiments, the invention encompasses antibodies comprising variant Fc regions that bind FcRn with an enhanced affinity, resulting in an increased antibody half life, e.g., a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. Although not intending to be bound by a particular mechanism of action the neonatal Fc receptor (FcRn) plays an important role in regulating the serum half-lives of IgG antibodies. A correlation has been established between the pH-dependent binding affinity of IgG antibodies to FcRn and their serum half-lives in mice. The increased half-lives of the antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. For example, antibodies or fragments thereof with increased in vivo half-lives can be generated by modifying (e.g., substituting, deleting or adding) amino acid residues identified as involved in the interaction between the Fc domain and the FcRn receptor. For example, the invention encompasses antibodies comprising variant Fc regions which have at least one or more modification that enhances the affinity to FcRn, e.g., a modification of one or more amino acid residues 251-256, 285-290, 308-314, 385-389, and 428-436, or a modification at positions 250 and 428, see, e.g., Hinton et al., 2004, *J. Biol. Chem.* 279(8): 6213-6; PCT Publication No. WO 97/34631; and WO 02/060919, all of which are incorporated herein by reference in their entirety.

In yet another embodiment, the invention provides a method of regulating immune-complex mediated cell activation in a patient, said method comprising administering to said patient a therapeutically effective amount of an antibody or fragment thereof that specifically binds the extracellular domain of human FcγRIIB and blocks the Fc binding site of human FcγRIIB. In a preferred embodiment, administration of the antibody or fragment thereof results in an enhanced immune response, such as an increase in an antibody-dependent cellular response. In another preferred embodiment, the immune complex mediated cell activation is B cell activation, mast cell activation, dendritic cell activation or macrophage activation.

In another embodiment, the invention provides a method of breaking tolerance to an antigen in a patient, said method comprising administering to a patient in need thereof (1) an antigen-antibody complex comprising said antigen and (2) an antibody or fragment thereof that specifically binds the extracellular domain of human FcγRIIB and blocks the Fc binding site of human FcγRIIB, thereby breaking tolerance in said patient to said antigen. The antibody or fragment thereof can be administered before, concurrently with, or after administration of said antigen-antibody complex.

In another embodiment, the invention provides a method of enhancing an antibody mediated cytotoxic effect in a subject being treated with a cytotoxic antibody, said method comprising administering to said patient a humanized antibody of the invention, or a fragment thereof, in an amount sufficient to enhance the cytotoxic effect of said cytotoxic antibody. In yet another embodiment, the invention provides a method of enhancing an antibody-mediated cytotoxic effect in a subject being treated with a cytotoxic antibody, said method comprising administering to said patient a humanized antibody of the invention, or a fragment thereof, further having an enhanced affinity for an Fc inhibitory receptor, when monomeric, in an amount sufficient to enhance the cytotoxic effect of said cytotoxic antibody. In yet another embodiment, the invention provides a method further comprising the administration of one or more additional cancer therapies.

The invention encompasses the use of the humanized antibodies of the invention in combination with any therapeutic antibody that mediates its therapeutic effect through cell killing to potentiate the antibody's therapeutic activity. In one particular embodiment, the humanized antibodies of the invention potentiate the antibody's therapeutic activity by enhancing antibody-mediated effector function. In another embodiment of the invention, the humanized antibodies of the invention potentiate the cytotoxic antibody's therapeutic activity by enhancing phagocytosis and opsonization of the targeted tumor cells. In yet another embodiment of the invention, the humanized antibodies of the invention potentiate the antibody's therapeutic activity by enhancing antibody-dependent cell-mediated cytotoxicity ("ADCC") in destruction of the targeted tumor cells. In certain embodiments, the antibodies of the invention are used in combination with Fc fusion proteins to enhance ADCC.

Although not intending to be bound by a particular mechanism of action, the combination of a humanized antibody of the invention in combination with a therapeutic antibody has an enhanced therapeutic effect due, in part, to the cytotoxic ability of the FcγRIIB specific humanized antibody to eliminate macrophages expressing the inhibitory Crib receptors. Therefore, there is a higher concentration of cells expressing activating Fig receptors remaining per dose of the therapeutic antibody.

In some embodiments, the invention encompasses use of the humanized antibodies of the invention in combination with a therapeutic antibody that does not mediate its therapeutic effect through cell killing to potentiate the antibody's therapeutic activity. In a specific embodiment, the invention encompasses use of the humanized antibodies of the invention in combination with a therapeutic apoptosis inducing antibody with agonistic activity, e.g., anti-Fas antibody. Therapeutic apoptosis inducing antibodies may be specific for any death receptor known in the art for the modulation of apoptotic pathway, e.g., TNFR receptor family member or a TRAIL family member.

The invention encompasses using the humanized antibodies of the invention to block macrophage mediated tumor cell progression and metastasis. The humanized antibodies of the invention are particularly useful in the treatment of solid tumors, where macrophage infiltration occurs. The antagonistic humanized antibodies of the invention are particularly useful for controlling, e.g., reducing or eliminating, tumor cell metastasis, by reducing or eliminating the population of macrophages that are localized at the tumor site. The invention further encompasses humanized antibodies that effectively deplete or eliminate immune effector cells other than macrophages that express FcγRIIB, e.g., dendritic cells. Effective depletion or elimination of immune effector cells using the antibodies of the invention may range from a reduction in population of the effector cells by 50%, 60%, 70%, 80%, preferably 90%, and most preferably 99%.

In some embodiments, the invention encompasses use of the humanized antibodies of the invention in combination with therapeutic antibodies that immunospecifically bind to tumor antigens that are not expressed on the tumor cells themselves, but rather on the surrounding reactive and tumor supporting, non-malignant cells comprising the tumor stroma. In a preferred embodiment, a humanized antibody of the invention is used in combination with an antibody that immunospecifically binds a tumor antigen on a fibroblast cell, e.g., fibroblast activation protein (FAP).

The invention provides a method of treating an autoimmune disorder in a patient in need thereof, said method comprising administering to said patient a therapeutically effective amount of one or more humanized antibodies of the invention. The invention also provides a method of treating an autoimmune disorder in a patient in need thereof, said method further comprising administering to said patient a therapeutically effective amount of one or more anti-inflammatory agents, and/or one or more immunomodulatory agents. The invention provides methods of treating or ameliorating the symptoms of autoimmune diseases including, but not limited to, Type I Diabetes, psoriasis, rheumatoid arthritis, lupus (particularly, cutaneous), inflammatory bowel disease (IBD), Crohn's disease, ulcerative colitis, multiple sclerosis. In certain embodiments, the he methods of the invention are for use in subjects with early stage disease to slow or reduce the damage from the autoimmunity and maintain a high level of function and/or reduce the need for or prevent an increase in the level of other therapy, e.g., administrations of an immunosuppressants or an anti-inflammatory.

The invention also provides a method of treating an inflammatory disorder in a patient in need thereof, said method comprising administering to said patient a therapeutically effective amount of one or more humanized antibodies of the invention. The invention also provides a method of treating an inflammatory disorder in a patient in need thereof, said method further comprising administering to said patient a therapeutically effective amount of one or more anti-inflammatory agents, and/or one or more immunomodulatory agents.

The invention provides a method of enhancing an immune response to a vaccine composition in a subject, said method comprising administering to said subject a humanized antibody or an antigen-binding fragment thereof that specifically binds FcγRIIB with greater affinity than said antibody or a fragment thereof binds FcγRIIA, and a vaccine composition, such that said antibody or a fragment thereof is administered in an amount effective to enhance the immune response to said vaccine composition in said subject. The humanized antibodies of the invention may be used to enhance a humoral and/or cell mediated response against the antigen(s) of the vaccine composition. The antibodies of the invention may be used in combination with any vaccines known in the art. The invention encompasses the use of the humanized antibodies of the invention to either prevent or treat a particular disorder, where an enhanced immune response against a particular antigen or antigens is effective to treat or prevent the disease or disorder.

The invention also provides a method for enhancing immune therapy for an infectious agent wherein the humanized antibodies of the invention are administered to a patient that is already infected by a pathogen, such as HIV, HCV or HSV, to enhance opsonization and phagocytosis of infected cells. In yet other embodiments, the invention encompasses method for treating sepsis or septic shock using the humanized antibodies of the invention. The role of FcγRIIB in sepsis has been described in Clatworthy et al., 2004, J Exp Med 199:717-723; incorporated herein by reference in its entirety.

The invention provides a method of treating diseases with impaired apoptotic mediated signaling, e.g., cancer, autoimmune disease In a specific embodiment, the invention encompasses a method of treating a disease with deficient Fas-mediated apoptosis, said method comprising administering a humanized antibody of the invention in combination with an anti-Fas antibody.

The invention further provides a method for treating or preventing an IgE-mediated allergic disorder in a patient in need thereof, comprising administering to said patient a therapeutically effective amount of the humanized agonistic antibodies of the invention. The invention also provides a method for treating or preventing an IgE-mediated allergic disorder in a patient in need thereof, comprising administering to said patient the humanized antibodies of the invention in combination with other therapeutic antibodies or vaccine compositions used for the treatment or prevention of IgE-mediated allergic disorders.

In another embodiment, the invention provides for the use of a FcγRIIB-specific antibody conjugated to a therapeutic agent or drug. Examples of therapeutic agents which may be conjugated to an anti-FcγRIIB antibody or an antigen-binding fragment thereof include, but are not limited to, cytokines, toxins, radioactive elements, and antimetabolites.

In another embodiment, the invention provides a method of diagnosis of an autoimmune disease in a subject comprising: (i) contacting a biological sample from said subject with an effective amount of a humanized antibody of the invention; and (ii) detecting binding of said humanized antibody or a fragment thereof, wherein detection of said detectable marker above a background or standard level indicates that said subject has an autoimmune disease.

The invention further provides a pharmaceutical composition comprising (i) a therapeutically effective amount of a humanized antibody or a fragment thereof that specifically binds FcγRIIB with greater affinity than said antibody or a fragment thereof binds FcγRIIA; and (ii) a pharmaceutically acceptable carrier. The invention additionally provides a pharmaceutical composition comprising (i) a therapeutically effective amount of a humanized antibody or a fragment thereof that specifically binds FcγRIIB with greater affinity than said antibody or a fragment thereof binds FcγRIIA; (ii) a cytotoxic antibody that specifically binds a cancer antigen; and (iii) a pharmaceutically acceptable carrier. In a specific embodiment, the antibody or fragment thereof specifically binds the extracellular domain of human FcγRIIB, blocks the Fc binding site of human FcγRIIB, and also blocks crosslinking of FcγRIIB to a Fc receptor. In a specific embodiment, Fc region of the antibody of the invention comprises one or more of an alanine at position 265, a glutamine at position 297, leucine at position 243, a proline at position 292, a leucine at position 300, an isoleucine at position 305, or a leucine at position 396. the In yet another embodiment, the antibody or fragment thereof that specifically binds the extracellular domain of human FcγRIIB and blocks the Fc binding site of human FcγRIIB comprises a Fc region comprising at least one amino acid modification relative to a wild-type Fc region, such that the modified Fc region has an altered binding affinity to a Fc receptor. In a specific embodiment, the amino acid modification comprises a substitution at position 265 or 297, preferably a substitution at position 265 with alanine or a substitution at position 297 with glutamine. In another embodiment, the amino acid modification comprises a substitution at position 243, 292, 300, 305 and 396, preferably a substitution at 243 with leucine, a substitution at position 292 with proline, a substitution at position 300 with leucine, a substitution at position 305 with isoleucine, and a substitution at position 396 with leucine.

The invention also provides combination therapy methods. The methods of the invention can be carried out in combination with any standard treatment for the particular indication, e.g., in the case of treatment of cancer, standard chemotherapy and/or anti-angiogenic agents and, in the case of the treatment of an autoimmune disorder, standard immunosuppressant and/or anti-inflammatory treatments. The antibodies and/or compositions of the invention may be administered with other therapies such as anti-inflammatory agents, steroidal therapies (for example, but not limited to, glucocorticoids, dexamethasone, cortisone, hydrocortisone, prednisone, prednisolone, triamcinolone, azulfidine, etc.), non-steroidal anti-inflammatories (NSAIDS) (for example, but not limited to, COX-2 inhibitors, aspirin, ibuprofen, diclofenac, etodolac, fenoprofen, indomethacin, ketolorac, oxaprozin, nabumetone, sulindac, tolmentin, naproxen, ketoprofen, etc.), beta-agonists, anti-cholinergic agents, immunomodulatory agents (for example, but not limited to, T cell receptor modulators, cytokine receptor modulators, T cell depleting agents, cytokine antagonists, monokine agonists, lymphokine inhibitors, etc.), immunosuppressants (such as, but not limited to, methotrexate or cyclosporin), anti-angiogenic agents (e.g., angiostatin and TNF-.alpha. antagonists and/or inhibitors (for example, but not limited to, etanercept and infliximab)), dapsone and psoralens. In certain embodiments of the invention, subjects which have become refractory to conventional treatments are treated using methods of the invention.

In certain embodiments of the invention, pharmaceutical compositions are provided for use in accordance with the methods of the invention, said pharmaceutical compositions comprising a humanized FcγRIIB antibody or an antigen-binding fragment thereof, in an amount effective to prevent, treat, manage, or ameliorate a B-cell malignancy, or one or more symptoms thereof, and a pharmaceutically acceptable carrier. The invention also provides pharmaceutical compositions for use in accordance with the methods of the invention, said pharmaceutical compositions comprising a humanized FcγRIIB antibody or an antigen-binding fragment thereof, a prophylactic or therapeutic agent other than a FcγRIIB antagonist, and a pharmaceutically acceptable carrier.

The antibodies and/or compositions of the invention may be administered parenterally, for example, intravenously, intramuscularly or subcutaneously, or, alternatively, may be administered orally. The antibodies and/or compostions of the invention may also be administered as a sustained release formulation.

4.1 Definitions

As used herein, the term "specifically binds to FcγRIIB" and analogous terms refer to antibodies or fragments thereof (or any other FcγRIIB binding molecules) that specifically bind to FcγRIIB or a fragment thereof and do not specifically bind to other Fc receptors, in particular to FcγRIIA. Further it is understood to one skilled in the art, that an antibody that specifically binds to FcγRIIB, may bind through the variable domain or the constant domain of the antibody. If the antibody that specifically binds to FcγRIIB binds through its variable domain, it is understood to one skilled in the art that it is not aggregated, i.e., is monomeric. An antibody that specifically binds to FcγRIIB may bind to other peptides or polypeptides with lower affinity as determined by, e.g., immunoassays, BIAcore, or other assays known in the art. Preferably, antibodies or fragments that specifically bind to FcγRIIB or a fragment thereof do not cross-react with other antigens. Antibodies or fragments that specifically bind to FcγRIIB can be identified, for example, by immunoassays, BIAcore, or other techniques known to those of skill in the art. An antibody or a fragment thereof binds specifically to a FcγRIIB when it binds to FcγRIIB with higher affinity than to any cross-reactive antigen as determined using experimental techniques, such as western blots, radioimmunoassays (RIA) and enzyme-linked immunosorbent assays (ELISAs). See, e.g., Paul, ed., 1989, Fundamental Immunology Second Edition, Raven Press, New York at pages 332-336 for a discussion regarding antibody specificity (incorporated herein by reference in its entirety).

As used herein, the term "native FcγRIIB" refers to FcγRIIB which is endogenously expressed and present on the surface of a cell. In some embodiments, "native FcγRIIB" encompasses a protein that is recombinantly expressed in a mammalian cell. Preferably, the native FcγRIIB is not expressed in a bacterial cell, i.e., $E.\ coli$. Most preferably the native FcγRIIB is not denatured, i.e., it is in its biologically active conformation.

As used herein, the term "endogenous" in the context of a cellular protein refers to protein naturally occurring and/or expressed by the cell in the absence of recombinant manipulation; accordingly, the terms "endogenously expressed protein" or "endogenous protein" excludes cellular proteins expressed by means of recombinant technology.

As used herein, the terms "antibody" and "antibodies" refer to monoclonal antibodies, multispecific antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies (including, e.g., anti-Id and anti-anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

Unless otherwise indicated, when referring to antibodies (as broadly defined herein), reference to antibody domains and/or amino acid positions within antibodies, or fragments thereof, is in accordance with the definition and assignment of amino acids to each domain in Kabat et al, SEQUENCES OF PROTEINS OF IMMUNOLOGICAL INTEREST, $5^{th}$ Ed. Public Health Service (National Institutes of Health, Bethesda, Md., 1987 and 1991); incorporated herein by reference in its entirety. Amino acids from the variable regions of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid. Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain. Thus, as used herein in the context of humanized antibodies, a reference such as "at position 297 of the Fc region" refers to the amino acid position in an immunoglobulin chain, region of an a immunoglobulin chain, or region of a polypeptide derived from an immunoglobulin chain, that corresponds to position 297 of the corresponding human immunoglobulin.

As used herein, the terms "B-cell malignancies" and "B-cell malignancy" refer to any B-cell lymphoproliferative disorder. B-cell malignancies include tumors of B-cell origin. B-cell malignancies include, but are not limited to, lymphomas, chronic lymphocytic leukemias, acute lymphoblastic leukemias, multiple myeloma, Hodgkin's and non-Hodgkin's disease, diffuse large B cell lymphoma, follicular lymphoma with areas of diffuse large B cell lymphoma, small lymphocytic lymphoma, mantle cell lymphoma, and diffuse small cleaved cell lymphoma.

As used herein, the term "derivative" in the context of a polypeptide or protein, e.g. an antibody, refers to a polypeptide or protein that comprises an amino acid sequence which has been altered by the introduction of amino acid residue substitutions, deletions or additions. The term "derivative" as used herein also refers to a polypeptide or protein which has been modified, i.e., by the covalent attachment of any type of molecule to the antibody. For example, but not by way of limitation, a polypeptide or protein may be modified, e.g., by glycosylation, acetylation, pegylation, phosphorylation, amidation, derivatization by known protecting/blocking groups, proteolytic cleavage, linkage to a cellular ligand or other protein, etc. A derivative a polypeptide or protein may be produced by chemical modifications using techniques known to those of skill in the art, including, but not limited to specific chemical cleavage, acetylation, formylation, metabolic synthesis of tunicamycin, etc. Further, a derivative a polypeptide or protein possesses a similar or identical function as the a polypeptide or protein from which it was derived.

The term "derivative" as used herein in the context of a FcγRIIB antibody refers to an antibody that immunospecifically binds to a FcγRIIB polypeptide, or an antibody fragment that immunospecifically binds to a FcγRIIB polypeptide, that has been altered by the introduction of one or more amino acid residue substitutions, deletions or additions (i.e., mutations) in one or more regions/domains of the antibody (e.g., CDRs, Fc region, hinge region, framework regions). The antibody derivative may have substantially the same binding, better binding, or worse binding when compared to a non-derivative antibody. In specific embodiments, one, two, three, four, or five amino acid residues of the CDR and/or Fc region have been substituted, deleted or added (i.e., mutated). The term "derivative" as used herein in conjunction with FcγRIIB also refers to an antibody that immunospecifically binds to a FcγRIIB polypeptide, or an antibody fragment that immunospecifically binds to a FcγRIIB polypeptide which has been modified, i.e., by the covalent attachment of any type of molecule to the polypeptide. For example, but not by way of limitation, an antibody, or antibody fragment may be modified, e.g., by glycosylation, acetylation, pegylation, phosphorylation, amidation, derivatization by known protecting/blocking groups, proteolytic cleavage, linkage to a cellular ligand or other protein, etc. A derivative antibody, or antibody fragment may be modified by chemical modifications using techniques known to those of skill in the art, including, but not limited to, specific chemical cleavage, acetylation, formulation, metabolic synthesis of tunicamycin, etc. Further, a derivative of an antibody, or antibody fragment may contain one or more non-classical amino acids. In one embodiment, an antibody derivative possesses a similar or identical function as the parent antibody. In another embodiment, a derivative of an antibody, or antibody fragment has an altered activity when compared to an unaltered antibody. For example, a derivative antibody or fragment thereof can bind to its epitope more tightly or be more resistant to proteolysis.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

As used herein, the term "cancer" refers to a neoplasm or tumor resulting from abnormal uncontrolled growth of cells. As used herein, cancer explicitly includes, leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or weblike matrices in a three-dimensional basement membrane or extracellular matrix preparation. Non-cancer cells do not form colonies in soft agar and form distinct sphere-like structures in three-dimensional basement membrane or extracellular matrix preparations. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen.

As used herein, the term "immunomodulatory agent" and variations thereof including, but not limited to, immunomodulatory agents, refer to an agent that modulates a host's immune system. In certain embodiments, an immunomodulatory agent is an immunosuppressant agent. In certain other embodiments, an immunomodulatory agent is an immunostimulatory agent. Immunomodatory agents include, but are not limited to, small molecules, peptides, polypeptides, fusion proteins, antibodies, inorganic molecules, mimetic agents, and organic molecules.

As used herein, the term "epitope" refers to a fragment of a polypeptide or protein having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide. Preferably, antibody fragments are epitope binding fragments.

As used herein, the term "humanized antibody" refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody, because, e.g., the entire variable region of a chimeric antibody is non-human. The term "humanization" refers to the process of creating the humanized antibody. The resultant humanized antibody is expected to bind to the same antigen as the donor antibody that provides the CDRs. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to a FcγRIIB polypeptide, that has been altered by the introduction of amino acid residue substitutions, deletions or additions (i.e., mutations). In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated). For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al., 1994, *PNAS* 91:969-973; Tan et al., 2002, *J. Immunol.* 169:1119-25; Caldas et al., 2000, *Protein Eng.* 13:353-60; Morea et al., 2000, *Methods* 20:267-79; Baca et al., 1997, *J. Biol. Chem.* 272:10678-84; Roguska et al., 1996, *Protein Eng.* 9:895-904; Couto et al., 1995, *Cancer Res.* 55 (23 Supp):5973s-5977s; Couto et al., 1995, *Cancer Res.* 55:1717-22; Sandhu, 1994, *Gene* 150:409-10; Pedersen et al., 1994, *J. Mol. Biol.* 235:959-73; Jones et al., 1986, *Nature* 321:522-525; Reichmann et al., 1988, *Nature* 332:323-329; and Presta, 1992, *Curr. Op. Struct. Biol.* 2:593-596; each of which is incorporated herein by reference in its entirety.

As used herein, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain according to Kabat et al., *Sequences of Proteins of Immunological Interest*, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917; incorporated herein by reference in its entirety). "Framework Region" or "FR" residues are those variable domain residues other than the hypervariable region residues as herein defined.

As used herein, the terms "single-chain Fv" or "scFv" refer to antibody fragments comprise the VH and VL domains of antibody, wherein these domains are present in a single polypeptide chain. Generally, the Fv polypeptide further comprises a polypeptide linker between the VH and VL domains which enables the scFv to form the desired structure for antigen binding. For a review of sFv, see Pluckthun in *The Pharmacology of Monoclonal Antibodies*, vol. 113, Rosenburg and Moore eds. Springer-Verlag, New York, pp. 269-315 (1994); incorporated herein by reference in its entirety. In specific embodiments, scFvs include bi-specific scFvs and humanized scFvs.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

As used herein, the terms "treat," "treating" and "treatment" refer to the eradication, reduction or amelioration of symptoms of a disease or disorder related to the loss of regulation in the Fc receptor signaling pathway or to enhance the therapeutic efficacy of another therapy, e.g., a therapeutic antibody, vaccine therapy or prophylaxis. In some embodiments, treatment refers to the eradication, removal, modification, or control of primary, regional, or metastatic cancer tissue that results from the administration of one or more therapeutic agents. In certain embodiments, such terms refer to the minimizing or delaying the spread of cancer resulting from the administration of one or more therapeutic agents to a subject with such a disease. In other embodiments, such terms refer to elimination of disease causing cells.

As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects from chemotherapy include, but are not limited to, gastrointestinal toxicity such as, but not limited to, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art, see, e.g., the *Physicians' Desk Reference* (56th ed., 2002), which is incorporated herein by reference in its entirety.

As used herein, a "therapeutically effective amount" refers to that amount of the therapeutic agent sufficient to treat or manage a disease or disorder associated with FcγRIIB and any disease related to the loss of regulation in the Fc receptor signaling pathway or to enhance the therapeutic efficacy of another therapy, e.g., therapeutic antibody, vaccine therapy or prophylaxis, etc. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease. Further, a therapeutically effective amount with respect to a therapeutic agent of the invention means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease. Used in connection with an amount of FcγRIIB antibody of the invention, the term can encompass an amount that improves overall therapy, reduces or avoids unwanted effects, or enhances the therapeutic efficacy of or synergies with another therapeutic agent.

As used herein, the terms "prophylactic agent" and "prophylactic agents" refer to any agent(s) which can be used in the prevention of a disorder, or prevention of recurrence or spread of a disorder. A prophylactically effective amount may refer to the amount of prophylactic agent sufficient to prevent the recurrence or spread of hyperproliferative disease, particularly cancer, or the occurrence of such in a patient, including but not limited to those predisposed to hyperproliferative disease, for example those genetically predisposed to cancer or previously exposed to carcinogens. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease. Used in connection with an amount of an FcγRIIB antibody of the invention, the term can encompass an amount that improves overall prophylaxis or enhances the prophylactic efficacy of or synergies with another prophylactic agent, such as but not limited to a therapeutic antibody. In certain embodiments, the term "prophylactic agent" refers to an agonistic FcγRIIB-specific antibody. In other embodiments, the term "prophylactic agent" refers to an antagonistic FcγRIIB-specific antibody. In certain other embodiments, the term "prophylactic agent" refers to cancer chemotherapeutics, radiation therapy, hormonal therapy, biological therapy (e.g., immunotherapy), and/or FcγRIIB antibodies of the invention. In other embodiments, more than one prophylactic agent may be administered in combination.

As used herein, the terms "manage," "managing" and "management" refer to the beneficial effects that a subject derives from administration of a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the terms "prevent", "preventing" and "prevention" refer to the prevention of the occurrence and/or recurrence or onset of one or more symptoms of a disorder in a subject resulting from the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder, e.g., hyperproliferative cell disorder, especially cancer. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a disorder. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

5. BRIEF DESCRIPTION OF THE DRAWINGS

FIGS. 1A and B. A. AMINO ACID ALIGNMENTS. The alignment of the amino acid sequences of mouse 2B6 VH (SEQ ID NO:28), humanized 2B6 VH-1 (SEQ ID NO:24), VH1-18 (SEQ ID NOS:4-6; SEQ ID NOS:71-72) and human JH6 (SEQ ID NOS:4-7, SEQ ID NOS:71-73) is shown in FIG. 1A. B. AMINO ACID ALIGNMENTS. This figure shows the alignment of amino acid sequences of murine 2B6 VL (SEQ ID NO:26), human 2B6 VL-1 (SEQ ID NO:18), human 2B6 VL-2 (SEQ ID NO:20); human 2B6 VL-3 (SEQ ID NO:22), and human VK-A26 (SEQ ID NOS:13-15; SEQ ID NOS:74-76) and Jκ4 (SEQ ID NOS:13-16; SEQ ID NOS; 74-76).

FIGS. 2A and 2B A. AMINO ACID ALIGNMENTS. The alignment of the amino acid sequences of humanized 2B6 VH-1 (SEQ ID NO:24) and humanized 2B6 VH3 (SEQ ID NO:68) is shown in FIG. 2A. B. AMINO ACID ALIGNMENTS. This figure shows the alignment of amino acid sequences of humanized 2B6 VL-1 (SEQ ID NO:18), 2B6 VL-2 (SEQ ID NO:20), 2B6 VL-3 (SEQ ID NO:22), and 2B6 VL-5 (SEQ ID NO:62). For FIGS. 2A and 2B, CDRs are indicated by underlining, and differences in amino acid sequence are indicated by bold lettering.

FIG. 3. BINDING OF hu2B6HC/ch2B6LC mAb AND ch2B6 mAb TO FcγRIIB. Binding to dimeric soluble FcγRIIB-Fc was determined by ELISA. hu2B6HC/ch2B6LC monoclonal antibody bound to the receptor with similar affinity to the ch2B6 monoclonal antibody.

Figure 4:
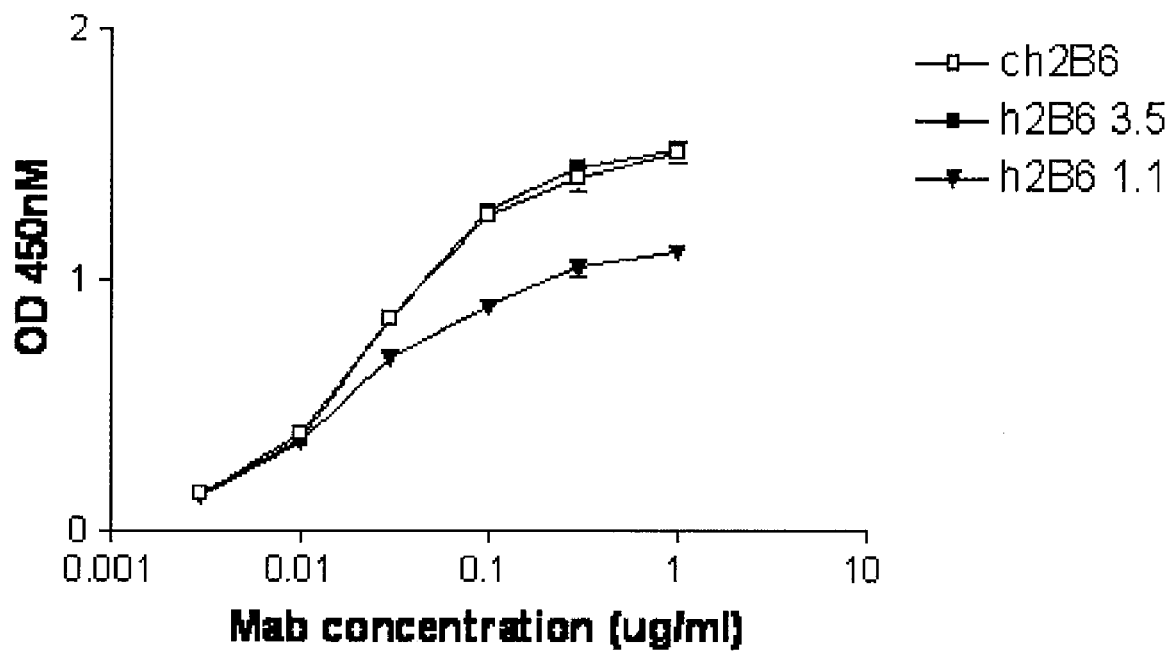
Figure 5:
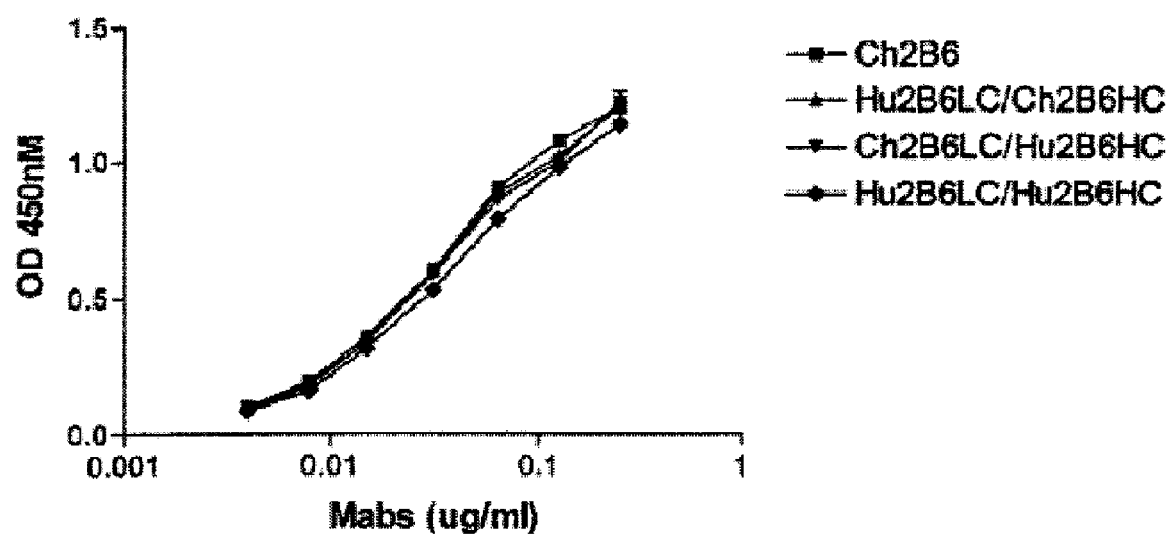

FIG. 4. BINDING OF ch2B6 mAb, h2B6 (v3.5) mAb and h2B6 (v1.1) mAb to FcγRIIB. Binding to dimeric soluble FcγRIIB-Fc was determined by ELISA. A hu2B6 (v3.5) monoclonal antibody bound to the receptor with similar affinity to the ch2B6 monoclonal antibody. Antibody FIG. 5. BINDING OF hu2B6LC/ch2B6HC mAB, ch2B6LC/hu2B6HC, AND ch2B6 mAb TO FcγRIIB. Binding to dimeric soluble FcγRIIB-Fc was determined by ELISA. hu2B6HC/ch2B6LC mAb and ch2B6HC/hu2B6LC mAB bound to the receptor with similar affinity to the ch2B6 mAb.

Figure 6:
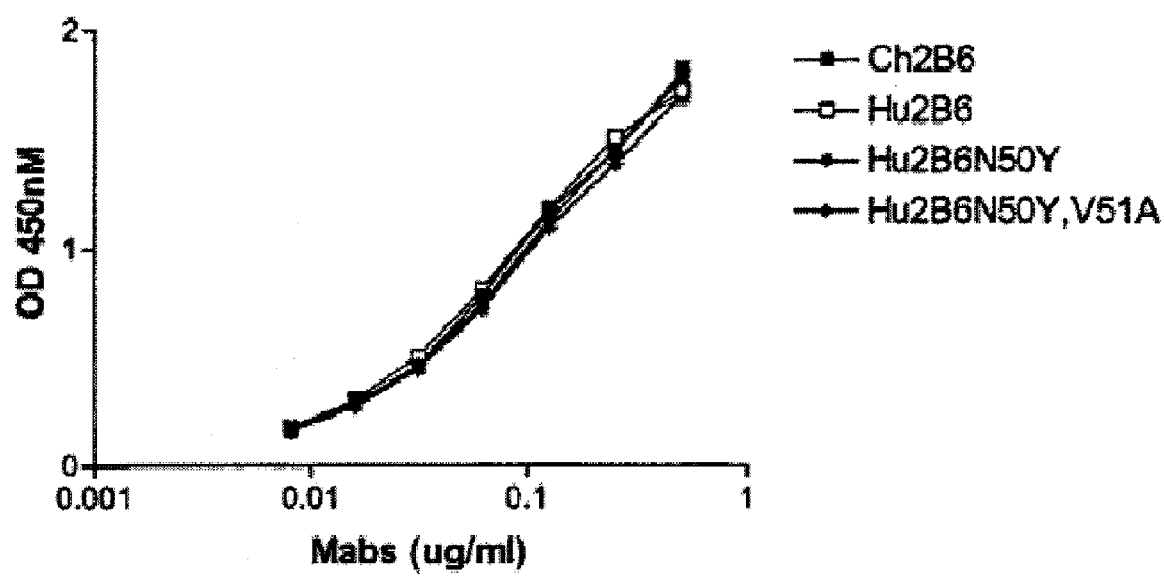

FIG. 6. BINDING OF hu2B6 VARIANTS TO FcγRIIB. Binding of Hu2B6N50Y; Hu2B6N50Y,V51A; Ch2B6, and Hu2B6 to dimeric soluble FcγRIIb-Fc was determined by ELISA. All of the mAbs bound to the receptor with similar affinity.

Figure 7:
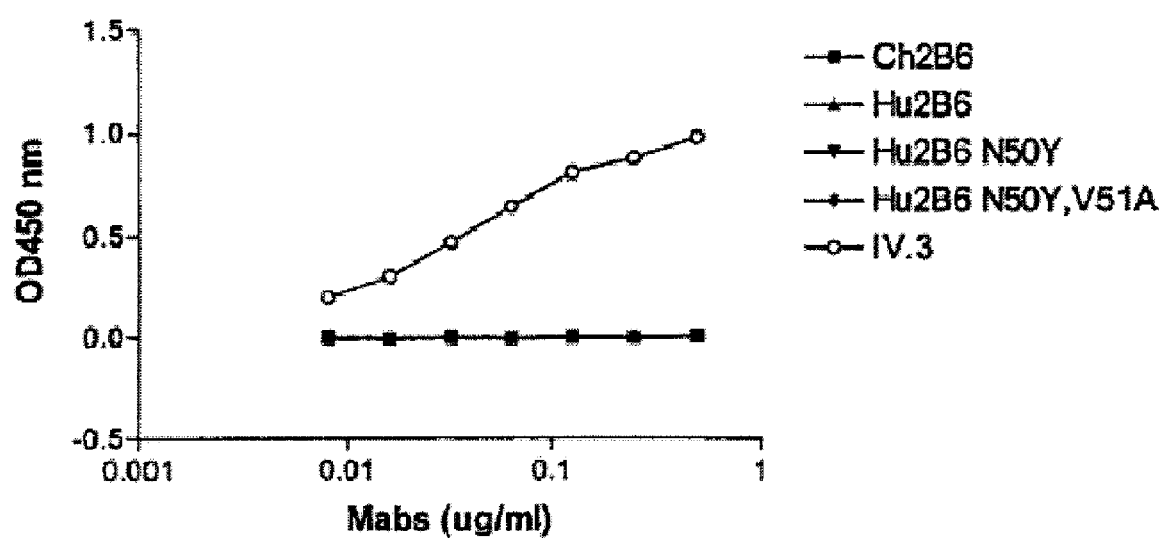

FIG. 7. BINDING OF hu2B6 VARIANTS TO FcγRIIA. Binding of Hu2B6N50Y; Hu2B6N50Y,V51A; Ch2B6, and Hu2B6 to dimeric soluble FcγRIIa-Fc was determined by ELISA. The humanized 2B6 mAbs selectively bind to CD32B. All of the solid data points fall on top of each other and are only displayed as a solid square.

Figure 8A:
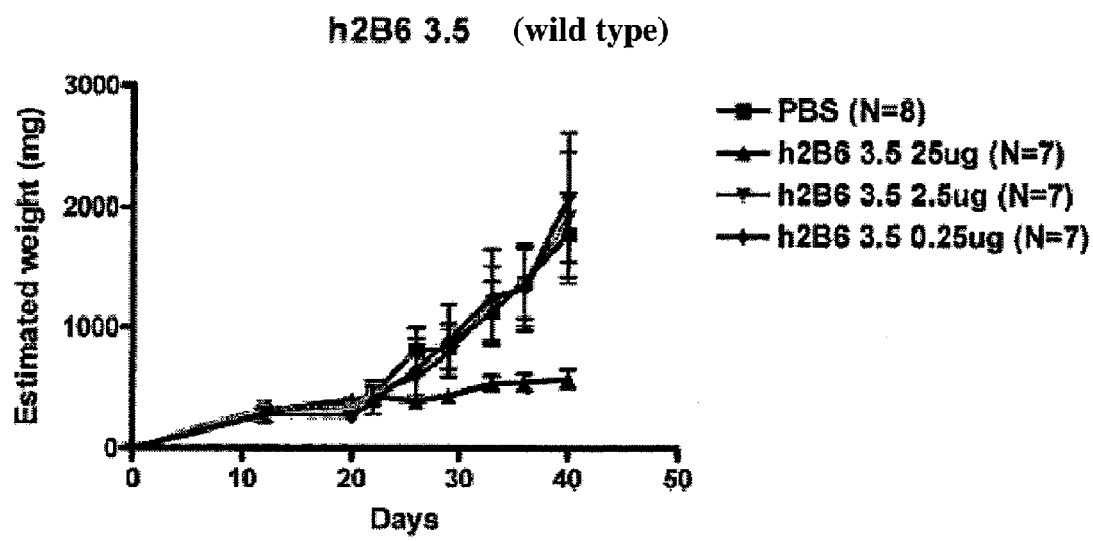
Figure 8B:
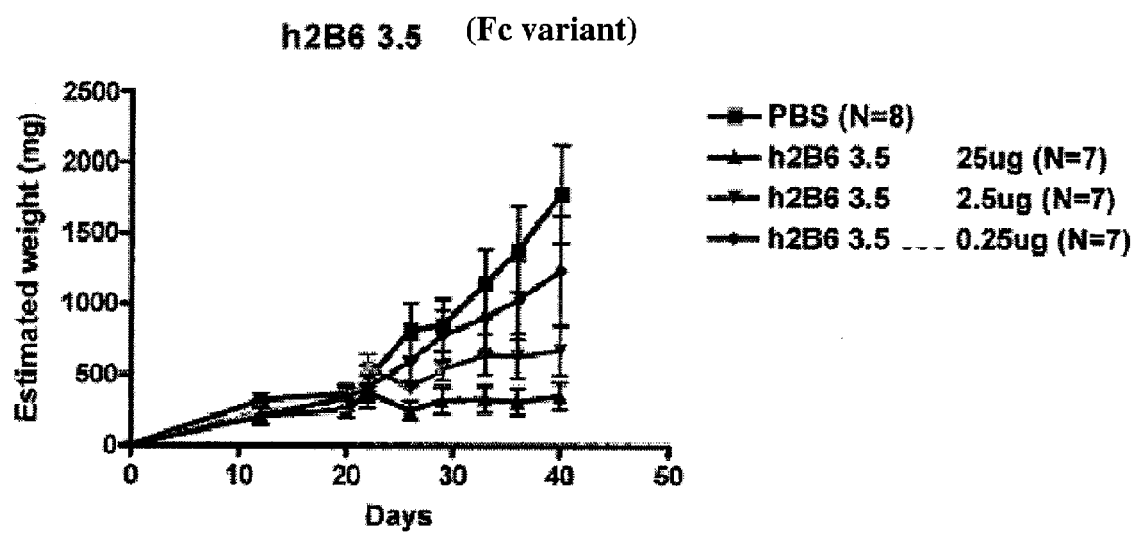

FIGS. 8A and 8B. ESTIMATED TUMOR WEIGHT IN MICE TREATED WITH WILD-TYPE OR Fc MUTANT h2B6. Balb/c nude mice were inoculated subcutaneously with Daudi cells and administered 25 µg, 2.5 µg or 0.25 µg weekly doses of either wild-type h2B6 (A) or a variant h2B6 comprising an Fc domain with a leucine at position 243, a proline at position 292, a leucine at position 300, an isoleucine at position 305, and a leucine at position 396; (B). Mice administered buffer alone were used as control. Tumor weight was calculated based on the estimated volume of the subcutaneous tumor according to the formula (width$^2$× length)/2.

Figure 9A:
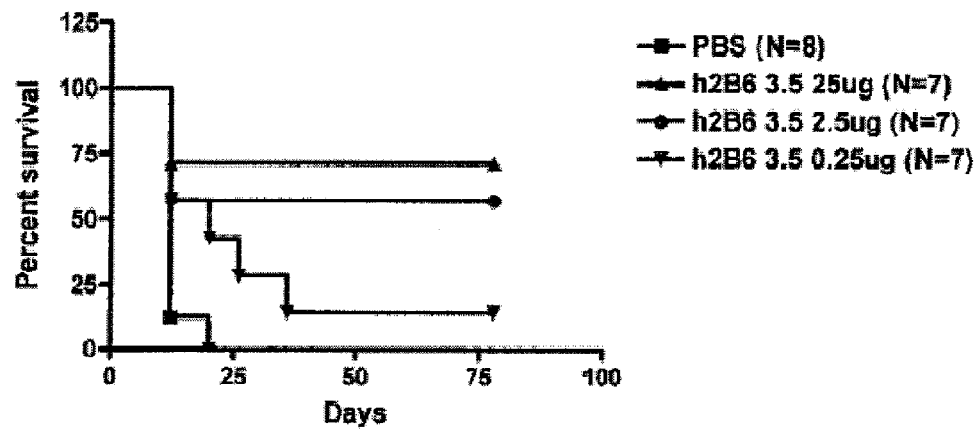
Figure 9B:
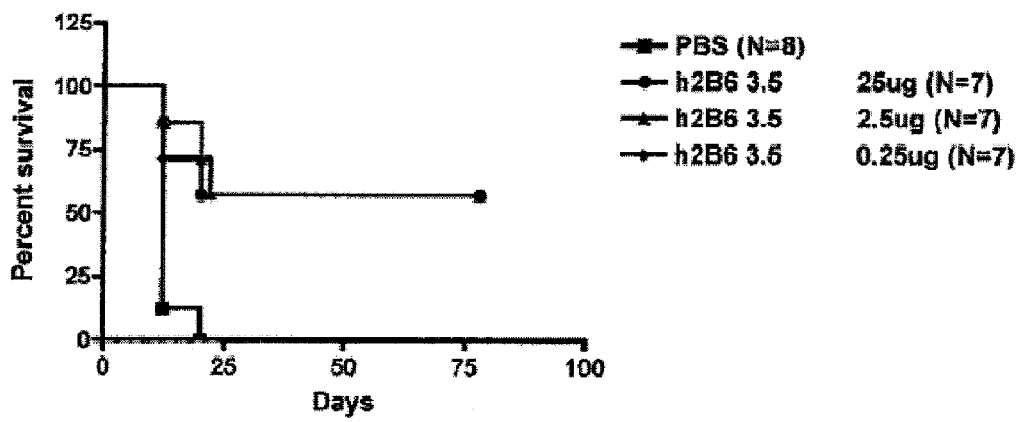

FIGS. 9A and 9B. SURVIVAL IN TUMOR BEARING MICE TREATED WITH WILD-TYPE OR Fc MUTANT h2B6. Nude mice were inoculated with Daudi cells and administered 25 µg, 2.5 µg or 0.25 µg weekly doses of either wild-type h2B6 (A) or a variant h2B6 comprising an Fc domain with 243L, 292P, 300L, 305I, and 396L; (B). Mice administered buffer alone were used as control.

6. DESCRIPTION OF THE PREFERRED EMBODIMENTS

6.1 FcγRIIB-Specific Antibodies

The present invention encompasses humanized antibodies (preferably humanized monoclonal antibodies) or fragments thereof that specifically bind FcγRIIB, preferably human FcγRIIB, more preferably native human FcγRIIB with a greater affinity than said antibodies or fragments thereof bind FcγRIIA, preferably human FcγRIIA, more preferably native human FcγRIIA. Preferably, the humanized antibodies of the invention bind the extracellular domain of native human FcγRIIB. In certain embodiments, the humanized antibodies or fragments thereof bind to FcγRIIB with an affinity greater than two-fold, four fold, 6 fold, 10 fold, 20 fold, 50 fold, 100 fold, 1000 fold, $10^4$ fold, $10^5$ fold, $10^6$ fold, $10^7$ fold, or $10^8$ fold than said antibodies or fragments thereof bind FcγRIIA. In one particular embodiment, the humanized antibody of the invention is derived from a mouse monoclonal antibody produced by clone 2B6 or 3H7, having ATCC accession numbers PTA-4591 and PTA-4592, respectively. In another embodiment, the humanized antibody of the invention is derived from a mouse monoclonal antibody produced by clone 1D5, 2E1, 2H9, 2D11, or 1F2, having ATCC Accession numbers, PTA-5958, PTA-5961, PTA-5962, PTA-5960, and PTA-5959, respectively. Hybridomas producing antibodies 2B6 and 3H7 have been deposited with the American Type Culture Collection (10801 University Blvd., Manassas, Va. 20110-2209) on Aug. 13, 2002 under the provisions of the Budapest Treaty on the International Recognition of the Deposit of Microorganisms for the Purposes of Patent Procedures, and assigned accession numbers PTA-4591 (for hybridoma producing 2B6) and PTA-4592 (for hybridoma producing 3H7), respectively, and are incorporated herein by reference. Hybridomas producing 1D5, 2E1, 2H9, 2D11, and 1F2 were deposited under the provisions of the Budapest Treaty with the American Type Culture Collection (10801 University Blvd., Manassas, Va. 20110-2209) on May 7, 2004, and assigned accession numbers PTA-5958, PTA-5961, PTA-5962, PTA-5960, and PTA-5959, respectively and are incorporated herein by reference.

In yet other embodiments, the invention encompasses humanized FcγRIIB antibodies that bind exclusively to FcγRIIB and have no affinity for FcγRIIA using standard methods known in the art and disclosed herein.

In a specific embodiment, the invention encompasses a humanized antibody comprising the CDRs of 2B6 or of 3H7. In particular, the invention encompasses a humanized antibody with the heavy chain variable domain having the amino acid sequence of SEQ ID NO: 24, SEQ ID NO:60 or SEQ ID NO:68 and the light chain variable domain having the amino acid sequence of SEQ ID NO: 18, SEQ ID NO: 20, SEQ ID NO: 22, SEQ ID NO:62. In a specific embodiment, the invention encompasses a humanized antibody with the heavy chain variable domain having the amino acid sequence of SEQ ID NO: 37 and the light chain variable domain having the amino acid sequence of SEQ ID NO: 46. In a preferred embodiment, the invention encompasses a humanized antibody with the heavy chain variable domain having the amino acid sequence of SEQ ID NO:68 and the light chain variable domain having the amino acid sequence of SEQ ID NO:62. In yet another preferred embodiment, the humanized antibodies of the invention further do not bind Fc activation receptors, e.g., FcγIIIA, FcγIIIB, etc. In one embodiment, the humanized FcγRIIB-specific antibody in accordance with the invention is not derived from the monoclonal antibody designated KB61, as disclosed in Pulford et al., 1986 (*Immunology,* 57: 71-76) or the monoclonal antibody designated MAbII8D2 as disclosed in Weinrich et al., 1996, (*Hybridoma,* 15(2):109-6); each of which reference is incorporated herein by reference in its entirety. In a specific embodiment, the FcγRIIB-specific antibody of the invention does not bind to the same epitope and/or does not compete with binding with the monoclonal antibody KB61 or II 8D2. Preferably, the humanized FcγRIIB-specific antibodies of the invention do not bind the amino acid sequence SDPNFSI corresponding to positions 135-141 of FcγRIIb2 isoform.

The constant domains of the humanized antibodies of the invention may be selected with respect to the proposed function of the antibody, in particular with regard to the effector function which may be required. In some embodiments, the constant domains of the humanized antibodies of the invention are human IgA, IgE, IgG or IgM domains. In a specific embodiment, human IgG constant domains, especially of the IgG1 and IgG3 isotypes are used, especially when the humanized antibodies of the invention are intended for therapeutic uses and antibody effector functions are needed. In alternative embodiments, IgG2 and IgG4 isotypes are used when the humanized antibody of the invention is intended for therapeutic purposes and antibody effector function is not required. In other embodiments, the invention encompasses humanized antibodies comprising one or more amino acid modifications in the Fc region such as those disclosed in International Publication Nos. WO 04/063351, WO 04/029207, WO 04/029092, WO 04/028564, WO 99/58572, WO 99/51642, WO 98/23289, WO 89/07142, WO 88/07089; U.S. Patent Application Publication Nos. 2005/0037000; and 2005/0064514 and U.S. Pat. Nos. 5,843,597 and 5,642,821; U.S. patent application Ser. Nos. 10/902,588 (filed Jul. 28, 2004) and 11/271,140 (filed Nov. 10, 2005); U.S. Provisional Application Nos. 60/707,419; and 60/781,564 filed on Aug. 10, 2005, and Mar. 10, 2006, respectively; and U.S. Pat. Nos. 5,624,821 and 5,648,260 and European Patent No. EP 0 307 434; all of which are incorporated herein by reference in their entireties. In a specific embodiment, the amino acid modification of the Fc regions of the humanized antibodies of the invention relative to a wild-type Fc region comprise a substitution at position 243, 292, 300, 305 and 396. In a preferred embodiment, the amino acid modification of the Fc regions of the humanized antibodies of the invention relative to a wild-type Fc region comprise a substitution at position 243 with leucine, at position 292 with proline, at position 300 with leucine, at position 305 with isoleucine and at position 396 with leucine.

Preferably, the humanized antibodies of the invention bind the extracellular domain of native human FcγRIIB that is endogenously expressed on the surface of a cell. The humanized anti-FcγRIIB antibodies of the invention may have a heavy chain variable region comprising the amino acid sequence of a CDR1 (e.g., SEQ ID NO:1, SEQ ID NO:29, an amino acid sequence corresponding to amino acids 31-35 as set forth in SEQ ID NO:60, or an amino acid sequence corresponding to amino acids 31-35 as set forth in SEQ ID NO:68) and/or a CDR2 (e.g., SEQ ID NO:2, SEQ ID NO:30, an amino acid sequence corresponding to amino acids 50-66 as set forth in SEQ ID NO:60, or an amino acid sequence corresponding to amino acids 50-66 as set forth in SEQ ID NO:68) and/or a CDR3 (e.g., SEQ ID NO:3, SEQ ID NO:31, an amino acid sequence corresponding to amino acids 99-110 as set forth in SEQ ID NO:60, or an amino acid sequence corresponding to amino acids 99-110 as set forth in SEQ ID NO:68) and/or a light chain variable region comprising the amino acid sequence of a CDR1 (e.g., SEQ ID NO:8, SEQ ID NO:38, or an amino acid sequence corresponding to amino acids 24-34 as set forth in SEQ ID NO:62) and/or a CDR2 (e.g., SEQ ID NO:9, SEQ ID NO:10, SEQ ID NO:11, SEQ ID NO:39, or an amino acid sequence corresponding to amino acids 50-56 as set forth in SEQ ID NO:62) and/or a CDR3 (e.g., SEQ ID NO:12, SEQ ID NO:40, or an amino acid sequence corresponding to amino acids 90-98 as set forth in SEQ ID NO:62).

In a specific embodiment, the invention provides a humanized 2B6 antibody, wherein the VH region consists of the FR segments from the human germline VH segment VH1-18 (Matsuda et al., 1998, J. Exp. Med. 188:2151062) and JH6 (Ravetch et al., 1981, Cell 27(3 Pt. 2): 583-91) (each of which reference is incorporated herein by reference in its entirety), and one or more CDR regions of the 2B6 VH, having the amino acid sequence of SEQ ID NO. 1, SEQ ID NO. 2, or SEQ ID NO. 3. In specific embodiments, the 2B6 VH has the amino acid sequence of SEQ ID NO. 24, SEQ ID NO:60, or SEQ ID NO:68. In another specific embodiment, the humanized 2B6 antibody further comprises a VL region, which consists of the FR segments of the human germline VL segment VK-A26 (Lautner-Rieske et al., 1992, Eur. J. Immunol. 22:1023-1029) and JK4 (Hieter et al., 1982, J. Biol. Chem. 257:1516-22) (each of which reference is incorporated herein by reference in its entirety), and one or more CDR regions of 2B6 VL, having the amino acid sequence of SEQ ID NO: 8, SEQ ID NO. 9, SEQ ID NO. 10, SEQ ID NO. 11, and SEQ ID NO. 12. In one embodiment, the 2B6 VL has the amino acid sequence of SEQ ID NO. 18; SEQ ID NO: 20, SEQ ID NO: 22, or SEQ ID NO:62. In a preferred embodiment, the 2B6 antibody of the invention comprises a VL comprising the amino acid sequence SEQ ID NO:62 and a VH comprising the amino acid sequence SEQ ID NO:68.

In another specific embodiment, the invention provides a humanized 3H7 antibody, wherein the VH region consists of the FR segments from a human germline VH segment and the CDR regions of the 3H7 VH, having the amino acid sequence of SEQ ID NO. 37. In another specific embodiment, the humanized 3H7 antibody further comprises a VL regions, which consists of the FR segments of a human germline VL segment and the CDR regions of 3H7 VL, having the amino acid sequence of SEQ ID NO. 46.

In particular, the invention provides a humanized antibody that immunospecifically binds to extracellular domain of native human FcγRIIB, said antibody comprising (or alternatively, consisting of) CDR sequences of 2B6 or 3H7, in any of the following combinations: a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR1, a VH CDR3, a VL CDR2 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs disclosed herein.

The present invention provides humanized antibody molecules specific for FcγRIIB in which one or more regions of one or more CDRs of the heavy and/or light chain variable regions of a human antibody (the recipient antibody) have been substituted by analogous parts of one or more CDRs of a donor monoclonal antibody which specifically binds FcγRIIB, with a greater affinity than FcγRIIA, e.g., a monoclonal antibody produced by clone 2B6 or 3H7, having ATCC accession numbers PTA-4591, and PTA-4592, respectively, or a monoclonal antibody produced by clone 1D5, 2E1, 2H9, 2D11, or 1F2, having ATCC Accession numbers, PTA-5958, PTA-5961, PTA-5962, PTA-5960, and PTA-5959, respectively. In other embodiments, the humanized antibodies of the invention bind to the same epitope as 2B6, 3H7, 1D5, 2E1, 2H9, 2D11, or 1F2. In a most preferred embodiment, the humanized antibody specifically binds to the same epitope as the donor murine antibody. It will be appreciated by one skilled in the art that the invention encompasses CDR grafting of antibodies in general. Thus, the donor and acceptor antibodies may be derived from animals of the same species and even same antibody class or sub-class. More usually, however, the donor and acceptor antibodies are derived from animals of different species. Typically the donor antibody is a non-human antibody, such as a rodent MAb, and the acceptor antibody is a human antibody.

In some embodiments, at least one CDR from the donor antibody is grafted onto the human antibody. In other embodiments, at least two and preferably all three CDRs of each of the heavy and/or light chain variable regions are grafted onto the human antibody. The CDRs may comprise the Kabat CDRs, the structural loop CDRs or a combination thereof. In some embodiments, the invention encompasses a humanized FcγRIIB antibody comprising at least one CDR grafted heavy chain and at least one CDR-grafted light chain.

In a preferred embodiment, the CDR regions of the humanized FcγRIIB specific antibody are derived from a murine antibody specific for FcγRIIB. In some embodiments, the humanized antibodies described herein comprise alterations, including but not limited to amino acid deletions, insertions, modifications, of the acceptor antibody, i.e., human, heavy and/or light chain variable domain framework regions that are necessary for retaining binding specificity of the donor monoclonal antibody. In some embodiments, the framework regions of the humanized antibodies described herein does not necessarily consist of the precise amino acid sequence of the framework region of a natural occurring human antibody variable region, but contains various alterations, including but not limited to amino acid deletions, insertions, modifications that alter the property of the humanized antibody, for example, improve the binding properties of a humanized antibody region that is specific for the same target as the murine FcγRIIB specific antibody. In most preferred embodiments, a minimal number of alterations are made to the framework region in order to avoid large-scale introductions of non-human framework residues and to ensure minimal immunogenicity of the humanized antibody in humans. The donor monoclonal antibody of the present invention is preferably a monoclonal antibody produced by clones 2B6 and 3H7 (having ATCC accession numbers PTA-4591, and PTA-4592, respectively) which bind FcγRIIB or a monoclonal antibody produced by clones 1D5, 2E1, 2H9, 2D11, or 1F2 (having ATCC Accession numbers, PTA-5958, PTA-5961, PTA-5962, PTA-5960, and PTA-5959, respectively).

In a specific embodiment, the invention encompasses a CDR-grafted antibody which specifically binds FcγRIIB with a greater affinity than said antibody binds FcγRIIA, wherein the CDR-grafted antibody comprises a heavy chain variable region domain comprising framework residues of the recipient antibody and residues from the donor monoclonal antibody, which specifically binds FcγRIIB with a greater affinity than said antibody binds FcγRIIA, e.g., monoclonal antibody produced from clones 2B6, 3H7, 1D5, 2E1, 2H9, 2D11, or 1F2. In a specific embodiment, the heavy chain variable domain of the antibodies of the invention comprise the amino acid sequence SEQ ID NO:60. In another specific embodiment, the heavy chain variable domain of the antibodies of the invention comprise the amino acid sequence SEQ ID NO:68. In other embodiments, the invention encompasses a CDR-grafted antibody which specifically binds FcγRIIB with a greater affinity than said antibody binds FcγRIIA, wherein the CDR-grafted antibody comprises a light chain variable region domain comprising framework residues of the recipient antibody and residues from the donor monoclonal antibody, which specifically binds FcγRIIB with a greater affinity than said antibody binds FcγRIIA, e.g., monoclonal antibody produced from clones 2B6, 3H7, 1D5, 2E1, 2H9, 2D11, or 1F2. In a specific embodiment, the light chain variable domain of the antibodies of the invention comprise the amino acid sequence SEQ ID NO:62.

A humanized FcγRIIB specific antibody of the invention may comprise substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized antibody of the invention also comprises at least a portion of an immunoglobulin constant region (Fc), typically that of a human immunoglobulin. The constant domains of the humanized antibodies of the invention may be selected with respect to the proposed function of the antibody, in particular the effector function which may be required. In some embodiments, the constant domains of the humanized antibodies of the invention are human IgA, IgE, IgG or IgM domains. In a specific embodiment, human IgG constant domains, especially of the IgG1 and IgG3 isotypes are used, when the humanized antibodies of the invention is intended for therapeutic uses and antibody effector functions are needed. In alternative embodiments, IgG2 and IgG4 isotypes are used when the humanized antibody of the invention is intended for therapeutic purposes and antibody effector function is not required. The invention encompasses Fc constant domains comprising one or more amino acid modifications which alter antibody effector functions such as those disclosed in U.S. Patent Application Publication Nos. 2005/0037000 and 2005/0064514; U.S. Provisional Application Nos. 60/439,498; 60/456,041; and 60/514,549 filed on Jan. 9, 2003; Mar. 19, 2003, and Oct. 23, 2003 respectively; all of which are incorporated herein by reference in their entireties. In a specific embodiment, the antibody of the invention comprises an Fc domain having a laucine at position 243, a praline at position 292, a leucine at position 300, an isoleucine at position 305, and a leucine at position 396. In other embodiment, the antibody of the invention comprises amino acid modification(s) of the Fc region relative to a wild-type Fc region, which modification comprise a substitution at position 243, 292, 300, 305 and 396, preferably a substitution at position 243 with leucine, at position 292 with proline, at position 300 with leucine, at position 305 with isoleucine and at position 396 with leucine.

In some embodiments, the humanized antibody of the invention contains both the light chain as well as at least the variable domain of a heavy chain. In other embodiments, the humanized antibody of the invention may further comprise one or more of the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the humanized antibody exhibit cytotoxic activity, and the class is typically $IgG_1$. In other embodiments, where such cytotoxic activity is not desirable, the constant domain may be of the $IgG_2$ class. The humanized antibody of the invention may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *Proc. Natl. Acad. Sci.* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct Biol.* 2:593-596; each of which is incorporated herein by reference in its entirety. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al, U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, Nature 332:323, all of which are incorporated herein by reference in their entireties.)

In a particular embodiment, the humanized antibodies of the invention, or fragments thereof, agonize at least one activity of FcγRIIB. In one embodiment of the invention, said activity is inhibition of B cell receptor-mediated signaling. In another embodiment, the humanized agonistic antibodies of the invention inhibit activation of B cells, B cell proliferation, antibody production, intracellular calcium influx of B cells, cell cycle progression, or activity of one or more downstream signaling molecules in the FcγRIIB signal transduction pathway. In yet another embodiment, the humanized agonistic antibodies of the invention enhance phosphorylation of FcγRIIB or SHIP recruitment. In a further embodiment of the invention, the humanized agonistic antibodies inhibit MAP kinase activity or Akt recruitment in the B cell receptor-mediated signaling pathway. In another embodiment, the humanized agonistic antibodies of the invention agonize FcγRIIB-mediated inhibition of FcεRI signaling. In a particular embodiment, said humanized antibodies inhibit FcεRI-induced mast cell activation, calcium mobilization, degranulation, cytokine production, or serotonin release. In another embodiment, the humanized agonistic antibodies of the invention stimulate phosphorylation of FcγRIIB, stimulate recruitment of SHIP, stimulate SHIP phosphorylation and its association with Shc, or inhibit activation of MAP kinase family members (e.g., Erk1, Erk2, JNK, p38, etc.). In yet another embodiment, the humanized agonistic antibodies of the invention enhance tyrosine phosphorylation of p62dok and its association with SHIP and rasGAP. In another embodiment, the humanized agonistic antibodies of the invention inhibit FcγR-mediated phagocytosis in monocytes or macrophages.

In another embodiment, the humanized antibodies of the invention, or fragments thereof, antagonize at least one activity of FcγRIIB. In one embodiment, said activity is activation of B cell receptor-mediated signaling. In a particular embodiment, the humanized antagonistic antibodies of the invention enhance B cell activity, B cell proliferation, antibody production, intracellular calcium influx, or activity of one or more downstream signaling molecules in the FcγRIIB signal transduction pathway. In yet another particular embodiment, the humanized antagonistic antibodies of the invention decrease phosphorylation of FcγRIIB or SHIP recruitment. In a further embodiment of the invention, the humanized antagonistic antibodies enhance MAP kinase activity or Akt recruitment in the B cell receptor mediated signaling pathway. In another embodiment, the humanized antagonistic antibodies of the invention antagonize FcγRIIB-mediated inhibition of FcεRI signaling. In a particular embodiment, the humanized antagonistic antibodies of the invention enhance FcεRI-induced mast cell activation, calcium mobilization, degranulation, cytokine production, or serotonin release. In another embodiment, the humanized antagonistic antibodies of the invention inhibit phosphorylation of FcγRIIB, inhibit recruitment of SHIP, inhibit SHIP phosphorylation and its association with Shc, enhance activation of MAP kinase family members (e.g., Erk1, Erk2, JNK, p38, etc.). In yet another embodiment, the humanized antagonistic antibodies of the invention inhibit tyrosine phosphorylation of p62dok and its association with SHIP and rasGAP. In another embodiment, the humanized antagonistic antibodies of the invention enhance FcγR-mediated phagocytosis in monocytes or macrophages. In another embodiment, the humanized antagonistic antibodies of the invention prevent phagocytosis, clearance of opsonized particles by splenic macrophages.

Antibodies of the invention include, but are not limited to, monoclonal antibodies, synthetic antibodies, recombinantly produced antibodies, multispecific antibodies, human antibodies, chimeric antibodies, camelized antibodies, single-chain Fvs (scFv), single chain antibodies, Fab fragments, F(ab') fragments, disulfide-linked Fvs (sdFv), intrabodies, and epitope-binding fragments of any of the above. In particular, antibodies used in the methods of the present invention include immunoglobulin molecules and immunologically active portions of immunoglobulin molecules, i.e., molecules that contain an antigen binding site that immunospecifically binds to FcγRIIB with greater affinity than said immunoglobulin molecule binds FcγRIIA and/or immunospecifically binds FcγRIIB and blocks the Fc binding domain of FcγRIIB. Antibody analogs may also include FcγRIIB-specific T-cell receptors, for example, chimeric T-cell receptors (see, e.g., U.S. Patent Application Publication No. 2004/0043401), a single-chain T-cell receptor linked to a single-chain antibody (see, e.g., U.S. Pat. No. 6,534,633), and protein scaffolds (see, e.g., U.S. Pat. No. 6,818,418) (each of which reference is incorporated herein by reference in its entirety). In certain embodiments, an antibody analog of the invention is not a monoclonal antibody.

The humanized antibodies used in the methods of the invention may be from any animal origin including birds and mammals (e.g., human, non-human primate, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or libraries of synthetic human immunoglobulin coding sequences or from mice that express antibodies from human genes.

The humanized antibodies used in the methods of the present invention may be monospecific, bispecific, trispecific or of greater multispecificity. Multispecific antibodies may immunospecifically bind to different epitopes of FcγRIIB or immunospecifically bind to both an epitope of FcγRIIB as well a heterologous epitope, such as a heterologous polypeptide or solid support material. See, e.g., International Publication Nos. WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, and 5,601,819; and Kostelny et al, 1992, J. Immunol. 148:1547-1553; Todorovska et al., 2001 Journal of Immunological Methods, 248:47-66; each of which is incorporated herein by reference in its entirety. In particular embodiments, the humanized antibodies of the invention are multispecific with specificities for FcγRIIB and for a cancer antigen or any other cell surface marker specific for a cell (e.g., an immune cell such as a T-cell or B-cell) designed to be killed, e.g., in treating or preventing a particular disease or disorder, or for other Fc receptors, e.g., FcγRIIIA, FcγRIIIB, etc.

In a specific embodiment, an antibody used in the methods of the present invention is an antibody or an antigen-binding fragment thereof (e.g., comprising one or more complementarity determining regions (CDRs), preferably all 6 CDRs) of the antibody produced by clone 2B6, 3H7, 1D5, 2E1, 2H9, 2D11, or 1F2, with ATCC accession numbers PTA-4591, PTA-4592, PTA-5958, PTA-5961, PTA-5962, PTA-5960, and PTA-5959, respectively (e.g., the heavy chain CDR3). In another embodiment, an antibody used in the methods of the present invention binds to the same epitope as the mouse monoclonal antibody produced from clone 2B6, 3H7, 1D5, 2E1, 2H9, 2D11, or 1F2, with ATCC accession numbers PTA-4591, PTA-4592, PTA-5958, PTA-5961, PTA-5962, PTA-5960, and PTA-5959, respectively and/or competes with the mouse monoclonal antibody produced from clone 2B6, 3H7, 1D5, 2E1, 2H9, 2D11, or 1F2, with ATCC accession numbers PTA-4591, PTA-4592, PTA-5958, PTA-5961, PTA-5962, PTA-5960, and PTA-5959, respectively as determined, e.g., in an ELISA assay or other appropriate competitive immunoassay, and also binds FcγRIIB with a greater affinity than said antibody or a fragment thereof binds FcγRIIA.

The humanized antibodies used in the methods of the invention include derivatives that are modified, i.e., by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

For some uses, including in vivo use of humanized antibodies in humans and in vitro detection assays, it may be preferable to use human, chimeric or humanized antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A chimeric antibody is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807,715, 4,816,567, and 4,816,397, which are incorporated herein by reference in their entirety. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519, 596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332). Each of the above-identified references is incorporated herein by reference in its entirety.

Further, the antibodies of the invention can, in turn, be utilized to generate anti-idiotype antibodies using techniques well known to those skilled in the art. (See, e.g., Greenspan & Bona, 1989, FASEB J. 7:437-444; and Nissinoff, 1991, J. Immunol. 147:2429-2438; incorporated herein by reference in its entirety). The invention provides methods employing the use of polynucleotides comprising a nucleotide sequence encoding an antibody of the invention or a fragment thereof.

The present invention encompasses single domain antibodies, including camelized single domain antibodies (See e.g., Muyldermans et al., 2001, Trends Biochem. Sci. 26:230; Nuttall et al., 2000, Cur. Pharm. Biotech. 1:253; Reichmann and Muyldermans, 1999, J. Immunol. Meth. 231:25; International Publication Nos. WO 94/04678 and WO 94/25591; U.S. Pat. No. 6,005,079; which are incorporated herein by reference in their entireties). In one embodiment, the present invention provides single domain antibodies comprising two VH domains with modifications such that single domain antibodies are formed.

The methods of the present invention also encompass the use of humanized antibodies or fragments thereof that have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The humanized antibodies of the invention may be engineered by methods described in Ward et al. to increase biological half-lives (See U.S. Pat. No. 6,277,375 B1; incorporated herein by reference in its entirety). For example, humanized antibodies of the invention may be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The humanized antibodies of the invention may also be modified by the methods and coupling agents described by Davis et al. (See U.S. Pat. No. 4,179,337; incorporated herein by reference in its entirety) in order to provide compositions that can be injected into the mammalian circulatory system with substantially no immunogenic response.

The present invention also encompasses the use of humanized antibodies or antibody fragments comprising the amino acid sequence of any of the antibodies of the invention with mutations (e.g., one or more amino acid substitutions) in the framework or CDR regions. Preferably, mutations in these humanized antibodies maintain or enhance the avidity and/or affinity of the antibodies for CD32B to which they immunospecifically bind. Standard techniques known to those skilled in the art (e.g., immunoassays) can be used to assay the affinity of an antibody for a particular antigen.

The invention encompasses modification of framework residues of the humanized antibodies of the invention. Framework residues in the framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al., 1988, *Nature* 332:323, which are incorporated herein by reference in their entireties). In certain embodiments, the invention encompases a humanized antibody having phenylalanine at amino acid number 21 of the light chain variable domain framework region 1 (e.g., corresponding to amino acid number 21 of SEQ ID NO:62). In other embodiments, the invention encompases a humanized antibody having one or more of an isoleucine at amino acid number 13 of the heavy chain variable domain framework region 2 (e.g., corresponding to amino acid number 48 of SEQ ID NO:60), a valine at amino acid number 6 of the heavy chain variable domain framework region 3 (e.g., corresponding to amino acid number 72 of SEQ ID NO:60), a valine at amino acid number 7 of the heavy chain variable domain framework region 3 (e.g., corresponding to amino acid number 73 of SEQ ID NO:60), a valine at amino acid number 8 of the heavy chain variable domain framework region 3 (e.g., corresponding to amino acid number 74 of SEQ ID NO:60), or any combination thereof. In still other embodiments, the invention encompasses a humanized antibody having one or more of an isoleucine at amino acid number 13 of the heavy chain variable domain framework region 2 (e.g., corresponding to amino acid number 48 of SEQ ID NO:68), a valine at amino acid number 6 of the heavy chain variable domain framework region 3 (e.g., corresponding to amino acid number 72 of SEQ ID NO:68), an aspartic acid at amino acid number 7 of the heavy chain variable domain framework region 3 (e.g., corresponding to amino acid number 73 of SEQ ID NO:68), a threonine at amino acid number 8 of the heavy chain variable domain framework region 3 (e.g., corresponding to amino acid number 74 of SEQ ID NO:68), or any combination thereof. In certain embodiments, the invention encompasses humanized antibodies comprising at least one amino acid modification (e.g., insertion, deletion, substitution) in one or more of the light chain variable domain framework regions. In a specific example in accordance with this embodiment, the invention encompasses a humanized antibody comprising a modification at amino acid 21 of the light chain variable domain framework region 1, which modification is preferably a substitution with phenylalanine (e.g., corresponding to amino acid number 21 in SEQ ID NO:62). In other embodiments, the invention encompasses humanized antibodies comprising at least one amino acid modification (e.g., insertion, deletion, substitution) in one or more of the heavy chain variable domain framework regions. In a specific example in accordance with this embodiment, the invention encompasses a humanized antibody comprising a modification at amino acid 13 of the heavy chain variable domain framework region 2, which modification is a substitution with isoleucine (e.g., corresponding to amino acid number 48 in SEQ ID NO:60), and/or a modification at amino acid 6 of the heavy chain variable domain framework region 3, which modification is a substitution with valine (e.g., corresponding to amino acid number 72 in SEQ ID NO:60), and/or a modification at amino acid 7 of the heavy chain variable domain framework region 3, which modification is a substitution with valine (e.g., corresponding to amino acid number 73 in SEQ ID NO:60), and/or a modification at amino acid 8 of the heavy chain variable domain framework region 3, which modification is a substitution with valine (e.g., corresponding to amino acid number 74 in SEQ ID NO:60). In another specific example in accordance with this embodiment, the invention encompasses a humanized antibody comprising a modification at amino acid 13 of the heavy chain variable domain framework region 2, which modification is a substitution with isoleucine (e.g., corresponding to amino acid number 48 in SEQ ID NO:68), and/or a modification at amino acid 6 of the heavy chain variable domain framework region 3, which modification is a substitution with valine (e.g., corresponding to amino acid number 72 in SEQ ID NO:68), and/or a modification at amino acid 7 of the heavy chain variable domain framework region 3, which modification is a substitution with aspartic acid (e.g., corresponding to amino acid number 73 in SEQ ID NO:68), and/or a modification at amino acid 8 of the heavy chain variable domain framework region 3, which modification is a substitution with threonine (e.g., corresponding to amino acid number 74 in SEQ ID NO:68). The invention further encompasses any combination of the foregoing amino acid modifications the heavy and or light chain variable domain framework regions.

The present invention encompasses humanized antibodies comprising modifications preferably, in the Fc region that modify the binding affinity of the antibody to one or more FcγR. Methods for modifying antibodies with modified binding to one or more FcγR are known in the art, see, e.g., International Publication Nos. WO 04/063351, WO 04/029207, WO 04/029092, WO 04/028564, WO 99/58572, WO 99/51642, WO 98/23289, WO 89/07142, WO 88/07089; U.S. Publication serial Nos. 2005/0037000; and 2005/0064514 and U.S. Pat. Nos. 5,843,597 and 5,642,821, each of which is incorporated herein by reference in their entirety. The invention encompasses any of the mutations disclosed in International Publication Nos. WO 04/063351, WO 04/029207, WO 04/029092, WO 04/028564, WO 99/58572, WO 99/51642, WO 98/23289, WO 89/07142, WO 88/07089; U.S. Patent Application Publication Nos. 2005/0037000; and 2005/0064514 and U.S. Pat. Nos. 5,843,597 and 5,642,821, each of which is incorporated herein by reference in their entirety. The invention also encompasses any of the mutations disclosed in U.S. patent application Ser. Nos. 10/902,588 (filed Jul. 28, 2004) and 11/271,140 (filed Nov. 10, 2005), and U.S. Provisional Application Nos. 60/707,419; and 60/781, 564 filed on Aug. 10, 2005, and Mar. 10, 2006, respectively, each of which is incorporated herein by reference in their entirety. In some embodiments, the invention encompasses antibodies that have altered affinity for an activating FcγR, e.g., FcγRIIIA. Preferably such modifications also have an altered Fc-mediated effector function. Modifications that affect Fc-mediated effector function are well known in the art (See U.S. Pat. No. 6,194,551, which is incorporated herein by reference in its entirety). In a specific embodiment, the amino acids that can be modified in accordance with the method of the invention include, but are not limited to, Proline 329, Proline 331, and Lysine 322. In certain embodiments, Proline 329, Proline 331 and Lysine 322 are replaced with alanine; however, substitution with any other amino acid is contemplated. See International Publication No.: WO 00/42072 and U.S. Pat. No. 6,194,551 which are incorporated herein by reference in their entirety. In preferred embodiments, the amino acids that are modified in accordance with the methods of the invention comprise the amino acids at positions 243, 292, 300, 305 and 396; in a specific example in accordance with this embodiment, the amino acids that are modified are phenylalanine 243, arginine 292, tyrosine 300, valine 305 and proline 396, and are preferably replaced with leucine, proline, leucine, isoleucine and leucine, respectively.

In one particular embodiment, the modification of the Fc region comprises one or more mutations in the Fc region. The one or more mutations in the Fc region may result in an antibody with an altered antibody-mediated effector function, an altered binding to other Fc receptors (e.g., Fc activation receptors), an altered ADCC activity, an altered C1q binding activity, an altered complement dependent cytotoxicity activity, an altered phagocytic activity, or any combination thereof.

The invention also provides humanized antibodies with altered oligosaccharide content. Oligosaccharides, as used herein, refer to carbohydrates containing two or more simple sugars and the two terms may be used interchangeably herein. Carbohydrate moieties of the instant invention will be described with reference to commonly used nomenclature in the art. For a review of carbohydrate chemistry, see, e.g., Hubbard et al., 1981 *Ann. Rev. Biochem.*, 50: 555-583, which is incorporated herein by reference in its entirety. This nomenclature includes, for example, Man which represents mannose; GlcNAc which represents 2-N-acetylglucosamine; Gal which represents galactose; Fuc for fucose and Glc for glucose. Sialic acids are described by the shorthand notation NeuNAc for 5-N-acetylneuraminic acid, and NeuNGc for 5-glycolneuraminic.

In general, antibodies contain carbohydrate moieties at conserved positions in the constant region of the heavy chain, and up to 30% of human IgGs have a glycosylated Fab region. IgG has a single N-linked biantennary carbohydrate structure at Asn 297 which resides in the CH2 domain (Jefferis et al., 1998, *Immunol. Rev.* 163: 59-76; Wright et al., 1997, *Trends Biotech* 15: 26-32). Human IgG typically has a carbohydrate of the following structure; GlcNAc(Fucose)-GlcNAc-Man-(ManGlcNAc)$_2$. However variations among IgGs in carbohydrate content does occur which leads to altered function, see, e.g., Jassal et al., 2001 *Biochem. Biophys. Res. Commun.* 288: 243-9; Groenink et al., 1996 *J. Immunol.* 26: 1404-7; Boyd et al., 1995 *Mol. Immunol.* 32: 1311-8; Kumpel et al., 1994, *Human Antibody Hybridomas*, 5: 143-51. The invention encompasses humanized antibodies comprising a variation in the carbohydrate moiety that is attached to Asn 297. In one embodiment, the carbohydrate moiety has a galactose and/or galactose-sialic acid at one or both of the terminal GlcNAc and/or a third GlcNac arm (bisecting GlcNAc). Each of the foregoing references is incorporated herein by reference in its entirety.

In some embodiments, the humanized antibodies of the invention are substantially free of one or more selected sugar groups, e.g., one or more sialic acid residues, one or more galactose residues, one or more fucose residues. An antibody that is substantially free of one or more selected sugar groups may be prepared using common methods known to one skilled in the art, including, for example, recombinantly producing an antibody of the invention in a host cell that is defective in the addition of the selected sugar groups(s) to the carbohydrate moiety of the antibody, such that about 90-100% of the antibody in the composition lacks the selected sugar group(s) attached to the carbohydrate moiety. Alternative methods for preparing such antibodies include, for example, culturing cells under conditions which prevent or reduce the addition of one or more selected sugar groups, or post-translational removal of one or more selected sugar groups.

In a specific embodiment, the invention encompasses a method of producing a substantially homogenous antibody preparation, wherein about 80-100% of the antibody in the composition lacks a fucose on its carbohydrate moiety, e.g., the carbohydrate attachment on Asn 297. The antibody may be prepared, for example, by (a) use of an engineered host cell that is deficient in fucose metabolism such that it has a reduced ability to fucosylate proteins expressed therein; (b) culturing cells under conditions which prevent or reduce fusocylation; (c) post-translational removal of fucose, e.g., with a fucosidase enzyme; or (d) purification of the antibody so as to select for the product which is not fucosylated. Most preferably, a nucleic acid encoding the desired antibody is expressed in a host cell that has a reduced ability to fucosylate the antibody expressed therein. Preferably, the host cell is a dihydrofolate reductase deficient chinese hamster ovary cell (CHO), e.g., a Lee 13 CHO cell (lectin resistant CHO mutant cell line; (see, e.g., U.S. Patent Application Publication No. 2003/0115614; PCT Publication No. WO 00/61739; European Patent Application EP 1 229 125; Ribka & Stanley, 1986, *Somatic Cell & Molec. Gen.* 12(1): 51-62; Ripka et al., 1986 *Arch. Biochem. Biophys.* 249(2): 533-45); each of which is incorporated by reference herein in its entirety), or a CHO-K1 cell, a DUX-B11 cell, a CHO-DP12 cell or a CHO-DG44 cell, which has been modified so that the antibody is not substantially fucosylated. Thus, the cell may display altered expression and/or activity for the fucosyltransferase enzyme, or another enzyme or substrate involved in adding fucose to the N-linked oligosaccharide so that the enzyme has a diminished activity and/or reduced expression level in the cell. For methods to produce antibodies with altered fucose content, see, e.g., WO 03/035835 and Shields et al., 2002, *J. Biol. Chem.* 277(30): 26733-40; both of which are incorporated herein by reference in their entirety.

In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields R. L. et al., 2001, *J. Biol. Chem.* 277 (30): 26733-40; Davies J. et al., 2001, *Biotechnology & Bioengineering*, 74(4): 288-294; each of which is incorporated herein by reference in its entirety). In another specific embodiment, the altered carbohydrate modifications enhance the binding of antibodies of the invention to FcγRIIB receptor. Altering carbohydrate modifications in accordance with the methods of the invention includes, for example, increasing the carbohydrate content of the antibody or decreasing the carbohydrate content of the antibody. Methods of altering carbohydrate contents are known to those skilled in the art, see, e.g., Wallick et al., 1988, *Journal of Exp. Med.* 168(3): 1099-1109; Tao et al., 1989 Journal of Immunology, 143(8): 2595-2601; Routledge et al., 1995 *Transplantation*, 60(8): 847-53; Elliott et al. 2003; *Nature Biotechnology*, 21: 414-21; Shields et al. 2002 *Journal of Biological Chemistry*, 277(30): 26733-40; all of which are incorporated herein by reference in their entirety.

In some embodiments, the invention encompasses humanized antibodies comprising one or more glycosylation sites, so that one or more carbohydrate moieties are covalently attached to the antibody. In other embodiments, the invention encompasses humanized antibodies comprising one or more glycosylation sites and one or more modifications in the Fc region, such as those disclosed supra and those known to one skilled in the art. In preferred embodiments, the one or more modifications in the Fc region enhance the affinity of the antibody for an activating FcγR, e.g., FcγRIIIA, relative to the antibody comprising the wild type Fc regions. Humanized antibodies of the invention with one or more glycosylation sites and/or one or more modifications in the Fc region have an enhanced antibody mediated effector function, e.g., enhanced ADCC activity. In some embodiments, the invention further comprises humanized antibodies comprising one or more modifications of amino acids that are directly or indirectly known to interact with a carbohydrate moiety of the antibody, including, but not limited to, amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al., 1995 *Immunology Letters*, 44: 111-7, which is incorporated herein by reference in its entirety.

The invention encompasses humanized antibodies that have been modified by introducing one or more glycosylation sites into one or more sites of the antibodies, preferably without altering the functionality of the antibody, e.g., binding activity to FcγRIIB. Glycosylation sites may be introduced into the variable and/or constant region of the antibodies of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The antibodies of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention, is the amino acid sequence: Asn-X-Thr/Ser, wherein X may be any amino acid and Thr/Ser indicates a threonine or a serine. Such a site or sites may be introduced into an antibody of the invention using methods well known in the art to which this invention pertains. See, for example, "In Vitro Mutagenesis," Recombinant DNA: A Short Course, J. D. Watson, et al. W.H. Freeman and Company, New York, 1983, chapter 8, pp. 106-116, which is incorporated herein by reference in its entirety. An exemplary method for introducing a glycosylation site into an antibody of the invention may comprise: modifying or mutating an amino acid sequence of the antibody so that the desired Asn-X-Thr/Ser sequence is obtained.

In some specific embodiments, the invention encompasses modified humanized FcγRIIB antibodies wherein the N-glysosylation consensenus site $Asn_{50}$-Val-Ser of the CDR2 region has been modified, so that the glycosylation site at position 50 is eliminated. Although not intending to be bound by a particular mechanism of action, removal of the glycosylation site may limit potential variation in production of the antibody as well as potential immunogenicity in a pharmaceutical application. In a specific embodiment, the invention encompasses a humanized FcγRIIB antibody wherein the amino acid at position 50 has been modified, e.g., deleted or substituted. In another specific embodiment, the invention further encompasses an amino acid modification, e.g., deletion or substitution, at position 51. In one specific embodiment, the invention encompasses a humanized FcγRIIB antibody wherein the amino acid at position 50 has been replaced with tyrosine. In another more specific embodiment, the invention encompasses a humanized FcγRIIB antibody wherein the amino acid at position 50 has been replaced with tyrosine and the amino acid at position 51 has been replaced with alanine.

In some embodiments, the invention encompasses methods of modifying the carbohydrate content of an antibody of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Patent Application Publication No. US 2002/0028486; WO 03/035835; U.S. Publication No. 2003/0115614; U.S. Pat.

No. 6,218,149; U.S. Pat. No. 6,472,511; all of which are incorporated herein by reference in their entirety. In other embodiments, the invention encompasses methods of modifying the carbohydrate content of an antibody of the invention by deleting one or more endogenous carbohydrate moieties of the antibody.

The invention further encompasses methods of modifying an effector function of an antibody of the invention, wherein the method comprises modifying the carbohydrate content of the antibody using the methods disclosed herein or known in the art.

Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. Preferably, the derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more predicted nonessential amino acid residues.

The present invention also encompasses humanized antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody produced by clone 2B6, 3H7, 1D5, 2E1, 2H9, 2D11, or 1F2, with ATCC accession numbers PTA-4591, PTA-4592, PTA-5958, PTA-5961, PTA-5962, PTA-5960, and PTA-5959, respectively. In preferred embodiments of the invention, the humanized antibody or fragment thereof comprises a heavy chain having the amino acid sequence SEQ ID NO:70 and/or light chain having the amino acid sequence SEQ ID NO:66. The present invention further encompasses antibodies or fragments thereof that specifically bind FcγRIIB with greater affinity than said antibody or fragment thereof binds FcγRIIA and/or bind to FcγRIIB and block the Fc binding domain of FcγRIIB, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the mouse monoclonal antibody produced by clone 2B6, 3H7, 1D5, 2E1, 2H9, 2D-11, or 1F2, with ATCC accession numbers PTA-4591, PTA-4592, PTA-5958, PTA-5961, PTA-5962, PTA-5960, and PTA-5959, respectively. The determination of percent identity of two amino acid sequences can be determined by any method known to one skilled in the art, including BLAST protein searches.

The present invention also encompasses the use of humanized antibodies or antibody fragments that specifically bind FcγRIIB with greater affinity than said antibodies or fragments thereof binds FcγRIIA and/or bind to FcγRIIB and block the Fc binding domain of FcγRIIB, wherein said antibodies or antibody fragments are encoded by a nucleotide sequence that hybridizes to the nucleotide sequence of the mouse monoclonal antibody produced by clone 2B6, 3H7, 1D5, 2E1, 2H9, 2D11, or 1F2, with ATCC accession numbers PTA-4591, PTA-4592, PTA-5958, PTA-5961, PTA-5962, PTA-5960, and PTA-5959, respectively, under stringent conditions. In a specific embodiments, the invention encompasses the use of humanized antibodies or antibody fragments that specifically bind FcγRIIB with greater affinity than said antibodies or fragments thereof binds FcγRIIA and/or bind to FcγRIIB and block the Fc binding domain of FcγRIIB, wherein said antibodies or antibody fragments are encoded by a nucleotide sequence that hybridizes under stringent conditions to the nucleotide sequence encoding a heavy chain variable domain or the complete heavy chain of a humanized 2B6 antibody of the invention, e.g., SEQ ID NO:67 or SEQ ID NO:69, respectively. In yet other embodiments, the invention encompasses the use of humanized antibodies or antibody fragments that specifically bind FcγRIIB with greater affinity than said antibodies or fragments thereof binds FcγRIIA and/or bind to FcγRIIB and block the Fc binding domain of FcγRIIB, wherein said antibodies or antibody fragments are encoded a nucleotide sequence that hybridizes under stringent conditions to the nucleotide sequence encoding the light chain variable domain or the light chain of a humanized 2B6 antibody of the invention, e.g., SEQ ID NO:61 or SEQ ID NO:65, respectively. In a preferred embodiment, the invention provides antibodies or fragments thereof that specifically bind FcγRIIB with greater affinity than said antibodies or fragments thereof bind FcγRIIA, said antibodies or antibody fragments comprising a variable light chain and/or variable heavy chain encoded by a nucleotide sequence that hybridizes under stringent conditions to the nucleotide sequence of the variable light chain and/or variable heavy chain of the mouse monoclonal antibody produced by clone 2B6, 3H7, 1D5, 2E1, 2H9, 2D11, or 1F2, with ATCC accession numbers PTA-4591, PTA-4592, PTA-5958, PTA-5961, PTA-5962, PTA-5960, and PTA-5959, respectively, under stringent conditions. In another preferred embodiment, the invention provides antibodies or fragments thereof that specifically bind FcγRIIB with greater affinity than said antibodies or fragments thereof bind FcγRIIA, said antibodies or antibody fragments comprising one or more CDRs encoded by a nucleotide sequence that hybridizes under stringent conditions to the nucleotide sequence of one or more CDRs of the mouse monoclonal antibody produced by clone 2B6, 3H7, 1D5, 2E1, 2H9, 2D11, or 1F2, with ATCC accession numbers PTA-4591, PTA-4592, PTA-5958, PTA-5961, PTA-5962, PTA-5960, and PTA-5959, respectively. Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3, incorporated herein by reference).

6.1.1 Antibody Conjugates

The present invention encompasses humanized antibodies recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. Humanized antibodies may be used for example to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., PCT Publication No. WO 93/21232; EP 439,095; Naramura et al., 1994 *Immunol. Lett.,* 39:91-99; U.S. Pat. No. 5,474,981; Gillies et al., 1992 *Proc. Natl. Acad. Sci. USA,* 89:1428-1432; and Fell et al., 1991, *J. Immunol.,* 146:2446-2452, all of which are incorporated herein by reference in their entireties.

Further, a humanized antibody may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin (i.e., PE-40), or diphtheria toxin, ricin, gelonin, and pokeweed antiviral protein, a protein such as tumor necrosis factor, interferons including, but not limited to, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, e.g., PCT Publication No. WO 97/34911), Fas Ligand (Takahashi et al., 1994 *J. Immunol.,* 6:1567-1574), and VEGI (PCT Publication No. WO 99/23105), a thrombotic agent or an anti-angiogenic agent (e.g., angiostatin or endostatin), or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), macrophage colony stimulating factor, ("M-CSF"), or a growth factor (e.g., growth hormone ("GH"); a protease, or a ribonuclease. Each of the foregoing references is incorporated herein by reference in its entirety.

Humanized antibodies can be fused to marker sequences, such as a peptide, to facilitate purification. In preferred embodiments, the marker amino acid sequence is a hexa-histidine peptide, such as the tag provided in a pQE™ vector (QIAGEN, Inc., 9259 Eton Avenue, Chatsworth, Calif., 91311), among others, many of which are commercially available. As described in Gentz et al., 1989 *Proc. Natl. Acad. Sci. USA,* 86:821-824 (incorporated herein by reference in its entirety), for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984 *Cell,* 37:767) and the "flag" tag (Knappik et al., 1994 *Biotechniques,* 17(4):754-761) (both of which references are incorporated herein by reference in its entirety).

The present invention further includes compositions comprising heterologous polypeptides fused or conjugated to antibody fragments. For example, the heterologous polypeptides may be fused or conjugated to a Fab fragment, Fd fragment, Fv fragment, F(ab)$_2$ fragment, or portion thereof. Methods for fusing or conjugating polypeptides to antibody portions are known in the art. See, e.g., U.S. Pat. Nos. 5,336,603, 5,622,929, 5,359,046, 5,349,053, 5,447,851, and 5,112,946; EP 307,434; EP 367,166; International Publication Nos. WO 96/04388 and WO 91/06570; Ashkenazi et al., 1991, *Proc. Natl. Acad. Sci. USA* 88: 10535-10539; Zheng et al., 1995, *J. Immunol.* 154:5590-5600; and Vil et al., 1992, *Proc. Natl. Acad. Sci. USA* 89:11337-11341 (said references incorporated by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.* 8:724-33; Harayama, 1998, *Trends Biotechnol.* 16:76; Hansson, et al., 1999, *J. Mol. Biol.* 287:265; and Lorenzo and Blasco, 1998, *BioTechniques* 24:308 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to FcγRIIB may be recombined with one or more components, motifs, sections, parts, domains, fragments, etc. of one or more heterologous molecules.

The present invention also encompasses humanized antibodies conjugated to a diagnostic or therapeutic agent or any other molecule for which serum half-life is desired to be increased. The humanized antibodies can be used diagnostically to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 (incorporated herein by reference in its entirety) for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$in, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

An antibody may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Moreover, a humanized antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraaza-cyclododecane-N,N',N'',N'''-tetraacetic acid (DOTA) which can be attached to the antibody via a linker molecule. Such linker molecules are commonly known in the art and described in Denardo et al., 1998, *Clin Cancer Res.* 4:2483-90; Peterson et al., 1999, *Bioconjug. Chem.* 10:553; and Zimmerman et al., 1999, *Nucl. Med. Biol.* 26:943-50 each incorporated by reference in their entireties.

Techniques for conjugating such therapeutic moieties to antibodies are well known; see, e.g., Arnon et al., "Monoclonal Antibodies For Immunotargeting Of Drugs In Cancer Therapy", in *Monoclonal Antibodies And Cancer Therapy*, Reisfeld et al. (eds.), 1985, pp. 243-56, Alan R. Liss, Inc.); Hellstrom et al., "Antibodies For Drug Delivery", in *Controlled Drug Delivery* (2nd Ed.), Robinson et al. (eds.), 1987, pp. 623-53, Marcel Dekker, Inc.); Thorpe, "Antibody Carriers Of Cytotoxic Agents In Cancer Therapy: A Review", in *Monoclonal Antibodies '84: Biological And Clinical Applications*, Pinchera et al. (eds.), 1985, pp. 475-506); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), 1985, pp. 303-16, Academic Press; and Thorpe et al., *Immunol. Rev.*, 62:119-58, 1982; each incorporated by reference in its entirety.

An antibody or fragment thereof, with or without a therapeutic moiety conjugated to it, administered alone or in combination with cytotoxic factor(s) and/or cytokine(s) can be used as a therapeutic.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

6.2 Preparation Of FcγRIIB Humanized Antibodies

The invention encompasses nucleotide sequences that encode the CDR-grafted heavy and light chains, cloning and expression vectors containing the nucleotide sequences, host cells transformed with the nucleotide sequences, and methods for the production of the CDR-grafted chains and antibody molecules comprising the nucleotide sequences in the transformed host cells. In specific embodiments, the invention encompasses any of the nucleotide sequences of SEQ ID NOS. 17, 19, 21, 23, 36 or 45.

The invention encompasses donor amino acid sequences, which encode antibodies that bind FcγRIIB with a greater affinity that FcγRIIA, such as those disclosed in U.S. Provisional Application No. 60/403,366, filed on Aug. 14, 2002 and U.S. Patent Application Publication No. 2004/0185045, both of which are incorporated herein by reference in their entireties. In a specific embodiment, the donor amino acid sequence encodes for the monoclonal antibody produced from clone 2B6, 3H7, 1D5, 2E1, 2H9, 2D11, or 1F2, with ATCC accession numbers PTA-4591, PTA-4592, PTA-5958, PTA-5961, PTA-5962, PTA-5960, and PTA-5959, respectively, or other monoclonal antibodies produced by immunization methods of the invention as disclosed in U.S. Provisional Application No. 60/403,366, filed on Aug. 14, 2002 and U.S. Patent Application Publication No. 2004/0185045, both of which are incorporated herein by reference in their entireties. The invention also encompass polynucleotides that encode for donor amino acid sequences that hybridize under various stringency, e.g., high stringency, intermediate or low stringency conditions, to polynucleotides that encode for the monoclonal antibody produced from clone 2B6, 3H7, 1D5, 2E1, 2H9, 2D11, or 1F2, with ATCC accession numbers PTA-4591, PTA-4592, PTA-5958, PTA-5961, PTA-5962, PTA-5960, and PTA-5959, respectively, or other monoclonal antibodies produced by immunization methods of the invention as disclosed in U.S. Provisional Application No. 60/403, 366, filed on Aug. 14, 2002 and U.S. Patent Application Publication No. 2004/0185045; both of which are incorporated herein by reference in their entirety. The hybridization can be performed under various conditions of stringency. By way of example and not limitation, procedures using conditions of low stringency are as follows (see also Shilo and Weinberg, 1981, *Proc. Natl. Acad. Sci. U.S.A.* 78, 6789-6792; incorporated herein by reference in its entirety). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20× $10^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations). By way of example and not limitation, procedures using conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987-1997, Current Protocols, © 1994-1997 John Wiley and Sons, Inc.; see especially, Dyson, 1991, "Immobilization of nucleic acids and hybridization analysis," In: Essential Molecular Biology: A Practical Approach, Vol. 2, T. A. Brown, ed., pp. 111-156, IRL Press at Oxford University Press, Oxford, UK; each of which reference is incorporated herein by reference in its entirety). The polynucleotides may be obtained, and the nucleotide sequence of the polynucleotides determined, by any method known in the art.

DNA sequences which encode the acceptor amino acid sequences may be obtained by any method known to one skilled in the art. For example, DNA sequences coding for preferred human acceptor framework sequences include but are not limited to FR segments from the human germline VH segment VH1-8 and JH6 and the human germline VL segment VK-A26 and JK4.

In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, *J. Mol. Biol.* 278: 457-479 for a listing of human framework regions; incorporated herein by reference in its entirety). Preferably, the polynucleotide generated by the combination of the framework regions and CDRs encodes an antibody that specifically binds to FcγRIIB with greater affinity than said antibody binds FcγRIIA. Preferably, as discussed supra, one or more amino acid substitutions may be made within the framework regions, and, preferably, the amino acid substitutions improve binding of the antibodies of the invention to FcγRIIB.

In another embodiment, human libraries or any other libraries available in the art, can be screened by standard techniques known in the art, to clone the nucleic acids encoding the antibodies of the invention.

The humanized antibodies of the present invention may be produced by any method known in the art useful for the production of polypeptides, e.g., in vitro synthesis, recombinant DNA production, and the like. Preferably, the humanized antibodies are produced by recombinant DNA technology. The humanized FcγRIM specific antibodies of the invention may be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757; all of which are incorporated herein by reference in their entireties. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W.H. Freeman (1992) (both of which are incorporated herein by reference in their entirety. Additional information concerning the generation, design and expression of recombinant antibodies can be found in Mayforth, Designing Antibodies, Academic Press, San Diego (1993).

An exemplary process for the production of the recombinant humanized antibodies of the invention may comprise the following: a) constructing, by conventional molecular biology methods, an expression vector comprising an operon that encodes an antibody heavy chain in which the CDRs and a minimal portion of the variable region framework that are required to retain donor antibody binding specificity are derived from a non-human immunoglobulin, such as the murine FcγRIIB monoclonal antibody, and the remainder of the antibody is derived from a human immunoglobulin, thereby producing a vector for the expression of a humanized antibody heavy chain; b) constructing, by conventional molecular biology methods, an expression vector comprising an operon that encodes an antibody light chain in which the CDRs and a minimal portion of the variable region framework that are required to retain donor antibody binding specificity are derived from a non-human immunoglobulin, such as the murine FcγRIIB monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized anti-FcγRIIB antibodies; and d) culturing the transfected cell by conventional cell culture techniques so as to produce humanized anti-FcγRIIB antibodies. Host cells may be cotransfected with two expression vectors of the invention, the first vector containing an operon encoding a heavy chain derived polypeptide and the second containing an operon encoding a light chain derived polypeptide. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant antibody of the invention may be either a bacterial cell such as *Escherichia coli*, or preferably a eukaryotic cell. Preferably, a mammalian cell such as a chinese hamster ovary cell or HEK-293 cells, may be used. The choice of expression vector is dependent upon the choice of host cell, and may be selected so as to have the desired expression and regulatory characteristics in the selected host cell. Other cell lines that may be used include, but are not limited to, CHO-K1, NSO, and PER.C6 (Crucell, Leiden, Netherlands).

In a specific embodiment the method for producing a humanized FcγRIIB 2B6 antibody comprises the following: RNA from hybridoma cells of 2B6 is converted to cDNA and the VH and VL segments are PCR amplified using, for example, the RLM-RACE kit (Ambion, Inc.). Gene specific primers for the VH are used. Examples of such primers for VH include: SJ15R, SEQ ID NO: 47 (5' GGT CAC TGT CAC TGG CTC AGG G 3') and SJ16R, SEQ ID NO: 48 (5' AGG CGG ATC CAG GGG CCA GTG GAT AGA C 3'), and for VL include SJ17R, SEQ ID NO: 49(5' GCA CAC GAC TGA GGC ACC TCC AGA TG 3') and SJ18R, SEQ ID NO. 50 (5'CGG CGG ATC CGA TGG ATA CAG TTG GTG CAG CAT C 3'). The RACE product is inserted into a plasmid, e.g., pCR2.1-TOPO using a TOPO TA Cloning kit (Invitrogen, Inc.). The resulting plasmids are then subjected to DNA sequencing to determine the VH and VL sequences for 2B6.

The resulting sequences are translated and the predicted amino acid sequence determined for each. From these sequences the framework (FR) and complementarity determining (CDR) regions are identified as defined by Kabat. The mouse VH is then joined to a human C-Gammal constant region and an Ig leader sequence and inserted into pCI-neo for mammalian expression. The mouse VL is joined to a human C-kappa segment and an Ig leader sequence and also cloned into pCI-neo for mammalian expression. The humanized 2B6 VH consists of the FR segments from the human germline VH segment VH1-18 and JH6, and the CDR regions of the 2B6 VH. The humanized 2B6 VL consists of the FR segments of the human germline VL segment VK-A26 and JK4, and the CDR regions of 2B6 VL. The humanized VH and VL segments are assembled de novo from oligonucleotides combined and amplified by PCR. The resulting fragment is then combined by PCR with a leader sequence and the appropriate constant region segment cloned into the expression vector pCI-neo. The DNA sequence of the resulting plasmids is confirmed by sequence analysis. After this procedure light chain segments having predicted humanized 2B6 VL sequence are identified. Representative plasmids, pMGx608 (containing a humanized 2B6 heavy chain) and pMGx611 (containing a humanized 2B6 light chain with $N_{50} \rightarrow Y$ and $V_{51} \rightarrow A$ in CDR2), having ATCC Accession numbers PTA-5963 and PTA-5964, respectively, were deposited under the provisions of the Budapest Treaty with the American Type Culture Collection (10801 University Blvd., Manassas, Va. 20110-2209) on May 7, 2004, respectively, and are incorporated herein by reference.

The general methods for construction of the vectors of the invention, transfection of cells to produce the host cell of the invention, culture of cells to produce the antibody of the invention are all conventional molecular biology methods. Likewise, once produced, the recombinant humanized antibodies of the invention may be purified by standard procedures of the art, including cross-flow filtration, ammonium sulphate precipitation, affinity column chromatography, gel electrophoresis and the like.

The humanized FcγRIIB specific antibodies of the present invention may be used in conjunction with, or attached to, other antibodies (or parts thereof) such as human or humanized monoclonal antibodies. These other antibodies may be reactive with other markers (epitopes) characteristic for the disease against which the antibodies of the invention are directed or may have different specificities chosen, for example, to recruit molecules or cells of the human immune system to the diseased cells. The antibodies of the invention (or parts thereof) may be administered with such antibodies (or parts thereof) as separately administered compositions or as a single composition with the two agents linked by conventional chemical or by molecular biological methods. Additionally the diagnostic and therapeutic value of the antibodies of the invention may be augmented by labelling the humanized antibodies with labels that produce a detectable signal (either in vitro or in vivo) or with a label having a therapeutic property. Some labels, e.g., radionucleotides, may produce a detectable signal and have a therapeutic property. Examples of radionuclide labels include, but are not limited to, $^{125}I$, $^{131}I$, and $^{14}C$. Examples of other detectable labels include a fluorescent chromophore such as fluorescein, phycobiliprotein or tetraethyl rhodamine for fluorescence microscopy, an enzyme which produces a fluorescent or colored product for detection by fluorescence, absorbance, visible color or agglutination, which produces an electron dense product for demonstration by electron microscopy; or an electron dense molecule such as ferritin, peroxidase or gold beads for direct or indirect electron microscopic visualization. Labels having therapeutic properties include drugs for the treatment of cancer, such as methotrexate and the like.

The subject invention provide numerous humanized antibodies specific for the FcγRIIB based on the discovery that the CDR regions of the murine monoclonal antibody could be spliced into a human acceptor framework so as to produce a humanized recombinant antibody specific for the FcγRIIB. Preferred humanized FcγRIIB specific antibodies contain an additional change in the framework region (or in other regions) to increasing binding for FcγRIIB. Particularly preferred embodiments of the invention are the exemplified humanized antibody molecules that have superior binding properties for FcγRIIB.

The invention encompasses standard recombinant DNA methods for preparing DNA sequences which code for the CDR-grafted antibodies of the invention. DNA sequences may be synthesized completely or in part using oligonucleotide synthesis techniques. Methods for oliogonucleotide directed synthesis are well known in the art. The invention further encompasses site-directed mutagenesis methods such as those known in the art.

Any suitable host cell/vector system may be used for expression of the DNA sequences coding for the CDR-grafted heavy and light chains. Bacterial, e.g., E. coli, and other microbial systems may be used, in particular for expression of antibody fragments such as Fab and (Fab')2 fragments, and especially FV fragments and single chain antibody fragments, e.g., single chain FVs. Eucaryotic systems, e.g., mammalian host cell expression systems, may be used for production of larger CDR-grafted antibody products, including complete antibody molecules. Suitable mammalian host cells include CHO cells and myeloma or hybridoma cell lines. Other cell lines that may be used include, but are not limited to, CHO-K1, NSO, and PER.C6 (Crucell, Leiden, Netherlands).

The donor murine antibodies of the invention may be produced using any method known in the art, including those disclosed in U.S. Patent Application Publication Nos. 2004/0185045; 2005/02157667; 2005/060213; and 2006/0013810; International Publication Nos. WO 04/016750; WO 2005/110474; and WO 2005/115452; and Provisional Application No. 60/636,663 (filed Dec. 15, 2004); each of which are incorporated herein by reference in their entireties.

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and at least a portion of the hinge region of the heavy chain.

For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., *J. Immunol. Methods*, 182:41-50, 1995; Ames et al., *J. Immunol. Methods*, 184:177-186, 1995; Kettleborough et al., *Eur. J. Immunol.*, 24:952-958, 1994; Persic et al., *Gene*, 187:9-18, 1997; Burton et al., *Advances in Immunology*, 57:191-280, 1994; PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT Publication WO 92/22324; Mullinax et al., *BioTechniques*, 12(6):864-869, 1992; and Sawai et al, *AJRI*, 34:26-34, 1995; and Better et al., *Science*, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., *Methods in Enzymology*, 203:46-88, 1991; Shu et al., *Proc. Natl. Acad. Sci. USA*, 90:7995-7999, 1993; and Skerra et al., *Science*, 240:1038-1040, 1988 (each of which is incorporated by reference in its entirety).

Phage display technology can be used to increase the affinity of an antibody of the invention for FcγRIIB. This technique would be useful in obtaining high affinity antibodies that could be used in the combinatorial methods of the invention. This technology, referred to as affinity maturation, employs mutagenesis or CDR walking and re-selection using FcγRIIB or an antigenic fragment thereof to identify antibodies that bind with higher affinity to the antigen when compared with the initial or parental antibody (See, e.g., Glaser et al., 1992, *J. Immunology* 149:3903; incorporated by reference in its entirety). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (See Wu et al., 1998, *Proc Natl. Acad. Sci. USA* 95:6037; Yelton et al., 1995, *J. Immunology* 155:1994; each of which is incorporated by reference in its entirety). CDR walking which randomizes the light chain is also possible (See Schier et al., 1996, *J. Mol. Bio.* 263:551; incorporated by reference in its entirety).

6.2.1 Screening for Biological Properties

The humanized antibodies of the invention may be characterized for specific binding to FcγRIIB using any immunological or biochemical based method known in the art for characterizing, including quantitating the interaction of the antibody to FcγRIIB. Specific binding of a humanized antibody of the invention to FcγRIIB may be determined, for example, using immunological or biochemical based methods including, but not limited to, an ELISA assay, surface plasmon resonance assays, immunoprecipitation assay, affinity chromatography, fluorescence activated cell sorting (FACS), and equilibrium dialysis. Immunoassays which can be used to analyze immunospecific binding and cross-reactivity of the antibodies of the invention include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety).

Humanized antibodies of the invention may be characterized for binding to FcγRIIB using an in vitro ELISA assay. An exemplary ELISA assay for use in the methods of the invention may comprise the following: 2.5 ng/well of soluble FcγRIIb-Fc fusion protein which is prepared in accordance with methods disclosed in U.S. Provisional Application No. 60/439,709 and U.S. application Ser. No. 10/756,153, both of which are incorporated herein by reference in its entirety, is captured on 96-well Maxisorp plates by mouse anti-FcγRIIb antibody 3H7 at room temperature for 1 hour. A serial of two-fold dilution of conditioned medium of ch2B6 or hu2B6Hc/Ch2B6Lc starting from 25 ng/well is added to the each well. The plate is incubated at room temperature for 1 hour, then binding is detected by HRP conjugated F(ab')$_2$ goat anti human IgG F(ab)'2 specific secondary antibody. After incubation with the secondary antibody for approximately 45 minutes, the plate is developed using a TMB substrate. After 5 minutes incubation, the reaction is stopped by 1% $H_2SO_4$. The OD 450 nm is read by SOFTmax program. Between each step, the plates are washed 3 times with PBS/0.1% Tween 20. Plates are blocked by 0.5% BSA in PBS/0.1% Tween 20 for 30 mins at room temperature before adding soluble FcγRIIb-Fc.

Humanized antibodies of the invention may be characterized for binding to FcγRIIB expressing cells, such as Daudi cells and Rajii cells using fluorescence activated cell sorting (FACS), using any of the techniques known to those skilled in the art. Flow sorters are capable of rapidly examining a large number of individual cells (e.g., 10-100 million cells per hour) (Shapiro et al., *Practical Flow Cytometry*, 1995). Flow cytometers for sorting and examining biological cells are well known in the art. Known flow cytometers are described, for example, in U.S. Pat. Nos. 4,347,935; 5,464,581; 5,483,469; 5,602,039; 5,643,796; and 6,211,477; the entire contents of which are incorporated by reference herein. Other known flow cytometers are the FACS Vantage™ system manufactured by Becton Dickinson and Company, and the COPAS™ system manufactured by Union Biometrica. An exemplary FACS analysis for characterizing the humanized antibodies of the invention may comprise the following: Approximately $10^6$ FcγRIIB expressing cells, e.g., Daudi cells and Rajii cells, are washed at least once with a buffer such as PBS. Primary antibodies (e.g., Ch2B6, Hu2B6Hc/ch2B6Lc, human IgG1) are diluted, e.g., into 0.5, 0.1, 0.02 µg/mL in PBS/1% BSA and 100 µl of diluted antibodies are transferred to the cells. After 30 mins incubation at 4° C., cells are washed once with 1 ml PBS/1% BSA. PE conjugated F(ab')$_2$ fragment of goat anti human IgG Fc specific (Jackson ImmunoReseach, Inc.)

is used as secondary antibody at 1:1000 dilution. After 30 mins incubation at 4° C., the cells are washed once with 1 ml PBS/1% BSA. Then the cells are resuspended in 500 µl of PBS/1% BSA and subjected to FACS analysis. Other cell lines that may be used in the methods of the invention include, but are not limited to, CHO-K1 (hamster cell line) cells transfected with CD32B; CHO-K1 (hamster cell line) cells transfected with CD32A; 293H (human epithelial cell line) cells transfected with CD32B; 293H (human epithelial cell line) cells transfected with CD32A; Raji (human Burkitt's lymphoma cell line) cells; Daudi (human Burkitt's lymphoma cell line) cells [Raji and Daudi B cell lines express only endogenous CD32B]; THP-1 (human monocytic cell line) cells expressing only endogenous CD32A; U937 (human monocytic cell line) cells expressing endogenous CD32A and CD32B; K526; HL60.

Humanized antibodies of the invention may be further characterized by epitope mapping, so that antibodies may be selected that have the greatest specificity for FcγRIIB compared to FcγRIIA. Epitope mapping methods of antibodies are well known in the art and encompassed within the methods of the invention. In certain embodiments, FcγRIIB, or a fusion protein comprising one or more regions of FcγRIIB, may be used in mapping the epitope of an antibody of the invention. In a specific embodiment, the fusion protein contains the amino acid sequence of a region of an FcγRIIB fused to the Fc portion of human IgG2. Each fusion protein may further comprise amino acid substitutions and/or replacements of certain regions of the receptor with the corresponding region from a homolog receptor, e.g., FcγRIIA, as shown in Table 2 below. pMGX125 and pMGX132 contain the IgG binding site of the FcγRIIB receptor, the former with the C-terminus of FcγRIIB and the latter with the C-terminus of FcγRIIA and can be used to differentiate C-terminus binding. The others have FcγRIIA substitutions in the IgG binding site and either the FcγIIA or FcγIIB N-terminus. These molecules can help determine the part of the receptor molecule where the antibodies bind.

The fusion proteins may be used in any biochemical assay for determination of binding to an anti-FcγRIIB antibody of the invention, e.g., an ELISA. In other embodiments, further confirmation of the epitope specificity may be done by using peptides with specific residues replaced with those from the FcγRIIA sequence.

The antibodies of the invention may be characterized for specific binding to FcγRIIB using any immunological or biochemical based method known in the art for characterizing including quantitating, the interaction of the antibody to FcγRIIB. Specific binding of an antibody of the invention to FcγRIIB may be determined for example using immunological or biochemical based methods including, but not limited to, an ELISA assay, surface plasmon resonance assays, immunoprecipitation assay, affinity chromatography, and equilibrium dialysis. Immunoassays which can be used to analyze immunospecific binding and cross-reactivity of the antibodies of the invention include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety).

Humanized antibodies of the invention may also be assayed using any surface plasmon resonance based assays known in the art for characterizing the kinetic parameters of the interaction of the antibody with FcγRIIB. Any SPR instrument commercially available including, but not limited to, BIACORE™ Instruments, available from Biacore AB (Uppsala, Sweden); IASYS™ instruments available from Affinity Sensors (Franklin, Mass.); IBIS™ system available from Windsor Scientific Limited (Berks, UK); SPR-CELLIA™ systems available from Nippon Laser and Electronics Lab (Hokkaido, Japan); and SPR Detector SPREETA® available from Texas Instruments (Dallas, Tex.) can be used in the instant invention. For a review of SPR-based technology, see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, the methods of the invention contemplate the use of any of the SPR instruments and SPR based methods for measuring protein-protein interactions described in U.S. Pat. Nos. 6,373,577; 6,289,286; 5,322,798; 5,341,215; and 6,268,125, all of which are incorporated herein by reference in their entirety, are contemplated in the methods of the invention.

TABLE 2

List of the fusion proteins that may be used to investigate the epitope of the monoclonal anti-FcγRIIB antibodies. Residues 172 to 180 belong to the IgG binding site of FcγRIIA and B. The specific amino acids from FcγRIIA sequence are in bold.

| Plasmid | Receptor | N-terminus | 172-180 | SEQ ID NO: | C-terminus | SEQ ID NO: |
|---------|----------|------------|---------|------------|------------|------------|
| pMGX125 | RIIb | IIb | KKFSRSDPN | 51 | APS------SS (IIb) | 57 |
| pMGX126 | RIIa/b | IIa | QKFSRLDPN | 52 | APS------SS (IIb) | 57 |
| pMGX127 | | IIa | QKFSRLDPT | 53 | APS------SS (IIb) | 57 |
| pMGX128 | | IIb | KKFSRLDPT | 54 | APS------SS (IIb) | 57 |
| pMGX129 | | IIa | QKFSHLDPT | 55 | APS------SS (IIb) | 57 |
| pMGX130 | | IIb | KKFSHLDPT | 56 | APS------SS (IIb) | 57 |
| pMGX131 | | IIa | QKFSRLDPN | 52 | VPSMGSSS(IIa) | 58 |
| pMGX132 | | IIb | KKFSRSDPN | 51 | VPSMGSSS(IIa) | 58 |
| pMGX133 | RIIa-131R | IIa | QKFSRLDPT | 53 | VPSMGSSS(IIa) | 58 |
| pMGX134 | RIIa-131H | IIa | QKFSHLDPT | 55 | VPSMGSSS(IIa) | 58 |
| pMGX135 | | IIb | KKFSRLDPT | 54 | VPSMGSSS(IIa) | 58 |
| pMGX136 | | IIb | KKFSHLDPT | 56 | VPSMGSSS(IIa) | 58 |

Briefly, SPR based assays involve immobilizing a member of a binding pair on a surface, and monitoring its interaction with the other member of the binding pair in solution in real time. SPR is based on measuring the change in refractive index of the solvent near the surface that occurs upon complex formation or dissociation. The surface onto which the immobilization occur is the sensor chip, which is at the heart of the SPR technology; the sensor chip consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Examples of sensor chips include those available from BIAcore AB, Inc., e.g., Sensor Chip™ CM5™, SA™, NTA™, and HPA™. A molecule of the invention may be immobilized onto the surface of a sensor chip using any of the immobilization methods and chemistries known in the art, including, but not limited to, direct covalent coupling via amine groups, direct covalent coupling via sulfhydryl groups, biotin attachment to avidin coated surface, aldehyde coupling to carbohydrate groups, and attachment through the histidine tag with NTA chips.

The invention encompasses characterization of the humanized antibodies produced by the methods of the invention using certain characterization assays for identifying the function of the antibodies of the invention, particularly the activity to modulate FcγRIIB signaling. For example, characterization assays of the invention can measure phosphorylation of tyrosine residues in the ITIM motif of FcγRIIB, or measure the inhibition of B cell receptor-generated calcium mobilization. The characterization assays of the invention can be cell-based or cell-free assays.

It has been well established in the art that in mast cells coaggregation of FcγRIIB with the high affinity IgE receptor, FcεRI, leads to inhibition of antigen-induced degranulation, calcium mobilization, and cytokine production (Metcalfe D. D. et al. 1997, *Physiol. Rev.* 77:1033; Long E. O. 1999 *Annu Rev. Immunol* 17: 875). The molecular details of this signaling pathway have been recently elucidated (Ott V. L., 2002, *J. Immunol.* 162(9):4430-9). Once coaggregated with FcεRI, FcγRIIB is rapidly phosphorylated on tyrosine in its ITIM motif, and then recruits Src Homology-2 containing inositol-5-phosphatase (SHIP), an SH2 domain-containing inositol polyphosphate 5-phosphatase, which is in turn phosphorylated and associates with Shc and p62$^{dok}$ (p62$^{dok}$ is the prototype of a family of adaptor molecules, which includes signaling domains such as an aminoterminal pleckstrin homology domain (PH domain), a PTB domain, and a carboxy terminal region containing PXXP motifs and numerous phosphorylation sites (Carpino et al., 1997 *Cell,* 88: 197; Yamanshi et al., 1997, *Cell,* 88:205)). Each of the foregoing references are incorporated herein by reference in its entirety.

The invention encompasses characterizing the anti-FcγRIIB humanized antibodies of the invention in modulating one or more IgE mediated responses. Preferably, cells lines co-expressing the high affinity receptor for IgE and the low affinity receptor for FcγRIIB will be used in characterizing the anti-FcγRIIB antibodies of the invention in modulating IgE mediated responses. In a specific embodiment, cells from a rat basophilic leukemia cell line (RBL-H23; Barsumian E. L. et al. 1981 *Eur. J. Immunol.* 11:317, which is incorporated herein by reference in its entirety) transfected with full length human FcγRIIB will be used in the methods of the invention. RBL-2H3 is a well characterized rat cell line that has been used extensively to study the signaling mechanisms following IgE-mediated cell activation. When expressed in RBL-2H3 cells and coaggregated with FcεRI, FcγRIIB inhibits FcεRI-induced calcium mobilization, degranulation, and cytokine production (Malbec et al., 1998, *J. Immunol.* 160: 1647; Daeron et al., 1995 *J. Clin. Invest.* 95:577; Ott et al., 2002 *J. of Immunol.* 168:4430-4439; (each of which is incorporated by reference in its entirety)).

In some embodiments, the invention encompasses characterizing the anti-FcγRIIB humanized antibodies of the invention for inhibition of FcεRI induced mast cell activation. For example, cells from a rat basophilic leukemia cell line (RBL-H23; Barsumian E. L. et al. 1981 *Eur. J. Immunol.* 11:317; incorporated by reference in its entirety) that have been transfected with FcγRIIB are sensitized with IgE and stimulated either with F(ab')$_2$ fragments of rabbit anti-mouse IgG, to aggregate FcεRI alone, or with whole rabbit anti-mouse IgG to coaggregate FcγRIIB and FcεRI. In this system, indirect modulation of down stream signaling molecules can be assayed upon addition of antibodies of the invention to the sensitized and stimulated cells. For example, tyrosine phosphorylation of FcγRIIB and recruitment and phosphorylation of SHIP, activation of MAP kinase family members, including, but not limited to Erk1, Erk2, JNK, or p38; and tyrosine phosphorylation of p62$^{dok}$ and its association with SHIP and RasGAP can be assayed.

One exemplary assay for determining the inhibition of FcεRI induced mast cell activation by the antibodies of the invention can comprise of the following: transfecting RBL-H23 cells with human FcγRIIB; sensitizing the RBL-H23 cells with IgE; stimulating RBL-H23 cells with either F(ab')$_2$ of rabbit anti-mouse IgG (to aggregate FcεRI alone and elicit FcεRI-mediated signaling, as a control), or stimulating RBL-H23 cells with whole rabbit anti-mouse IgG to (to coaggregate FcγRIIB and FcεRI, resulting in inhibition of FcεRI-mediated signaling). Cells that have been stimulated with whole rabbit anti-mouse IgG antibodies can be further pre-incubated with the antibodies of the invention. Measuring FcεRI-dependent activity of cells that have been pre-incubated with the antibodies of the invention and cells that have not been pre-incubated with the antibodies of the invention, and comparing levels of FcεRI-dependent activity in these cells, would indicate a modulation of FcεRI-dependent activity by the antibodies of the invention.

The exemplary assay described above can be used, for example, to identify antibodies that block ligand (IgG) binding to FcγRIIB receptor and antagonize FcγRIIB-mediated inhibition of FcεRI signaling by preventing coaggregating of FcγRIIB and FcεRI. This assay likewise identifies antibodies that enhance coaggregation of FcγRIIB and FcεRI and agonize FcγRIIB-mediated inhibition of FcεRI signaling by promoting coaggregating of FcγRIIB and FcεRI.

In a preferred embodiment, FcεRI-dependent activity is at least one or more of the following: modulation of downstream signaling molecules, e.g., modulation of phosphorylation state of FcγRIIB, modulation of SHIP recruitment, modulation of MAP Kinase activity, modulation of phosphorylation state of SHIP, modulation of SHIP and Shc association SHIP and Shc, modulation of the phosphorylation state of p62$^{dok}$, modulation of p62$^{dok}$ and SHIP association, modulation of p62$^{dok}$ and RasGAP association, modulation of calcium mobilization, modulation of degranulation, and modulation of cytokine production. In yet another preferred embodiment, FcεRI-dependent activity is serotonin release and/or extracellular Ca$^{++}$ influx and/or IgE dependent mast cell activation. It is known to one skilled in the art that coaggregation of FcγRIIB and FcεRI stimulates FcγRIIB tyrosine phosphorylation, stimulates recruitment of SHIP, stimulates SHIP tyrosine phosphorylation and association with Shc, and inhibits activation of MAP kinase family members including, but not limited to, Erk1, Erk2, JNK, p38. It is also known to those skilled in the art that coaggregation of FcγRIIB and FcεRI stimulates enhanced tyrosine phosphorylation of p62$^{dok}$ and its association with SHIP and RasGAP.

In some embodiments, the anti-FcγRIIB humanized antibodies of the invention are characterized for their ability to modulate an IgE mediated response by monitoring and/or measuring degranulation of mast cells or basophils, preferably in a cell-based assay. Preferably, mast cells or basophils for use in such assays have been engineered to contain human FcγRIIB using standard recombinant methods known to one skilled in the art. In a specific embodiment the anti-FcγRIIB antibodies of the invention are characterized for their ability to modulate an IgE mediated response in a cell-based β-hexosaminidase (enzyme contained in the granules) release assay. β-hexosaminidase release from mast cells and basophils is a primary event in acute allergic and inflammatory condition (Aketani et al., 2001 Immunol Lett. 75: 185-9; Aketani et al., 2000 Anal. Chem. 72: 2653-8 (each of which is incorporated by reference in its entirety)). Release of other inflammatory mediators including, but not limited to, serotonin and histamine may be assayed to measure an IgE mediated response in accordance with the methods of the invention. Although not intending to be bound by a particular mechanism of action, release of granules such as those containing β-hexosaminidase from mast cells and basophils is an intracellular calcium concentration dependent process that is initiated by the cross-linking of FcεRIs with multivalent antigen.

One exemplary assay for characterizing the anti-FcγRIIB humanized antibodies of the invention in mediating an IgE mediated response is a β-hexosaminidase release assay comprising the following: transfecting RBL-H23 cells with human FcγRIIB; sensitizing the cells with mouse IgE alone or with mouse IgE and an anti-FcγRIIB antibody of the invention; stimulating the cells with various concentrations of goat anti-mouse F(ab)$_2$, preferably in a range from 0.03 μg/mL to 30 μg/mL for about 1 hour; collecting the supernatant; lysing the cells; and measuring the β-hexosaminidase activity released in the supernatant by a colorometric assay, e.g., using p-nitrophenyl N-acetyl-β-D-glucosaminide. The released β-hexosaminidase activity is expressed as a percentage of the released activity to the total activity. The released β-hexosaminidase activity will be measured and compared in cells treated with antigen alone; IgE alone; IgE and an anti-FcγRIIB antibody of the invention. Although not intending to be bound by a particular mechanism of action, once cells are sensitized with mouse IgE alone and challenged with F(ab)$_2$ fragments of a polyclonal goat anti-mouse IgG, aggregation and cross linking of FcεRI occurs since the polyclonal antibody recognizes the light chain of the murine IgE bound to the FcεRI, which in turn leads to mast cell activation and degranulation. On the other hand, when cells are sensitized with mouse IgE and an anti-FcγRIIB antibody of the invention and challenged with F(ab)$_2$ fragments of a polyclonal goat anti-mouse IgG; cross linking of FcεRI and FcγRIIB occurs, resulting in inhibition of FcεRI induced degranulation. In either case, goat anti mouse F(ab)$_2$ induces a dose-dependent β-hexoaminidase release. In some embodiments, the anti-FcγRIIB antibodies bound to the FcγRIIB receptor and cross linked to FcεRI do not affect the activation of the inhibitory pathway, i.e., there is no alteration in the level of degranulation in the presence of an anti-FcγRIIB antibody. In other embodiments, the anti-FcγRIIB antibodies mediate a stronger activation of the inhibitory receptor, FcγRIIB, when bound by the anti-FcγRIIB antibody, allowing effective cross linking to FCεRI and activation of the inhibitory pathway of homo-aggregated FcγRIIB.

The invention also encompasses characterizing the effect of the anti-FcγRIIB humanized antibodies of the invention on IgE mediated cell response using calcium mobilization assays using methodologies known to one skilled in the art. An exemplary calcium mobilization assay may comprise the following: priming basophils or mast cells with IgE; incubating the cells with a calcium indicator, e.g., Fura 2; stimulating cells as described supra; and monitoring and/or quantitating intracellular calcium concentration for example by using flow cytometry. The invention encompasses monitoring and/or quantitating intracellular calcium concentration by any method known to one skilled in the art. See, e.g., Immunology Letters, 2001, 75:185-9; British J. of Pharm, 2002, 136:837-45; J. of Immunology, 168:4430-9 and J. of Cell Biol., 153 (2):339-49; all of which are incorporated herein by reference.

In preferred embodiments, anti-FcγRIIB humanized antibodies of the invention inhibit IgE mediated cell activation. In other embodiments, the anti-FcγRIIB antibodies of the invention block the inhibitory pathways regulated by FcγRIIB or block the ligand binding site on FcγRIIB and thus enhance immune response.

The ability to study human mast cells has been limited by the absence of suitable long term human mast cell cultures. Recently two novel stem cell factor dependent human mast cell lines, designated LAD 1 and LAD2, were established from bone marrow aspirates from a patient with mast cell sarcoma/leukemia (Kirshenbaum et al., 2003, Leukemia research, 27:677-82, which is incorporated herein by reference in its entirety). Both cell lines have been described to express FcεRI and several human mast cell markers. The invention encompasses using LAD 1 and 2 cells in the methods of the invention for assessing the effect of the humanized antibodies of the invention on IgE mediated responses. In a specific embodiment, cell-based P-hexosaminidase release assays such as those described supra may be used in LAD cells to determine any modulation of the IgE-mediated response by the humanized anti-FcγRIIB antibodies of the invention. In an exemplary assay, human mast cells, e.g., LAD 1, are primed with chimaeric human IgE anti-nitrophenol (NP) and challenged with BSA-NP, the polyvalent antigen, and cell degranulation is monitored by measuring the β-hexosaminidase released in the supernatant (Kirshenbaum et al., 2003, Leukemia research, 27:677-682, which is incorporated herein by reference in its entirety).

In some embodiments, if human mast cells have a low expression of endogenous FcγRIIB, as determined using standard methods known in the art, e.g., FACS staining, it may be difficult to monitor and/or detect differences in the activation of the inhibitory pathway mediated by the anti-FcγRIIB antibodies of the invention. The invention thus encompasses alternative methods, whereby the FcγRIIB expression may be upregulated using cytokines and particular growth conditions. FcγRIIB has been described to be highly up-regulated in human monocyte cell lines, e.g., THP1 and U937, (Tridandapani et al., 2002, J. Biol. Chem., 277(7): 5082-5089) and in primary human monocytes (Pricop et al., 2001, J. of Immunol., 166: 531-537) by IL4. Differentiation of U937 cells with dibutyryl cyclic AMP has been described to increase expression of FcγRII (Cameron et al., 2002 Immunology Letters 83, 171-179). Thus, the endogenous FcγRIIB expression in human mast cells for use in the methods of the invention may be up-regulated using cytokines, e.g., IL-4, IL-13, in order to enhance sensitivity of detection. Each of the foregoing references is hereby incorporated by reference in its entirety.

The invention also encompasses characterizing the humanized anti-FcγRIIB antibodies of the invention for inhibition of B-cell receptor (BCR)-mediated signaling. BCR-mediated signaling can include at least one or more down stream biological responses, such as activation and proliferation of B cells, antibody production, etc. Coaggregation of FcγRIIIB and BCR leads to inhibition of cell cycle progression and cellular survival. Further, coaggregation of FcγRIIB and BCR leads to inhibition of BCR-mediated signaling.

Specifically, BCR-mediated signaling comprises at least one or more of the following: modulation of down stream signaling molecules (e.g., phosphorylation state of FcγRIIB, SHIP recruitment, localization of Btk and/or PLCγ, MAP kinase activity, recruitment of Akt (anti-apoptotic signal), calcium mobilization, cell cycle progression, and cell proliferation.

Although numerous effector functions of FcγRIIB-mediated inhibition of BCR signaling are mediated through SHIP, recently it has been demonstrated that lipopolysaccharide (LPS)-activated B cells from SHIP deficient mice exhibit significant FcγRIIB-mediated inhibition of calcium mobilization, $Ins(1,4,5)P_3$ production, and Erk and Akt phosphorylation (Brauweiler A. et al., 2001, *Journal of Immunology*, 167(1): 204-211; incorporated by reference in its entirety). Accordingly, ex vivo B cells from SHIP deficient mice can be used to characterize the antibodies of the invention. One exemplary assay for determining FcγRIIB-mediated inhibition of BCR signaling by the antibodies of the invention can comprise the following: isolating splenic B cells from SHIP deficient mice, activating said cells with lipopolysachharide, and stimulating said cells with either $F(ab')_2$ anti-IgM to aggregate BCR or with anti-IgM to coaggregate BCR with FcγRIIB. Cells that have been stimulated with intact anti-IgM to coaggregate BCR with FcγRI 1B can be further pre-incubated with the antibodies of the invention. FcγRIIB-dependent activity of cells can be measured by standard techniques known in the art and used for, e.g., comparing the level of FcγRIIB-dependent activity in cells that have been pre-incubated with the antibodies of the invention and cells that have not been pre-incubated, and comparing the levels would indicate a modulation of FcγRIIB-dependent activity by the antibodies of the invention.

Measuring FcγRIIB-dependent activity can include, for example, measuring intracellular calcium mobilization by flow cytometry, measuring phosphorylation of Akt and/or Erk, measuring BCR-mediated accumulation of $PI(3,4,5)P_3$, or measuring FcγRIIB-mediated proliferation B cells.

The assays can be used, for example, to identify antibodies that modulate FcγRIIB-mediated inhibition of BCR signaling by blocking the ligand (IgG) binding site to FcγRIIB receptor and antagonizing FcγRIIB-mediated inhibition of BCR signaling by preventing coaggregation of FcγRIIB and BCR. The assays can also be used to identify antibodies that enhance coaggregation of FcγRIIB and BCR and agonize FcγRIIB-mediated inhibition of BCR signaling.

The invention relates to characterizing the humanized anti-FcγRIIB antibodies of the invention for FcγRII-mediated signaling in human monocytes/macrophages. Coaggregation of FcγRIIB with a receptor bearing the immunoreceptor tyrosine-based activation motif (ITAM) acts to down-regulate FcγR-mediated phagocytosis using SHIP as its effector (Tridandapani et al. 2002, *J. Biol. Chem.* 277(7):5082-9; incorporated by reference in its entirety). Coaggregation of FcγRIIA with FcγRIIB results in rapid phosphorylation of the tyrosine residue on FcγRIIB's ITIM motif, leading to an enhancement in phosphorylation of SHIP, association of SHIP with Shc, and phosphorylation of proteins having the molecular weight of 120 and 60-65 kDa. In addition, coaggregation of FcγRIIA with FcγRIIB results in down-regulation of phosphorylation of Akt, which is a serine-threonine kinase that is involved in cellular regulation and serves to suppress apoptosis.

The invention further encompasses characterizing the humanized anti-FcγRIIB antibodies of the invention for their inhibition of FcγR-mediated phagocytosis in human monocytes/macrophages. For example, cells from a human monocytic cell line, THP-1 can be stimulated either with Fab fragments of mouse monoclonal antibody IV.3 against FcγRIIA (Medarex, Inc.) and goat anti-mouse antibody (to aggregate FcγRIIA alone), or with whole IV.3 mouse monoclonal antibody and goat anti-mouse antibody (to coaggregate FcγRIIA and FcγRIIB). In this system, modulation of down stream signaling molecules, such as tyrosine phosphorylation of FcγRIIB, phosphorylation of SHIP, association of SHIP with Shc, phosphorylation of Akt, and phosphorylation of proteins having the molecular weight of 120 and 60-65 kDa can be assayed upon addition of antibodies of the invention to the stimulated cells. In addition, FcγRIIB-dependent phagocytic efficiency of the monocyte cell line can be directly measured in the presence and absence of the antibodies of the invention.

Another exemplary assay for determining inhibition of FcγR-mediated phagocytosis in human monocytes/macrophages by the antibodies of the invention can comprise the following: stimulating THP-1 cells with either Fab of IV.3 mouse anti-FcγRIIA antibody and goat anti-mouse antibody (to aggregate FcγRIIA alone and elicit FcγRIIA-mediated signaling); or with mouse anti-FcγRII antibody and goat anti-mouse antibody (to coaggregate FcγRIIA and FcγRIIB and inhibiting FcγRIIA-mediated signaling). Cells that have been stimulated with mouse anti-FcγRII antibody and goat anti-mouse antibody can be further pre-incubated with the antibodies of the invention. Measuring FcγRIIA-dependent activity of stimulated cells that have been pre-incubated with antibodies of the invention and cells that have not been pre-incubated with the antibodies of the invention and comparing levels of FcγRIIA-dependent activity in these cells would indicate a modulation of FcγRIIA-dependent activity by the antibodies of the invention.

The exemplary assay described can be used, for example, to identify antibodies that block ligand binding of FcγRI 1B receptor and antagonize FcγRIIB-mediated inhibition of FcγRIIA signaling by preventing coaggregation of FcγRIIB and FcγRIIA. This assay likewise identifies antibodies that enhance coaggregation of FcγRIIB and FcγRIIA and agonize FcγRIIB-mediated inhibition of FcγRIIA signaling.

In another embodiment of the invention, the invention relates to characterizing the function of the humanized antibodies of the invention by measuring the ability of THP-1 cells to phagocytose fluoresceinated IgG-opsonized sheep red blood cells (SRBC) by methods previously described (Tridandapani et al., 2000, *J. Biol. Chem.* 275: 20480-7; incorporated by reference in its entirety). For example, an exemplary assay for measuring phagocytosis comprises: treating THP-1 cells with the antibodies of the invention or with a control antibody that does not bind to FcγRII, comparing the activity levels of said cells, wherein a difference in the activities of the cells (e.g., rosetting activity (the number of THP-1 cells binding IgG-coated SRBC), adherence activity (the total number of SRBC bound to THP-1 cells), and phagocytic rate) would indicate a modulation of FcγRIIA-dependent activity by the antibodies of the invention. This assay can be used to identify, for example, antibodies that block ligand binding of FcγRIIB receptor and antagonize FcγRIIB-mediated inhibition of phagocytosis. This assay can also identify antibodies that enhance FcγRIIB-mediated inhibition of FcγRIIA signaling.

In a preferred embodiment, the humanized antibodies of the invention modulate FcγRIIB-dependent activity in human monocytes/macrophages in at least one or more of the following ways: modulation of downstream signaling molecules (e.g., modulation of phosphorylation state of FcγRIIB, modulation of SHIP phosphorylation, modulation of SHIP and Shc association, modulation of phosphorylation of Akt, modulation of phosphorylation of additional proteins around 120 and 60-65 kDa) and modulation of phagocytosis.

The invention encompasses characterization of the humanized antibodies of the invention using assays known to those skilled in the art for identifying the effect of the antibodies on effector cell function of therapeutic antibodies, e.g., their ability to enhance tumor-specific ADCC activity of therapeutic antibodies. Therapeutic antibodies that may be used in accordance with the methods of the invention include, but are not limited to, anti-tumor antibodies, anti-viral antibodies, anti-microbial antibodies (e.g., bacterial and unicellular parasites), examples of which are disclosed herein (Section 5.3.6). In particular, the invention encompasses characterizing the antibodies of the invention for their effect on FcγR-mediated effector cell function of therapeutic antibodies, e.g., tumor-specific monoclonal antibodies. Examples of effector cell functions that can be assayed in accordance with the invention, include, but are not limited to, antibody-dependent cell mediated cytotoxicity, phagocytosis, opsonization, opsonophagocytosis, C1q binding, and complement dependent cell mediated cytotoxicity. Any cell-based or cell free assay known to those skilled in the art for determining effector cell function activity can be used (for effector cell assays, see Perussia et al., 2000, *Methods Mol. Biol.* 121: 179-92; Baggiolini et al., 1998 *Experientia*, 44(10): 841-8; Lehmann et al., 2000 *J. Immunol. Methods*, 243(1-2): 229-42; Brown E J. 1994, *Methods Cell Biol.*, 45: 147-64; Munn et al., 1990 *J. Exp. Med.*, 172: 231-237, Abdul-Majid et al., 2002 *Scand. J. Immunol.* 55: 70-81; Ding et al., 1998, *Immunity* 8:403-411, each of which is incorporated by reference herein in its entirety).

Antibodies of the invention can be assayed for their effect on FcγR-mediated ADCC activity of therapeutic antibodies in effector cells, e.g., natural killer cells, using any of the standard methods known to those skilled in the art (see e.g., Perussia et al., 2000, *Methods Mol. Biol.* 121: 179-92). "Antibody-dependent cell-mediated cytotoxicity" and "ADCC", as used herein, carry their ordinary and customary meaning in the art and refer to an in vitro cell-mediated reaction in which nonspecific cytotoxic cells that express FcγRs (e.g., monocytic cells such as Natural Killer (NK) cells and macrophages) recognize bound antibody on a target cell and subsequently cause lysis of the target cell. In principle, any effector cell with an activating FcγR can be triggered to mediate ADCC. The primary cells for mediating ADCC are NK cells which express only FcγRIII, whereas monocytes, depending on their state of activation, localization, or differentiation, can express FcγRI, FcγRII, and FcγRIII. For a review of FcγR expression on hematopoietic cells, see, e.g., Ravetch et al., 1991, *Annu. Rev. Immunol.*, 9:457-92, which is incorporated herein by reference in its entirety.

Effector cells are leukocytes which express one or more FcγRs and perform effector functions. Preferably, the cells express at least FcγRIII and perform ADCC effector function. Effector cells that may be used in the methods of the invention include, but are not limited to, peripheral blood mononuclear cells (PBMC), natural killer (NK) cells, monocytes, and neutrophils; with PBMCs and NK cells being preferred. The effector cells may be isolated from a native source thereof, e.g., from blood or PBMCs as described herein. Preferably, the effector cells used in the ADCC assays of the invention are peripheral blood mononuclear cells (PBMC) that are preferably purified from normal human blood, using standard methods known to one skilled in the art, e.g., using Ficoll-Paque density gradient centrifugation. For example, PBMCs may be isolated by layering whole blood onto Ficoll-Hypaque and spinning the cells at 500 g, at room temperature for 30 minutes. The leukocyte layer can be harvested as effector cells. Other effector cells that may be used in the ADCC assays of the invention include, but are not limited to, monocyte-derived macrophages (MDMs). MDMs that are used as effector cells in the methods of the invention are preferably obtained as frozen stocks or used fresh (e.g., from Advanced Biotechnologies, MD). In most preferred embodiments, elutriated human monocytes are used as effector cells in the methods of the invention. Elutriated human monocytes express activating receptors, FcγRIIIA and FcγRIIA and the inhibitory receptor, FcγRIIB. Human monocytes are commercially available and may be obtained as frozen stocks, thawed in basal medium containing 10% human AB serum or in basal medium with human serum containing cytokines. Levels of expression of FcγRs in the cells may be directly determined; e.g. using FACS analysis. Alternatively, cells may also be allowed to mature to macrophages in culture. The level of FcγRIIB expression may be increased in macrophages. Antibodies that may be used in determining the expression level of FcγRs include but are not limited to anti-human FcγRIIA antibodies, e.g., IV.3-FITC; anti-FcγRI antibodies, e.g., 32.2 FITC; and anti-FcγRIIIA antibodies, e.g., 3G8-PE.

Target cells used in the ADCC assays of the invention include, but are not limited to, breast cancer cell lines, e.g., SK-BR-3 with ATCC accession number HTB-30 (see, e.g., Tremp et al., 1976, *Cancer Res.* 33-41); B-lymphocytes; cells derived from Burkitts lymphoma, e.g., Raji cells with ATCC accession number CCL-86 (see, e.g., Epstein et al., 1965, *J. Natl. Cancer Inst.* 34: 231-240), Daudi cells with ATCC accession number CCL-213 (see, e.g., Klein et al., 1968, *Cancer Res.* 28: 1300-10); ovarian carcinoma cell lines, e.g., OVCAR-3 with ATCC accession number HTB-161 (see, e.g., Hamilton, Young et al., 1983), SK-OV-3, PA-1, CAOV3, OV-90, and IGROV-1 (available from the NCI repository; Benard et al., 1985, *Cancer Research*, 45:4970-9; which is incorporated herein by reference in its entirety. The target cells must be recognized by the antigen binding site of the antibody to be assayed. The target cells for use in the methods of the invention may have low, medium, or high expression level of a cancer antigen. The expression levels of the cancer antigen may be determined using common methods known to one skilled in the art, e.g., FACS analysis. For example, the invention encompasses the use of ovarian cancer cells such as IGROV-1, wherein Her2/neu is expressed at different levels, or OV-CAR-3 (ATCC Assession Number HTB-161; characterized by a lower expression of Her2/neu than SK-BR-3, the breast carcinoma cell line). Other ovarian carcinoma cell lines that may be used as target cells in the methods of the invention include OVCAR-8 (Hamilton et al., 1983, *Cancer Res.* 43:5379-89,which is incorporated herein by reference in its entirety); SK-OV-3 (ATCC Accession Number HTB-77); Caov-3 (ATCC Accession Number HTB-75); PA-1 (ATCC Accession Number CRL-1572); OV-90 (ATCC Accession Number CRL-11732); and OVCAR-4. Other breast cancer cell lines that may be used in the methods of the invention include BT-549 (ATCC Accession Number HTB-122), MCF7 (ATCC Accession Number HTB-22), and Hs578T (ATCC Accession Number HTB-126), all of which are available from the NCI repository and ATCC and which are incorporated herein by reference. Other cell lines that may be used in the methods of the invention include, but are not limited to, CCRF-CEM (leukemia); HL-60 (TB, leukemia); MOLT-4 (leukemia); RPMI-8226 (leukemia); SR (leukemia); A549 (Non-small cell lung); EKVX (Non-small cell lung); HOP-62 (Non-small cell lung); HOP-92 (Non-small cell lung); NC1-H226 (Non-small cell lung); NC1-H23 (Non-small cell lung); NC1-H322M (Non-small cell lung); NC1-H460 (Non-small cell lung); NC1-H522 (Non-small cell lung); COLO 205 (Colon); HCC-2998 (Colon); HCT-116 (Colon); HCT-15 (Colon); HT29 (Colon); KM12 (Colon); SW-620 (Colon); SF-268 (CNS); SF-295 (CNS); SF-539 (CNS); SNB-19 (CNS); SNB-75 (CNS); U251 (CNS); LOX 1MV1 (Melanoma); MALME-3M (Melanoma); M14 (Melanoma); SK-MEL-2 (Melanoma); SK-MEL-28 (Melanoma); SK-MEL-5 (Melanoma); UACC-257 (Melanoma); UACC-62 (Melanoma); IGR-OV1 (Ovarian); OVCAR-3,4,5,8 (Ovarian); SK-OV-3 (Ovarian); 786-0 (Renal); A498 (Renal); ACHN (Renal); CAKl-1 (Renal); SN12C(Renal); TK-10 (Renal); UO-31 (Renal); PC-3C (Prostate); DU-145 (Prostate); NC1/ADR-RES (Breast); MDA-MB-231/ATCC (Breast); MDA-MB-435 (Breast); DMS 114 (Small-cell lung); and SHP-77 (Small-cell lung); all of which are available from the NCl and which are incorporated herein by reference.

An exemplary assay for determining the effect of the antibodies of the invention on the ADCC activity of therapeutic antibodies is based on a $^{51}$Cr release assay comprising: labeling target cells with [$^{51}$Cr]Na$_2$CrO$_4$ (this cell-membrane permeable molecule is commonly used for labeling since it binds cytoplasmic proteins and although spontaneously released from the cells with slow kinetics, it is released massively following target cell lysis); preferably, the target cells express one or more tumor antigens, osponizing the target cells with one or more antibodies that immunospecifically bind the tumor antigens expressed on the cell surface of the target cells, in the presence and absence of an antibody of the invention, e.g., 2B6, 3H7, combining the opsonized radiolabeled target cells with effector cells in a microtitre plate at an appropriate ratio of target cells to effector cells; incubating the mixture of cells preferably for 16-18 hours, preferably at 37° C.; collecting supernatants; and analyzing the radioactivity in the supernatant samples. The cytotoxicity of the therapeutic antibodies in the presence and absence of the antibodies of the invention can then be determined, for example using the following formula: Percent specific lysis=(Experimental lysis-antibody-independent lysis/maximal lysis-antibody independent lysis)×100%. A graph can be generated by varying either the target: effector cell ratio or antibody concentration.

In yet another embodiment, the antibodies of the invention are characterized for antibody dependent cellular cytotoxicity (ADCC) in accordance with the method described earlier; see, e.g., Ding et al, *Immunity*, 1998, 8:403-11, which is incorporated herein by reference in its entirety.

In some embodiments, the invention encompasses characterizing the function of the antibodies of the invention in enhancing ADCC activity of therapeutic antibodies in an in vitro based assay and/or in an animal model.

In a specific embodiment, the invention encompasses determining the function of the humanized antibodies of the invention in enhancing tumor specific ADCC using an ovarian cancer model and/or breast cancer model.

Preferably, the ADCC assays of the invention are done using more than one cancer cell line, characterized by the expression of at least one cancer antigen, wherein the expression level of the cancer antigen is varied among the cancer cell lines used. Although not intending to be bound by a particular mechanism of action, performing ADCC assays in more than one cell line wherein the expression level of the cancer antigen is varied, will allow determination of stringency of tumor clearance of the antibodies of the invention. In one embodiment, the ADCC assays of the invention are done using cancer cell lines with different levels of expression of a cancer antigen.

In an exemplary assay, OVCAR3, an ovarian carcinoma cell line, can serve as the tumor target expressing the tumor antigens, Her2/neu and TAG-72; human monocytes that express the activating FcγRIIIA and FcγRIIA and inhibitory FcγRIIB, can be used as effectors; and tumor specific murine antibodies, ch4D5 and chCC49, can be used as the tumor specific antibodies. OVCAR-3 cells are available from ATCC (Accession Number HTB-161). Preferably, OVCAR-3 cells are propagated in medium supplemented with 0.01 mg/ml bovine insulin. 5×10$^6$ viable OVCAR-3 cells may be injected subcutaneously (s.c) into age and weight matched nude athymic mice with MATRIGEL® (Becton Dickinson). The estimated weight of the tumor can be calculated by the formula: length-(width)$^2$/2, and preferably does not exceed 3 grams. Anchorage-dependent tumor can be isolated after 6-8 weeks, and the cells can be dissociated by adding 1 µg of Collagenase (Sigma) per gram of tumor and a 5 mg/mL RNase, passed through a cell strainer and nylon mesh to isolate cells. Cells can then be frozen for long-term storage for s.c. injection for establishment of the xenograft model.

Hybridomas secreting CC49 and 4D5 antibodies are available with ATCC Accession Numbers HB-9459 and CRL-3D463 and the heavy chain and light chain nucleotide sequences are in the public domain (see, e.g., Murray et al., 1994 *Cancer* 73 (35):1057-66, Yamamoto et al., 1986 *Nature*, 319:230-4; both of which are incorporated herein by reference in their entirety). Preferably, the 4D5 and CC49 antibodies are chimerized using standard methods known to one skilled in the art so that the human Fc sequence, e.g., human constant region of IgG1, is grafted onto the variable region of the murine antibodies in order to provide the effector function. The chimeric 4D5 and CC49 antibodies bind via their variable region to the target cell lines and via their Fc region to FcγRs expressed on human effector cells. CC49 is directed to TAG-72, a high molecular weight mucin that is highly expressed on many adenocarcinoma cells and ovarian carcinoma (Lottich et al., 1985 *Breast Cancer Res. Treat.* 6(1):49-56; Mansi et al., 1989 *Int. J. Rad. Appl. Instrum B*. 16(2):127-35; Colcher et al., 1991 *Int. J. Rad. Appl. Instrum B*. 18:395-41; all of which are incorporated herein by reference in their entirety). 4D5 is directed to human epidermal growth factor receptor 2 (Carter et al., 1992, *Proc. Natl. Acad. Sci. USA*, 89: 4285-9, which is incorporated herein by reference). Antibodies of the invention can then be utilized to investigate the enhancement of ADCC activity of the tumor specific antibodies, by blocking the inhibitory FcγRIIB. Although not intending to be bound by a particular mechanism of action, upon activation of effector cells that express at least one activating FcγR, e.g., FcγRIIA, the expression of the inhibitory receptor (FcγRIIB) is enhanced and this limits the clearance of tumors as the ADCC activity of FcγRIIA is suppressed. However, antibodies of the invention can serve as a blocking antibody, i.e., an antibody that will prevent the inhibitory signal from being activated and thus, the activation signal, e.g., ADCC activity, will be sustained for a longer period and may result in potent tumor clearance.

Preferably, the humanized antibodies of the invention for use in enhancement of ADCC activity have been modified to comprise at least one amino acid modification so that binding of their Fc region to FcγR has been diminished, most preferably abolished. In some embodiments, the antibodies of the invention have been modified to comprise at least one amino acid modification which reduces the binding of the constant domain to an activating FcγR, e.g., FcγRIIIA, FcγRIIA, as compared to a wild type antibody of the invention while retaining maximal FcγRIIB blocking activity. Antibodies of the invention may be modified in accordance with any method known to one skilled in the art or disclosed herein. Any amino acid modification which is known to disrupt effector function may be used in accordance with the methods of the invention such as those disclosed in International Publication Nos. WO 04/063351, WO 04/029207, WO 04/029092, WO 04/028564, WO 99/58572, WO 99/51642, WO 98/23289, WO 89/07142, WO 88/07089; U.S. Patent Application Publication Nos. 2005/0037000; and 2005/0064514 and U.S. Pat. Nos. 5,843, 597 and 5,642,821, each of which is incorporated herein by reference in their entirety. The invention also encompasses any of the mutations disclosed in U.S. patent application Ser. Nos. 10/902,588 (filed Jul. 28, 2004) and 11/271,140 (filed Nov. 10, 2005), and U.S. Provisional Application Nos. 60/707,419; and 60/781,564 filed on Aug. 10, 2005, and Mar. 10, 2006, respectively, each of which are incorporated herein by reference in their entireties. In some embodiments, antibodies of the invention are modified so that position 265 is modified, e.g., position 265 is substituted with alanine. In preferred embodiments, the murine constant region of an antibody of the invention is swapped with the corresponding human constant region comprising a substitution of the amino acid at position 265 with alanine, so that the effector function is abolished while FcγRIIB blocking activity is maintained. A single amino acid change at position 265 of IgG1 heavy chain has been shown to significantly reduce binding to FcγR based on ELISA assays, and has resulted in tumor mass reduction (Shields et al., 2001, *J. Biol. Chem.*, 276:6591-6604, which is incorporated herein by reference in its entirety). In other embodiments, antibodies of the invention are modified so that position 297 is modified, e.g., position 297 is substituted with glutamine, so that the N-linked glycosylation site is eliminated (see, e.g., Jefferies et al., 1995, *Immunol. lett* 44:111-7; Lund et al., 1996, *J. Immunol.*, 157:4963-69; Wright et al., 1994, *J. Exp. Med.* 180:1087-96; White et al., 1997; *J. Immunol.* 158:426-35; all of which are incorporated herein by reference in their entireties. Modification at this site has been reported to abolish all interaction with FcγRs. In preferred embodiments, the murine constant region of an antibody of the invention is swapped with the corresponding human constant region comprising a substitution of the amino acid at position 265 and/or 297, so that the effector function is abolished while FcγRIIB blocking activity is maintained.

An exemplary assay for determining the ADCC activity of the tumor specific antibodies in the presence and absence of the antibodies of the invention is a non-radioactive europium based fluorescent assay (BATDA®, Perkin Elmer) and may comprise the following: labeling the targets cells with an acteoxylmethyl ester of fluorescence-enhancing ester that forms a hydrophilic ligand (TDA) with the membrane of cells by hydrolysis of the esters (this complex is unable to leave the cell and is released only upon lysis of the cell by the effectors); adding the labeled targets to the effector cells in presence of anti-tumor antibodies and an antibody of the invention; and incubating the mixture of the target and effector cells for 6 to 16 hours, preferably at 37° C. The extent of ADCC activity can be assayed by measuring the amount of ligand that is released and interacts with europium (DELFIA® reagent; PerkinElmer). The ligand and the europium form a very stable and highly fluorescent chelate (EuTDA) and the measured fluorescence is directly proportional to the number of cells lysed. Percent specific lysis can be calculated using the formula: (Experimental lysis–antibody-independent lysis/maximal lysis antibody-independent lysis×100%).

In some embodiments, if the sensitivity of the fluorescence-based ADCC assay is too low to detect ADCC activity of the therapeutic antibodies, the invention encompasses using radioactive-based ADCC assays, such as $^{51}$Cr release assay. Radioactive-based assays may be done instead of, or in combination with, fluorescent-based ADCC assays.

An exemplary $^{51}$Cr release assay for characterizing the antibodies of the invention can comprise the following: labeling 1–2×$10^6$ target cells such as OVCAR-3 cells with $^{51}$Cr; opsonizing the target cells with antibodies 4D5 and CC49 in the presence and absence of an antibody of the invention and adding 5×$10^3$ cells to 96 well plate (preferably 4D5 and CC49 are at a concentration varying from 1-15 µg/mL); adding the opsonized target cells to monocyte-derived macrophages (MDM) (effector cells), preferably at a ratio varying from 10:1 to 100:1; incubating the mixture of cells for 16-18 hours at 37° C.; collecting supernatants; and analyzing the radioactivity in the supernatant. The cytotoxicity of 4D5 and CC49 in the presence and absence of an antibody of the invention can then be determined, for example, using the following formula percent specific lysis=(experimental lysis–antibody independent lysis/maximal lysis–antibody independent lysis)×100%.

In some embodiments, the in vivo activity of the FcγRIIB humanized antibodies of the invention is determined in xenograft human tumor models. Tumors may be established using any of the cancer cell lines described supra. In some embodiments, the tumors will be established with two cancer cell lines, wherein the first cancer cell line is characterized by a low expression of a cancer antigen and a second cancer cell line, wherein the second cancer cell line is characterized by a high expression of the same cancer antigen. Tumor clearance may then be determined using methods known to one skilled in the art, using an anti-tumor antibody which immunospecifically binds the cancer antigen on the first and second cancer cell line, and an appropriate mouse model, e.g., a Balb/c nude mouse model (e.g., Jackson Laboratories, Taconic), with adoptively transferred human monocytes and MDMs as effector cells. Any of the antibodies described supra may then be tested in this animal model to evaluate the role of anti-FcγRIIB antibody of the invention in tumor clearance. Mice that may be used in the invention include for example FcγRIII –/– (where FcγRIIIA is knocked out); Fcγ–/– nude mice (where FcγRI and FcγRIIIA are knocked out); or human FcγRIIB knock in mice or a transgenic knock-in mice, where mouse fcgr2 and fcgr3 loci on chromosome 1 are inactivated and the mice express human FcγRIIA, human FcγRIIA human FcγRIIB, human FcγRIIC, human FcγRIIIA, and human FcγRIIIB.

An exemplary method for testing the in vivo activity of an antibody of the invention may comprise the following: establishing a xenograft murine model using a cancer cell line characterized by the expression of a cancer antigen and determining the effect of an antibody of the invention on an antibody specific for the cancer antigen expressed in the cancer cell line in mediating tumor clearance. Preferably, the in vivo activity is tested parallel using two cancer cell lines, wherein the first cancer cell line is characterized by a first cancer antigen expressed at low levels and a second cancer cell line, characterized by the same cancer antigen expressed at a higher level relative to the first cancer cell line. These experiments will thus increase the stringency of the evaluation of the role of an antibody of the invention in tumor clearance. For example, tumors may be established with the IGROV-1 cell line and the effect of an anti-FcγRIIB antibody of the invention in tumor clearance of a Her2/neu specific antibody may be assessed. In order to establish the xenograft tumor models, $5 \times 10^6$ viable cells, e.g., IGROV-1, SKBR3, may be injected, e.g., s.c. into mice, e.g., 8 age and weight matched femal nude athymic mice using, for example, MATRIGEL® (Becton Dickinson). The estimated weight of the tumor may be determined by the formula: length×(width)$^2$/2; and preferably does not exceed 3 grams. Injection of IGROV-1 cells s.c. gives rise to fast growing tumors while the i.p. route induces a peritoneal carcinomatosis which kills mice in 2 months (Benard et al., 1985, *Cancer Res.*. 45:4970-9; incorporated by reference in its entirety). Since the IGROV-1 cells form tumors within 5 weeks, at day 1 after tumor cell injection, monocytes as effectors are co-injected i.p. along with a therapeutic antibody specific for Her2/neu, e.g., Ch4D5, and an antibody of the invention; e.g. chimeric 2B6 or 3H7 as described supra. Preferably, the antibodies are injected at 4 μg each per gram of mouse body weight (mbw). The initial injection will be followed by weekly injections of antibodies for 4-6 weeks thereafter at 2 μg/wk. Human effector cells will be replenished once in 2 weeks. A group of mice will receive no therapeutic antibody but will be injected with a chimeric 4D5 comprising a N297A mutation and human IgG1 as isotype control antibodies for the anti-tumor and anti-FcγRIIB antibodies, respectively. Mice may be placed in groups of 4 and monitored three times weekly.

Table 3 below is an exemplary setup for tumor clearance studies in accordance with the invention. As shown in Table 3, six groups of 8 mice each will be needed for testing the role of an antibody of the invention in tumor clearance, wherein one target and effector cell combination is used and wherein two different combinations of the antibody concentration are used. In group A, only tumor cells are injected; in group B, tumor cells and monocytes are injected; in group C, tumor cells, monocytes, an anti-tumor antibody (ch4D5) are injected; in group D, tumor cells, monocytes, anti-tumor antibody, and an anti-FcγRII antibody are injected; in group E, tumor cells, monocytes and an anti-FcγRIIB antibody are injected; in group F, tumor cells, monocytes, Ch4D5 (N297Q), and human IgG1 are injected. It will be appreciated by one skilled in the art that various antibody concentrations of various antibody combinations may be tested in the tumor models described. Preferably, studies using a breast cancer cell line, e.g., SKBR3, is carried out in parallel to the above-described experiment.

TABLE 3

EXEMPLARY EXPERIMENTAL SET UP IN MICE

| 8 mice/group | Tumor cell s.c day 0 | Monocytes i.p at day 1 | ch4D5 at 4 μg/gm of mbw day 1 i.p | ch4D5 N297Q at 4 μg/gm of mbw day 1 i.p | ch2B6 N297Q at 4 μg/gm of mbw day 1 i.p | Human IgG1 4 μg/gm of mbw day 1 i.p |
|---|---|---|---|---|---|---|
| A | + | − | − | − | − | − |
| B | + | + | − | − | − | − |
| C | + | + | + | − | − | − |
| D | + | + | + | − | + | − |
| E | + | + | − | − | + | − |
| F | + | + | − | + | − | + |

The endpoint of the xenograft tumor models is determined based on the size of the tumors, weight of mice, survival time and histochemical and histopathological examination of the cancer, using methods known to one skilled in the art. Each of the groups of mice in Table 3 will be evaluated. Mice are preferably monitored three times a week. Criteria for tumor growth may be abdominal distention, presence of palpable mass in the peritoneal cavity. Preferably estimates of tumor weight versus days after inoculation will be calculated. A comparison of the aforementioned criteria of mice in Group D compared to those in other groups will define the role of an antibody of the invention in enhancement of tumor clearance. Preferably, antibody-treated animals will be under observation for an additional 2 months after the control group.

In alternative embodiments, human FcγRIIB "knock in" mice expressing human FcγRIIB on murine effector cells may be used in establishing the in vivo activity of the antibodies of the invention, rather than adoptively transferring effector cells. Founder mice expressing the human FcγRIIB may be generated by "knocking in" the human FcγRIIB onto the mouse FcγRIIB locus. The founders can then be backcrossed onto the nude background and will express the human FcγRIIB receptor. The resulting murine effector cells will express endogenous activating FcγRI and FcγRIIIA and inhibitory human FcγRIIB receptors.

The in vivo activity of the humanized antibodies of the invention may be further tested in a xenograft murine model with human primary tumor derived cells, such as human primary ovarian and breast carcinoma derived cells. Ascites and pleural effusion samples from cancer patients may be tested for expression of Her2/neu, using methods known to one skilled in the art. Samples from ovarian carcinoma patients may be processed by spinning down the ascites at 6370 g for 20 minutes at 4° C., lysing the red blood cells, and washing the cells with PBS. Once the expression of Her2/neu in tumor cells is determined, two samples, a median and a high expresser may be selected for s.c. inoculation to establish the xenograft tumor model. The isolated tumor cells will then be injected i.p. into mice to expand the cells. Approximately 10 mice may be injected i.p. and each mouse ascites further passaged into two mice to obtain ascites from a total of 20 mice which can be used to inject a group of 80 mice. Pleural effusion samples may be processed using a similar method as ascites. The Her2/neu+ tumor cells from pleural effusion samples may be injected into the upper right and left mammary pads of the mice.

In some embodiments, if the percentage of neoplastic cells in the ascites or pleural effusion samples is low compared to other cellular subsets, the neoplastic cells may be expanded in vitro. In other embodiments, tumor cells may be purified using CC49 antibody (anti-TAG-72)-coated magnetic beads as described previously, see, e.g., Barker et al., 2001, *Gynecol. Oncol* 82:57, 63, which is incorporated herein by reference in its entirety. Briefly, magnetic beads coated with CC49 antibody can be used to separate the ovarian tumor cells that will be detached from the beads by an overnight incubation at 37° C. In some embodiments, if the tumor cells lack the TAG-72 antigen, negative depletion using a cocktail of antibodies, such as those provided by Stem Cell Technologies, Inc., Canada, may be used to enrich the tumor cells.

In other embodiments, other tumors markers besides Her2/neu may be used to separate tumor cells obtained from the ascites and pleural effusion samples from non-tumor cells. In the case of pleural effusion or breast tissue, it has been recently reported that CD44 (an adhesion molecule), B38.1 (a breast/ovarian cancer-specific marker), CD24 (an adhesion molecule) may be used as markers, see, e.g., Al Hajj, et al., 2003, *Proc. Natl. Acad. Sci. USA* 100:3983, 8; which is incorporated herein by reference in its entirety. Once tumor cells are purified they may be injected s.c. into mice for expansion.

Preferably, immunohistochemistry and histochemistry is performed on ascites and pleural effusion of patients to analyze structural characteristics of the neoplasia. Such methods are known to one skilled in the art and encompassed within the invention. The markers that may be monitored include for example cytokeratin (to identify ovarian neoplastic and mesothelial cells from inflammatory and mesenchymal cells); calretinin (to separate mesothelial from Her2neu positive neoplastic cells); and CD45 (to separate inflammatory cells from the rest of the cell population in the samples). Additional markers that may be followed include CD3 (T cells), CD20 (B cells), CD56 (NK cells), and CD14 (monocytes). It will be appreciated by one skilled in the art that the immunohistochemistry and histochemistry methods described supra, are analogously applied to any tumor cell for use in the methods of the invention. After s.c. inoculation of tumor cells, mice are followed for clinical and anatomical changes. As needed, mice may be necropsied to correlate total tumor burden with specific organ localization.

In a specific embodiment, tumors are established using carcinoma cell lines such as IGROV-1, OVCAR-8, SK-B, and OVCAR-3 cells and human ovarian carcinoma ascites and pleural effusion from breast cancer patients. The ascites preferably contain both the effectors and the tumor targets for the antibodies being tested. Human monocytes will be transferred as effectors.

The in vivo activity of the humanized antibodies of the invention may also be tested in an animal model, e.g., Balb/c nude mice, injected with cells expressing FcγRIIB, including but not limited to SK-BR-3 with ATCC accession number HTB-30 (see, e.g., Tremp et al., 1976, Cancer Res. 33-41); B-lymphocytes; cells derived from Burkitts lymphoma, e.g., Raji cells with ATCC accession number CCL-86 (see, e.g., Epstein et al., 1965, *J. Natl. Cancer Inst.* 34: 231-240), Daudi cells with ATCC accession number CCL-213 (see, e.g., Klein et al., 1968, *Cancer Res.* 28: 1300-10); ovarian carcinoma cell lines, e.g., OVCAR-3 with ATCC accession number HTB-161 (see, e.g., Hamilton, Young et al., 1983), SK-OV-3, PA-1, CAOV3, OV-90, and IGROV-1 (available from the NCI repository Benard et al., 1985, *Cancer Research,* 45:4970-9; each of which is incorporated herein by reference in its entirety.

An exemplary assay for measuring the in vivo activity of the humanized antibodies of the invention may comprise the following: Balb/c Nude female mice (Taconic, Md.) are injected at day 0 with cells expressing FcγRIIB such as $5 \times 10^6$ Daudi cells for example by the subcutaneous route. Mice (e.g., 5 mice per group) then receive i.p. injection of a humanized anti-FcγRIIB antibody of the invention (e.g. a h2B6 of the invention, e.g., at 10 μg/g), i.p. injection of PBS (negative control), ch 4.4.20 (anti-FITC antibody) as a negative control, and as a positive control another therapeutic cancer antibody such as those disclosed herein, e.g., Rituxan, (e.g., at 10 μg/g) once a week starting at day 0. Mice are observed, e.g., twice a week following injection, and tumor size (length and width) is determined using for example a caliper. Tumor weight in mg is estimated using the formula: $(\text{length} \times \text{width}^2)/2$.

Preferably, the humanized antibodies of the invention have an enhanced efficacy in decreasing tumor relative to a cancer therapeutic antibody when administered at the same dose, e.g., 10 μg/g, over a time period of at least 14 days, at least 21 days, at least 28 days, or at least 35 days. In most preferred embodiments, the humanized antibodies of the invention reduce tumor size by at least 10 fold, at least 100 fold, at least 1000 fold relative to administration of a cancer therapeutic antibody at the same dose. In yet another preferred embodiment, the antibodies of the invention completely abolish the tumor.

6.2.2 Polynucleotides Encoding an Antibody

The present invention also includes polynucleotides that encode the humanized antibodies of the invention (e.g., mouse monoclonal antibody produced from clone 2B6 or 3H7, with ATCC accession numbers PTA-4591 and PTA-4592, respectively). The present invention encompass the polynucleotide encoding the heavy chain of the 2B6 antibody, with ATCC accession number PTA-4591 and/or the polynucleotide encoding the heavy chain having the amino acid sequence SEQ ID NO:70. As a specific example in accordance with this embodiment, the invention encompasses the polynucleotide sequence SEQ ID NO:69, which encodes the amino acid sequende SEQ ID NO:70. The present invention also encompasses the polynucleotide encoding the light chain of the 2B6 antibody with ATCC accession number PTA-4591 and/or the polynucleotide encoding the light chain having the amino acid sequence SEQ ID NO:66. As a specific example in accordance with this embodiment, the invention encompasses the polynucleotide sequence SEQ ID NO:65, which encodes the amino acid sequende SEQ ID NO:66. In a specific embodiment, the invention encompasses the plasmid pMGxO675 that comprises nucleotide sequences SEQ ID NO:69 and SEQ ID NO:65 that encode the amino acid sequences of the heavy chain (SEQ ID NO:70) and light chain (SEQ ID NO:66), respectively, of a specific example of a h2B6 antibody of the invention, which plasmid has ATCC Accession number PTA-7609, and was deposited on May 23, 2006.

The methods of the invention also encompass polynucleotides that hybridize under various stringency, e.g., high stringency, intermediate or lower stringency conditions, to polynucleotides that encode a humanized antibody of the invention. The hybridization can be performed under various conditions of stringency. By way of example and not limitation, procedures using conditions of low stringency are as follows (see also Shilo and Weinberg, 1981, *Proc. Natl. Acad. Sci. U.S.A.* 78, 6789-6792; incorporated by reference in its entirety). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations). By way of example and not limitation, procedures using conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987-1997, Current Protocols, © 1994-1997 John Wiley and Sons, Inc.; see especially, Dyson, 1991, "Immobilization of nucleic acids and hybridization analysis," In: Essential Molecular Biology: A Practical Approach, Vol. 2, T. A. Brown, ed., pp. 111-156, IRL Press at Oxford University Press, Oxford, UK (each of which is incorporated by reference in its entirety)).

The polynucleotides may be obtained, and the nucleotide sequence of the polynucleotides determined, by any method known in the art.

A polynucleotide encoding a humanized antibody of the invention may be generated from nucleic acid from a suitable source (e.g., a cDNA library generated from, or nucleic acid, preferably poly A+ RNA, isolated from, any tissue or cells expressing the antibody, such as hybridoma cells selected to express an antibody of the invention, e.g., 2B6 or 3H7) by hybridization with Ig specific probes and/or PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the humanized antibody is determined, the nucleotide sequence of the humanized antibody may be manipulated using methods well known in the art for the manipulation of nucleotide sequences, e.g., recombinant DNA techniques, site directed mutagenesis, PCR, etc. (see, for example, the techniques described in Sambrook et al, 1990, Molecular Cloning A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In another embodiment, human libraries or any other libraries available in the art, can be screened by standard techniques known in the art, to clone the nucleic acids encoding the antibodies of the invention.

6.2.3 Recombinant Expression of Antibodies

Once a nucleic acid sequence encoding a humanized antibody of the invention has been obtained, the vector for the production of the antibody may be produced by recombinant DNA technology using techniques well known in the art, e.g. the vector pMGx0675, which encodes the heavy and light chain of a h2B6 antibody of the invention, deposited with ATCC on May 23, 2006 and having Accession number PTA-7609. Methods which are well known to those skilled in the art can be used to construct expression vectors containing the humanized antibody coding sequences and appropriate transcriptional and translational control signals. These methods include, for example, in vitro recombinant DNA techniques, synthetic techniques, and in vivo genetic recombination. (See, for example, the techniques described in Sambrook et al., 1990, Molecular Cloning, A Laboratory Manual, 2d Ed., Cold Spring Harbor Laboratory, Cold Spring Harbor, N.Y. and Ausubel et al. eds., 1998, Current Protocols in Molecular Biology, John Wiley & Sons, NY (each of which is incorporated by reference in its entirety)).

An expression vector comprising the nucleotide sequence of a humanized antibody of the invention can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the humanized antibody is regulated by a constitutive, an inducible or a tissue, specific promoter.

The host cells used to express the recombinant antibodies of the invention may be either bacterial cells such as Escherichia coli, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 1998, Gene 45:101; Cockett et al., 1990, Bio/Technology 8:2) (see paragraph 147). Preferably, the host cell is a dihydrofolate reductase deficient chinese hamster ovary cell (CHO), e.g., a Lec 13 CHO cell (lectin resistant CHO mutant cell line; (see, e.g., U.S. Patent Application Publication No. 2003/0115614; PCT Publication No. WO 00/61739; European Patent Application EP 1 229 125; Ribka & Stanley, 1986, Somatic Cell & Molec. Gen. 12(1): 51-62; Ripka et al., 1986 Arch. Biochem. Biophys. 249(2): 533-45); each of which is incorporated by reference herein in its entirety), or a CHO-K1cell, a DUX-B11 cell, a CHO-DP12 cell or a CHO-DG44 cell, which has been modified so that the antibody is not substantially fucosylated.

A variety of host-expression vector systems may be utilized to express the humanized antibodies of the invention. Such host-expression systems represent vehicles by which the coding sequences of the humanized antibodies may be produced and subsequently purified, but also represent cells which may, when transformed or transfected with the appropriate nucleotide coding sequences, express the humanized antibodies of the invention in situ. These include, but are not limited to, microorganisms such as bacteria (e.g., E. coli and B. subtilis) transformed with recombinant bacteriophage DNA, plasmid DNA or cosmid DNA expression vectors containing immunoglobulin coding sequences; yeast (e.g., *Saccharomyces Pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807,715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts. (e.g., see Logan & Shenk, 1984, *Proc. Natl. Acad. Sci. USA* 81:355-359; incorporated by reference in its entirety). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544; incorporated by reference in its entirety).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express a humanized antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 *Clinical Pharmacy* 12:488-505; Wu and Wu, 1991, 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al, 1981, *J. Mol. Biol.* 150:1; and hygro, which confers resistance to hygromycin (Santerre et al., 1984, *Gene* 30:147). Each of the foregoing references is incorporated herein by reference in its entirety.

The expression levels of a humanized antibody of the invention can be increased by vector amplification (for a review, see Bebbington and Hentschel, *The use of vectors based on gene amplification for the expression of cloned genes in mammalian cells in DNA cloning*, Vol. 3. (Academic Press, New York, 1987); incorporated by reference in its entirety). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell. Biol.* 3:257; incorporated by reference in its entirety).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides, e.g. pMGx0675 encoding the heavy and light chain of a h2B6 antibody of the invention, having ATCC accession number PTA-7609, deposited May 23, 2006. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197; incorporated by reference in its entirety). The coding sequences for the heavy and light chains may comprise cDNA or genomic DNA.

Once the humanized antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

6.3 Prophylactic and Therapeutic Methods

The present invention encompasses antibody-based therapies which involve administering one or more of the humanized antibodies of the invention to an animal, preferably a mammal, and most preferably a human, for preventing, treating, or ameliorating symptoms associated with a disease, disorder, or infection, associated with aberrant levels or activity of FcγRIIB and/or treatable by altering immune function associated with FcγRIIB activity or enhancing cytotoxic activity of a second therapeutic antibody or enhancing efficacy of a vaccine composition or breaking tolerance to an antigen. In some embodiments, therapy by administration of one or more antibodies of the invention is combined with administration of one or more therapies such as, but not limited to, chemotherapies, radiation therapies, hormonal therapies, and/or biological therapies/immunotherapies.

FcγRIIB (CD32B) has been found to be expressed in the following tissue types: adipose, b-cell, bone, brain, cartilage, colon, endocrine, eye, fetus, gastrointestinal tract, genitourinary, germ cell, head and neck, kidney, lung, lymph node, lymphoreticular, mammary gland, muscle, nervous, ovary, pancreas, pancreatic islet, pituitary gland, placenta, retina, skin, soft tissue, synovium, and uterus (data collected from the Cancer Genome Anatomy Project of the National Cancer Institute). Thus, the humanized antibodies of the invention can be used to agonize or antagonize the activity of FcγRIIB in any of these tissues. For example, FcγRIIB is expressed in the placenta and may play a role in transport of IgG to the fetus and also in scavenging immune complexes (Lyden et al., 2001, *J. Immunol.* 166:3882-3889). In certain embodiments of the invention, a humanized FcγRIIB antibody can used as an abortifacient.

Prophylactic and therapeutic compounds of the invention include, but are not limited to, proteinaceous molecules, including, but not limited to, peptides, polypeptides, proteins, including post-translationally modified proteins, antibodies, etc.; small molecules (less than 1000 daltons), inorganic or organic compounds; nucleic acid molecules including, but not limited to, double-stranded or single-stranded DNA, double-stranded or single-stranded RNA, as well as triple helix nucleic acid molecules. Prophylactic and therapeutic compounds can be derived from any known organism (including, but not limited to, animals, plants, bacteria, fungi, and protista, or viruses) or from a library of synthetic molecules.

Humanized antibodies may be provided in pharmaceutically acceptable compositions as known in the art or as described herein. As detailed below, the humanized antibodies of the invention can be used in methods of treating cancer (particularly to enhance passive immunotherapy or efficacy of a cancer vaccine), autoimmune disease, inflammatory disorders or allergies (e.g., to enhance efficacy of a vaccine for treatment of allergy).

Humanized antibodies of the present invention that function as a prophylactic and/or therapeutic agent of a disease, disorder, or infection can be administered to an animal, preferably, a mammal and most preferably, a human, to treat, prevent or ameliorate one or more symptoms associated with the disease, disorder, or infection. Antibodies of the invention can be administered in combination with one or more other prophylactic and/or therapeutic agents useful in the treatment, prevention or management of a disease, disorder, or infection associated with aberrant levels or activity of FcγRIIB and/or treatable by altering immune function associated with FcγRIIB activity. In certain embodiments, one or more antibodies of the invention are administered to a mammal, preferably, a human, concurrently with one or more other therapeutic agents useful for the treatment of cancer. The term "concurrently" is not limited to the administration of prophylactic or therapeutic agents at exactly the same time, but rather it is meant that antibodies of the invention and the other agent are administered to a subject in a sequence and within a time interval such that the antibodies of the invention can act together with the other agent to provide an increased benefit than if they were administered otherwise. For example, each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route.

In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56$^{th}$ ed., 2002).

The humanized antibodies of this invention may also be advantageously utilized in combination with other monoclonal or chimeric antibodies, Fc fusion proteins, or with lymphokines, cytokines or hematopoietic growth factors (such as, e.g., IL-2, IL-3, IL-4, IL-7, IL-10 and TGF-β), which enhance FcγRIIB, for example, serve to increase the number or activity of effector cells which interact with the antibodies and, increase immune response. In certain embodiments, a cytokine is conjugated to an anti-FcγRIIB antibody.

The humanized antibodies of this invention may also be advantageously utilized in combination with one or more drugs used to treat a disease, disorder, or infection such as, for example anti-cancer agents, anti-inflammatory agents or anti-viral agents, e.g., as detailed in sections 5.3.6 and 5.3.5 below.

6.3.1 Cancers

Humanized antibodies of the invention can be used alone or in combination with other therapeutic antibodies known in the art to prevent, inhibit or reduce the growth of primary tumores or metastasis of cancerous cells. In one embodiment, humanized antibodies of the invention can be used in combination with antibodies used in cancer immunotherapy. The invention encompasses the use of the humanized antibodies of the invention in combination with another therapeutic antibody to enhance the efficacy of such immunotherapy by increasing the potency of the therapeutic antibody's effector function, e.g., ADCC, CDC, phagocytosis, opsonization, etc. Although not intending to be bound by a particular mechanism of action antibodies of the invention block FcγRIIB, preferably on monocytes and macrophages and thus enhance the therapeutic benefits a clinical efficacy of tumor specific antibodies by, for example, enhancing clearance of the tumors mediated by activating fcγRs.

Accordingly, the invention provides methods of preventing or treating cancer characterized by a cancer antigen, when administered in combination with another antibody that specifically binds a cancer antigen and is cytotoxic. The humanized antibodies of the invention are useful for prevention or treatment of cancer, particularly in potentiating the cytotoxic activity of cancer antigen-specific therapeutic antibodies with cytotoxic activity to enhance tumor cell killing by the antibodies of the invention and/or enhancing, for example, ADCC activity or CDC activity of the therapeutic antibodies. In certain embodiments of the invention, humanized antibodies of the invention are administered with Fc fusion proteins. In a specific embodiment, a humanized antibody of the invention, when administered alone or in combination with a cytotoxic therapeutic antibody, inhibits or reduces the growth of primary tumor or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of primary tumor or metastasis in absence of said antibody of the invention. In a preferred embodiment, humanized antibodies of the invention in combination with a cytotoxic therapeutic antibody inhibit or reduce the growth of primary tumor or metastasis of cancer by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of said antibodies.

The transition from a normal to a malignant state is a multistep process involving genetic and epigenetic changes. In fact, numerous alterations occur in the cellular regulatory circuits that facilitate this progression which enables tumor cells to evade the commitment to terminal differentiation and quiescence that normally regulate tissue homeostasis. Certain genes have been implicated in invasiveness and metastatic potential of cancer cells such as CSF-1 (colony stimulating factor 1 or macrophage colony stimulating factor). Although not intending to be bound by a particular mechanism of action, CSF-1 may mediate tumor progression and metastasis by recruiting macrophages to the tumor site where they promote progression of tumor. It is believed that macrophages have a trophic role in mediating tumor progression and metastasis perhaps by the secretion of angiogenic factors, e.g., thymidine phosphorylase, vascular endothelial-derived growth factor; secretion of growth factors such as epidermal growth factor that could act as a paracrine factor on tumor cells, and thus promoting tumor cell migration and invasion into blood vessels. (See, e.g., Lin et al., 2001, *J. Exp. Med.* 193(6): 727-739; Lin et al., 2002, *Journal of Mammary Gland Biology and Neoplasam* 7(2): 147-162; Scholl et al., 1993, *Molecular Carcinogenesis*, 7: 207-11; Clynes et al., 2000, *Nature Medicine*, 6(4): 443-446; Fidler et al., 1985, *Cancer Research*, 45: 4714-26 (each of which is incorporated by reference in its entirety)).

The invention encompasses using the humanized antibodies of the invention to block macrophage mediated tumor cell progression and metastasis. The antibodies of the invention are particularly useful in the treatment of solid tumors, where macrophage infiltration occurs. The antagonistic antibodies of the invention are particularly useful for controlling, e.g., reducing or eliminating, tumor cell metastasis, by reducing or eliminating the population of macrophages that are localized at the tumor site. In some embodiments, the humanized antibodies of the invention are used alone to control tumor cell metastasis. Although not intending to be bound by a particular mechanism of action, the antagonistic antibodies of the invention, when administered alone bind the inhibitory FcγRIIB on macrophages and effectively reduce the population of macrophages and thus restrict tumor cell progression. The antagonistic antibodies of the invention reduce, or preferably, eliminate macrophages that are localized at the tumor site, since FcγRIIB is preferentially expressed on activated monocytes and macrophages including tumor-infiltrating macrophages. In some embodiments, the humanized antibodies of the invention are used in the treatment of cancers that are characterized by the overexpression of CSF-1, including, but not limited to, breast, uterine, and ovarian cancers.

The invention further encompasses humanized antibodies that effectively deplete or eliminate immune cells other than macrophages that express FcγRIIB, e.g., dendritic cells and B-cells. Effective depletion or elimination of immune cells using the antibodies of the invention may range from a reduction in population of the immune cells by 50%, 60%, 70%, 80%, preferably 90%, and most preferably 99%. Thus, the humanized antibodies of the invention have enhanced therapeutic efficacy either alone or in combination with a second antibody, e.g., a therapeutic antibody such as anti-tumor antibodes, anti-viral antibodies, and anti-microbial antibodies. In some embodiments, the therapeutic antibodies have specificity for a cancer cell or an inflammatory cell. In other embodiments, the second antibody binds a normal cell. Although not intending to be bound by a particular mechanism of action, when the antibodies of the invention are used alone to deplete FcγRIIB-expressing immune cells, the population of cells is redistributed so that effectively the cells that are remaining have the activating Fc receptors and thus the suppression by FcγRIIB is alleviated. When used in combination with a second antibody, e.g., a therapeutic antibody the efficacy of the second antibody is enhanced by increasing the Fc-mediated effector function of the antibody.

The humanized antibodies and fragments thereof of the invention and methods of treatment ae believed to be effective for the treatment of both liquid and solid cancers. By liquid cancers it is meant cancers of the bone marrow, such as leukemias. Solid cancers generally refer to cancers of organs and/or other tissues. Cancers and related disorders that can be treated or prevented by methods and compositions of the present invention include, but are not limited to, the following: leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, pappillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, non-seminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America (each of which is incorporated by reference in its entirety)).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

Cancers associated with the cancer antigens may be treated or prevented by administration of the antibodies of the invention in combination with an antibody that binds the cancer antigen and is cytotoxic. In one particular embodiment, the antibodies of the invention enhance the antibody mediated cytotoxic effect of the antibody directed at the particular cancer antigen. For example, but not by way of limitation, cancers associated with the following cancer antigens may be treated or prevented by the methods and compositions of the invention: KS ¼ pan-carcinoma antigen (Perez and Walker, 1990, *J. Immunol.* 142:32-37; Bumal, 1988, *Hybridoma* 7(4): 407-415), ovarian carcinoma antigen (CA125) (Yu et al., 1991, *Cancer Res.* 51(2):48-475), prostatic acid phosphate (Tailor et al., 1990, *Nucl. Acids Res.* 18(1):4928), prostate specific antigen (Henttu and Vihko, 1989, *Biochem. Biophys. Res. Comm.* 10(2):903-910; Israeli et al., 1993, *Cancer Res.* 53:227-230), melanoma-associated antigen p97 (Estin et al., 1989, *J. Natl. Cancer Instit.* 81(6):445-44), melanoma antigen gp75 (Vijayasardahl et al., 1990, *J. Exp. Med.* 171(4): 1375-1380), high molecular weight melanoma antigen (HMW-MAA) (Natali et al., 1987, *Cancer* 59:55-3; Mittelman et al., 1990, *J. Clin. Invest.* 86:2136-2144)), prostate specific membrane antigen, carcinoembryonic antigen (CEA) (Foon et al, 1994, *Proc. Am. Soc. Clin. Oncol.* 13:294), polymorphic epithelial mucin antigen, human milk fat globule antigen, Colorectal tumor-associated antigens such as: CEA, TAG-72 (Yokata et al., 1992, *Cancer Res.* 52:3402-3408), CO17-1A (Ragnhammar et al., 1993, *Int. J. Cancer* 53:751-758); GICA 19-9 (Herlyn et al., 1982, *J. Clin. Immunol.* 2:135), CTA-1 and LEA, Burkitt's lymphoma antigen-38.13, CD19 (Ghetie et al., 1994, *Blood* 83:1329-1336), human B-lymphoma antigen-CD20 (Reff et al., 1994, *Blood* 83:435-445), CD33 (Sgouros et al., 1993, *J. Nucl. Med.* 34:422-430), melanoma specific antigens such as ganglioside GD2 (Saleh et al., 1993, *J. Immunol.*, 151, 3390-3398), ganglioside GD3 (Shitara et al., 1993, *Cancer Immunol. Immunother.* 36:373-380), ganglioside GM2 (Livingston et al., 1994, *J. Clin. Oncol.* 12:1036-1044), ganglioside GM3 (Hoon et al., 1993, *Cancer Res.* 53:5244-5250), tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellstrom et al., 1985, *Cancer. Res.* 45:2210-2188), differentiation antigen such as human lung carcinoma antigen L6, L20 (Hellstrom et al., 1986, *Cancer Res.* 46:3917-3923), antigens of fibrosarcoma, human leukemia T cell antigen-Gp37 (Bhattacharya-Chatterjee et al., 1988, *J. of Immun.* 141:1398-1403), neoglycoprotein, sphingolipids, breast cancer antigen such as EGFR (Epidermal growth factor receptor), HER2 antigen ($p185^{HER2}$), polymorphic epithelial mucin (PEM) (Hilkens et al., 1992, *Trends in Bio. Chem. Sci.* 17:359), malignant human lymphocyte antigen-APO-1 (Bernhard et al., 1989, *Science* 245:301-304), differentiation antigen (Feizi, 1985, *Nature* 314:53-57) such as I antigen found in fetal erthrocytes and primary endoderm, I(Ma) found in gastric adencarcinomas, M18 and M39 found in breast epithelium, SSEA-1 found in myeloid cells, VEP8, VEP9, Myl, VIM-D5, and $D_1$56-22 found in colorectal cancer, TRA-1-85 (blood group H), C14 found in colonic adenocarcinoma, F3 found in lung adenocarcinoma, AH6 found in gastric cancer, Y hapten, $Le^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma, CO-514 (blood group $Le^a$) found in adenocarcinoma, NS-10 found in adenocarcinomas, CO-43 (blood group $Le^b$), G49, EGF receptor, (blood group $ALe^b/Le^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, M1:22:25:8 found in embryonal carcinoma cells and SSEA-3, SSEA-4 found in 4-8-cell stage embryos. In another embodiment, the antigen is a T cell receptor derived peptide from a cutaneous T cell lymphoma (see Edelson, 1998, *The Cancer Journal* 4:62). Each of the foregoing references is hereby incorporated herein in its entirety.

The humanized antibodies of the invention can be used in combination with any therapeutic cancer antibodies known in the art to enhance the efficacy of treatment. For example, the humanized antibodies of the invention can be used with any of the antibodies in Table 4 that have demonstrated therapeutic utility in cancer treatment. The humanized antibodies of the invention enhance the efficacy of treatment of the therapeutic cancer antibodies by enhancing at least one antibody-mediated effector function of said therapeutic cancer antibodies. In one particular embodiment, the humanized antibodies enhance the efficacy of treatment by enhancing the complement dependent cascade of said therapeutic cancer antibodies. In another embodiment of the invention, the humanized antibodies of the invention enhance the efficacy of treatment by enhancing the phagocytosis and opsonization of the targeted tumor cells. In another embodiment of the invention, the humanized antibodies of the invention enhance the efficacy of treatment by enhancing antibody-dependent cell-mediated cytotoxicity ("ADCC") in destruction of the targeted tumor cells.

Humanized antibodies of the invention can also be used in combination with cytosine-guanine dinucleotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of cancer (See also Warren et al., 2002, *Semin Oncol.*, 29(1 Suppl 2):93-7; Warren et al., 2000, *Clin Lymphoma*, 1(1):57-61, both of which are incorporated herein by reference).

Humanized antibodies of the invention can be used in combination with a therapeutic antibody that does not mediate its therapeutic effect through cell killing to potentiate the antibody's therapeutic activity. In a specific embodiment, the invention encompasses use of the antibodies of the invention in combination with a therapeutic apoptosis inducing antibody with agonisitc activity, e.g., an anti-Fas antibody. Anti-Fas antibodies are known in the art and include, for example, Jo2 (Ogasawara et al., 1993, *Nature* 364: 806) and HFE7 (Ichikawa et al., 2000, *Int. Immunol* 12: 555) (each of which is incorporated by reference in its entirety). Although not intending to be bound by a particular mechanisms of action, FcγRIIB has been implicated in promoting anti-Fas mediated apoptosis, see, e.g., Xu et al., 2003, *Journal of Immunology*, 171: 562-568; incorporated by reference in its entirety. In fact, the extracellular domain of FcγRIIB may serve as a cross-linking agent for Fas receptors, leading to a functional complex and promoting Fas dependent apoptosis. In some embodiments, the antibodies of the invention block the interaction of anti-Fas antibodies and FcγRIIB, leading to a reduction in Fas-mediated apoptotic activity. Antibodies of the invention that result in a reduction in Fas-mediated apoptotic activity are particularly useful in combination with anti-Fas antibodies that have undesirable side effects, e.g., hepatotoxicity. In other embodiments, the antibodies of the invention enhance the interaction of anti-Fas antibodies and FcγRIIB, leading to an enhancement of Fas-mediated apoptotic activity. Combination of the antibodies of the invention with therapeutic apoptosis inducing antibodies with agonisitc activity have an enhanced therapeutic efficacy.

Therapeutic apoptosis inducing antibodies used in the methods of the invention may be specific for any death receptor known in the art for the modulation of apoptotic pathway, e.g., TNFR receptor family.

The invention provides a method of treating diseases with impaired apoptotic mediated signaling, e.g., cancer or autoimmune disease. In a specific embodiment, the invention encompasses a method of treating a disease with deficient Fas-mediated apoptosis, said method comprising administering an antibody of the invention in combination with an anti-Fas antibody.

In some embodiments, the agonistic antibodies of the invention are particularly useful for the treatment of tumors of non-hematopoietic origin, including tumors of melanoma cells. Although not intending to be bound by a particular mechanism of action, the efficacy of the agonistic antibodies of the invention is due, in part, to activation of FcγRIIB inhibitory pathway, as tumors of non-hematopoietic origin, including tumors of melanoma cells express FcγRIIB. Recent experiments have in fact shown that expression of FcγRIIB in melanoma cells modulates tumor growth by direct interaction with anti-tumor antibodies (e.g., by binding the Fc region of the anti-tumor antibodies) in an intracytoplasmic-dependent manner (Cassard et al., 2002, *Journal of Clinical Investigation*, 110(10): 1549-1557; incorporated by reference in its entirety).

In some embodiments, the invention encompasses use of the antibodies of the invention in combination with therapeutic antibodies that immunospecifically bind to tumor antigens that are not expressed on the tumor cells themselves, but rather on the surrounding reactive and tumor supporting non-malignant cells comprising the tumor stroma. The tumor stroma comprises endothelial cells forming new blood vessels and stromal fibroblasts surrounding the tumor vasculature. In a specific embodiment, an antibody of the invention is used in combination with an antibody that immunospecifically binds a tumor antigen on an endothelial cell. In a preferred embodiment, an antibody of the invention is used in combination with an antibody that immunospecifically binds a tumor antigen on a fibroblast cell, e.g., fibroblast activation protein (FAP). FAP is a 95 KDa homodimeric type II glycoprotein which is highly expressed in stromal fibroblasts of many solid tumors, including, but not limited to, lung, breast, and colorectal carcinomas. (See, e.g., Scanlan et al, 1994; *Proc. Natl. Acad. USA*, 91: 5657-61; Park et al., 1999, *J. Biol. Chem.*, 274: 36505-12; Rettig et al., 1988, *Proc. Natl. Acad. Sci. USA* 85: 3110-3114; Garin-Chesea et al., 1990, *Proc. Natl. Acad. Sci. USA* 87: 7235-7239). Antibodies that immunospecifically bind FAP are known in the art and encompassed within the invention, see, e.g., Wuest et al., 2001, *Journal of Biotechnology*, 159-168; Mersmann et al., 2001, *Int. J. Cancer,* 92: 240-248; U.S. Pat. No. 6,455,677; all of which are incorporated herein in by reference in their entireties.

Recently IgE's have been implicated as mediators of tumor growth and, in fact, IgE-targeted immediate hypersensitivity and allergic inflammation reactions have been proposed as possible natural mechanisms involved in anti-tumor responses (for a review, see, e.g., Mills et al., 1992, *Am. Journal of Epidemiol.* 122: 66-74; Eriksson et al., 1995, Allergy 50: 718-722 (each of which is incorporated by reference in its entirety)). In fact, a recent study has shown loading tumor cells with IgEs reduces tumor growth, leading in some instances to tumor rejection. According to the study, IgE loaded tumor cells not only possess a therapeutic potential but also confer long term antitumor immunity, including activation of innate immunity effector mechanism and T-cell mediated adaptive immune response, see Reali et al., 2001, *Cancer Res.* 61: 5516-22; which is incorporated herein by reference in its entirety. The antagonistic antibodies of the invention may be used in the treatment and/or prevention of cancer in combination with administration of IgEs in order to enhance the efficacy of IgE-mediated cancer therapy. Although not intending to be bound by a particular mechanism of action the antibodies of the invention enhance the therapeutic efficacy of IgE treatment of tumors, by blocking the inhibitory pathway. The antagonistic antibodies of the invention may enhance the therapeutic efficacy of IgE mediated cancer therapy by (i) enhancing the delay in tumor growth; (ii) enhancing the decrease in the rate of tumor progression; (iii) enhancing tumor rejection; or (iv) enhancing protective immune relative to treatment of cancer with IgE alone.

Cancer therapies and their dosages, routes of administration and recommended usage are known in the art and have been described in the literature, see, e.g., *Physician's Desk Reference* (56$^{th}$ ed., 2002, which is incorporated herein by reference).

6.3.2 B Cell Malignancies

The agonistic antibodies of the invention are useful for treating or preventing any B cell malignancies, particularly non-Hodgkin's lymphoma and chronic lymphocytic leukemia. Other B-cell malignancies include small lymphocytic lymphoma, Burkitt's lymphoma, mantle cell lymphomas diffuse small cleaved cell lymphomas, most follicular lymphomas and some diffuse large B cell lymphomas (DLBCL). FcγRIIB, is a target for deregulation by chromosomal translocation in malignant lymphoma, particularly in B-cell non-Hodgkin's lymphoma (See Callanan M. B. et al., 2000 *Proc. Natl. Acad. Sci. U.S.A.*, 97(1):309-314). Thus, the antibodies of the invention are useful for treating or preventing any chronic lymphocytic leukemia of the B cell lineage. Chronic lymphocytic leukemia of the B cell lineage are reviewed by Freedman (See review by Freedman, 1990, *Hemtaol. Oncol. Clin. North Am.* 4:405). Although not intending to be bound by any mechanism of action, the agonistic antibodies of the invention inhibit or prevent B cell malignancies inhibiting B cell proliferation and/or activation. The invention also encompasses the use of the agonistic antibodies of the invention in combination with other therapies known (e.g., chemotherapy and radiotherapy) in the art for the prevention and/or treatment of B cell malignancies. The invention also encompasses the use of the agonistic antibodies of the invention in combination with other antibodies known in the art for the treatment and or prevention of B-cell malignancies. For example, the agonistic antibodies of the invention can be used in combination with the anti-C22 or anti-CD19 antibodies disclosed by Goldenberg et al. (U.S. Pat. No. 6,306,393), anti-$CD_{20}$ antibodies, anti-CD33 antibodies, or anti-CD52 antibodies.

Antibodies of the invention can also be used in combination with, for example, Oncoscint (target: CEA), Verluma (target: GP40), Prostascint (target: PSMA), CEA-SCAN(target: CEA), Rituxin (target: CD20), Herceptin (target: HER-2), Campath (target: CD52), Mylotarge (target: CD33), LymphoCide (target: CD22), Lymphocide Y-90 (target: CD22) and Zevalin (target: CD20).

6.3.3 Autoimmune Disease and Inflammatory Diseases

The agonistic antibodies of the invention may be used to treat or prevent autoimmune diseases or inflammatory diseases. The present invention provides methods of preventing, treating, or managing one or more symptoms associated with an autoimmune or inflammatory disorder in a subject, comprising administering to said subject a therapeutically effective amount of the antibodies or fragments thereof of the invention. The invention also provides methods for preventing, treating, or managing one or more symptoms associated with an inflammatory disorder in a subject further comprising, administering to said subject a therapeutically effective amount of one or more anti-inflammatory agents. The invention also provides methods for preventing, treating, or managing one or more symptoms associated with an autoimmune disease further comprising, administering to said subject a therapeutically effective amount of one or more immunomodulatory agents. Section 5.4.5 provides non-limiting examples of anti-inflammatory agents and immunomodulatory agents.

The humanized antibodies of the invention can also be used in combination with any of the antibodies known in the art for the treatment and/or prevention of autoimmune disease or inflammatory disease. A non-limiting example of the antibodies or Fc fusion proteins that are used for the treatment or prevention of inflammatory disorders is presented in Table 4A, and a non-limiting example of the antibodies or Fc fusion proteins that are used for the treatment or prevention of autoimmune disorder is presented in Table 4B. The humanized antibodies of the invention can, for example, enhance the efficacy of treatment of the therapeutic antibodies or Fc fusion proteins presented in Tables 5A and 5B. For example, but not by way of limitation, the antibodies of the invention can enhance the immune response in the subject being treated with any of the antibodies or Fc fusion proteins in Tables 5A or 5B.

Humanized antibodies of the invention can also be used in combination with for example, but not by way of limitation, Orthoclone OKT3, ReoPro, Zenapax, Simulec, Rituximab, Synagis, and Remicade.

Humanized antibodies of the invention can also be used in combination with cytosine-guanine dinucleotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of autoimmune or inflammatory disorders (Weeratna et al., 2001, *FEMS Immunol Med. Microbiol.*, 32(1):65-71, which is incorporated herein by reference).

Examples of autoimmune disorders that may be treated by administering the antibodies of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis (including rheumatoid arthritis of the skin, eyes, lungs, heart, blood or nerves), sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. As described herein in Section 3.1, some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. The term arthritis is also generally used to describe disorders beyond rheumatoid arthritis, that are commonly associated with autoimmune inflammation. Nonlimiting examples of such disorders that can be prevented, treated or managed in accordance with the methods of the invention include psoriatic arthritis, Reiter's syndrome and ankylosing spondylitis arthritis.

Use of the invention in the context of an autoimmune disease (e.g., rheumatoid arthritis) therefore excompasses methods to treat the acute phases of the disease as well as to prevent recurrence of its symptoms. The response to the therapeutic methods of the invention in the context of the autoimmune disease (e.g., rheumatoid arthritis) may be assessed by methods described herein or by any method known to one of ordinary skill in the art. For example, in the case of rheumatoid arthritis, many, but not all, people have rheumatoid-factor antibody in their blood; however, the presence of rheumatoid factor is not in itself definitive for a positive diagnosis of RA as other conditions are know which cause the rheumatoid factor to be produced. Therefore, the diagnosis and assessment of rheumatoid arthritis is most commonly based on a combination of factors, including, but not limited to: the specific location and symmetry of painful joints, the presence of joint stiffness in the morning, the presence of bumps and nodules under the skin (rheumatoid nodules), results of X-ray tests that suggest rheumatoid arthritis.

In certain embodiments of the invention, the humanized antibodies of the invention may be used to treat an autoimmune disease that is more prevalent in one sex. For example, the prevalence of Graves' disease in women has been associated with expression of FcγRIIB2 (see Estienne et al., 2002, FASEB J. 16:1087-1092; incorporated by reference in its entirety). Accordingly, humanized antibodies of the invention may be used to treat, prevent, ameliorate, or manage Graves' disease.

Humanized antibodies of the invention can also be used to reduce the inflammation experienced by animals, particularly mammals, with inflammatory disorders. In a specific embodiment, an antibody reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in the not administered said antibody. In another embodiment, a combination of antibodies reduce the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in not administered said antibodies.

Humanized antibodies of the invention can also be used to prevent the rejection of transplants.

TABLE 4A

Antibodies for Inflammatory Diseases and Autoimmune Diseases that can be used in combination with the antibodies of the invention.

| Antibody Name | Target Antigen | Product Type | Isotype | Sponsors | Indication |
|---|---|---|---|---|---|
| 5G1.1 | Complement (C5) | Humanised | IgG | Alexion Pharm Inc | Rheumatoid Arthritis |
| 5G1.1 | Complement (C5) | Humanised | IgG | Alexion Pharm Inc | SLE |
| 5G1.1 | Complement (C5) | Humanised | IgG | Alexion Pharm Inc | Nephritis |
| 5G1.1-SC | Complement (C5) | Humanised | ScFv | Alexion Pharm Inc | Cardiopulmano Bypass |
| 5G1.1-SC | Complement (C5) | Humanised | ScFv | Alexion Pharm Inc | Myocardial Infarction |
| 5G1.1-SC | Complement (C5) | Humanised | ScFv | Alexion Pharm Inc | Angioplasty |
| ABX-CBL ™ | CBL | Human | | Abgenix Inc | GvHD |
| ABX-CBL ™ | CD147 | Murine | IgG | Abgenix Inc | Allograft rejection |
| ABX-IL8 ™ | IL-8 | Human | IgG2 | Abgenix Inc | Psoriasis |
| ANTEGREN ™ | VLA-4 | Humanised | IgG | Athena/Elan | Multiple Sclerosis |
| Anti-CD11a | CD11a | Humanised | IgG1 | Genentech Inc/Xoma | Psoriasis |
| Anti-CD18 | CD18 | Humanised | Fab'2 | Genentech Inc | Myocardial infarction |
| Anti-LFA1 | CD18 | Murine | Fab'2 | Pasteur-Merieux/Immunotech | Allograft rejection |
| ANTOVA ™ | CD40L | Humanised | IgG | Biogen | Allograft rejection |
| ANTOVA ™ | CD40L | Humanised | IgG | Biogen | SLE |
| BTI-322 | CD2 | Rat | IgG | Medimmune Inc | GvHD, Psoriasis |
| CDP571 | TNF-alpha | Humanised | IgG4 | Celltech | Crohn's |
| CDP571 | TNF-alpha | Humanised | IgG4 | Celltech | Rheumatoid Arthritis |
| CDP850 | E-selectin | Humanised | | Celltech | Psoriasis |
| CORSEVIN M ™ | Fact VII | Chimeric | | Centocor | Anticoagulant |
| D2E7 | TNF-alpha | Human | | Abbott | Rheumatoid Arthritis |
| Hu23F2G | CD11/18 | Humanised | | ICOS Pharm Inc | Multiple Sclerosis |
| Hu23F2G | CD11/18 | Humanised | IgG | ICOS Pharm Inc | Stroke |
| IC14 | CD14 | | | ICOS Pharm Inc | Toxic shock |
| ICM3 | ICAM-3 | Humanised | | ICOS Pharm Inc | Psoriasis |
| IDEC-114 ™ | CD80 | Primatised | | IDEC Pharm/Mitsubishi | Psoriasis |
| IDEC-131 ™ | CD40L | Humanised | | IDEC Pharm/Eisai | SLE |
| IDEC-131 ™ | CD40L | Humanised | | IDEC Pharm/Eisai | Multiple Sclerosis |
| IDEC-151 ™ | CD4 | Primatised | IgG1 | IDEC Pharm/GlaxoSmithKline | Rheumatoid Arthritis |
| IDEC-152 | CD23 | Primatised | | IDEC Pharm | Asthma/Allergy |
| Infliximab | TNF-alpha | Chimeric | IgG1 | Centocor | Rheumatoid Arthritis |
| Infliximab | TNF-alpha | Chimeric | IgG1 | Centocor | Crohn's |
| LDP-01 ™ | beta2-integrin | Humanised | IgG | Millennium Inc (LeukoSite Inc.) | Stroke |
| LDP-01 ™ | beta2-integrin | Humanised | IgG | Millennium Inc (LeukoSite Inc.) | Allograft rejection |
| LDP-02 ™ | alpha4beta7 | Humanised | | Millennium Inc (LeukoSite Inc.) | Ulcerative Colitis |
| MAK-195F ™ | TNF alpha | Murine | Fab'2 | Knoll Pharm, BASF | Toxic shock |

TABLE 4A-continued

Antibodies for Inflammatory Diseases and Autoimmune Diseases that can be used in combination with the antibodies of the invention.

| Antibody Name | Target Antigen | Product Type | Isotype | Sponsors | Indication |
|---|---|---|---|---|---|
| MDX-33 ™ | CD64 (FcR) | Human | | Medarex/Centeon | Autoimmune haematogical disorders |
| MDX-CD4 ™ | CD4 | Human | IgG | Medarex/Eisai/Genmab | Rheumatoid Arthritis |
| MEDI-507 ™ | CD2 | Humanised | | Medimmune Inc | Psoriasis |
| MEDI-507 ™ | CD2 | Humanised | | Medimmune Inc | GvHD |
| OKT4A ® | CD4 | Humanised | IgG | Ortho Biotech | Allograft rejection |
| OrthoClone OKT4A ® | CD4 | Humanised | IgG | Ortho Biotech | Autoimmune disease |
| Orthoclone/anti-CD3 OKT3 ® | CD3 | Murine | mIgG2a | Ortho Biotech | Allograft rejection |
| RepPro/Abciximab | gpIIbIIIa | Chimeric | Fab | Centocor/Lilly | Complications of coronary angioplasty |
| rhuMab-E25 ™ | IgE | Humanised | IgG1 | Genentech/Novartis/Tanox Biosystems | Asthma/Allergy |
| SB-240563 | IL5 | Humanised | | GlaxoSmithKline | Asthma/Allergy |
| SB-240683 | IL-4 | Humanised | | GlaxoSmithKline | Asthma/Allergy |
| SCH55700 | IL-5 | Humanised | | Celltech/Schering | Asthma/Allergy |
| Simulect | CD25 | Chimeric | IgG1 | Novartis Pharm | Allograft rejection |
| SMART a-CD3 ® | CD3 | Humanised | | Protein Design Lab | Autoimmune disease |
| SMART a-CD3 ® | CD3 | Humanised | | Protein Design Lab | Allograft rejection |
| SMART a-CD3 ® | CD3 | Humanised | IgG | Protein Design Lab | Psoriasis |
| Zenapax ® | CD25 | Humanised | IgG1 | Protein Design Lab/Hoffman-La Roche | Allograft rejection |

TABLE 4B

Antibodies and Fc fusion proteins for Autoimmune Disorders

| Antibody | Indication | Target Antigen |
|---|---|---|
| ABX-RB2 ™ | | antibody to CBL antigen on T cells, B cells and NK cells fully human antibody from the Xenomouse |
| IL1-ra | rheumatoid arthritis | recombinant anti-inflammatory protein |
| sTNF-RI | chronic inflammatory disease rheumatoid arthritis | soluble tumor necrosis factor a - receptor type I blocks TNF action |
| 5c8 (Anti CD-40 ligand antibody) | Phase II trials were halted in October 1999 examine "adverse events" | CD-40 |
| IDEC 131 ™ | systemic lupus erythyematous (SLE) | anti CD40 humanized |
| IDEC 151 ™ | rheumatoid arthritis | primatized; anti-CD4 |
| IDEC 152 ™ | Asthma | primatized; anti-CD23 |
| IDEC 114 ™ | Psoriasis | primatized anti-CD80 |
| MEDI-507 ™ | rheumatoid arthritis; multiple sclerosis Crohn's disease psoriasis | anti-CD2 |
| LDP-02 (anti-b7 mAb) ™ | inflammatory bowel disease Crohn's disease ulcerative colitis | a4b7 integrin receptor on white blood cells (leukocytes) |
| SMART ® Anti-Gamma Interferon antibody | autoimmune disorders | Anti-Gamma Interferon |
| VERTEPORTIN ™ | rheumatoid arthritis | |
| THALOMID ® (thalidomide) | leprosy - approved for market Chron's disease rheumatoid arthritis | inhibitor of tumor necrosis factor alpha (TNF alpha) |

TABLE 4B-continued

Antibodies and Fc fusion proteins for Autoimmune Disorders

| Antibody | Indication | Target Antigen |
|---|---|---|
| SelCIDs (selective cytokine inhibitory drugs) | | highly specific inhibitors of phosphodiesterase type 4 enzyme (PDE-4) increases levels of cAMP (cyclic adenosine monophosphate) activates protein kinase A (PKA) blocks transcription factor NK-kB prevents transcription of TNF-a gene decreases production of TNF-a |
| IMiDs (immunomodulatory drugs) | general autoimmune disorders | structural analogues of thalidomideinhibit TNF-a |
| MDX-33 ™ | blood disorders caused by autoimmune reactions Idiopathic Thrombocytopenia Purpurea (ITP) autoimmune hemolytic anemia | monoclonal antibody against FcRI receptors |
| MDX-CD4 ™ | treat rheumatoid arthritis and other autoimmunity | monoclonal antibody against CD4 receptor molecule |
| VX-497 ™ | autoimmune disorders multiple sclerosis rheumatoid arthritis inflammatory bowel disease lupus psoriasis | inhibitor of inosine monophosphate dehydrogenase (enzyme needed to make new RNA and DNA used in production of nucleotides needed for lymphocyte proliferation) |
| VX-740 ™ | rheumatoid arthritis | inhibitor of ICE interleukin-1 beta (converting enzyme controls pathways leading to aggressive immune response regulates cytokines) |
| VX-745 ™ | specific to inflammation involved in chemical signaling of immune response onset and progression of inflammation | inhibitor of P38MAP kinase mitogen activated protein kinase |
| ENBREL ® (etanercept) | | targets TNF (tumor necrosis factor) |
| IL-8 | | fully human MAB against IL-8 (interleukin 8) (blocks IL-8 blocks inflammatory response) |
| 5G1.1 | rheumatoid arthritis pemphigoid (dangerous skin rash) psoriasis lupus | a C5 complement inhibitor |
| APOGEN ® MP4 | | recombinant antigen selectively destroys disease associated T-cells induces apoptosis T-cells eliminated by programmed cell death no longer attack body's own cells specific apogens target specific T-cells |

6.3.4 Allergy

The invention provides methods for treating or preventing an IgE-mediated and or FcεRI mediated allergic disorder in a subject in need thereof, comprising administering to said subject a therapeutically effective amount of the agonistic antibodies or fragments thereof of the invention. Although not intending to be bound by a particular mechanism of action, antibodies of the invention are useful in inhibiting FcεRI-induced mast cell activation, which contributes to acute and late phase allergic responses (Metcalfe D. et al 1997, *Physiol. Rev.* 77:1033; incorporated by reference in its entirety). Preferably, the agonistic antibodies of the invention have enhanced therapeutic efficacy and/or reduced side effects in comparison with the conventional methods used in the art for the treatment and/or prevention of IgE mediated allergic disorders. Conventional methods for the treatment and/or prevention of IgE mediated allergic disorders include, but are not limited to, anti-inflammatory drugs (e.g., oral and inhaled corticosteroids for asthma), antihistamines (e.g., for allergic rhinitis and atopic dermatitis), cysteinyl leukotrienes (e.g., for the treatment of asthma); anti-IgE antibodies; and specific immunotherapy or desensitization.

Examples of IgE-mediated allergic responses include, but are not limited to, asthma, allergic rhinitis, gastrointestinal allergies, eosinophilia, conjunctivitis, atopic dermatitis, urticaria, anaphylaxis, or golmerular nephritis.

The invention encompasses molecules, e.g., immunoglobulins, engineered to form complexes with FcεRI and human FcγRIIB, i.e., specifically bind FcεRI and human FcγRIIB. Preferably, such molecules have therapeutic efficacy in IgE and FcεRI-mediated disorders. Although not intending to be bound by a particular mechanism of action, the therapeutic efficacy of these engineered molecules is, in part, due to their ability to inhibit mast cell and basophil function.

In a specific embodiment, molecules that specifically bind FcεRI and human FcγRIIB are chimeric fusion proteins comprising a binding site for FcεRI and a binding site for FcγRIIB. Such molecules may be engineered in accordance with standard recombinant DNA methodologies known to one skilled in the art. In a preferred specific embodiment, a chimeric fusion protein for use in the methods of the invention comprises an F(ab') single chain of an anti-FcγRIIB monoclonal antibody of the invention fused to a region used as a bridge to link the huFcε to the C-terminal region of the F(ab') single chain of the anti-FcγRIIB monoclonal antibody. One exemplary chimeric fusion protein for use in the methods of the invention comprises the following: $V_L/C_H$(FcγRIIB)-hinge-$V_H/C_H$ (FcγRIIB)-LINKER-$C_H2$-$C_H3$-$C_H4$. The linker for the chimeric molecules may be five, ten, preferably, fifteen amino acids in length. The length of the linker may vary to provide optimal binding of the molecule to both FcγRIIB and FcεRI. In a specific embodiment, the linker is a 15 amino acid linker, consisting of the sequence: $(Gly_4Ser)_3$. Although not intending to be bound by a particular mechanism of action, the flexible peptide linker facilitates chain pairing and minimizes possible refolding and it will also allow the chimeric molecule to reach the two receptors, i.e., FcγRIIB and FcεRI on the cells and cross-link them. Preferably, the chimeric molecule is cloned into a mammalian expression vector, e.g., pCI-neo, with a compatible promoter, e.g., cytomegalovirus promoter. The fusion protein prepared in accordance with the methods of the invention will contain the binding site for FcεRI ($CH_ε2CH_ε3$) and for FcγRIIB (VL/CL,-hinge-VH/CH). The nucleic acid encoding the fusion protein prepared in accordance with the methods of the invention is preferably transfected into 293 cells and the secreted protein is purified using common methods known in the art.

Binding of the chimeric molecules to both human FcεRI and FcγRIIB may be assessed using common methods known to one skilled in the art for determining binding to an FcγR. Preferably, the chimeric molecules of the invention have therapeutic efficacy in treating IgE mediated disorders, for example, by inhibiting antigen-driven degranulation and inhibition of cell activation. The efficacy of the chimeric molecules of the invention in blocking IgE driven FcεRI-mediated mast cell degranulation may be determined in transgenic mice, which have been engineered to express the human FcεRα and human FcγRIIB, prior to their use in humans.

The invention provides the use of bispecific antibodies for the treatment and/or prevention of IgE-mediated and/or FcεRI-mediated allergic disorders. A bispecific antibody (BsAb) binds to two different epitopes usually on distinct antigens. BsAbs have potential clinical utility and they have been used to target viruses, virally infected cells and bacterial pathogens as well as to deliver thrombolitic agents to blood clots (Cao Y., 1998 *Bioconj. Chem.* 9: 635-644; Koelemij et al., 1999, *J. Immunother.*, 22, 514-524; Segal et al., *Curr. Opin. Immunol.*, 11, 558-562). The technology for the production of BsIgG and other related bispecific molecules is available (see, e.g., Carter et al., 2001 *J. of Immunol. Methods,* 248, 7-15; Segal et al., 2001, *J. of Immunol. Methods,* 248, 7-15, which are incorporated herein by reference in their entirety). The instant invention provides bispecific antibodies containing one F(ab') of the anti-FcγRIIB antibody and one F(ab') of an available monoclonal anti-huIgE antibody which aggregates two receptors, FcγRIIB and FcεRI, on the surface of the same cell. Any methodology known in the art and disclosed herein may be employed to generate bispecific antibodies for use in the methods of the invention. In a specific embodiment, the BsAbs will be produced by chemically cross-linking F(ab') fragments of an anti-FcγRIIB antibody and an anti-huIgE antibody as described previously (see, e.g., Glennie et al., 1995, Tumor Immunobiology, Oxford University press, Oxford, p. 225; which is incorporated herein by reference in its entirety). The F(ab') fragments may be produced by limited proteolysis with pepsin and reduced with mercaptoethanol amine to provide Fab' fragments with free hinge-region sulfhydryl (SH) groups. The SH group on one of the Fab' (SH) fragments may be alkylated with excess O-phenylenedimaleimide (O-PDM) to provide a free maleimide group (mal). The two preparations Fab'(mal) and Fab'(SH) may be combined at an appropriate ratio, preferably, 1:1 to generate heterodimeric constructs. The BsAbs can be purified by size exclusion chromatography and characterized by HPLC using methods known to one skilled in the art.

In particular, the invention encompasses bispecific antibodies comprising a first heavy chain-light chain pair that binds FcγRIIB with greater affinity than said heavy chain-light chain pair binds FcγRIIA, and a second heavy chain-light chain pair that binds IgE receptor, with the provision that said first heavy chain-light chain pair binds FcγRIIB first. The bispecific antibodies of the invention can be engineered using standard techniques known in the art to ensure that the binding to FcγRIIB precedes the binding to the IgE receptor. It will be understood to one skilled in the art to engineer the bispecific antibodies, for example, such that said bispecific antibodies bind FcγRIIB with greater affinity than said antibodies bind IgE receptor. Additionally, the bispecific antibodies can be engineered by techniques known in the art, such that the hinge size of the antibody can be increased in length, for example, by adding linkers, to provide the bispecific antibodies with flexibility to bind the IgE receptor and FcγRIIB receptor on the same cell.

The humanized antibodies of the invention can also be used in combination with other therapeutic antibodies or drugs known in the art for the treatment or prevention of IgE-mediated allergic disorders. For example, the antibodies of the invention can be used in combination with any of the following: azelastine, Astelin, beclomethasone dipropionate inhaler, Vanceril, beclomethasone dipropionate nasal inhaler/spray, Vancenase, Beconase budesonide nasal inhaler/spray, Rhinocort cetirizine, Zyrtec chlorpheniramine, pseudoephedrine, Deconamine, Sudafed, cromolyn, Nasalcrom, Intal, Opticrom, desloratadine, Clarinex, fexofenadine and pseudoephedrine, Allegra-D, fexofenadine, Allegra flunisolide nasal spray, Nasalide fluticasone propionate nasal inhaler/spray, Flonase fluticasone propionate oral inhaler, Flovent, hydroxyzine, Vistaril, Ataraxloratadine, pseudoephedrine, Claritin-D, loratadine, Claritin, prednisolone, Prednisolone, Pediapred Oral Liquid, Medrol prednisone, Deltasone, Liquid Predsalmeterol, Serevent triamcinolone acetonide inhaler, Azmacort triamcinolone acetonide nasal inhaler/spray, Nasacort, or NasacortAQ. Antibodies of the invention can be used in combination with cytosine-guanine dinucleotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of IgE-mediated allergic disorders (See also Weeratna et al., 2001, *FEMS Immunol Med. Microbiol.*, 32(1):65-71, which is incorporated herein by reference).

The invention encompasses the use of the humanized antibodies of the invention in combination with any therapeutic antibodies known in the art for the treatment of allergy disorders, e.g., Xolair™ (Omalizumab; Genentech); rhuMAB-E25 (BioWorld Today, Nov. 10, 1998, p. 1; Genentech); CGP-51901 (humanized anti-IgE antibody), etc.

Additionally, the invention encompasses the use of the humanized antibodies of the invention in combination with other compositions known in the art for the treatment of allergy disorders. In particular methods and compositions disclosed in Carson et al. (U.S. Pat. No. 6,426,336; U.S. Patent Application Publication Nos. 2002/0035109 A1 and 2002/0010343, all of which are incorporated herein by reference in its entirety).

6.3.5 Immunomodulatory Agents and Anti-Inflammatory Agents

The method of the present invention provides methods of treatment for autoimmune diseases and inflammatory diseases comprising administration of the antibodies of the present invention in conjunction with other treatment agents. Examples of immunomodulatory agents include, but are not limited to, methothrexate, ENBREL®, REMICADE™, HUMIRA®, leflunomide, cyclophosphamide, cyclosporine A, and macrolide antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators.

Anti-inflammatory agents have exhibited success in treatment of inflammatory and autoimmune disorders and are now a common and a standard treatment for such disorders. Any anti-inflammatory agent well-known to one of skill in the art can be used in the methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumetone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

6.3.6 Anti-Cancer Agents and Therapeutic Antibodies

In a specific embodiment, the methods of the invention encompass the administration of one or more angiogenesis inhibitors such as, but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); EGFr blockers/inhibitors (Iressa®, Tarceva®, Erbitux®, and ABX-EGF) Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Anti-cancer agents that can be used in combination with antibodies of the invention in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used in methods of the invention include, but are not limited to, HERCEPTIN® (Trastuzumab) (Genentech, South San Francisco, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ (rituximab) which is a chimeric anti-CD20 IgG1 antibody (IDEC Pharm/Genentech, Roche/Zettyaku); LYMPHOCIDE™ (epratuzumab) which is a humanized anti-CD22 IgG antibody (Immunomedics); ICM3 which is a humanized anti-ICAM3 antibody (ICOS Pharm); IDEC-114 which is a primatied anti-CD80 antibody (IDEC Pharm/Mitsubishi); ZEVALIN™ which is a radiolabelled murine anti-CD20 antibody (IDEC/Schering AG); IDEC-131 which is a humanized anti-CD40L antibody (IDEC/Eisai); IDEC-151 which is a primatized anti-CD4 antibody (IDEC); IDEC-152 which is a primatized anti-CD23 antibody (IDEC/Seikagaku); SMART anti-CD3 which is a humanized anti-CD3 IgG (Protein Design Lab); 5G1.1 which is a humanized anti-complement factor 5 (C5) antibody (Alexion Pharm); D2E7 which is a humanized anti-TNF-α antibody (CAT/BASF); CDP870 which is a humanized anti-TNF-α Fab fragment (Celltech); IDEC-151 which is a primatized anti-CD4 IgG1 antibody (IDEC Pharm/SmithKline Beecham); MDX-CD4 which is a human anti-CD4 IgG antibody (Medarex/Eisai/Genmab); CDP571 which is a humanized anti-TNF-α IgG4 antibody (Celltech); LDP-02 which is a humanized anti-α4β7 antibody (LeukoSite/Genentech); OrthoClone OKT4A which is a humanized anti-CD4 IgG antibody (Ortho Biotech); ANTOVA™ which is a humanized anti-CD40L IgG antibody (Biogen); ANTEGREN™ which is a humanized anti-VLA-4 IgG antibody (Elan); and CAT-152 which is a human anti-TGF-$β_2$ antibody (Cambridge Ab Tech).

Other examples of therapeutic antibodies that can be used in combination with the antibodies of the invention are presented in Table 5.

TABLE 5

Monoclonal antibodies for Cancer Therapy that can be used in combination with the antibodies of the invention.

| Company | Product | Disease | Target |
|---|---|---|---|
| Abgenix | ABX-EGF | Cancer | EGF receptor |
| AltaRex | OvaRex ® | ovarian cancer | tumor antigen CA125 |
|  | BravaRex ® | metastatic cancers | tumor antigen MUC1 |
| Antisoma | Theragyn (pemtumomabytrrium-90) | ovarian cancer | PEM antigen |
|  | THEREX ® | breast cancer | PEM antigen |
| Boehringer Ingelheim | blvatuzumab | head & neck cancer | CD44 |
| Centocor/J&J | PANOREX ® | Colorectal cancer | 17-1A |
|  | REOPRO ® | PTCA | gp IIIb/IIIa |
|  | REOPRO ® | Acute MI | gp IIIb/IIIa |
|  | REOPRO ® | Ischemic stroke | gp IIIb/IIIa |
| Corixa | Bexocar | NHL | CD20 |
| CRC Technology | MAb, idiotypic 105AD7 | colorectal cancer vaccine | gp72 |
| Crucell | Anti-EpCAM | cancer | Ep-CAM |
| Cytoclonal | MAb, lung cancer | non-small cell lung cancer | NA |
| Genentech | HERCEPTIN ® | metastatic breast cancer | HER-2 |
|  | HERCEPTIN ® | early stage breast cancer | HER-2 |
|  | RITUXAN ® | Relapsed/refractory low-grade or follicular NHL | CD20 |
|  | RITUXAN ® | intermediate & high-grade NHL | CD20 |
|  | MAb-VEGF | NSCLC, metastatic | VEGF |
|  | MAb-VEGF | Colorectal cancer, metastatic | VEGF |
|  | AMD Fab | age-related macular degeneration | CD18 |
|  | E-26 ($2^{nd}$ gen. IgE) | allergic asthma & rhinitis | IgE |

TABLE 5-continued

Monoclonal antibodies for Cancer Therapy that can be used in combination with the antibodies of the invention.

| Company | Product | Disease | Target |
|---|---|---|---|
| IDEC | ZEVALIN ® (RITUXAN ® + yttrium-90) | low grade of follicular, relapsed or refractory, CD20-positive, B-cell NHL and Rituximab-refractory NHL | CD20 |
| ImClone | Cetuximab + innotecan | refractory colorectal carcinoma | EGF receptor |
| | Cetuximab + cisplatin & radiation | newly diagnosed or recurrent head & neck cancer | EGF receptor |
| | Cetuximab + gemcitabine | newly diagnosed metastatic pancreatic carcinoma | EGF receptor |
| | Cetuximab + cisplatin + 5FU or TAXOL ® | recurrent or metastatic head & neck cancer | EGF receptor |
| | Cetuximab + carboplatin + paclitaxel | newly diagnosed non-small cell lung carcinoma | EGF receptor |
| | Cetuximab + cisplatin | head & neck cancer (extensive incurable local-regional disease & distant metasteses) | EGF receptor |
| | Cetuximab + radiation | locally advanced head & neck carcinoma | EGF receptor |
| | BEC2 + Bacillus Calmette Guerin | small cell lung carcinoma | mimics ganglioside GD3 |
| | BEC2 + Bacillus Calmette Guerin | melanoma | mimics ganglioside GD3 |
| | IMC-1C11 | colorectal cancer with liver metasteses | VEGF-receptor |
| ImmonoGen | nuC242-DM1 | Colorectal, gastric, and pancreatic cancer | nuC242 |
| ImmunoMedics | LymphoCide | Non-Hodgkins lymphoma | CD22 |
| | LymphoCide Y-90 | Non-Hodgkins lymphoma | CD22 |
| | CEA-Cide | metastatic solid tumors | CEA |
| | CEA-Cide Y-90 | metastatic solid tumors | CEA |
| | CEA-Scan (Tc-99m-labeled arcitumomab) | colorectal cancer (radioimaging) | CEA |
| | CEA-Scan (Tc-99m-labeled arcitumomab) | Breast cancer (radioimaging) | CEA |
| | CEA-Scan (Tc-99m-labeled arcitumomab) | lung cancer (radioimaging) | CEA |
| | CEA-Scan (Tc-99m-labeled arcitumomab) | intraoperative tumors (radioimaging) | CEA |
| | LEUKOSCAN ® (Tc-99m-labeled sulesomab) | soft tissue infection (radioimaging) | CEA |
| | LYMPHOSCAN ® (Tc-99m-labeled) | lymphomas (radioimaging) | CD22 |
| | AFP-Scan (Tc-99m-labeled) | liver 7 gem-cell cancers (radioimaging) | AFP |
| Intracel | HumaRAD-HN (+yttrium-90) | head & neck cancer | NA |
| | HumaSPECT | colorectal imaging | NA |

TABLE 5-continued

Monoclonal antibodies for Cancer Therapy that can be used in combination with the antibodies of the invention.

| Company | Product | Disease | Target |
|---|---|---|---|
| Medarex | MDX-101 (CTLA-4) | Prostate and other cancers | CTLA-4 |
| | MDX-210 (her-2 overexpression) | Prostate cancer | HER-2 |
| | MDX-210/MAK | Cancer | HER-2 |
| MedImmune | Vitaxin | Cancer | $\alpha v \beta_3$ |
| Merck KGaA | MAb 425 | Various cancers | EGF receptor |
| | IS-IL-2 | Various cancers | Ep-CAM |
| Millennium | CAMPATH ® (alemtuzumab) | chronic lymphocytic leukemia | CD52 |
| NeoRx | CD20-streptavidin (+biotin-yttrium 90) | Non-Hodgkins lymphoma | CD20 |
| | Avidicin (albumin + NRLU13) | metastatic cancer | NA |
| Peregrine | Oncolym (+iodine-131) | Non-Hodgkins lymphoma | HLA-DR 10 beta |
| | COTARA ® (+iodine-131) | unresectable malignant glioma | DNA-associated proteins |
| Pharmacia Corporation | C215 (+staphylococcal enterotoxin) | pancreatic cancer | NA |
| | MAb, lung/kidney cancer | lung & kidney cancer | NA |
| | nacolomab tafenatox (C242 + staphylococcal enterotoxin) | colon & pancreatic cancer | NA |
| Protein Design Labs | Nuvion | T cell malignancies | CD3 |
| | SMART M195 ® | AML | CD33 |
| | SMART 1D10 ® | NHL | HLA-DR antigen |
| Titan | CEAVac | colorectal cancer, advanced | CEA |
| | TriGem | metastatic melanoma & small cell lung cancer | GD2-ganglioside |
| | TriAb | metastatic breast cancer | MUC-1 |
| Trilex | CEAVac | colorectal cancer, advanced | CEA |
| | TriGem | metastatic melanoma & small cell lung cancer | GD2-ganglioside |
| | TriAb | metastatic breast cancer | MUC-1 |
| Viventia Biotech | NovoMAb-G2 radiolabeled | Non-Hodgkins lymphoma | NA |
| | Monopharm C | colorectal & pancreatic carcinoma | SK-1 antigen |
| | GlioMAb-H (+gelonin toxin) | glioma, melanoma & neuroblastoma | NA |
| Xoma | RITUXAN ® | Relapsed/refractory low-grade or follicular NHL | CD20 |
| | RITUXAN ® | intermediate & high-grade NHL | CD20 |
| | ING-1 | adenomcarcinoma | Ep-CAM |

6.3.7 Vaccine Therapy and Prophylaxis

The invention provides a method for enhancing an immune response to a vaccine composition in a subject, said method comprising administering to said subject a humanized antibody of the invention or a fragment thereof that specifically binds FcγRIIB with greater affinity than said antibody or a fragment thereof binds FcγRIIA, and a vaccine composition, wherein said antibody or a fragment thereof enhances the immune response to said vaccine composition. In one particular embodiment, said antibody or a fragment thereof enhances the immune response to said vaccine composition by enhancing antigen presentation/and or antigen processing of the antigen to which the vaccine is directed at. Any vaccine composition known in the art is useful in combination with the antibodies or fragments thereof of the invention.

Although not intending to be bound by a particular mechanism of action, the antibodies of the invention may block activation of FcγRIIB that is expressed on certain populations and/or types of dendritic cells and thus enhance the activity of such dendritic cells during active vaccination. This enhanced dendritic cell activity may thus result in an enhanced or better response to prophylatic or therapeutic vaccination.

In one embodiment, the invention encompasses the use of the humanized antibodies of the invention in combination with any cancer vaccine known in the art, e.g., Canvaxin™ (Cancer Vax, Corporation, melanoma and colon cancer); Oncophage (HSPPC-96; Antigenics; metastatic melanoma); HER-2/neu cancer vaccine, etc. The cancer vaccines used in the methods and compositions of the invention can be, for example, antigen-specific vaccines, anti-idiotypic vaccines, dendritic cell vaccines, or DNA vaccines. In other embodiments, the invention encompasses use of the antibodies of the invention with vaccines against EGFRviii, CD44 splice variants, and PSMA. The invention encompasses the use of the antibodies of the invention with cell-based vaccines as described by Segal et al. (U.S. Pat. No. 6,403,080, which is incorporated herein by reference in its entirety). The cell based vaccines used in combination with the antibodies of the invention can be either autologous or allogeneic. Briefly, the cancer-based vaccines as described by Segal et al. are based on Opsonokine™ product by Genitrix, LLC. Opsonokines™ are genetically engineered cytokines that, when mixed with tumor cells, automatically attach to the surface of the cells. When the "decorated" cells are administered as a vaccine, the cytokine on the cells activates critical antigen presenting cells in the recipient, while also allowing the antigen presenting cells to ingest the tumor cells. The antigen presenting cells are then able to instruct "killer" T cells to find and destroy similar tumor cells throughout the body. Thus, the Opsonokine™ product converts the tumor cells into a potent anti-tumor immunotherapeutic.

In one embodiment, the invention encompasses the use of the humanized antibodies of the invention in combination with any allergy vaccine known in the art. The humanized antibodies of the invention, can be used, for example, in combination with recombinant hybrid molecules coding for the major timothy grass pollen allergens used for vaccination against grass pollen allergy, as described by Linhart et al. (2000, *FASEB Journal*, 16(10): 1301-3, which is incorporated by reference). In addition, the humanized antibodies of the invention can be used in combination with DNA-based vaccinations described by Horner et al. (2002, *Allergy*, 57 Suppl. 72:24-9, which is incorporated by reference). Antibodies of the invention can be used in combination with Bacille Clamett-Guerin ("BCG") vaccination as described by Choi et al. (2002, *Ann. Allergy Asthma Immunology*, 88(6): 584-91) and Barlan et al. (2002, *Journal Asthma*, 39(3):239-46), both of which are incorporated herein by reference in entirety, to downregulate IgE secretion. The humanized antibodies of the invention are useful in treating food allergies. In particular the humanized antibodies of the invention can be used in combination with vaccines or other immunotherapies known in the art (see Hourihane et al., 2002, *Curr. Opin. Allergy Clin. Immunol.* 2(3):227-31) for the treatment of peanut allergies.

The methods and compositions of the invention can be used in combination with vaccines, in which immunity for the antigen(s) is desired. Such antigens may be any antigen known in the art. The humanized antibodies of the invention can be used to enhance an immune response, for example, to infectious agents, diseased or abnormal cells such as, but not limited to, bacteria (e.g., gram positive bacteria, gram negative bacteria, aerobic bacteria, Spirochetes, *Mycobacteria, Rickettsias, Chlamydias*, etc.), parasites, fungi (e.g., *Candida albicans, Aspergillus*, etc.), viruses (e.g., DNA viruses, RNA viruses, etc.), or tumors. Viral infections include, but are not limited to, human immunodeficiency virus (HIV); hepatitis A virus, hepatitis B virus, hepatitis C virus, hepatitis D virus, or other hepatitis viruses; cytomegaloviruses, herpes simplex virus-1 (–2,–3,–4,–5,–6), human papilloma viruses; Respiratory syncytial virus (RSV), Parainfluenza virus (PIV), Epstein Barr virus, human metapneumovirus (HMPV), influenza virus, Severe Acute Respiratory Syndrome(SARS) or any other viral infections.

The invention encompasses methods and vaccine compositions comprising combinations of a humanized antibody of the invention, an antigen and a cytokine. Preferably, the cytokine is IL-4, IL-10, or TGF-β.

The invention encompasses the use of the humanized antibodies of the invention to enhance a humoral and/or cell mediated response against the antigen(s) of the vaccine composition. The invention further encompasses the use of the humanized antibodies of the invention to either prevent or treat a particular disorder, where an enhanced immune response against a particular antigen or antigens is effective to treat or prevent the disease or disorder. Such diseases and disorders include, but are not limited to, viral infections, such as HIV, CMV, hepatitis, herpes virus, measles, etc., bacterial infections, fungal and parasitic infections, cancers, and any other disease or disorder amenable to treatment or prevention by enhancing an immune response against a particular antigen or antigens.

6.3.8 Breaking Tolerance to an Antigen

Certain cancers may be associated with an ability of the tumors to circumvent an immune response against their antigens, i.e., tolerance to these antigens exists. See Mapara et al., 2004, J. Clin. Oncol. 22:1136-1151; incorporated by reference in its entirety. Accordingly, a goal in tumor immunotherapy is to break tolerance to tumor antigens in order to induce an antitumor response. Eliciting an immune response against a foreign antigen that is otherwise recognized by the host as a "self" antigen breaks tolerance to that antigen.

Thus, in certain embodiments, the invention provides a method for breaking tolerance to an antigen in a patient by administering to a patient in need thereof (1) an antigen-antibody complex comprising the antigen and (2) a humanized antibody or fragment thereof that specifically binds the extracellular domain of human FcγRIIB and blocks the Fc binding site of human FcγRIIB, thereby breaking tolerance in said patient to the antigen. The humanized antibody or fragment thereof can be administered before, concurrently with, or after administration of said antigen-antibody complex.

Antigen-presenting cells, such as dendritic cells, coexpress activating and inhibitory Fc gamma receptors. Without being bound by theory, when antibodies that block Fc binding to FcγRIIB are present, the antigen-antibody complexes comprising an antigen are primarily taken up by non-inhibitory receptors on antigen-presenting cells eliciting an immune response to the antigen.

In certain embodiments, the antigen is an antigen that is associated with a cancer or a neoplastic disease. In another aspect, the antigen is specific to a cancer cell or a neoplastic cell. The antigen can also be an antigen of a pathogen, such as, e.g., a virus, a bacterium, or a protozoa. Representative antigens have been disclosed herein.

6.4 Compositions and Methods of Administering

The invention provides methods and pharmaceutical compositions comprising the humanized antibodies of the invention. The invention also provides methods of treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or conjugated molecules of the invention. In a preferred aspect, an antibody or fusion protein or conjugated molecule, is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human.

Various delivery systems are known and can be used to administer a composition comprising humanized antibodies of the invention, e.g., encapsulation in liposomes, microparticles, microcapsules, recombinant cells capable of expressing the antibody or fusion protein, receptor-mediated endocytosis (see, e.g., Wu and Wu, 1987, *J. Biol. Chem.* 262:4429-4432; incorporated by reference in its entirety), construction of a nucleic acid as part of a retroviral or other vector, etc.

In some embodiments, the humanized antibodies of the invention are formulated in liposomes for targeted delivery of the antibodies of the invention. Liposomes are vesicles comprised of concentrically ordered phopsholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al., 1985, *Proc. Natl. Acad. Sci. USA*, 82: 3688; Hwang et al., 1980 *Proc. Natl. Acad. Sci. USA*, 77: 4030-4; U.S. Pat. Nos. 4,485,045 and 4,544,545; all of which are incorporated herein by reference in their entirety.

The invention also encompasses methods of preparing liposomes with a prolonged serum half-life, i.e., enhanced circulation time, such as those disclosed in U.S. Pat. No. 5,013,556. Preferred liposomes used in the methods of the invention are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome, see, e.g., Bendas et al., 2001 *BioDrugs*, 15(4): 215-224; Allen et al., 1987 *FEBS Lett.* 223: 42-6; Klibanov et al., 1990 *FEBS Lett*, 268: 235-7; Blum et al., 1990, *Biochim. Biophys. Acta.*, 1029: 91-7; Torchilin et al., 1996, *J. Liposome Res.* 6: 99-116; Litzinger et al., 1994, *Biochim. Biophys. Acta*, 1190: 99-107; Maruyama et al., 1991, *Chem. Pharm. Bull.*, 39: 1620-2; Klibanov et al., 1991, *Biochim Biophys Acta*, 1062: 142-8; Allen et al., 1994, *Adv. Drug Deliv. Rev*, 13: 285-309; all of which are incorporated herein by reference in their entirety. The invention also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody of the invention, e.g., F(ab'), may be conjugated to the liposomes using previously described methods, see, e.g., Martin et al., 1982, *J. Biol. Chem.* 257: 286-288, which is incorporated herein by reference in its entirety.

The humanized antibodies of the invention may also be formulated as immunoliposomes. Immunoliposomes refer to a liposomal composition, wherein an antibody of the invention or a fragment thereof is linked, covalently or non-covalently to the liposomal surface. The chemistry of linking an antibody to the liposomal surface is known in the art and encompassed within the invention, see, e.g., U.S. Pat. No. 6,787,153; Allen et al., 1995, Stealth Liposomes, Boca Rotan: CRC Press, 233-44; Hansen et al., 1995, *Biochim. Biophys. Acta*, 1239: 133-44; which are incorporated herein by reference in their entirety. In most preferred embodiments, immunoliposomes for use in the methods and compositions of the invention are further sterically stabilized. Preferably, the humanized antibodies of the invention are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phospahtidylinositol (PI). To achieve a covalent linkage between an antibody and a hydrophobic anchor, any of the known biochemical strategies in the art may be used, see, e.g., J. Thomas August, ed., 1997, Gene Therapy: Advances in Pharmacology, Volume 40, Academic Press, San Diego, Calif., p. 399-435, which is incorporated herein by reference in its entirety. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionyl-phosphatidylethanolamine. See, e.g., Dietrich et al., 1996, *Biochemistry*, 35: 1100-1105; Loughrey et al., 1987, *Biochim. Biophys. Acta*, 901: 157-160; Martin et al., 1982, *J. Biol. Chem.* 257: 286-288; Martin et al., 1981, *Biochemistry*, 20: 4429-38; all of which are incorporated herein by reference in their entirety. Although not intending to be bound by a particular mechanism of action, immunoliposomal formulations comprising an antibody of the invention are particularly effective as therapeutic agents, since they deliver the antibody to the cytoplasm of the target cell, i.e., the cell comprising the FcγRIIB receptor to which the antibody binds. The immunoliposomes preferably have an increased half-life in blood, specifically target cells, and can be internalized into the cytoplasm of the target cells thereby avoiding loss of the therapeutic agent or degradation by the endolysosomal pathway.

The invention encompasses immunoliposomes comprising a humanized antibody of the invention or a fragment thereof. In some embodiments, the immunoliposomes further comprise one or more additional therapeutic agents, such as those disclosed herein.

The immunoliposomal compositions of the invention comprise one or more vesicle forming lipids, an antibody of the invention or a fragment or derivative thereof, and, optionally, a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations of the invention are known to one skilled in the art and encompassed within the invention. In some embodiments, the immunoliposomal compositions further comprise a hydrophilic polymer, e.g., polyethylene glycol, and ganglioside GM1, which increases the serum half life of the liposome. Methods of conjugating hydrophilic polymers to liposomes are well known in the art and encompassed within the invention. For a review of immunoliposomes and methods of preparing them, see, e.g., U.S. Patent Application Publication No. 2003/0044407; PCT International Publication No. WO 97/38731, Vingerhoeads et al., 1994, Immunomethods, 4: 259-72; Maruyama, 2000, *Biol. Pharm. Bull.* 23(7): 791-799; Abra et al., 2002, Journal of Liposome Research, 12(1&2): 1-3; Park, 2002, *Bioscience Reports*, 22(2): 267-281; Bendas et al., 2001 *BioDrugs*, 14(4): 215-224, *J. Thomas August, ed.*, 1997, Gene Therapy Advances in Pharmacology, Volume 40, Academic Press, San Diego, Calif., p. 399-435, all of which are incorporated herein by reference in their entireties.

Methods of administering a humanized antibody of the invention include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the humanized antibodies of the invention are packaged in a hermetically sealed container, such as an ampoule or sachette, indicating the quantity of antibody. In one embodiment, the antibodies of the invention are supplied as a dry sterilized lyophilized powder or water free concentrate in a hermetically sealed container and can be reconstituted, e.g., with water or saline to the appropriate concentration for administration to a subject. Preferably, the antibodies of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies of the invention should be stored at between 2 and 8° C. in their original container and the antibodies should be administered within 12 hours, preferably within 6 hours, within 5 hours, within 3 hours, or within 1 hour after being reconstituted. In an alternative embodiment, antibodies of the invention are supplied in liquid form in a hermetically sealed container indicating the quantity and concentration of the antibody, fusion protein, or conjugated molecule. Preferably, the liquid form of the antibodies are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For antibodies encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In one embodiment, the dosage of the antibodies of the invention administered to a patient are 0.01 mg to 1000 mg/day, when used as single agent therapy. In another embodiment the antibodies of the invention are used in combination with other therapeutic compositions and the dosage administered to a patient are lower than when said antibodies are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an antibody of the invention, care must be taken to use materials to which the antibody or the fusion protein does not absorb.

In another embodiment, the compositions can be delivered in a vesicle, in particular a liposome (See Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.) (each of which is incorporated by reference in its entirety).

In yet another embodiment, the compositions can be delivered in a controlled release or sustained release system. Any technique known to one of skill in the art can be used to produce sustained release formulations comprising one or more antibodies of the invention. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al, 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760, each of which is incorporated herein by reference in its entirety. In one embodiment, a pump may be used in a controlled release system (See Langer, supra; Sefton, 1987, *CRC Crit. Ref Biomed. Eng.* 14:20; Buchwald et al., 1980, Surgery 88:507; and Saudek et al., 1989, *N. Engl. J. Med.* 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., *Macromol. Sci. Rev. Macromol. Chem.* 23:61; See also Levy et al., 1985, *Science* 228:190; During et al., 1989, Ann. Neurol. 25:351; Howard et al., 1989, *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533). Each of the foregoing references is incorporated herein in its entirety.

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

In a specific embodiment where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

For antibodies, the therapeutically or prophylactically effective dosage administered to a subject is typically 0.1 mg/kg to 200 mg/kg of the subject's body weight. Preferably, the dosage administered to a subject is between 0.1 mg/kg and 20 mg/kg of the subject's body weight and more preferably the dosage administered to a subject is between 1 mg/kg to 10 mg/kg of the subject's body weight. The dosage and frequency of administration of antibodies of the invention may be reduced also by enhancing uptake and tissue penetration (e.g., into the lung) of the antibodies or fusion proteins by modifications such as, for example, lipidation.

Treatment of a subject with a therapeutically or prophylactically effective amount of antibodies of the invention can include a single treatment or, preferably, can include a series of treatments. In a preferred example, a subject is treated with antibodies of the invention in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the antibodies used for treatment may increase or decrease over the course of a particular treatment.

6.4.1 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of humanized antibodies of the invention and a pharmaceutically acceptable carrier.

In one particular embodiment, the pharmaceutical composition comprises of a therapeutically effective amount of a humanized antibody or a fragment thereof that binds FcγRIIB with a greater affinity than said antibody or a fragment thereof binds FcγRIIA, a cytotoxic antibody that specifically binds a cancer antigen, and a pharmaceutically acceptable carrier. In another embodiment, said pharmaceutical composition further comprises one or more anti-cancer agents.

In another particular embodiment, the pharmaceutical composition comprises (i) a therapeutically effective amount of a humanized antibody or fragment thereof that specifically binds the extracellular domain of human FcγRIIB and blocks the Fc binding site of human FcγRIIB; (ii) a cytotoxic antibody that specifically binds a cancer antigen; and (iii) a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The present invention also provides pharmaceutical compositions and kits comprising a FcγRIIB antagonist for use in the prevention, treatment, management, or amelioration of a B-cell malignancy, or one or more symptoms thereof. In particular, the present invention provides pharmaceutical compositions and kits comprising a humanized FcγRIIB antibody or an antigen-binding fragment thereof.

6.4.2 Kits

The invention provides a pharmaceutical pack or kit comprising one or more containers filled with humanized antibodies of the invention. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more humanized antibodies of the invention. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

6.5 Characterization and Demonstration of Therapeutic Utility

Several aspects of the pharmaceutical compositions or prophylactic or therapeutic agents of the invention are preferably tested in vitro, e.g., in a cell culture system, and then in vivo, e.g., in an animal model organism, such as a rodent animal model system, for the desired therapeutic activity prior to use in humans. For example, assays which can be used to determine whether administration of a specific pharmaceutical composition is indicated, include cell culture assays in which a patient tissue sample is grown in culture, and exposed to or otherwise contacted with a pharmaceutical composition, and the effect of such composition upon the tissue sample is observed, e.g., inhibition of or decrease in growth and/or colony formation in soft agar or tubular network formation in three-dimensional basement membrane or extracellular matrix preparation. The tissue sample can be obtained by biopsy from the patient. This test allows the identification of the therapeutically most effective prophylactic or therapeutic molecule(s) for each individual patient. Alternatively, instead of culturing cells from a patient, therapeutic agents and methods may be screened using cells of a tumor or malignant cell line. In various specific embodiments, in vitro assays can be carried out with representative cells of cell types involved in an autoimmune or inflammatory disorder (e.g., T cells), to determine if a pharmaceutical composition of the invention has a desired effect upon such cell types. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc. Additional assays include raft association, CDC, ADCC and apoptosis assays as known in the art.

Combinations of prophylactic and/or therapeutic agents can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary such as the temporal regime of administering the prophylactic and/or therapeutic agents, and whether such agents are administered separately or as an admixture.

Preferred animal models for use in the methods of the invention are, for example, transgenic mice expressing FcγR on mouse effector cells, e.g., any mouse model described in U.S. Pat. No. 5,877,396 (which is incorporated herein by reference in its entirety). Transgenic mice for use in the methods of the invention include, but are not limited to, mice carrying human FcγRIIIA, mice carrying human FcγRIIA, mice carrying human FcγRIIB and human FcγRIIIA, mice carrying human FcγRIIB and human FcγRIIA.

Once the prophylactic and/or therapeutic agents of the invention have been tested in an animal model they can be tested in clinical trials to establish their efficacy. Establishing clinical trials will be done in accordance with common methodologies known to one skilled in the art, and the optimal dosages and routes of administration as well as toxicity profiles of the compositions of the invention can be established using routine experimentation.

The anti-inflammatory activity of the combination therapies of invention can be determined by using various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al.(eds.), Chapter 30 (Lee and Febiger, 1993). Experimental and spontaneous animal models of inflammatory arthritis and autoimmune rheumatic diseases can also be used to assess the anti-inflammatory activity of the combination therapies of invention. The following are some assays provided as examples, and not by limitation.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al.(eds.), Chapter 30 (Lee and Febiger, 1993), incorporated herein by reference in its entirety.

The anti-inflammatory activity of the combination therapies of invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al., "Carrageenan-Induced Arthritis in the Rat," Inflammation, 24(2): 141-155, (2000;) incorporated by reference in its entirety. Also commonly used are zymosan-induced inflammation animal models as known and described in the art. A collagen-induced arthritis (CIA) is an animal model for the human autoimmune disease rheumatoid arthritis (RA) (Trenthom et al., 1977, J. Exp. Med. 146:857, which is hereby incorporated by reference herein in its entirety). This disease can be induced in many species by the administration of heterologous type II collagen (Courtenay et al., 1980, Nature 283:665; and Cathcart et at, 1986, Lab. Invest. 54:26); with respect to animal models of arthritis see, in addition, e.g., Holmdahl, R., 1999, Curr. Biol. 15:R528-530 (each of these references is hereby incorporated by reference herein in its entirety).

The anti-inflammatory activity of the combination therapies of invention can also be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" Proc. Soc. Exp. Biol Med. 111, 544-547, (1962); incorporated by reference in its entirety. This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group.

Additionally, animal models for inflammatory bowel disease can also be used to assess the efficacy of the combination therapies of invention (Kim et al., 1992, Scand. J. Gastroentrol. 27:529-537; Strober, 1985, Dig. Dis. Sci. 30(12 Suppl): 3S-10S (each of which is incorporated by reference in its entirety)). Ulcerative cholitis and Crohn's disease are human inflammatory bowel diseases that can be induced in animals. Sulfated polysaccharides including, but not limited to, amylopectin, carrageen, amylopectin sulfate, and dextran sulfate or chemical irritants including, but not limited to, trinitrobenzenesulphonic acid (TNBS) and acetic acid can be administered to animals orally to induce inflammatory bowel diseases.

Animal models for asthma can also be used to assess the efficacy of the combination therapies of invention. An example of one such model is the murine adoptive transfer model in which aeroallergen provocation of TH1 or TH2 recipient mice results in TH effector cell migration to the airways and is associated with an intense neutrophilic (TH1) and eosinophilic (TH2) lung mucosal inflammatory response (Cohn et al., 1997, J. Exp. Med. 1861737-1747; incorporated by reference in its entirety).

Animal models for autoimmune disorders can also be used to assess the efficacy of the combination therapies of invention. Animal models for autoimmune disorders such as type 1 diabetes, thyroid autoimmunity, systemic lupus eruthematosus, and glomerulonephritis have been developed (Flanders et al., 1999, Autoimmunity 29:235-246; Krogh et al., 1999, Biochimie 81:511-515; Foster, 1999, Semin. Nephrol. 19:12-24 (each of which is incorporated by reference in its entirety)).

Further, any assays known to those skilled in the art can be used to evaluate the prophylactic and/or therapeutic utility of the combinatorial therapies disclosed herein for autoimmune and/or inflammatory diseases.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$ Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models for the study of cancer such as the SCID mouse model or transgenic mice or nude mice with human xenografts, animal models, such as hamsters, rabbits, etc. known in the art and described in *Relevance of Tumor Models for Anticancer Drug Development* (1999, eds. Fiebig and Burger); *Contributions to Oncology* (1999, Karger); *The Nude Mouse in Oncology Research* (1991, eds. Boven and Winograd); and *Anticancer Drug Development Guide* (1997 ed. Teicher), herein incorporated by reference in their entireties.

The protocols and compositions of the invention are preferably tested in vitro, and then in vivo, for the desired therapeutic or prophylactic activity, prior to use in humans. Therapeutic agents and methods may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of cancer, inflammatory disorder, or autoimmune disease.

6.6 Diagnostic Methods

Labeled antibodies of the invention can be used for diagnostic purposes to detect, diagnose, or monitor diseases, disorders or infections. The invention provides for the detection or diagnosis of a disease, disorder or infection, particularly an autoimmune disease comprising: (a) assaying the expression of FcγRIIB in cells or a tissue sample of a subject using one or more antibodies that immunospecifically bind to FcγRIIB; and (b) comparing the level of the antigen with a control level, e.g., levels in normal tissue samples, whereby an increase in the assayed level of antigen compared to the control level of the antigen is indicative of the disease, disorder or infection.

Antibodies of the invention can be used to assay FcγRIIB levels in a biological sample using classical immunohistological methods as described herein or as known to those of skill in the art (e.g., see Jalkanen et al., 1985, *J. Cell. Biol.* 101:976-985; Jalkanen et al., 1987, *J. Cell. Biol.* 105:3087-3096 (each of which is incorporated by reference in its entirety)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, alkaline phosphatase, glucose oxidase; radioisotopes, such as iodine ($^{125}$I, $^{131}$I), carbon ($^{14}$C), sulfur ($^{35}$S), tritium ($^3$H), indium ($^{121}$In), and technetium ($^{99m}$Tc); luminescent labels, such as luminol; and fluorescent labels, such as fluorescein and rhodamine.

One aspect of the invention is the detection and diagnosis of a disease, disorder, or infection in a human. In one embodiment, diagnosis comprises: a) administering (for example, parenterally, subcutaneously, or intraperitoneally) to a subject an effective amount of a labeled antibody that immunospecifically binds to FcγRIIB; b) waiting for a time interval following the administration for permitting the labeled antibody to preferentially concentrate at sites in the subject where FcγRIIB is expressed (and for unbound labeled molecule to be cleared to background level); c) determining background level; and d) detecting the labeled antibody in the subject, such that detection of labeled antibody above the background level indicates that the subject has the disease, disorder, or infection. In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982); incorporated by reference in its entirety.

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

7. EXAMPLES 7.1 Humanization of Mouse ANI-CD32B MAB 2B6

RNA was converted to cDNA and the VH and VL segments were PCR amplified using the RLM-RACE kit (Ambion, Inc.). Gene specific primers for the VH were SJ15R, SEQ ID NO. 47 (5' GGT CAC TGT CAC TGG CTC AGG G 3') and SJ16R, SEQ ID NO. 48 (5' AGG CGG ATC CAG GGG CCA GTG GAT AGA C 3'). Gene specific primers for the VL were SJ17R, SEQ ID NO. 49 (5'GCA CAC GAC TGA GGC ACC TCC AGA TG 3') and SJ18R, SEQ ID NO. 50 (5'CGG CGG ATC CGA TGG ATA CAG TTG GTG CAG CAT C 3'). The RACE product was inserted into the plasmid pCR2.1-TOPO using a TOPO TA Cloning kit (Invitrogen, Inc.). The resulting plasmids were then subjected to DNA sequencing to determine the VH and VL sequences for 2B6. The resulting sequences were then translated and the predicted amino acid sequence determined for each. From these sequences, the framework (FR) and complementarity determining (CDR) regions were identified as defined by Kabat. The mouse VH was then joined to a human C-Gammal constant region and an Ig leader sequence and inserted into pCI-neo for mammalian expression. The mouse VL was joined to a human C-kappa segment and an Ig leader sequence and also cloned into pCI-neo for mammalian expression.

The humanized 2B6 VH consists of the FR segments from the human germline VH segment VH1-18 and JH6, and the CDR regions of the 2B6 VH. The humanized 2B6 VL consists of the FR segments of the human germline VL segment VK-A26 and JK4, and the CDR regions of 2B6 VL. The humanized VH and VL segments were assembled de novo from oligonucleotides combined and amplified by PCR. The resulting fragment was then combined by PCR with a leader sequence and the appropriate constant region segment cloned into the expression vector pCI-neo as a Nhe I-EcoR I fragment. The DNA sequence of the resulting plasmids was confirmed by sequence analysis. For the VL, none of the plasmids analyzed had a perfectly correct sequence. The two best inserts were combined to reduce the number of incorrect positions, then these positions were corrected by site-directed mutagenesis. After this procedure light chain segments having predicted humanized 2B6 VL sequence were identified.

The alignment of the amino acid sequences of mouse 2B6 VH, humanized 2B6 VH1, VH1-18 and human JH6 is shown in FIG. 1A. FIG. 1B shows the alignment of amino acid sequences of murine 2B6VL, human 2B6VL-1, human 2B6VL-2; human 2B6VL-3, and human Jκ4. The first amino acid in the humanized 2B6VL CDR2 was found to be asparagine (see, e.g., amino acid number 1 of SEQ ID NO:9), presumably allowing N-linked glycosylation and possibly affecting binding of the antibody. For this reason amino acid number 1 of the light chain variable domain CDR2 was substituted with tyrosine (h2B6 VL-2, h2B6 VL-3) or glutamic acid (h2B6 VL-5; amino acid 50 of SEQ ID NO:62) to remove the glycosylation site (FIG. 2B). h2B6 VL-5 (SEQ ID NO:62) additionally contains a substitution with phenylalanine at amino acid number 21 of framework region 1 (amino acid number 21 of SEQ ID NO:62), which corresponds to the amino acid at the same position in the donor antibody light chain variable domain. FIG. 2A shows the alignment of the heavy chain variable regions, h2B6 VH-1 and h2B6 VH-3 (SEQ ID NO:68). h2B6 VH-3 contains a substitution at amino acid number 13 of framework region 2 (amino acid number 48 of SEQ ID NO:68), and substitutions with valine at amino acid number 6 of framework region 3 (amino acid 72 of SEQ ID NO:68), which corresponds to the amino acid at the same position in the donor antibody heavy chain variable domain.

7.2 Expression and Characterization of the Humanized 2B6 Heavy and Light Chains

Experiment 1: The hu2B6 heavy chain (HC) expression plasmid was co-transfected together with ch2B6 light chain (LC) into HEK-293 cells. At the same time, the ch2B6HC was co-transfected with the ch2B6LC. After three days in culture the amount of human IgG expressed was quantitated by ELISA. Binding to dimeric soluble FcγRIIb-Fc was then determined by ELISA assay.

Protocol for ELISA assay: 2.5 ng/well of soluble FcγRIIb-Fc was captured on 96-well Maxisorp plates by mouse anti-FcγRIIB antibody 3H7 at room temperature for 1 hour. A serial of two-fold dilution of conditioned medium of ch2B6, h2B6Hc/Ch2B6Lc, h2B6 v1.1 (comprising the heavy chain variable domain h2B6 VH-1 (FIG. 1A and FIG. 2A) and light chain variable domain h2B6 VL-1 (FIG. 1-B and FIG. 2B)) or h2B6 v3.5 (comprising the heavy chain variable domain h2B6 VH-3 (FIG. 2A; SEQ ID NO:68) and light chain variable domain h2B6 VL-5 (FIG. 2B; SEQ ID NO:62)) starting from 25 ng/well was added to the each well. The plate was incubated at room temperature for 1 hour, then binding was detected by HRP conjugated F(ab')$_2$ goat anti human IgG F(ab)'$_2$ specific secondary antibody. After incubation with the secondary antibody for approximately 45 minutes, the plate was developed using a TMB substrate. After 5 minutes incubation, the reaction was stopped by 1% $H_2SO_4$. The $OD_{450}$ nm was read by SOFTmax program. Between each step, the plates were washed 3 times with PBS/0.1% Tween20. Plates were blocked by 0.5% BSA in PBS/0.1% Tween 20 for 30 mins at room temperature before adding soluble FcγRIIb-Fc.

Results: The results of the ELISA assay with hu2B6HC/ch2B6LC and ch2B6 (ch2B6HC/ch2B6LC) are depicted in FIG. 3, which indicate that the hu2B6HC/ch2B6LC mAb bound to the receptor with similar affinity as the ch2B6HC/ch2B6LC mAb. A second ELISA was performed as for ch2B6, h2B6 1.1, and h2B6 3.5 as described with the exception that soluble FcγRIIB-Fc was captured directly on the 96-well Maxisorp plates at 4° C. over night (FIG. 4). The results indicate that h2B6 3.5 bound to the receptor with similar affinity to ch2B6, and substantially greater affinity than ch2B6 1.1, which comprises the glycosylation site in CDR of the light chain variable domain.

FACS analysis was then performed to measure the binding of the mAbs to Daudi cells.

Protocol for FACS analysis. Approximately $10^6$ Daudi cells were used for each antibody staining. Cells were washed once with PBS. Primary antibodies (Ch2B6, Hu2B6Hc/ch2B6Lc, human IgG1) were diluted into 0.5, 0.1, 0.02 µg/mL in PBS/1% BSA and 100 µL of diluted antibodies was transferred to the cells. After 30 mins incubation at 4° C., cells were washed once with 1 mL PBS/1% BSA. PE conjugated F(ab')$_2$ fragment of goat anti human IgG Fc specific (Jackson ImmunoReseach, Inc.) was used as secondary antibody at 1:1000 dilution. After 30 mins incubation at 4° C., cells were washed once with 1 mL PBS/1% BSA. The cells were then resuspended in 500 µL of PBS/1% BSA and subjected to be FACS analysis.

Results: The results indicate that hu2B6HC/ch2B6LC mAb binds to this human B cell tumor line with the same affinity as the chimeric mAb (Table 6).

TABLE 6

| Primary Antibody | Concentration (μg/ml) | Mean Fluorescence |
|---|---|---|
| Human IgG1 | 0.5 | 9.49 |
| | 0.1 | N/A |
| | 0.02 | N/A |
| Ch2B6 | 0.5 | 647.48 |
| | 0.1 | 511.85 |
| | 0.02 | 172.68 |
| Hu2B6Hc/Ch2B6Lc | 0.5 | 648.99 |
| | 0.1 | 546.46 |
| | 0.02 | 196.93 |

Experiment 2: Transfections of HEK-293 cells were performed using the following combinations: hu2B6HC/hu2B6LC, hu2B6HC/ch2B6LC, ch2B6HC/hu2B6LC and ch2B6HC/ch2B6LC. After three days in culture the amount of human IgG expressed was quantitated by ELISA using the protocol described above. Binding to dimeric soluble FcγRIIb-Fc was then determined by ELISA. The results of this experiment, depicted in FIG. 5, indicated that all of the mAbs bound to the receptor with similar affinity. FACS analysis was then performed using the protocol described above to measure the binding of the mAbs to Daudi cells (Table 7). The results indicate that hu2B6HC/hu2B6LC mAb binds to this human B cell tumor line with the same affinity as the ch2B6 mAb.

TABLE 7

| Primary Antibody | Concentration (ug/ml) | Mean Fluorescence |
|---|---|---|
| Human IgG1 | 0.5 | 6.07 |
| | 0.1 | N/A |
| | 0.02 | N/A |
| Ch2B6 | 0.5 | 551.52 |
| | 0.1 | 514.69 |
| | 0.02 | 168.17 |
| Hu2B6 | 0.5 | 628.82 |
| | 0.1 | 618.13 |
| | 0.02 | 228.74 |

7.3 Generation, Expression and Binding of HU2B6LC Variants

There is a consensus sequence of N-glycosylation site (Asn-Xaa-Ser/Thr) in the Hu2B6LC CDR2 region (Asn$_{50}$-Val-Ser). To eliminate the glycosylation at residue 50 and thus limit potential variation in production as well as potential immunogenicity in a pharmaceutical application, other amino acids were substituted at the position 50 using site-directed mutagenesis (Stratagene kit). Two different versions of Hu2B6LC were generated, Hu2B6LC-N50Y Hu2B6LC-N50Y,V51A. These amino acids were chosen because Tyrosine is the human acceptor residue at CDRL2 position 50 and Alanine is the residue at CDRL2 position 51 in the human germline gene segment.

Transfections of HEK-293 cells were performed using the following combinations: hu2B6HC/hu2B6LC; hu2B6HC/hu2B6LC(N50Y); hu2B6HC/hu2B6LC(N50Y,V51A); ch2B6HC/ch2B6LC. After three days in culture the amount of human IgG expressed was quantitated by an ELISA assay, using the method described above. Binding to dimeric soluble FcγRIIb-Fc was determined by ELISA assay. The results of this experiment, depicted in FIG. 6, indicated that all of the mAbs bound to the receptor with similar affinity. FACS analysis was then performed to measure the binding of the mAbs to Daudi cells (Table 8). The results demonstrate that the two variants of hu2B6LC/hu2B6HC mAbs bind to this human B cell tumor line with the same affinity as the ch2B6 mAb.

TABLE 8

| Primary Antibody | Concentration (μg/ml) | Mean Fluorescence |
|---|---|---|
| Human IgG1 | 0.5 | 1.23 |
| | 0.1 | N/A |
| | 0.02 | N/A |
| Ch2B6 | 0.5 | 192.88 |
| | 0.1 | 141.01 |
| | 0.02 | 45.59 |
| Hu2B6 | 0.5 | 201.69 |
| | 0.1 | 174.37 |
| | 0.02 | 58.65 |
| Hu2B6 N50Y | 0.5 | 191.16 |
| | 0.1 | 134.56 |
| | 0.02 | 40.14 |
| Hu2B6N50Y, V51A | 0.5 | 167.16 |
| | 0.1 | 133.83 |
| | 0.02 | 45.95 |

7.4 Binding of MAbs to FcRIIA

Protocol for ELISA assay: 100 ng/well of soluble FcγIIA in carbonate buffer was coated on 96-well Maxisorp plates at 4° C. overnight. A serial of two-fold dilution of conditioned medium of Ch2B6; hu2B6HC/hu2B6LC; hu2B6HC/hu2B6LC(N50Y); hu2B6HC/hu2B6LC(N50Y,V51A); and purified IV.3 starting from 25 ng/well was added to the each well. The plate was incubated at room temperature for 1 hour. The binding was detected by HRP conjugated F(ab')2 goat anti human IgG F(ab')2 specific secondary antibody for Ch2B6 and all hu2B6 samples and HRP conjugated F(ab')2 goat anti mouse IgG (H+L) secondary antibody for IV.3. After incubation with the secondary antibody for approximately 45 minutes, the plate was developed using a TMB substrate. After 5 mins incubation, the reaction was stopped by 1% $H_2SO_4$. The $OD_{450}$ nm was ready by SOFTmax program. Between each step, the plates were washed 3 times with PBS/0.1% Tween 20. The plates were blocked by 0.5% BSA in PBS/0.1% Tween 20 for 30 mins at room temperature before adding the serial diluted antibodies.

Results: These data show that the humanized 2B6 antibody did not lose its ability to selectively bind CD32B during the humanization process (FIG. 7). In summary UV.3 (a murine Mab against FcγIIA) binds FcγIIA while chimeric and humanized 2B6 does not.

7.5 Fc Mutant Mediated Tumor Growth Control in an In Vivo Tumor Model

Fc mutations previously identified as conferring enhanced affinity for FcγIIIA and/or FcγIIA to FcγRIIB antibodies were further analyzed for relative efficacy of tumor control using an in vivo tumor model system (see, U.S. Provisional Application 60/707,419 filed Aug. 10, 2005; hereby incorporated by reference in its entirety)).

Materials and Methods

Antibodies harboring Fc mutants were tested for anti-tumor activity in a murine xenograft system. Balbc/nude mice were subcutaneously injected with $5 \times 10^6$ Daudi cells and subsequently monitored for general signs of illness, e.g. weight gain/loss and grooming activity. Without treatment, this model system results in 100% mortality with an average survival time of approximately 2 weeks post tumor cell inoculation. Treatment consists of doses of wild-type antibody or antibody comprising a variant Fc region administered at weekly intervals. Animals administered buffer alone at the same intervals served as a control. Tumor weight was calculated based on the estimated volume of the subcutaneous tumor according to the formula (width$^2$×length)/2.

Results

At weekly intervals, mice inoculated with Daudi cells received wild-type humanized 2B6 ("h2B6"), humanized 2B6 comprising an Fc region having 243L, 292P, 300L, 305I, and 396L or buffer alone. Wild-type and Fc mutant h2B6 antibody showed similar levels of tumor suppression at the highest dose schedule tested, weekly doses of 25 μg (FIGS. 7A and B). However, significant differences in antibody efficacy were observed when dosages were reduced. 100 and 10 fold reduction in wild-type h2B6 dosages provided no greater tumor control than administration of buffer alone (FIG. 8A). In contrast, the Fc mutant h2B6 provided significant protection at weekly doses of 2.5 μg and at least limited protection at weekly doses of 0.25 μg (FIG. 8B).

The protection conferred by even the lowest dose of Fc mutant antibody was confirmed in survival comparisons. At 11 weeks, 4 out of 7 mice remained alive in the group treated with 0.25 μg doses of Fc mutant h2B6 compared to only 1 out of 7 in the group treated with the same dose of wild-type h2B6 (FIGS. 9A and 9B).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entirety.

The invention claimed is:

1. A humanized antibody that comprises a human Fc domain and an antigen-binding domain, wherein said antibody specifically binds the extracellular domain of human FcγRIIB via said antigen-binding domain; wherein said antigen-binding domain comprises a heavy chain variable domain comprising the amino acid sequence of SEQ ID NO:68 and a light chain variable domain comprising the amino acid sequence of SEQ ID NO: 62 or a fragment of said antibody that comprises said antigen-binding domain and specifically binds said extracellular domain of human FcγRIIB via said antigen-binding domain.

2. The fragment of the humanized antibody of claim 1, wherein said fragment specifically binds said extracellular domain of human FcγRIIB via said antigen-binding domain.

3. The humanized antibody of claim 1, wherein the Fc domain comprises at least one amino acid modification in the Fc domain.

4. The humanized antibody of claim 3, wherein the Fc domain comprises a leucine at position 243, a proline at position 292, a leucine at position 300, an isoleucine at position 305, and a leucine at position 396 and wherein said positions are according to Kabat.

5. A pharmaceutical composition comprising (i) a therapeutically effective amount of the humanized antibody of claim 1; (ii) a cytotoxic antibody that specifically binds a cancer antigen; and (iii) a pharmaceutically acceptable carrier.

* * * * *